(12) United States Patent
Guney et al.

(10) Patent No.: US 10,201,678 B2
(45) Date of Patent: Feb. 12, 2019

(54) ADJUSTABLE MASK SYSTEM AND RELATED METHODS

(75) Inventors: Memduh Guney, Killara (AU); David Anthony Pidcock, Fairlight (AU); Joel Edward Gibson, Balmain (AU); Gerard Michael Rummery, Woodford (AU); Lachlan Richard Goldspink, Elizabeth Bay (AU); Craig David Edwards, Annandale (AU); Andrew Hung, Peakhurst (AU); Renee Frances Flower, Eastwood (AU); Rupert Christian Scheiner, Davidson (AU)

(73) Assignee: RESMED LIMITED, Bella Vista (AU)

( * ) Notice: Subject to any disclaimer, the term of this patent is extended or adjusted under 35 U.S.C. 154(b) by 842 days.

(21) Appl. No.: 13/377,305

(22) PCT Filed: Jun. 24, 2010

(86) PCT No.: PCT/AU2010/000796
§ 371 (c)(1),
(2), (4) Date: Dec. 9, 2011

(87) PCT Pub. No.: WO2010/148453
PCT Pub. Date: Dec. 29, 2010

(65) Prior Publication Data
US 2012/0080035 A1 Apr. 5, 2012

Related U.S. Application Data

(60) Provisional application No. 61/213,611, filed on Jun. 24, 2009, provisional application No. 61/272,933,
(Continued)

(51) Int. Cl.
*A61M 16/00* (2006.01)
*A61M 16/06* (2006.01)

(52) U.S. Cl.
CPC ........ *A61M 16/06* (2013.01); *A61M 16/0611* (2014.02); *A61M 16/0616* (2014.02);
(Continued)

(58) Field of Classification Search
CPC .............. A61M 16/06; A61M 16/0611; A61M 16/0616; A61M 2016/0661; A61M 16/0683
(Continued)

(56) References Cited

U.S. PATENT DOCUMENTS 2,245,658 A 6/1941 Erickson
2,620,794 A * 12/1952 George ................ A62B 18/084
128/207.11
(Continued)

FOREIGN PATENT DOCUMENTS

AU 2009902524 6/2009
AU 2009906101 12/2009
(Continued)

OTHER PUBLICATIONS

Notice of Reasons for Rejection and English translation in corresponding JP 2012-516438, dated Feb. 24, 2014.
(Continued)

*Primary Examiner* — Gregory Anderson
*Assistant Examiner* — Victoria Murphy
(74) *Attorney, Agent, or Firm* — Nixon & Vanderhye, P.C.

(57) ABSTRACT

An adjustable mask system (100) includes a cushion with a seal (130) having the ability to change size and/or shape. The seal is preferably a one-piece, continuous member without interruptions. To effect adjustment of the size and/or shape of the seal, an actuator may be provided, which may take the form of a dial (190).

39 Claims, 134 Drawing Sheets

Related U.S. Application Data filed on Nov. 20, 2009, provisional application No. 61/285,026, filed on Dec. 9, 2009.

(52) U.S. Cl.
CPC ..... *A61M 16/0622* (2014.02); *A61M 16/0683* (2013.01); *A61M 2016/0661* (2013.01)

(58) Field of Classification Search
USPC ............ 128/206.24, 205.25, 206.21, 206.28, 128/207.11
See application file for complete search history.

(56) References Cited

U.S. PATENT DOCUMENTS

| | | | |
|---|---|---|---|
| 2,762,368 | A | 9/1956 | Bloomfield |
| 4,657,010 | A | 4/1987 | Wright |
| 4,739,755 | A | 4/1988 | White et al. |
| 4,944,310 | A | 7/1990 | Sullivan |
| 5,884,624 | A | 3/1999 | Barnett et al. |
| 6,012,503 | A * | 1/2000 | Balder ............ 156/578 |
| 6,196,223 | B1 * | 3/2001 | Belfer et al. ............ 128/206.25 |
| 8,353,294 | B2 | 1/2013 | Frater et al. |
| 8,701,667 | B1 | 4/2014 | Ho et al. |
| 2003/0005509 | A1 | 1/2003 | Kelzer |
| 2003/0075182 | A1 * | 4/2003 | Heidmann ............ A61M 16/06 128/207.11 |
| 2003/0168063 | A1 * | 9/2003 | Gambone et al. ........ 128/203.16 |
| 2004/0255949 | A1 | 12/2004 | Lang et al. |
| 2005/0056286 | A1 * | 3/2005 | Huddart ................ A61M 16/06 128/206.21 |
| 2006/0032504 | A1 | 2/2006 | Burton et al. |
| 2006/0042629 | A1 * | 3/2006 | Geist ..................... A61M 16/06 128/206.24 |
| 2006/0219246 | A1 * | 10/2006 | Dennis ..................... 128/205.25 |
| 2009/0014007 | A1 * | 1/2009 | Brambilla ............ A61M 16/06 128/206.24 |
| 2009/0151724 | A1 * | 6/2009 | Wondka et al. ......... 128/204.23 |
| 2009/0211582 | A1 | 8/2009 | Reese et al. |
| 2010/0043798 | A1 * | 2/2010 | Sullivan ................ A61M 16/06 128/205.25 |
| 2011/0232647 | A1 * | 9/2011 | Ho ........................... 128/206.28 |

FOREIGN PATENT DOCUMENTS

| | | |
|---|---|---|
| EP | 1057494 | 12/2000 |
| EP | 1982740 | 10/2008 |
| GB | 150232 | 9/1920 |
| JP | 2004-522481 | 7/2004 |
| JP | 2005-506156 | 3/2005 |
| JP | 2005-537906 | 12/2005 |
| JP | 2006-505373 | 2/2006 |
| JP | 2008-501438 | 1/2008 |
| JP | 2008-502380 | 1/2008 |
| WO | WO 2004/071565 | 8/2004 |
| WO | WO 2005/053781 | 6/2005 |
| WO | WO 2005/077214 | 8/2005 |
| WO | 2005/118042 | 12/2005 |
| WO | WO 2008/011682 | 1/2008 |
| WO | WO 2008/011683 | 1/2008 |
| WO | 2008/028014 | 3/2008 |
| WO | WO 2008/028014 | 3/2008 |
| WO | WO 2008/053715 | 5/2008 |
| WO | WO 2008/070929 | 6/2008 |
| WO | PCT/AU2009/000240 | 2/2009 |
| WO | WO 2009/062265 | 5/2009 |

OTHER PUBLICATIONS

Communication and European Search Report dated Feb. 19, 2016 in corresponding European Application No. 10791072.1-1662 (9 pages).
Japanese Office Action issued in Corresponding JP Appln. No. 2012-516438 dated Oct. 20, 2014, with English language translation thereof.
Decision of Rejection and Decision to Reject the Amendments issued in related Japanese Application No. 2015-116380 dated Sep. 25, 2017, with English translation, 16 pages.
Examination Report issued in related European Application No. 10791072.1 dated Mar. 6, 2017, 5 pages.
Second Office Action issued in related Japanese Application No. 2015-116380 dated Jan. 19, 2017 with English translation, 11 pages.
International Search Report for PCT/AU2010/000796 dated Oct. 5, 2010.
U.S. Appl. No. 61/213,326, filed May 2009, Dravitzki.
U.S. Appl. No. 61/222,711, filed Jul. 2009, Dravitzki.
U.S. Appl. No. 61/272,162, filed Aug. 2009, Dravitzki.
U.S. Appl. No. 61/272,250, filed Sep. 2009, Dravitzki.
U.S. Appl. No. 61/263,175, filed Nov. 2009, Dravitzki.
U.S. Appl. No. 61/282,693, filed Mar. 2010, Dravitzki.
Japanese First Office Action dated May 30, 2016 in corresponding Japanese Application No. 2015-116380 with English translation (9 pages).

* cited by examiner

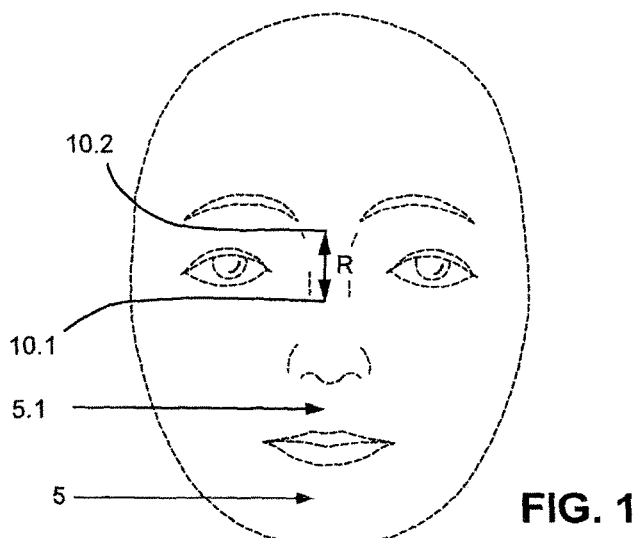
FIG. 1
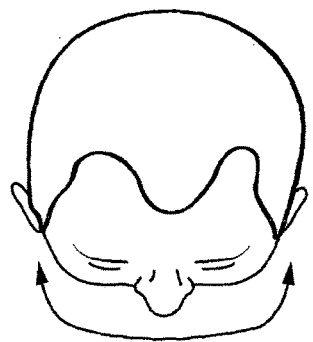
FIG. 1A
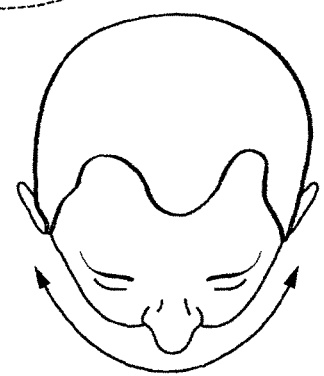
FIG. 1B
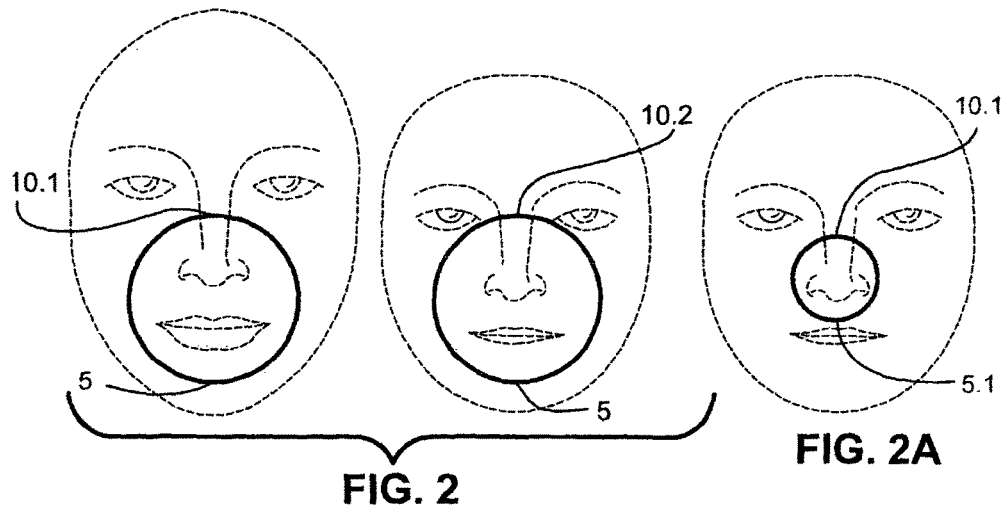
FIG. 2
FIG. 2A

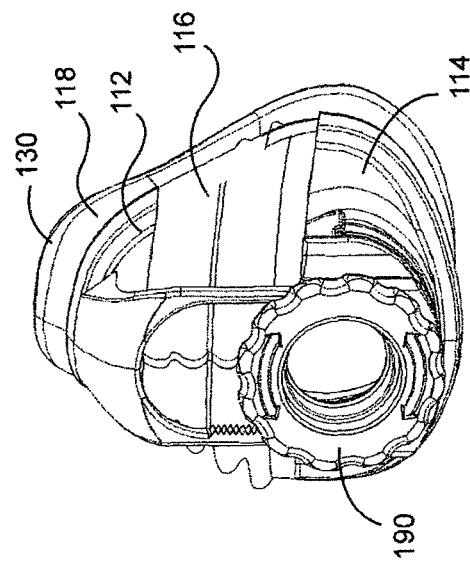
FIG. 9-6
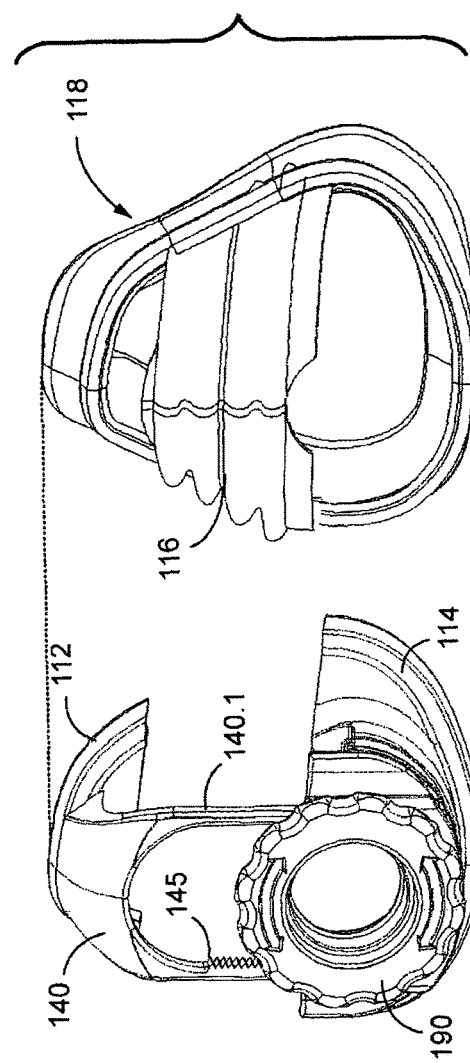
FIG. 9-5
FIG. 9-4

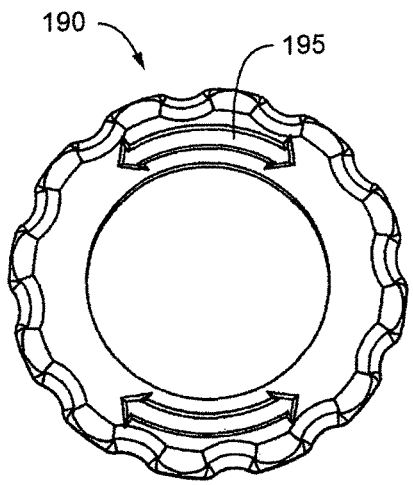
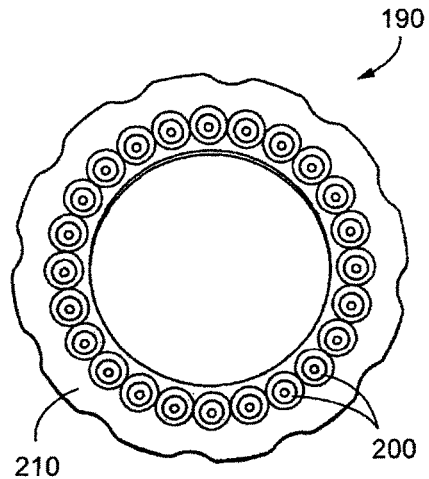
FIG. 12-1  FIG. 12-2
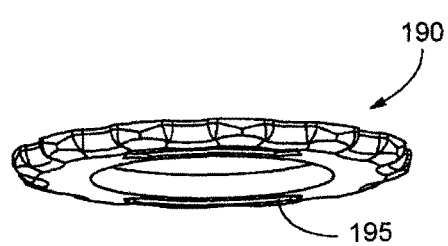
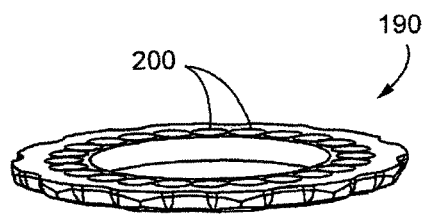
FIG. 12-3  FIG. 12-4
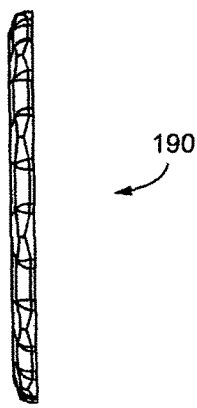
FIG. 12-5

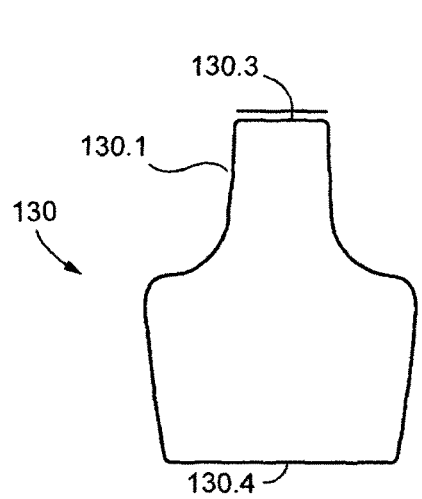
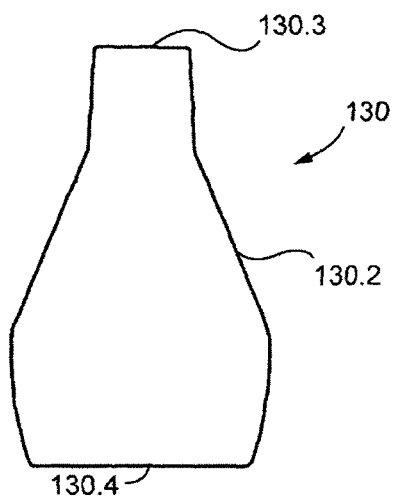
FIG. 17-1  FIG. 17-2
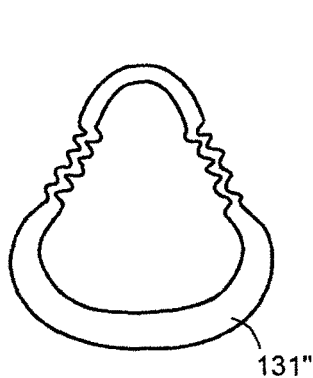
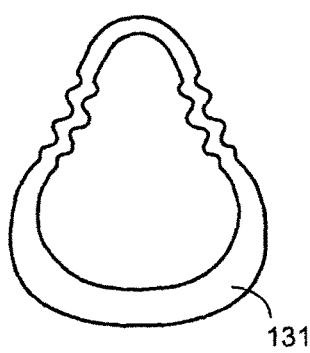
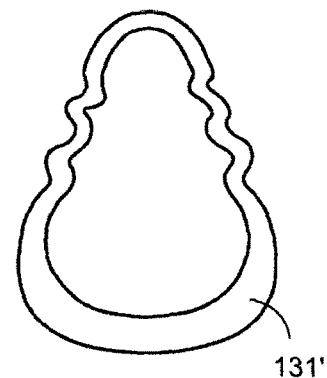
FIG. 18-3  FIG. 18-1  FIG. 18-2
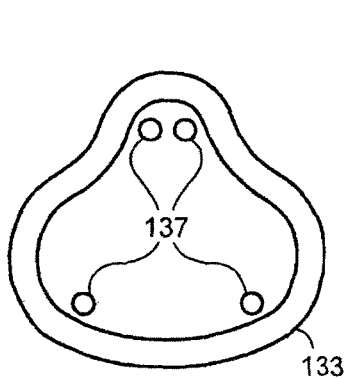
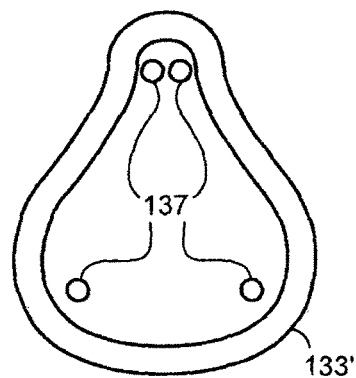
FIG. 18-4  FIG. 18-5

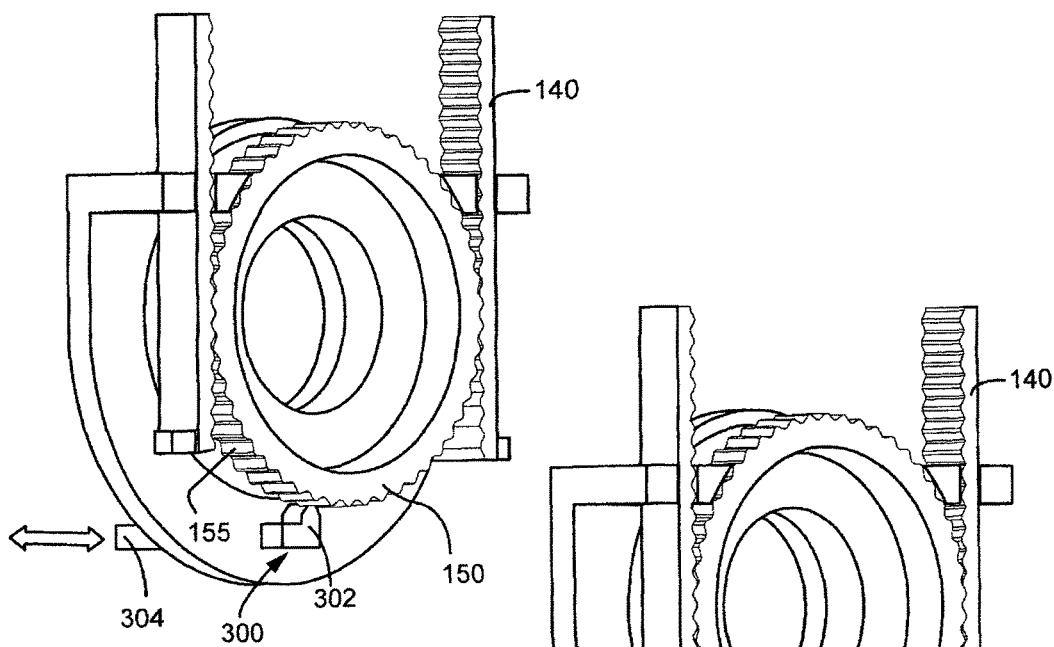
FIG. 21-1
FIG. 21-2
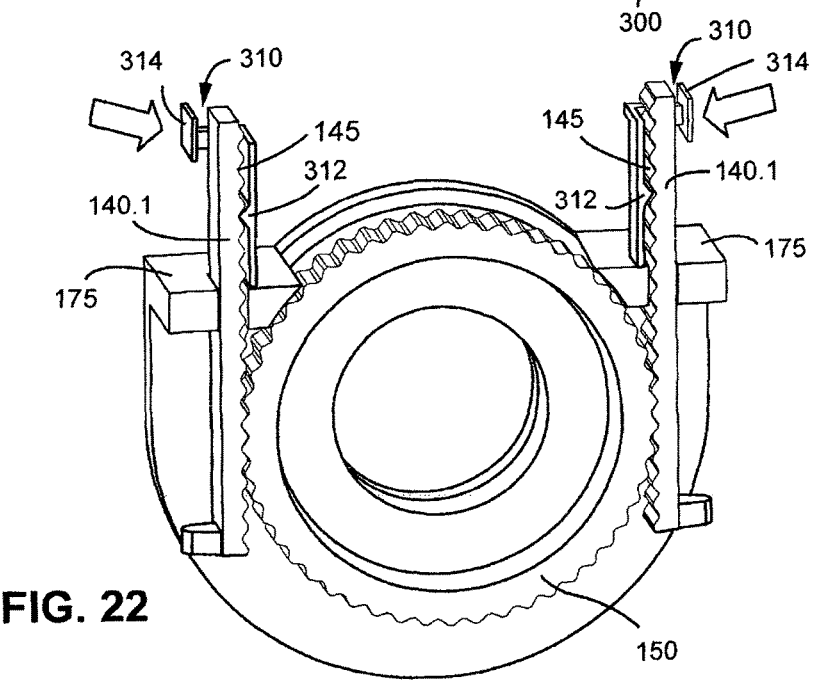
FIG. 22

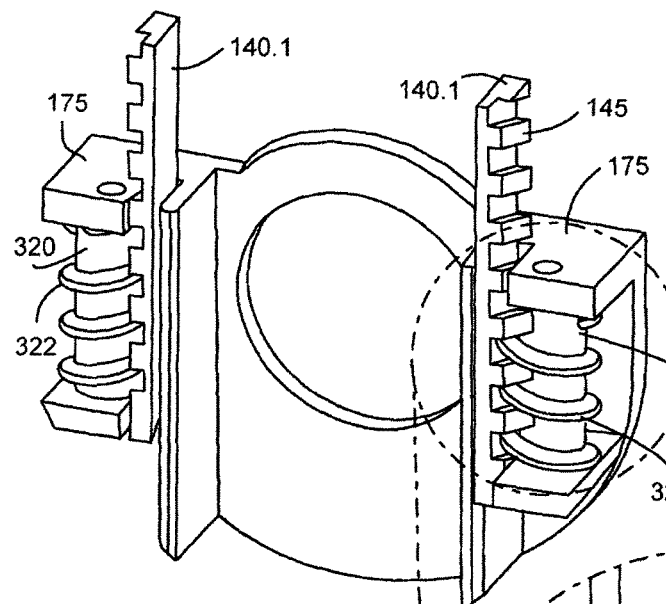
FIG. 23-1
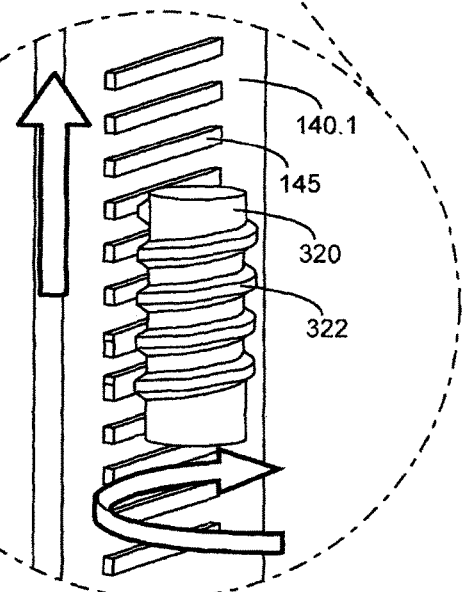
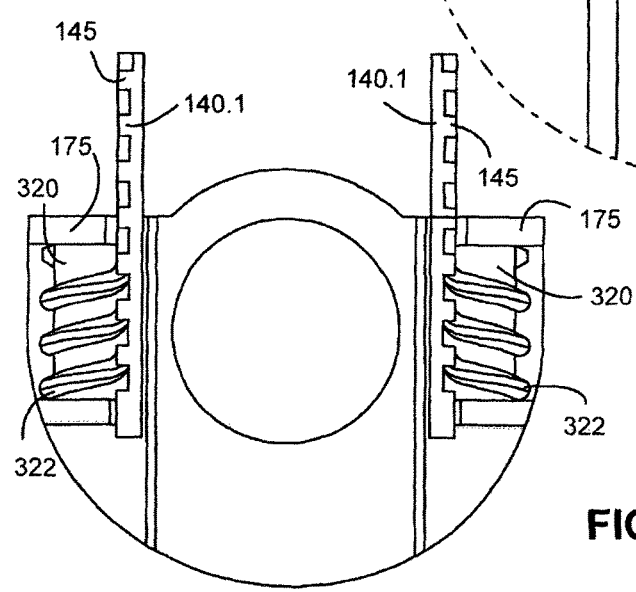
FIG. 23-2

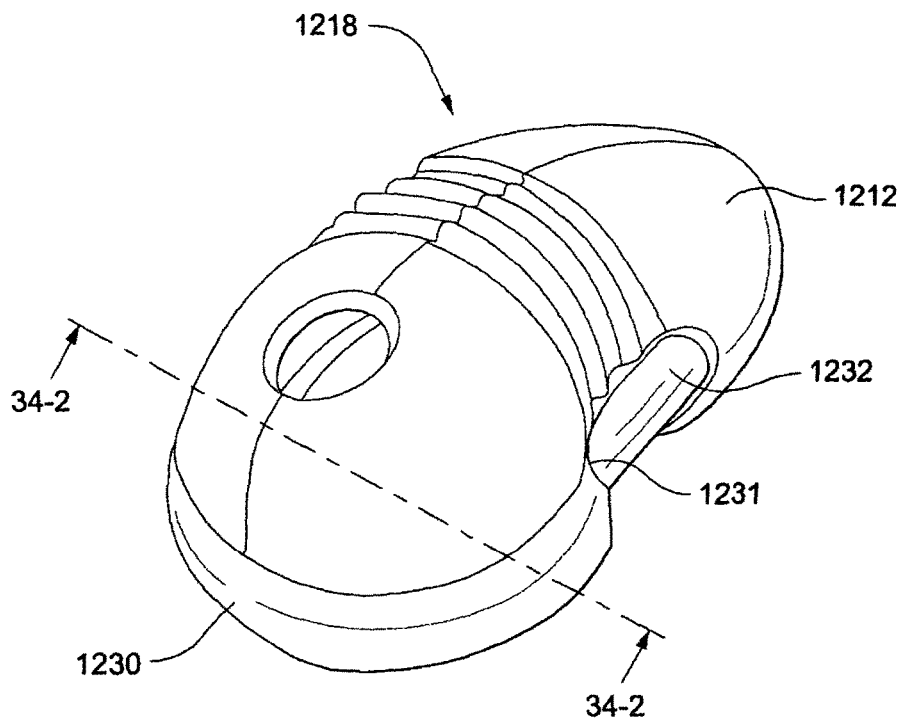
FIG. 34-1
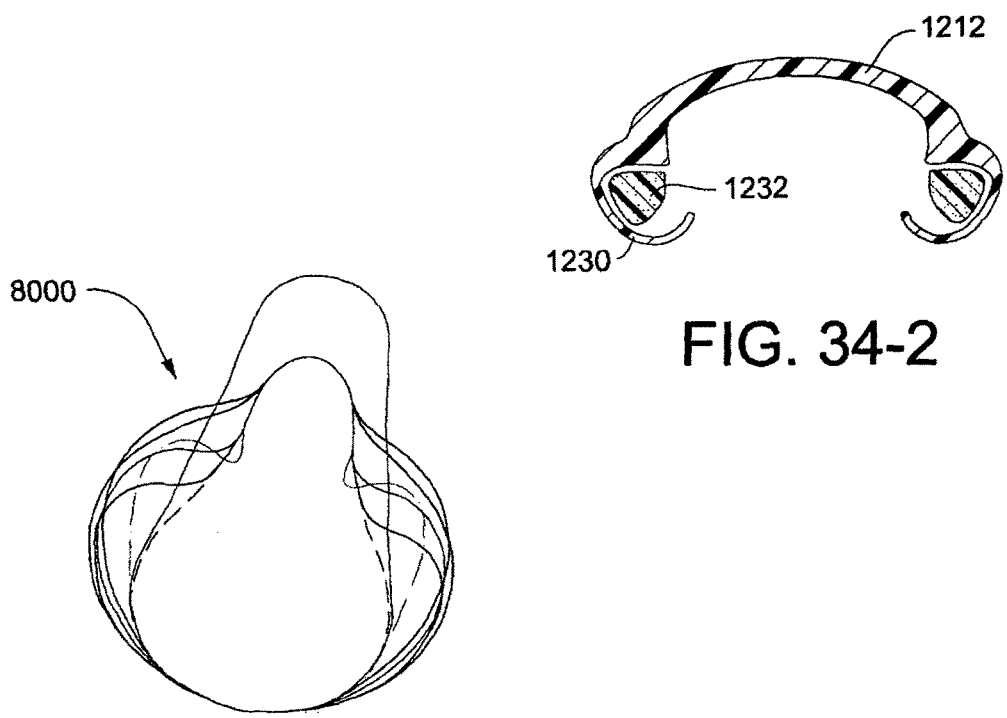
FIG. 34-2
FIG. 34-3

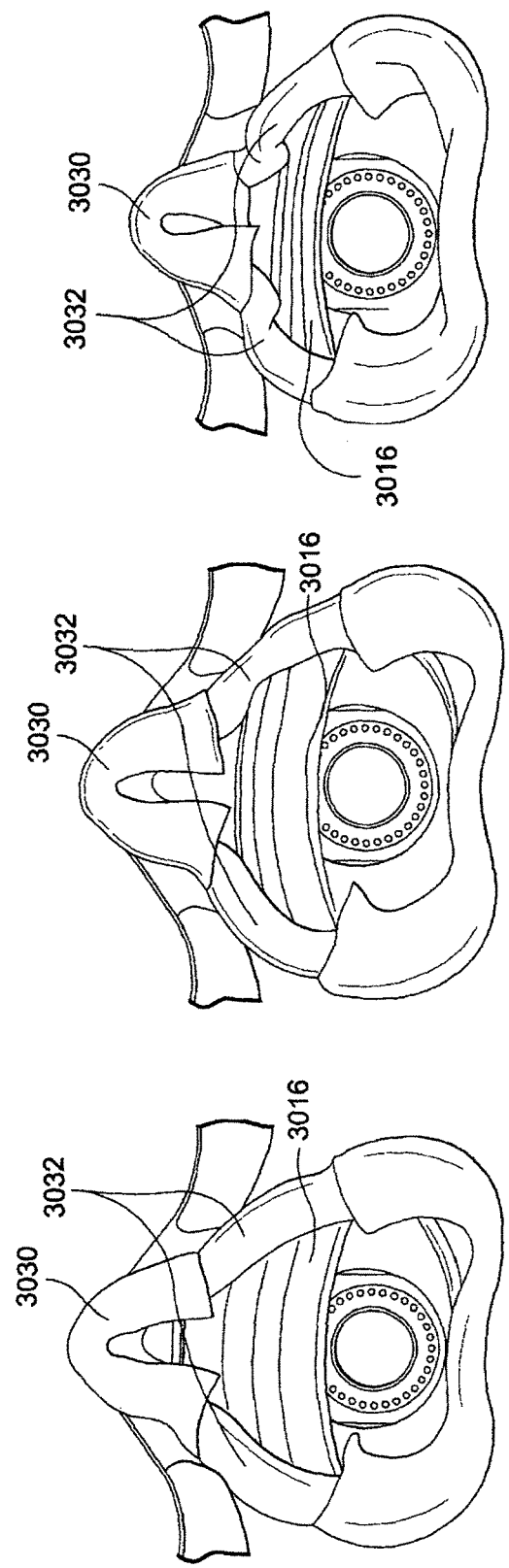

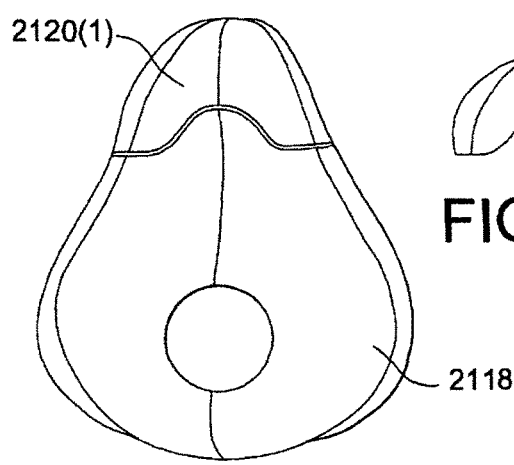
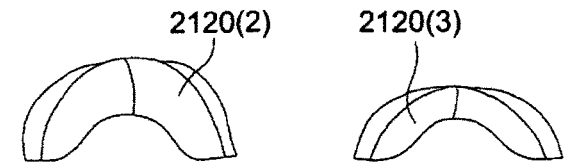
FIG. 43-1
FIG. 43-2
FIG. 43-3
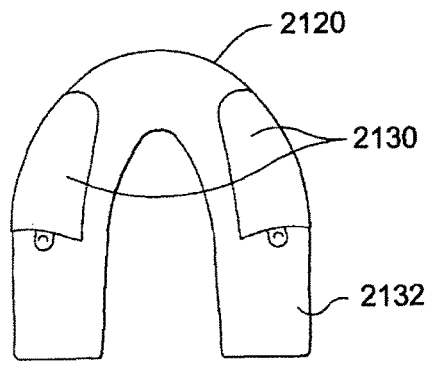
FIG. 43-4
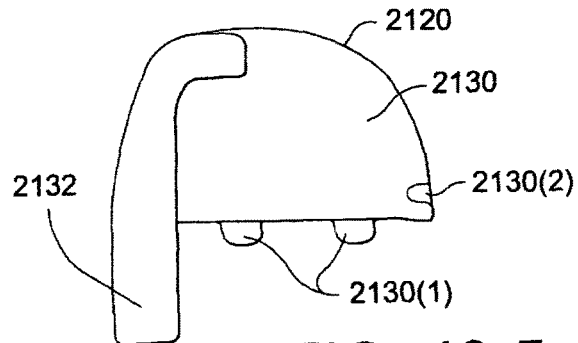
FIG. 43-5
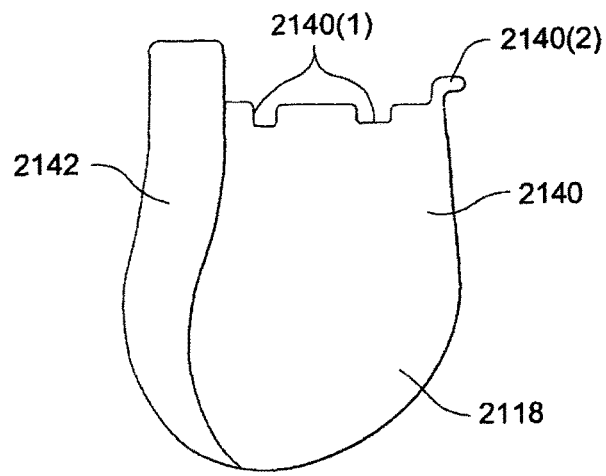
FIG. 43-6

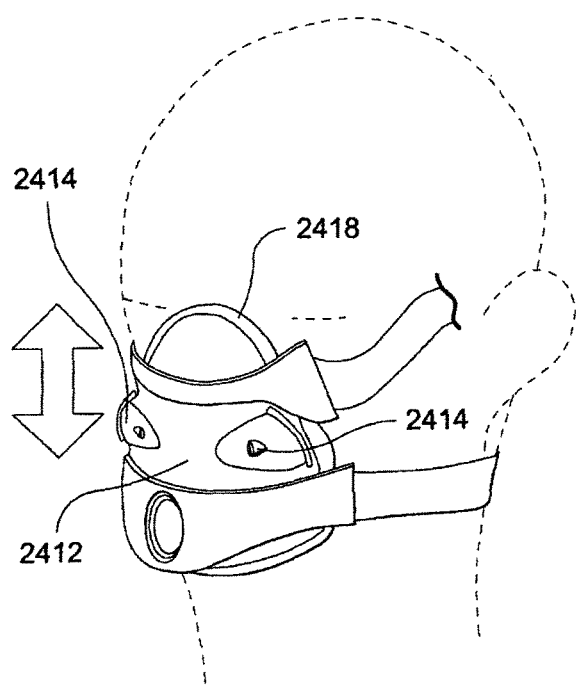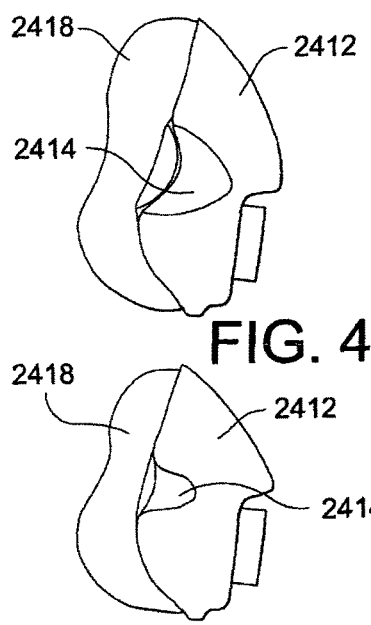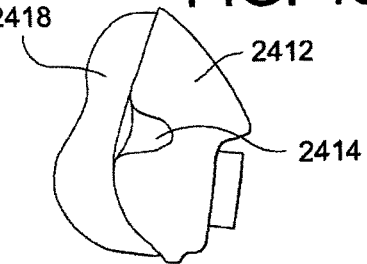
FIG. 46-1
FIG. 46-2
FIG. 46-3

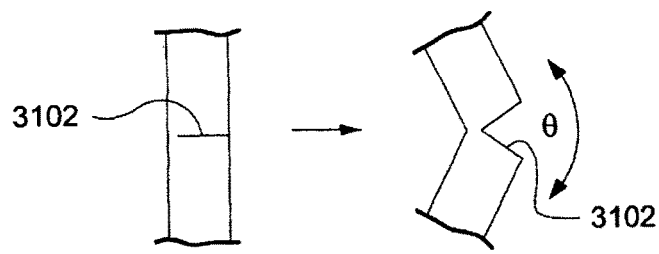
FIG. 51-1
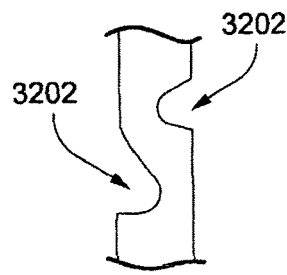    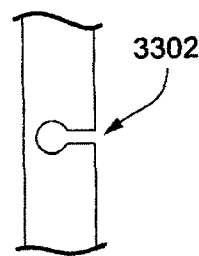
FIG. 51-2    FIG. 51-3
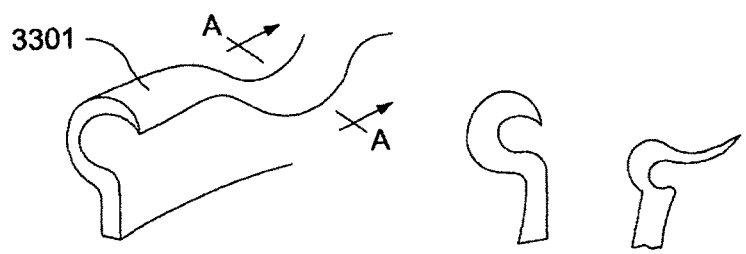
FIG. 51-4    A-A
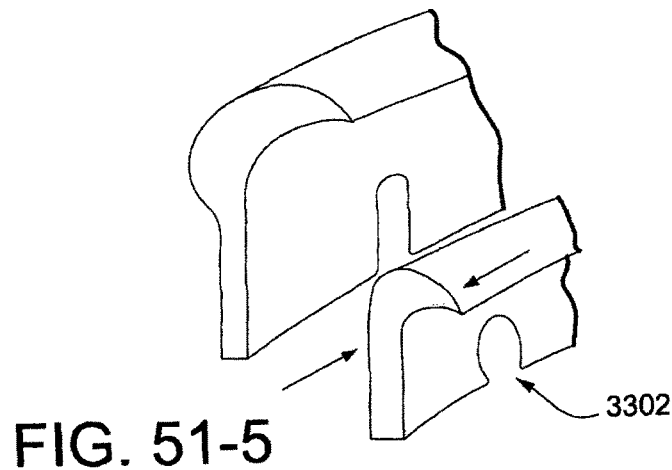
FIG. 51-5

ADJUSTABLE MASK SYSTEM AND RELATED METHODS

CROSS-REFERENCE TO APPLICATION

This application is the U.S. national phase of International Application No. PCT/AU2010/000796, filed Jun. 24, 2010, which designated the U.S. and claims the benefit of U.S. Provisional Application Nos. 61/213,611, filed Jun. 24 2009, 61/272,933, filed Nov. 20, 2009, and 61/285,026, filed Dec. 9, 2009, each of which is incorporated herein by reference in its entirety.

FIELD OF THE INVENTION

The present technology relates to respiratory masks, e.g., for delivery of air or breathable gas at positive pressure to one or more airways of a patient or wearer. In particular, the technology relates to adjustable mask systems and related methods.

BACKGROUND OF THE INVENTION

The use of Nasal Continuous Positive Airway Pressure (nasal CPAP) to treat Sleep Disordered Breathing (SDB) was pioneered by Sullivan, e.g., see U.S. Pat. No. 4,944,310. Apparatus for providing nasal CPAP typically comprises a source of air at positive pressure (for example, from 2-30 cm $H_2O$ provided by a blower or flow generator), some form of patient interface or respiratory mask system (for example a nasal or full-face mask system), and an air delivery tube.

Respiratory mask systems typically include some form of cushioning element (a "cushion"), a sealing element and some form of stabilizing element (for example, a frame and headgear). The cushioning and sealing elements may be formed in one piece, or more than one piece, or may be separate structures. Cushioning and sealing elements may be formed from different portions of a single structure. Headgear may include an assembly of soft, flexible, elastic straps. They may be constructed from a composite material such as foam and fabric.

The frame may be a rigid, semi-rigid, or soft structure that allows for the connection of the cushion, headgear and air delivery tube. The frame can be made of polycarbonate, silicone or various other materials.

In many conventional mask systems, it is necessary to provide a range of different sized components (cushions, frames) in order to fit a wide range of patients. While these mask systems are acceptable for their intended purpose, a need has developed in the art to provide a mask system to address limitations associated with conventional mask systems.

SUMMARY OF THE INVENTION

The present technology relates to a mask system and methods of using the mask system. An aspect of the present technology is a mask system that fits a wide range of sizes and/or shapes of faces. Another aspect of the present technology is a mask system that may be used to maintain positive airway pressure.

One aspect of the technology relates to a mask system that is adjustable. Another aspect of the present technology is a mask system that is sealable with a patient's face to maintain a positive pressure, and that is adjustable. In one form, the mask system is adjustable in length. In one form the mask system is adjustable while maintaining a seal. In one form a mask system in accordance with an aspect of the present technology includes an adjustable frame and a cushion, and the frame is adjustable in length and the cushion is adapted to elongate in response to an increase in the length of the frame.

A further aspect of the technology relates to a mask system comprising a sealing portion, wherein the sealing portion can change shape.

A further aspect of the technology relates to a mask system comprising a sealing portion, wherein the sealing portion can change shape and the length of the perimeter of the sealing portion remains constant.

A further aspect of the technology relates to a mask system comprising a sealing portion, wherein the sealing portion can compress and/or stretch.

A further aspect of the technology relates to a mask system comprising a sealing portion, wherein the sealing portion can compress and/or stretch and the length of the perimeter of the sealing portion is changeable.

A further aspect of the technology relates to a mask system comprising a sealing portion, wherein the sealing portion can compress and/or stretch and/or change shape.

A further aspect of the technology relates to a mask system comprising a sealing portion, wherein the sealing portion can compress and/or stretch and/or change shape and the length of the perimeter of the sealing portion is changeable.

In one form, the mask system in accordance with the present technology comprises a sealing portion having a first relatively fixed part and a second relatively changeable part. The mask system may be adjusted so that the second part is changed without a significant change to the first part. In one form, the first part may maintain a relatively fixed shape while the second part is adjustable in shape and/or length. In one form, the mask system may comprise two relatively fixed parts and a second relatively changeable part, with the relatively changeable part preferably located between the two relatively fixed parts. In one form of the present technology, a mask system has a relatively fixed nasal bridge region, a relatively fixed lip region and a relatively adjustable or changeable region therebetween.

Another aspect relates to a mask system that requires fewer components and/or less inventory to fit a wider range of patients.

Still another aspect relates to a mask system that more easily enables home fitting and/or diagnosis without the need for a clinician to choose the correct size mask system.

Yet another aspect relates to a mask seal that may change shape and/or size to fit a wide range of patient sizes and shapes, and still maintain a comfortable and adequate seal with the patient's or wearer's face.

Another aspect of the present technology relates to a means for adjusting a first portion of a mask with respect to a second portion of a mask.

Another aspect of the present technology relates to a skeleton or substantially inextensible frame that may be covered or otherwise connected to a skin or flexible membrane, where the flexible membrane allows adjustment of the position of the skeleton. The flexible membrane may be stretchable, foldable, and/or bendable.

Another aspect of the present technology relates to a cushion or sealing mechanism connected to a skeleton, such that when the skeleton is altered in shape, the sealing mechanism alters in shape while maintaining its ability to sealingly engage with a patient.

Another aspect of the present technology relates to a flexible or extensible covering or joining member that is arranged and positioned between portions of a skeleton or substantially elastic frame, such that the joining member can be deformed or moved to alter the positioning of the portion/s of the skeleton. Movement between a first position and a second position of the skeleton may be a change from a first mask size to a second mask size.

Another aspect of the present technology relates to a skeleton or frame portion that is movable from a first position to a second position. The second position may be substantially vertically aligned with the first position.

Another aspect of the present technology relates to a skeleton or frame portion that is movable from a first position to a second position. The second position may be substantially angular to the first position.

In one example, there is provided a mask system for a wearer, comprising a frame and a cushion provided to the frame, the cushion having a one-piece seal or more than one seal component working together to contact the wearer's skin, the seal being adjustable in size and/or shape relative to one or more dimensions of the wearer's face. The seal may include foam, TPE, silicone, or a hybrid of soft, semi-soft, and hard materials.

In another example, there is provided a method of making a mask system for a wearer, comprising providing a frame; providing a cushion to the frame, the cushion including a one-piece seal or more than one seal component working together; and structuring the seal such that it may be adjusted between an initial size and a plurality of different sizes for customization to the wearer, and from the different sizes back to the initial size.

According to yet another example, there is provided a method of fitting a CPAP mask system to deliver pressurized air in the range of 2-30 cm $H_2O$ to a patient, comprising fitting a one-piece seal or more than one seal component working together of the mask system to the wearer; and adjusting one or more dimensions of the seal tailored to the wearer's face.

According to still another example, there is provided a mask system, comprising: a frame; a cushion provided to the frame, the cushion including a seal; and an adjustment mechanism provided to adjust the size and/or shape of the seal, the adjustment mechanism including an actuator system to effect adjustment of the seal.

In one form of the present technology, a mask system is provided that includes a length adjustment mechanism that may be adjustable thereby in discrete positions between a minimum and a maximum length. In one form the mask system further comprises a locking or latching mechanism to hold a nasal bridge and a lip region in fixed relative displacement.

Another aspect of the technology relates to a mask system including a frame including an upper frame portion and a lower frame portion and a flexible member including an upper portion provided to the upper frame portion, a lower portion provided to the lower frame portion, and an adjustment portion between the upper and lower portions. The adjustment portion is structured to allow relative movement between the upper and lower portions and hence between the upper and lower frame portions.

Another aspect of the technology relates to a mask system including a structural element and a conforming element provided to the structural element and adapted to form a seal with the patient's face. At least a portion of the structural element and conforming element are encapsulated or coated with a membrane.

Another aspect of the technology relates to a mask system including a frame defining a mask interior breathing chamber adapted to receive pressurized air in the range of 2-30 cm $H_2O$ and a cushion provided to the frame and adapted to form a seal with the patient's face. The frame includes an adjustment portion to adjust the seal from at least a first size to a second size, and vice versa.

Another aspect of the technology relates to a mask system including a frame and a cushion provided to the frame. The frame includes a first frame portion and a second frame portion. The first and second frame portions are movable relative to one another. The cushion is adapted to form a seal with the patient's face. A portion of the seal is adapted to change size and/or shape based on the relative movement between the first and second frame portions without requiring detachment of the first and second frame portions and/or the seal relative to one another.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this technology. In such drawings:

FIGS. 1, 1A, 1B, 2, and 2A are schematic views of a model patient's head showing sealing topographies;

FIGS. 3-1 to 3-6 show various views of a nasal or full-face mask system according to an example of the present technology;

FIG. 4 is a sample frame thereof;

FIGS. 5-1 to 5-5 show various views of the upper frame in isolation;

FIGS. 6-1 to 6-6 show various views of an adjustment mechanism/actuator sub-assembly in isolation;

FIGS. 7-1 to 7-5 show various views of a rack in isolation;

FIGS. 8-1 to 8-3 show various views of a gear/pinion in isolation;

FIGS. 9-1 to 9-6 show various views of assembly steps of the mask system;

FIGS. 10-1 to 10-5 show various views of the inner shroud in isolation;

FIGS. 11-1 to 11-5 show various views of the outer shroud in isolation;

FIGS. 12-1 to 12-5 show various views of the dial in isolation;

FIGS. 13 and 13-1 show an alternative example;

FIGS. 14-1 to 14-2 show an alternative example;

FIGS. 15-1 to 15-5 show various views of the sub-assembly of the cushion and adjustable region or gusset;

FIGS. 16-1 to 16-5 show various views of the adjustable region or gusset in isolation;

FIGS. 17-1 to 17-2 shown an alternate seal arrangement;

FIGS. 18-1 to 18-5 show another alternate seal arrangement;

FIG. 19-1 shows a rotary gear and rack with closer spacing between teeth according to an embodiment of the present technology;

FIG. 19-2 shows a rotary gear and rack with wider spacing between teeth according to an embodiment of the present technology;

FIGS. 20-1 and 20-2 show a travel stop for an adjustment mechanism according to an embodiment of the present technology;

FIGS. 21-1 and 21-2 show a locking feature for an adjustment mechanism according to an embodiment of the present technology;

FIG. 22 shows a locking feature for an adjustment mechanism according to another embodiment of the present technology;

FIGS. 23-1 and 23-2 show a worm gear mechanism for an adjustment mechanism according to an embodiment of the present technology;

FIGS. 24-1 and 24-2 show a sliding mechanism for an adjustment mechanism according to an embodiment of the present technology;

FIGS. 26-1 to 26-7 show various views of a cushion according to an embodiment of the present technology;

FIGS. 26-8 to 26-11 alternative examples of cushion shape according to an embodiment of the present technology;

FIGS. 27-1 to 27-7 show various views of a cushion according to an embodiment of the present technology;

FIGS. 27-8 to 27-12 show alternative examples of cushion shape according to an embodiment of the present technology;

FIG. 28-1 shows a cushion according to an embodiment of the present technology;

FIG. 30-1 shows a cushion according to an embodiment of the present technology;

FIG. 31-1 shows a cushion according to an embodiment of the present technology;

FIGS. 33-1 to 33-8 show various views of a cushion according to an embodiment of the present technology;

FIGS. 33-9 to 33-17 show various views of a cushion according to an embodiment of the present technology;

FIGS. 33-18 to 33-25 show alternative examples of a cushion with a silicone membrane part and a foam undercushion part;

FIGS. 34-1 to 34-2 show various views of a cushion according to an embodiment of the present technology;

FIG. 34-3 is a schematic view showing a cushion with various shape change shapes;

FIGS. 34-4 to 34-10 show various views of a cushion according to an embodiment of the present technology;

FIGS. 35-1 to 35-3 show various views of a cushion according to an embodiment of the present technology;

FIGS. 36-1 to 36-2 show various views of a cushion according to an embodiment of the present technology;

FIGS. 37-1 to 37-2 show various views of a cushion according to an embodiment of the present technology;

FIGS. 38-1 to 38-4 show various views of a cushion according to an embodiment of the present technology;

FIG. 39 shows a cushion according to an embodiment of the present technology;

FIGS. 40-1 to 40-2 show various views of a cushion according to an embodiment of the present technology;

FIGS. 41-1 to 41-2 show various views of a cushion according to an embodiment of the present technology;

FIGS. 42-1 to 42-2 show various views of a cushion according to an embodiment of the present technology;

FIGS. 43-1 to 43-8 show various views of a cushion according to an embodiment of the present technology;

FIGS. 44-1 to 44-2 and 45 show various views of a cushion according to an embodiment of the present technology;

FIGS. 46-1 to 46-6 show various views of a cushion according to an embodiment of the present technology;

FIGS. 48-1 to 48-3 show various views of a cushion according to an embodiment of the present technology;

FIGS. 51-1 to 51-5 show alternative examples to shape change a cushion according to an embodiment of the present technology;

FIGS. 52-1 to 52-4 show various views of a cushion according to an embodiment of the present technology;

FIGS. 52-5 to 52-6 show various views of a cushion according to an embodiment of the present technology;

FIG. 52-7 shows a frame for a cushion according to an embodiment of the present technology;

FIGS. 52-8 to 52-9 show various views of a cushion according to an embodiment of the present technology;

FIGS. 52-10 to 52-12 show alternative examples to stiffen a cushion according to an embodiment of the present technology;

FIGS. 52-13 to 52-14 show various views of a cushion according to an embodiment of the present technology;

FIGS. 52-15 to 52-22 show various views of a cushion and adjustment mechanism according to an embodiment of the present technology;

FIGS. 75-1 and 75-2 show actuation of the pinch type adjustment mechanism of FIG. 74 in use;

FIGS. 82 and 82-1 are schematic and perspective views of a slide type adjuster according to an embodiment of the technology;

FIGS. 133 to 135 are cross-sectional views through the cushion of FIG. 132;

FIG. 136 is a front view of an integrated cushion and frame according to another embodiment of the technology; and FIGS. 137 to 141 are cross-sectional views through the integrated cushion and frame of FIG. 136.

DETAILED DESCRIPTION OF ILLUSTRATED EMBODIMENTS

Figures 1, 3:
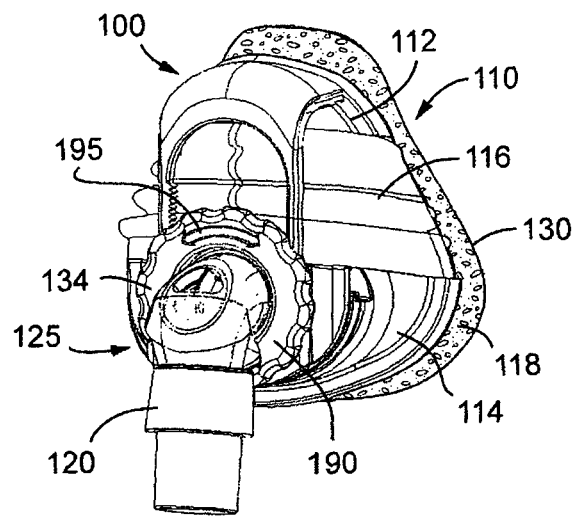

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the blowers used with the mask system, described herein may be designed to pump fluids other than air.

1.1 Overview

The present technology relates to a mask system aimed at providing a "one-size-fits-all" solution, e.g., an adjustable mask system, such as an adjustable full face mask, an adjustable nasal mask, or a mask that converts between a full face mask and a nasal mask, and vice versa. The term one size fits all refers to a single mask system that is capable of fitting over 70-80% of the population, preferable up to 95% or more. Many conventional mask systems typically require 2, 3, or more sizes to cover up to 95% of the population. In the illustrated embodiments, the mask system is a CPAP mask system used in CPAP therapy in which pressurized air in the range of 2-30 cm $H_2O$ is provided to a patient.

However, it should be appreciated that aspects of the technology may be applicable to other suitable mask systems.

Benefits that a one size fits all mask would create include those for sleep labs as well as home use. For example, for sleep labs, the adjustable mask provides simplified fitting, removes the need to initially determine patient size, and simplifies selection. Moreover, an adjustable mask system effectively overcomes the issue of mouth breathing/leaking, for example, if the patient has the mask adjusted to a nasal mask but finds they are mouth breathing, they may adjust the mask to a full face mask. The adjustable mask system also reduces inventory due to only needing to stock a single product or a reduced number of parts for that product, thus reducing the amount of capital tied up in inventory and/or reducing the space required to store excessive inventory.

As applied to a durable medical equipment (DME) or home medical equipment (HME) manufacturer, an adjustable mask system can likely provide a fit with the first mask that is tried on, which results in simplified fitting and removes the need to initially determine patient size and simplifies selection. One-size-fits-all mask systems should result in less call backs or re-sizings because it may not be possible to provide an incorrect size. Moreover, the simplified fitting process (preferably, only one size is available) promotes customer loyalty, and helps increase the chances for compliance with therapy due to ease of fitting and ordering, especially when there is a need to replace a spent or soiled mask system. A one-size-fits-all mask system also provides the option to adjust mask size to fit patient facial profile better than the predetermined few fixed-size mask system (e.g., small, medium, large, etc.). In addition, the adjustability of the mask system allows the ability to effectively overcome leaking, e.g., in situ. In exemplary embodiments, the one-size-fits-all mask system is adjustable without requiring detachment of components (e.g., frame parts, seal, etc.) relative to one another, which allows the mask system to be easily adjusted while on the patient's face in use (e.g., mask system adjustable to remove leaks while in use).

1.1.1 General Concept

The mask system according to an embodiment of the present technology may comprise some or all of the following: a sealing portion, a frame portion, an adjustable portion, a mechanism, a supporting system and an air delivery system.

Sealing Portion

The sealing portion may comprise an interface provided to the mask system to seal with a patient's airways in use. The sealing portion may be formed from a generally flexible material. The sealing portion may be resilient. The sealing portion may be selectively formable for example with the application of heat. The sealing portion may be flexible so as to allow a mechanism to change the shape of the sealing portion from a first position to a second position. The sealing portion may be compressible and/or stretchable so as to allow a mechanism to change the length of the perimeter of the sealing portion from a first position to a second position. Alternatively, the sealing portion may be flexible, compressible and/or stretchable so as to allow a mechanism to change the length of the perimeter of the sealing portion and the shape of the sealing portion from a first position to a second position. The sealing portion may be formed from a foam, gel, silicone, thermoplastic elastomer, or any other material suitable for the functions described above. The sealing portion may be more flexible in tension and less flexible in compression. The sealing portion may be constructed of one or more materials, with one or more regions having different durometers.

Frame Portion

The frame portion may comprise a structure adapted to support or otherwise shape at least a portion of the sealing portion. In an embodiment, the frame portion may have a nasal bridge portion adapted to support and maintain the structure of the nasal bridge portion of the sealing portion. The frame portion may further comprise a chin portion adapted to support and maintain the structure of the chin portion of the sealing portion. The frame portion may be resilient. The frame portion may be stiffer than the sealing portion. The frame portion may further act as an anchor, securing the supporting system to the sealing portion. The frame portion may be formed from foam, gel, silicone, nylon, polycarbonate, polypropylene, metal or any other suitable material for the functions described above. the frame portion may include overlapping sections (e.g., telescoping arrangement) so the sealing portion is never unsupported during adjustment.

Adjustable Portion

The adjustable portion may be a substantially flexible region adapted to translate adjustment from the mechanism to the sealing portion. The adjustment portion may be intermediate the sealing portion and the mechanism. In one embodiment, the adjustment portion may be integrally formed with the sealing portion. The adjustment portion may be part of the sealing portion. The adjustment portion may be a part of the frame, wherein the frame translates the adjustment from the mechanism to the sealing portion. The adjustment portion may be resilient so as to return to its originally formed shape and permit re-use of the mask system. The adjustment portion may be formed from silicone, foam, gel, nylon, thermoplastic elastomers, or any other material suitable for the functions described above.

Mechanism

A mechanism may be provided to the mask system to mechanically adjust or change its shape, thereby changing the shape or size of the sealing portion. The mechanism be connected to the frame, adjustment portion or sealing portion. The mechanism may comprise parts that are selectively movable from at least a first position to a second position, and vice versa. The parts may be movable by gears, pivots, cranks, cams, ratchet, or any other mechanism. The parts may be selectively movable by a person or a machine, i.e., controlled by inputs or automatically moveable. For example, the parts may be selectively movable by one hand operation (e.g., dial, pinch mechanism, etc.), or may be movable by a motor.

Supporting System

A supporting system may also be provided to the mask system to support and/or stabilize the mask system in position in use. The supporting system may comprise straps to engage the rear and sides of the patient's head and connect or be formed with the mask system.

Air Delivery System

An air delivery system may be connected to the mask system, including an elbow and a tube. The elbow may be positioned between the mask system and the tube. The tube may deliver breathable gas from a CPAP apparatus to the elbow and hence mask system and patient.

1.1.1.2 Shape Change

Shape change of the sealing portion means that the profile or outline of the sealing portion is able to change or adapt depending on the mechanisms position. Generally, the sealing portion will have a substantially constant perimeter length. The material of the sealing portion may be sufficiently stiff so as not to compress or stretch, rather it will move into an alternative arrangement as dictated by the adjustment portion and mechanism.

1.1.1.3 Compression/Stretch

Compression or stretch of the sealing portion means that the profile or outline of the sealing portion is changed or adapted depending on the mechanism position. The sealing portion may change perimeter length. The material of the sealing portion may be flexible, resilient and/or compressible to allow the sealing portion profile to change.

1.2 Anthropometric Data

By examining analysis done in mask product designs (e.g., ResMed's Mirage Quattro™ mask or Mirage Micro™ mask) it was discovered that there is no significant correlation between face height and other main anthropometric measurements (e.g., mouth width, nose width, nostril size, etc.). Hence the one anthropometric variable that varies across at least the Mirage Quattro™ mask system sizes is face height, e.g., a measure of distance from the nasal bridge region to the chin region. The cushion design over the nasal bridge and chin region remains generally constant across all sizes. Thus, the present technology is directed, in one example, to a full face mask that has the ability to adjust facial height over the required range and has the same seal performance, particularly at the sides of the nose and the cheeks as well as over the nasal bridge and chin region as current products. In a further example, an aspect of the technology is directed to a mask that may be adjustable from a nasal mask to a full face mask, and vice versa, and is able to seal over the nose bridge, on the sides of the nose, along the cheeks, over the chin and over the top lip region. In an additional example, as aspect of the technology is directed to a nasal mask that is lengthwise adjustable and has the same seal performance as current products, particularly at the nose bridge, sides of the nose and top lip region. In an additional example, as aspect of the technology is directed to a mouth seal that is lengthwise adjustable to seal over a patient's mouth.

1.3 Sealing Topology

The required range of facial height adjustment will be dependant on the intended sealing topography and the ability of the seal design to seal over a range of positions within the intended seal topography.

As shown in FIG. 1, for the bottom (e.g., chin) sealing position, one exemplary sealing location 5 for a full face cushion under the mouth is in the groove between the lower lip and chin (across the sublabiale point). For a nasal mask, the bottom sealing position 5.1 would be the upper lip of the wearer. For the top (e.g., nasal bridge) sealing position—for both full face and nasal masks—there is a range R of sealing positions, ranging between a minimum position 10.1 and a maximum position 10.2. The minimum sealing topology of the cushion should be located above the bone to cartilage joint on the nose. This is because if excess pressure (from the seal) is applied to the soft cartilage of the nose this could cause the nostrils to occlude thus increasing nasal resistance and reducing efficacy of treatment. In an alternative embodiment, the cushion may seal on the cartilage of the nose as long as there is minimal force on the cartilage to prevent occlusion of the nares.

The maximum sealing topology for the seal over the nasal bridge is the level of perceived obtrusiveness of the system that is acceptable. The more the cushion obstructs the field of view of the patient, the more physically obtrusive the product is. Also, to maintain an acceptable level of comfort, the seal should not protrude over into the eyes of the patient.

Shown in FIGS. 1A and 1B are exemplary facial profiles. In FIG. 1A, the face is substantially flat as indicated by the arrow. In FIG. 1B, the face is rounded or curved, also indicated by the arrow. In a further embodiment of the present technology, the mask system may be laterally adjustable to accommodate rounded faces as well as flat faces. This may be achieved similarly to the methods described below, however instead of the adjustment mechanism modifying the shape and/or size of the cushion in the vertical direction, the adjustment mechanism may modify the shape and/or size of the cushion in the horizontal direction.

1.4 Ability to Seal Over Different Nasal Bridge Geometries

The mask system should seal somewhere between the maximum and minimum nasal bridge regions 10.1, 10.2 as indicated above. Thus, the seal is capable of adapting to the change in geometry of the nasal bridge over this region. For example, the height of the nose bridge may vary between some patients. The seal may be able to seal on the highest nose bridge as well as the lowest nose bridge.

1.4.1 Dimension/Size Adjustment

The shape and/or one or more dimensions, e.g., height, width, depth, etc., of the mask system can be adjusted to cover a range of patients having different facial topographies, in particular, height or facial profile (curvature). In one example for a full face mask, the height of the mask system can be varied over a range of between about 5 to about 75 mm, e.g., at least 10 mm, or between about 25 to about 35 mm, or between about 30 to about 40 mm. Preferably, the height of the mask system may be adjusted by about 5 to 25 mm. Preferably, the height of the mask system may be adjusted by about 10 to 20 mm. Most preferably, the height of the mask system may be adjusted by about 12 to 18 mm. Most preferably, the height of the mask system may be adjusted by about 16 mm. Most preferably, the height of the mask system may be adjusted by about 12 mm.

Figures 2, 3:
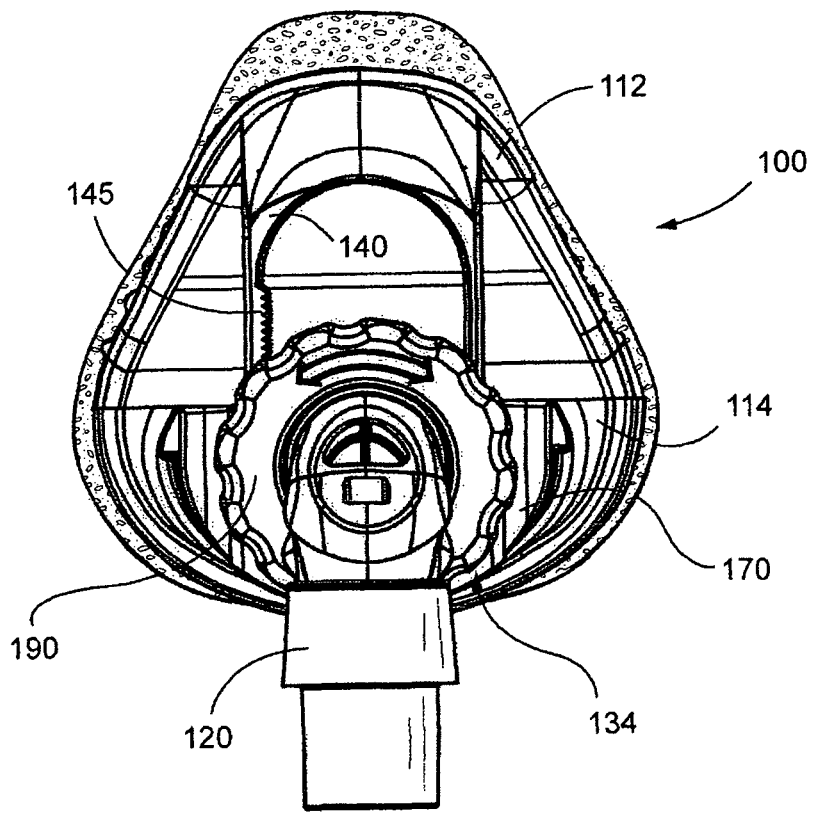
Figure 3:
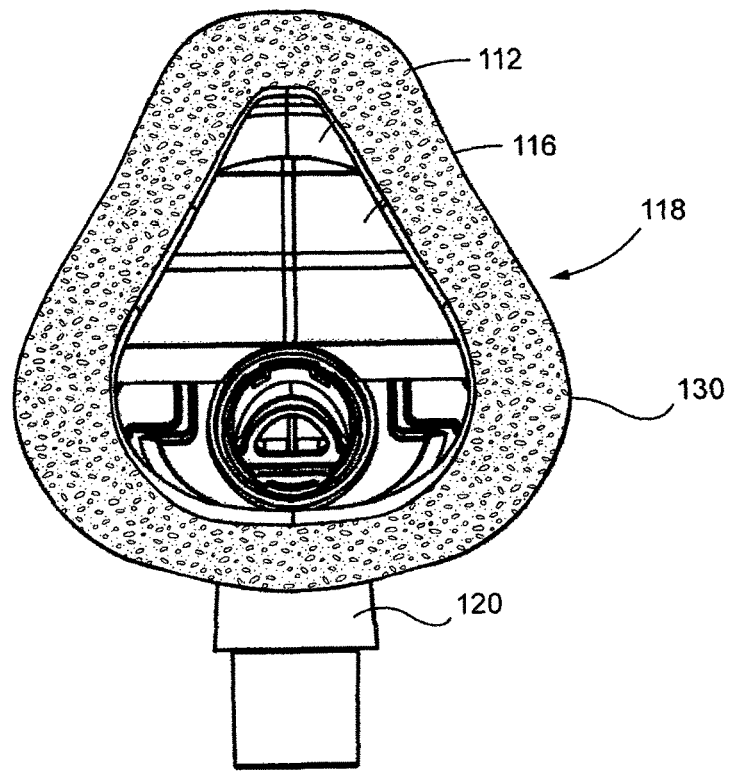

In general, as shown in FIG. 2, the mask in one example is designed, for a relatively taller or the tallest face, to seal near the minimum nasal bridge sealing position 10.1 as identified previously, and, for a relatively smaller or the smallest face, to seal at the maximum nasal bridge sealing position 10.2 as identified previously. FIG. 2A shows one example for a nasal mask designed to seal along the upper lip sealing position 5.1 and a nasal bridge sealing position 10.1.

2.1 First Embodiment

FIG. 3-1 is a perspective view of an adjustable mask system 100 according to one example of the present technology. FIGS. 3-2 to 3-6 show additional views of the mask system 100. The mask system includes a frame 110, e.g., including upper and lower frame portions 112, 114, at least one intermediate member or adjustable portion 116, e.g., an adjustable region or gusset extending between the upper and lower frame portions, a cushion or sealing portion 118 provided to the intermediate member and frame, and an elbow 120 (shown with a swivel) which is coupled to or otherwise provided to the frame (e.g., via an aperture in the frame). A mechanism 125 is provided to change the size of the cushion, in particular the seal 130 of the cushion. The mechanism may include an actuator 134 (e.g., a dial, lever, switch, etc.).

2.2 Frame

Figures 3, 4:
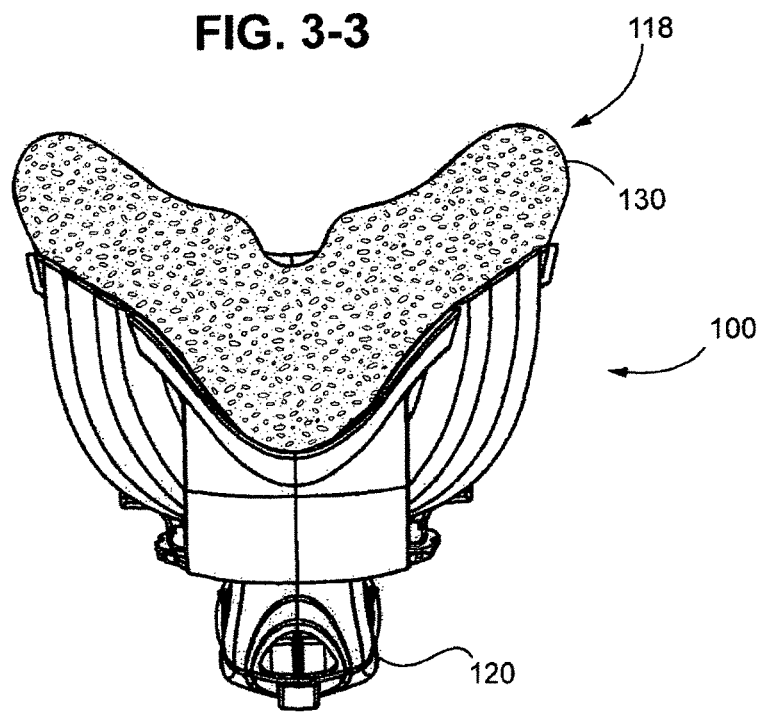
Figures 3, 4, 5:
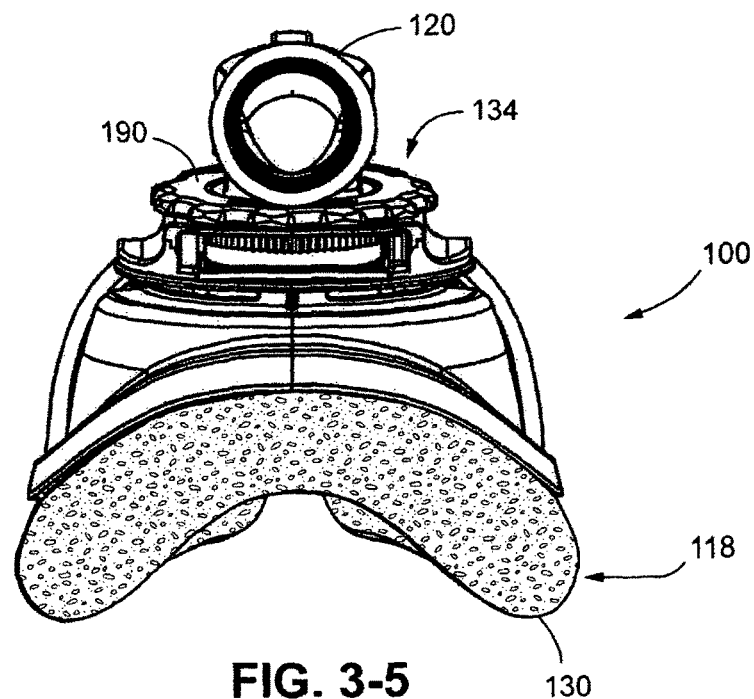

As shown in FIG. 4, the frame 110 functions to provide structural support to the cushion. FIGS. 5-1 to 5-5 show additional views of the upper frame 112. Frame 110 also maintains cushion geometry in the static upper and lower seal positions, e.g., for a full face mask, the chin and nasal bridge region. Frame 110 further provides a rigid, semi-rigid or otherwise non-occludable elbow connection point, e.g., where the aperture 135 is provided in lower frame 114. The frame, or each of the upper and lower frames, may include one or more headgear or supporting system connection points to couple the mask system with appropriate headgear, e.g., for a full face mask, a four or five strap arrangement; for a nasal mask a two or three strap arrangement, or for a convertible mask (e.g., nasal to full face), expansion of the adjustable region or gusset or adjustable portion could be arranged to expose an additional (upper or lower) set of connection points. Frame(s) can be made from stiff materials such as molded plastics, metal, etc. such as polycarbonate, polypropylene, or polyurethane.

The frame(s) may be integrated into a "cushion clip" or any other component (as long as substantial functionality is maintained).

The frame may connect to the sealing portion by an interference fit. The frame may be integrally formed with the sealing portion and the adjustment portion. The frame may interface with the mechanism.

2.3 Mechanism

Preferably, the mechanism 125 is constructed from a stiff material to ensure the mechanism is able to maintain the adjusted positions of the mask system (i.e., in certain positions, there may be some force or resistance provided by the mask system, to which the mechanism will need to overcome).

Preferably, the mechanism 125 is constructed from a material with low creep to ensure longevity of the mechanism and hence mask system.

The components of the mechanism (e.g., rack and gear) may be constructed of different materials to reduce the likelihood of the components squeaking in use.

2.3.1 Rack & Pinion

Figures 3, 4, 5, 6:
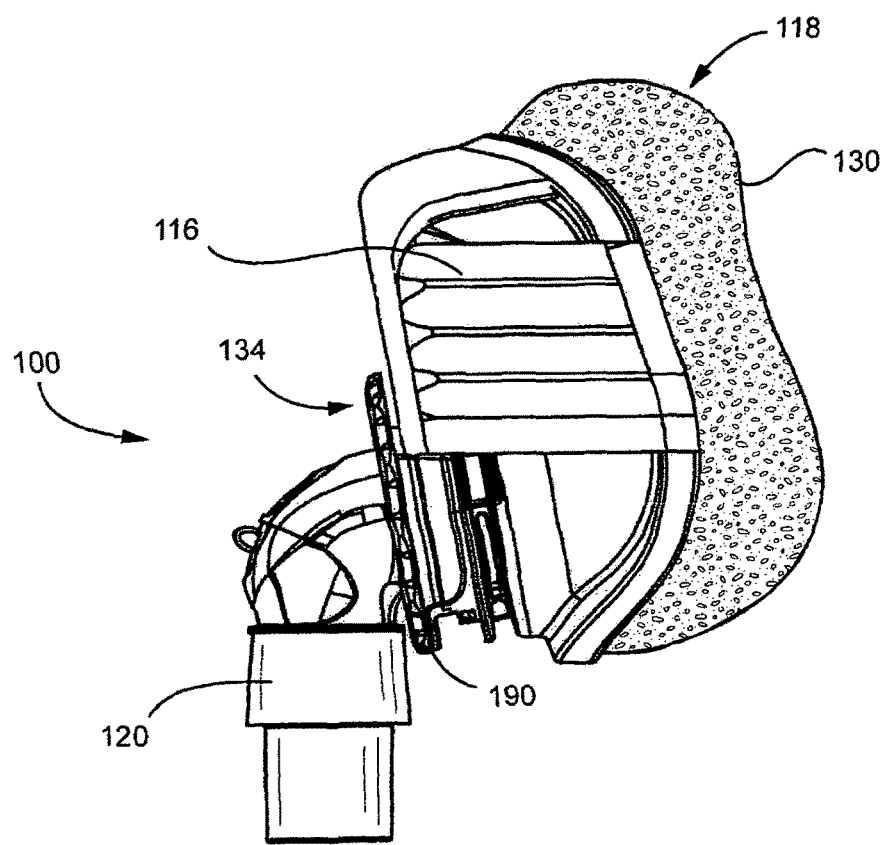
Figure 4:
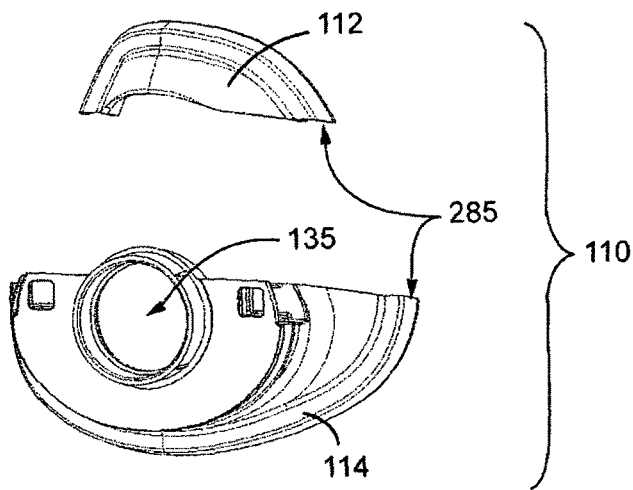
Figures 1, 5:
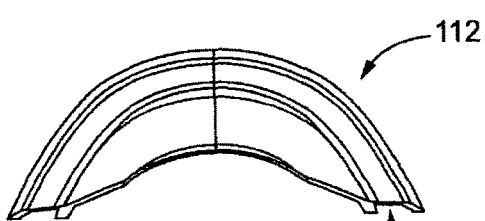
Figures 2, 5:
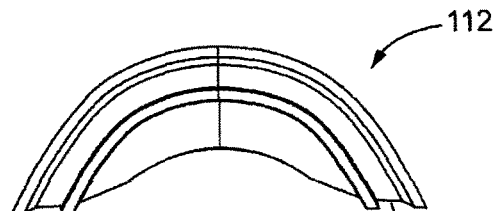
Figures 3, 5:
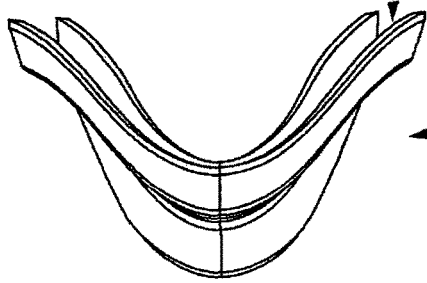
Figures 4, 5:
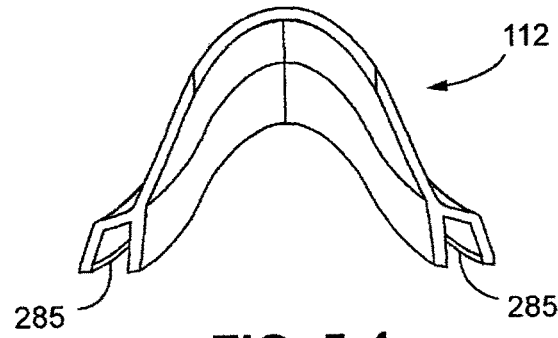
Figure 5:
Figures 1, 6:
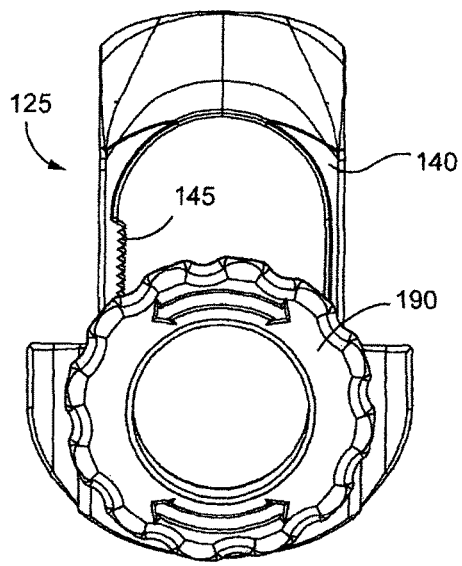
Figures 2, 6:
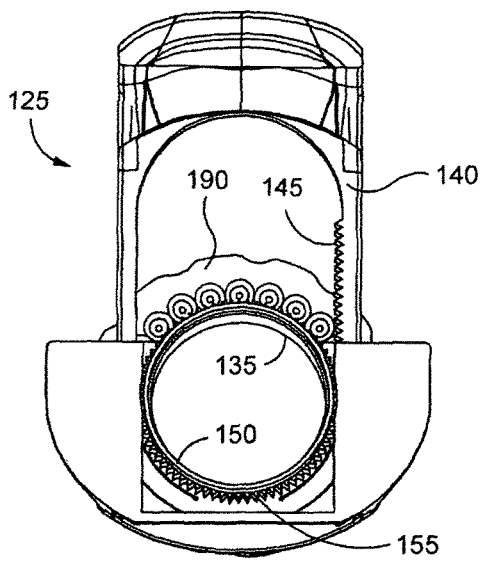
Figures 3, 6:
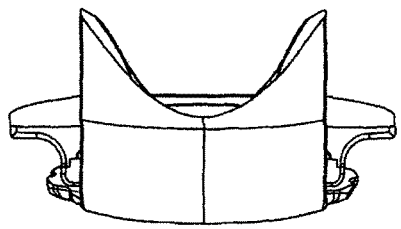
Figures 4, 6:
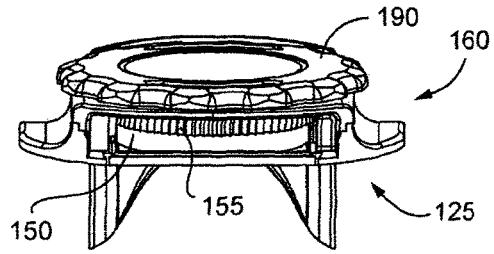
Figures 5, 6:
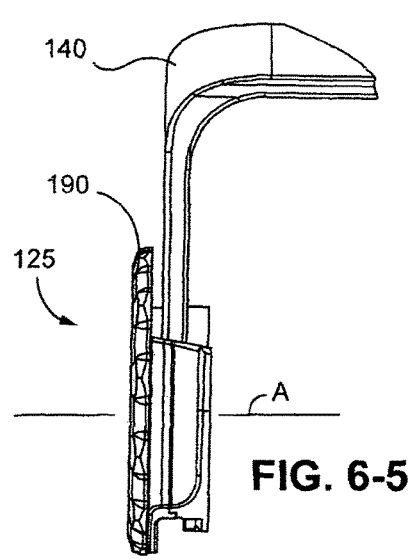
Figure 6:
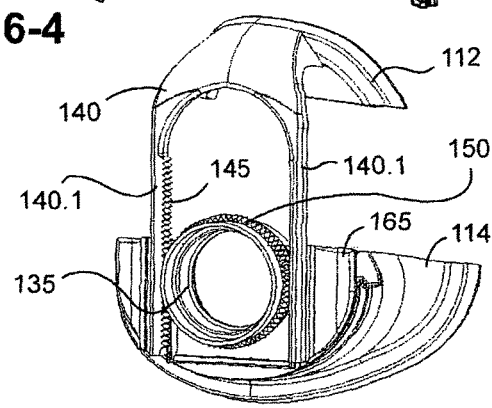

Mask system 100 includes a mechanism 125, which is shown in isolation as a sub-assembly in FIGS. 6-1 to 6-6. In one example, the mechanism takes the form of a rack and pinion mechanism provided to the frame. The rack and pinion mechanism includes a rack 140 having a linear row of gear teeth 145, and a rotary gear 150 having teeth 155 to interact with the teeth 145 of the rack.

Rack 140 is connected or otherwise provided to the upper frame 112 element, as best shown in FIG. 6-6, to provide relative movement between the upper and lower frame portions 112, 114 through the rack and pinion mechanism. Rack 140 is designed to fit around the gear 150 and elbow aperture 135 to allow for maximum travel. Maximum travel is possible if the mechanism is located at an end of the upper or lower frame portions.

Figures 1, 19:
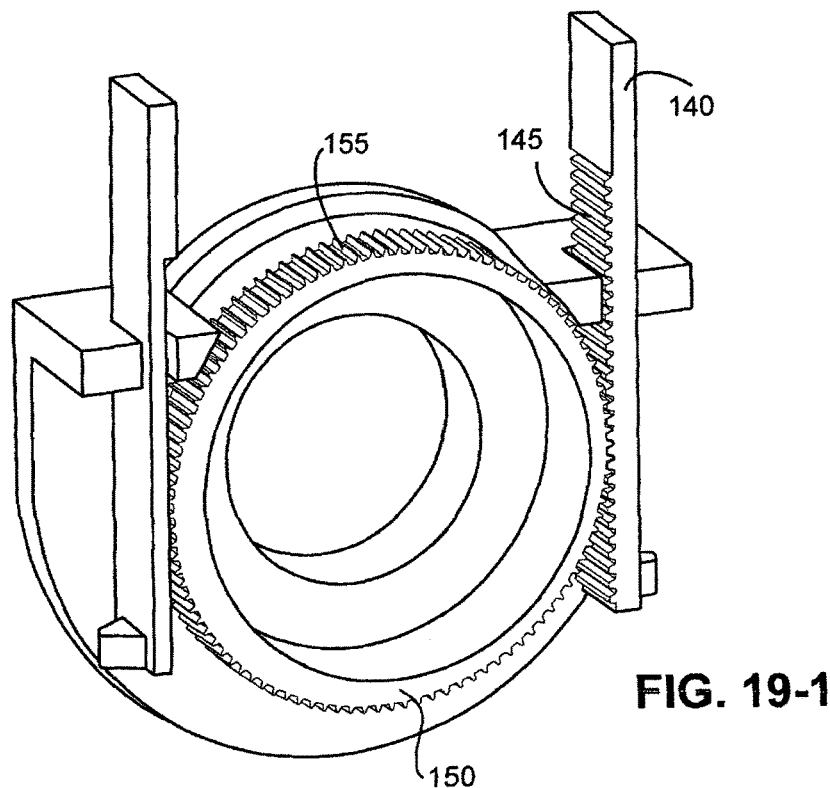
Figures 2, 19:
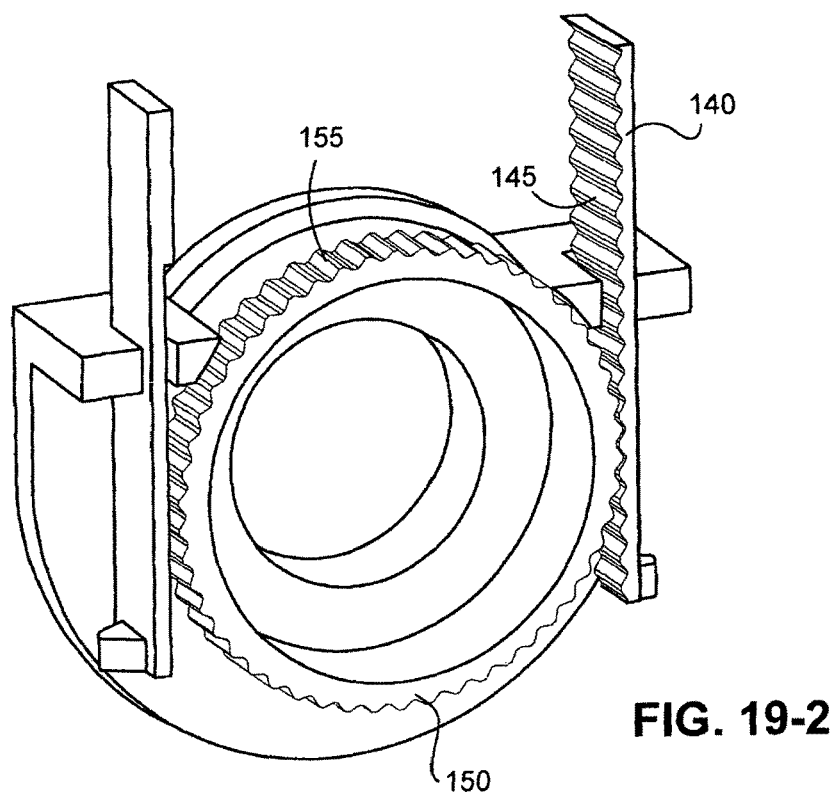

The teeth 145 on the rack 140 can either provide smooth height adjustment or be designed to provide more discrete or step-wise adjustment. Teeth can be designed to be self locking to prevent unintended height change during use. Teeth can be sized and spaced to be tuned to alter the level of adjustment by the gear. For example, FIG. 19-1 shows a rotary gear 150 and rack 140 wherein respective teeth 155, 145 are smaller with closer spacing between teeth so as to provide finer adjustment. Alternatively, FIG. 19-2 shows a rotary gear 150 and rack 140 wherein respective teeth 155, 145 are larger with wider spacing between teeth so as to provide more gross or coarse adjustment.

Figures 1, 7:
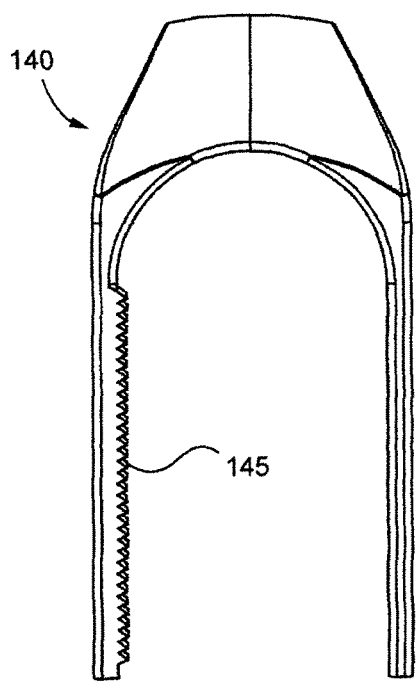
Figures 2, 7:
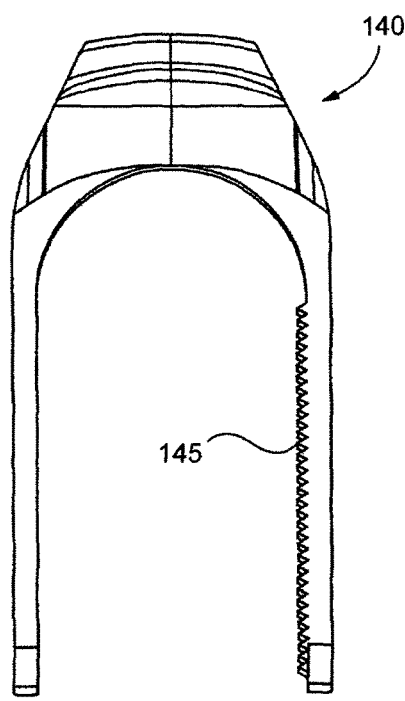
Figures 3, 7:
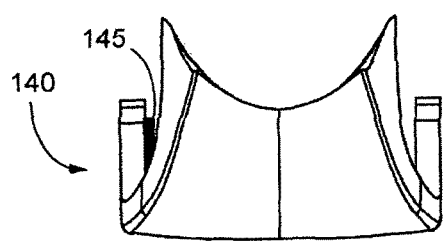
Figures 4, 7:
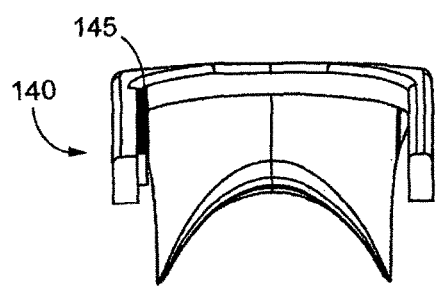
Figures 5, 7:
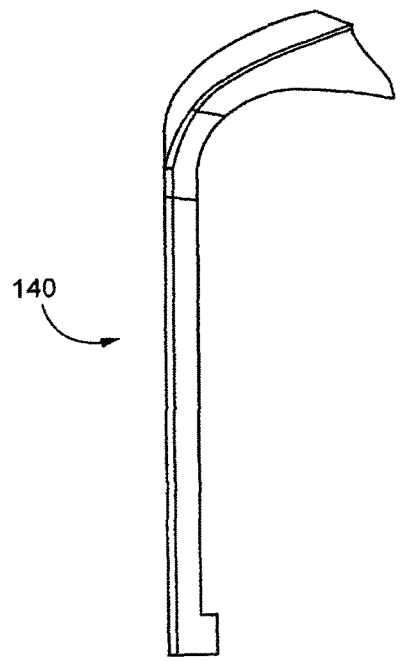

Rack 140 can be made from stiff materials such as molded plastics (such as polycarbonate or polypropylene), metal, etc. Rack 140 may be incorporated into the upper frame portion and as such made of the same material. Rack 140 may be made as a permanent assembly with the rack and pinion mechanism and hence made of same or different material as this sub assembly. FIGS. 7-1 to 7-5 show isolated views of the rack 140.

2.3.2 Gear

Figures 1, 8:
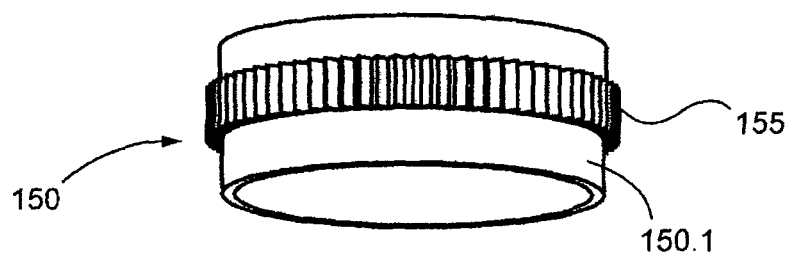
Figures 2, 8:
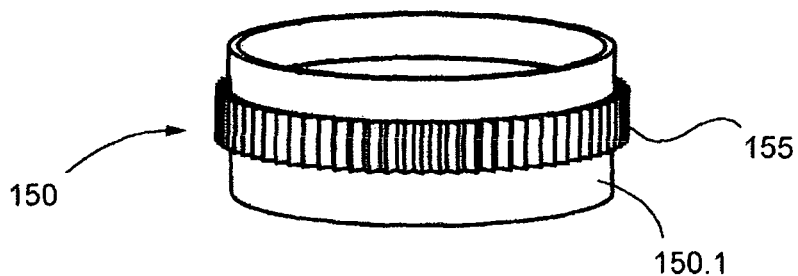
Figures 3, 8:
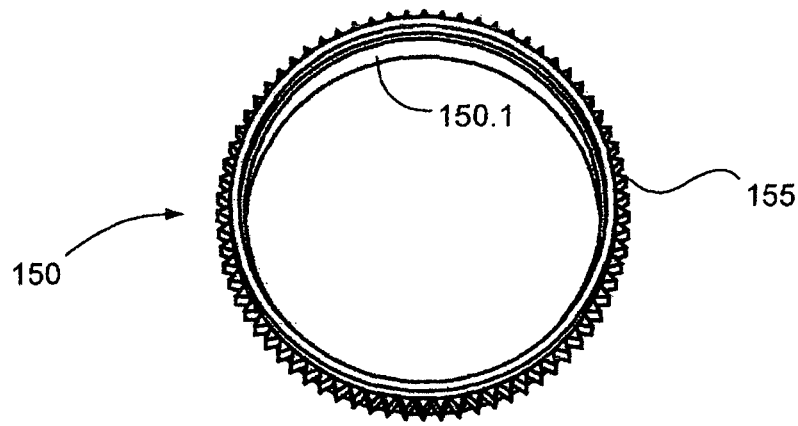

Gear 150 is located co-axially with the elbow 120 in this example, to minimize the size of the system, allow a large dial for easy use and maximize the possible adjustment range. Gear and elbow may individually rotate about a common axis A (FIG. 6-5). However, the gear and the adjustment mechanism in general can be located at other positions, e.g., the mask frames, shrouds, etc. Gear may be formed as a cylinder 150.1, with the teeth 155 being formed over at least a portion of the width and circumference of the cylinders, as shown in FIGS. 8-1 to 8-3.

Gear 150 can be made from stiff materials such as molded plastics (such as polycarbonate or polypropylene), metal, etc. Gear 150 may be made as a permanent assembly with the rack and pinion system and hence made of same or different material as this sub assembly.

2.3.3 Support Arrangement for Adjustment Mechanism

Figures 1, 9:
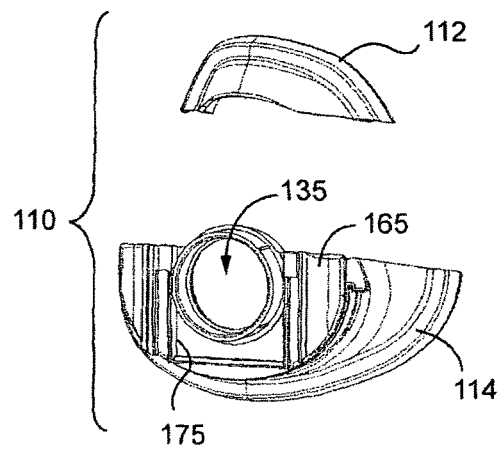
Figures 2, 9:
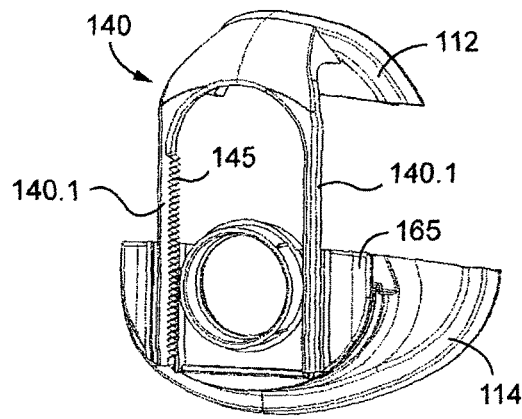
Figures 3, 9:
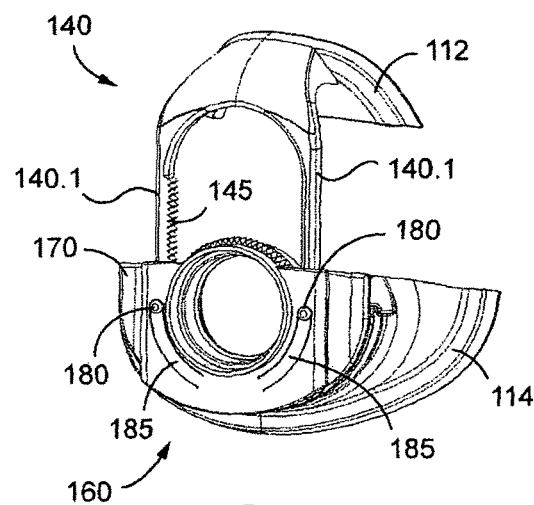

As shown in FIGS. 6-4 and 9-1 to 9-6, adjustment mechanism 125 may be supported relative to the frame via a support arrangement 160. The support arrangement may include an inner shroud 165 and/or an outer shroud 170. FIGS. 9-1 to 9-6 show a sequence when adding the various components. FIG. 9-6 shows the assembly of the frame and adjustment mechanism sub-assembly of FIG. 9-4 with the cushion and intermediate member sub-assembly of FIG. 9-5.

Figures 1, 20:
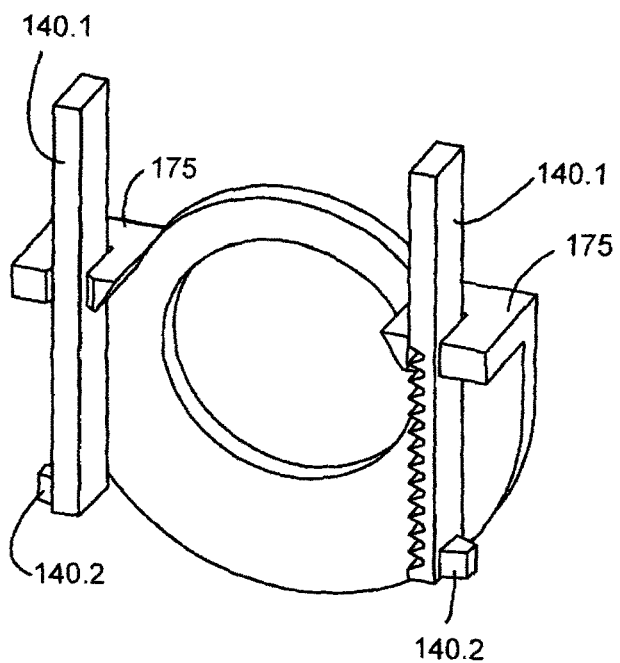
Figures 2, 20:
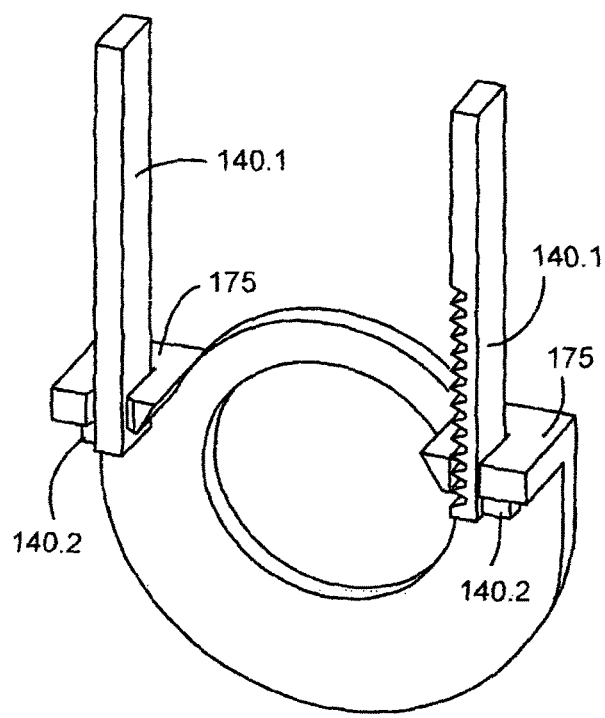

Inner shroud 165 (FIG. 9-1) is provided to the lower frame 114. Inner shroud 165 functions to aid the location of gear element 150 positioned around aperture 135 for the elbow 120. Specifically, the inner shroud 165 locates the gear element 150 by aligning the back wall of the gear element 150 and restricting axial movement of the gear element 150. Inner shroud 165 also aids in locating rack 140 to ensure it interfaces robustly with the gear 150. For example, inner shroud 165 may include one or more integrated vertical guides or rails 175 that are designed to receive the rack 140 and restrict lateral movement of the rack 140. Preferably, the guides or rails 175 will have a locking mechanism to prevent arms 140.1 of the rack 140 from extending past the rails and thus disassembling the system. For example, FIG. 20-1 shows a locking feature or protrusion 140.2 provided to a free end of each arm 140.1 that acts as a travel stop for the arms. As shown in FIG. 20-2, when the arms 140.1 of the rack reach the highest position, the locking feature 140.2 of each arm 140.1 engages or catches on respective guides 175 and prevents the arms 140.1 from further movement and disassembling of the system.

Figures 1, 10:
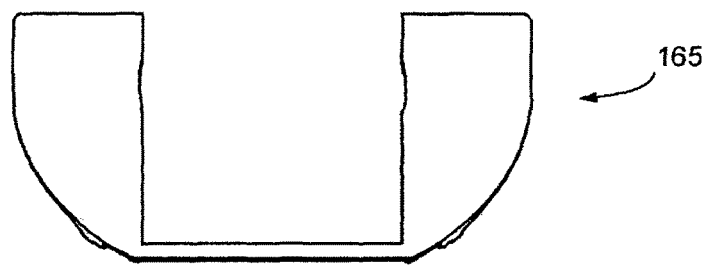
Figures 2, 10:
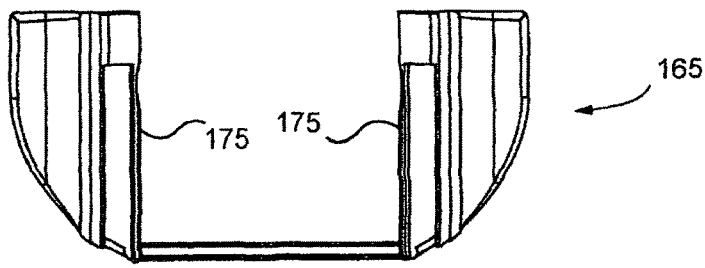
Figures 3, 10:
Figures 4, 10:
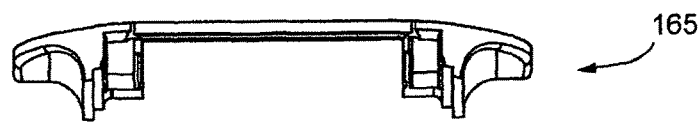
Figures 5, 10:
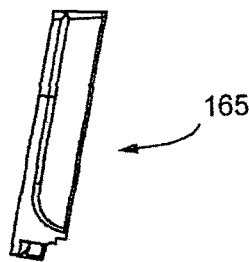

Inner shroud 165 could be made from stiff materials such as molded plastics (such as polycarbonate or polypropylene), metal, etc. FIGS. 10-1 to 10-5 show the inner shroud in isolation.

Inner shroud 165 may be incorporated into lower frame portion 114 and as such made of the same material. Alternatively, inner shroud 165 may be made as a permanent assembly with the rack and pinion mechanism and hence made of same or different material as this sub assembly. However, it should be noted that selecting different materials for elements that move relative to each other can reduce risks of squeak etc.

Outer shroud 170 (which is shown in isolation in FIGS. 11-1 to 11-5) functions to aid the location of the gear 150 around the elbow aperture 135. Specifically, the outer shroud 170 includes a round aperture to locate the gear 150 coaxially with the elbow aperture 135 and restrict lateral movement of the gear 150. In addition, the outer shroud 170 locates the gear 150 by aligning the front wall of the gear 150 and restricting axial movement of the gear 150. Outer shroud 170 also aids the location of the rack 140 to ensure it interfaces robustly with the gear 150. Outer shroud 170 may have one or more locking features (e.g., a bump feature 180 on flexible arm 185) that prevent the dial from rotating unintentionally. This may be implemented using other structure but preferably the system should not move when external or inadvertent forces such as headgear, treatment pressure or reaction force from the face is applied.

Figures 1, 33:
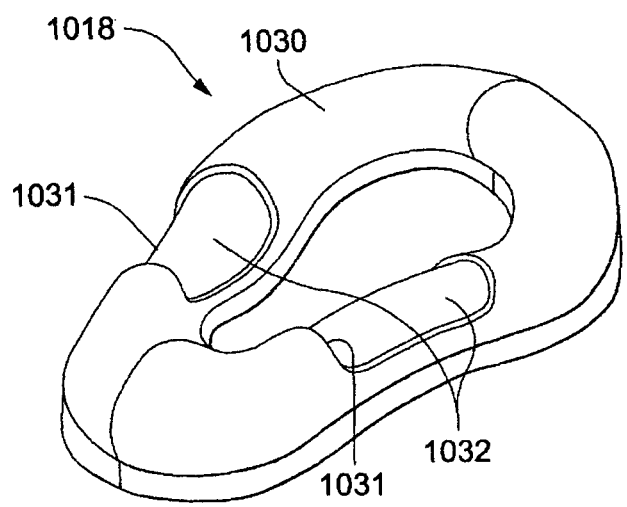
Figures 2, 33:
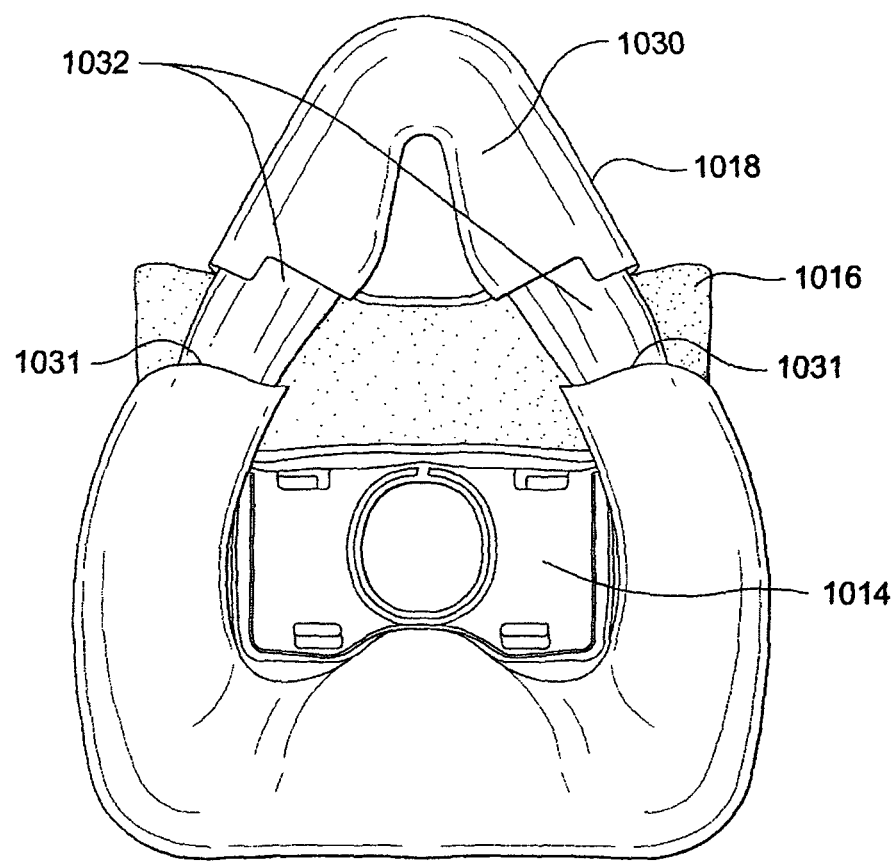
Figures 3, 33:
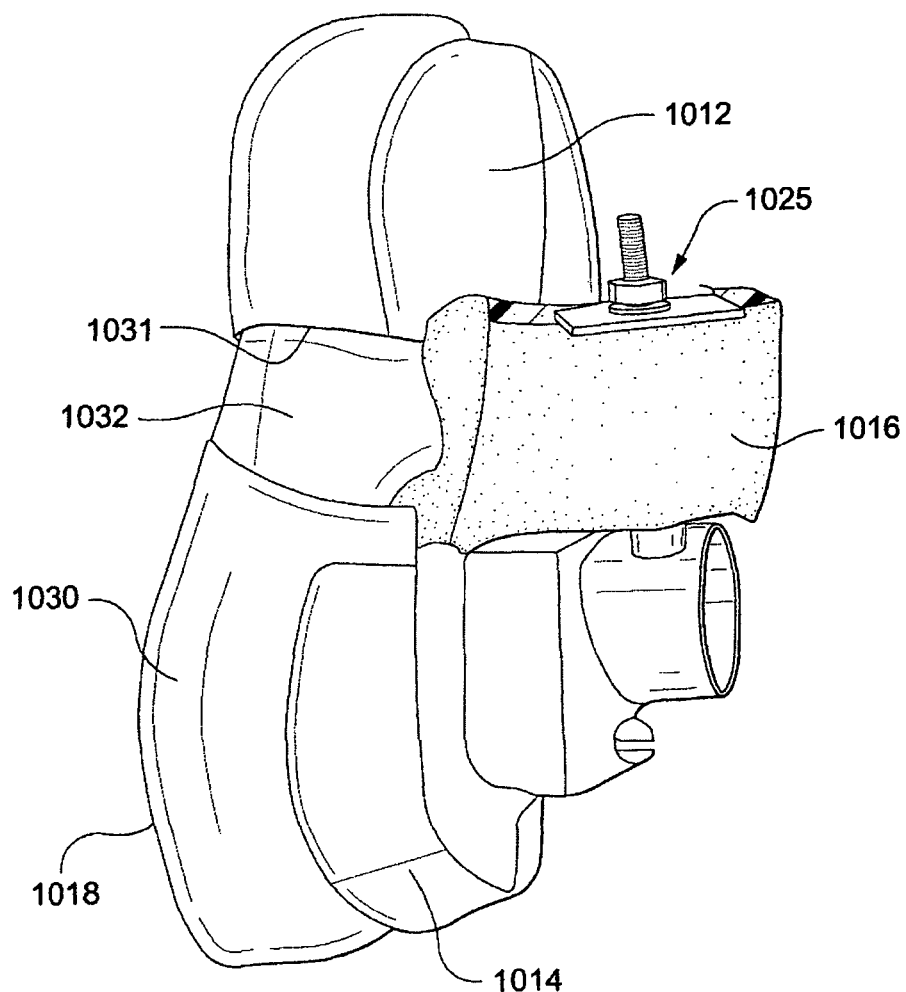
Figures 6, 33:
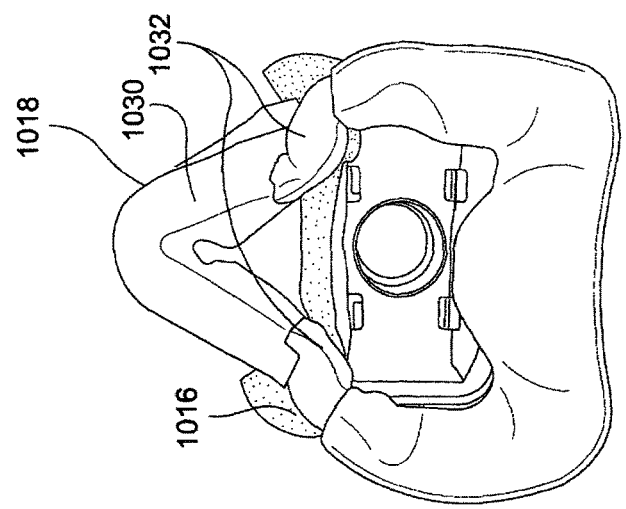
Figures 5, 33:
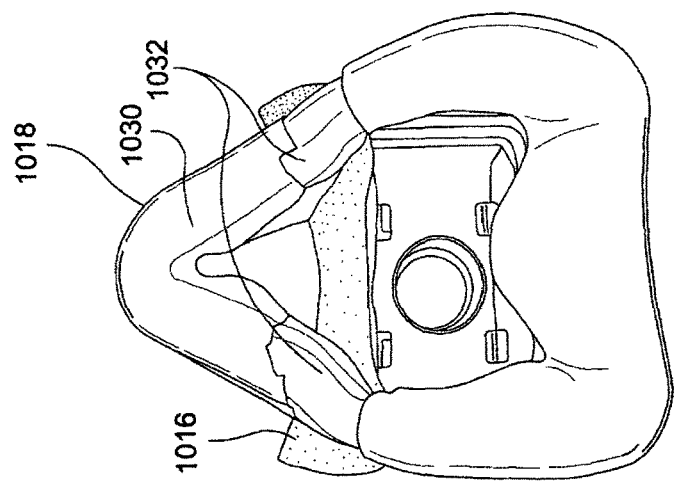
Figures 4, 33:
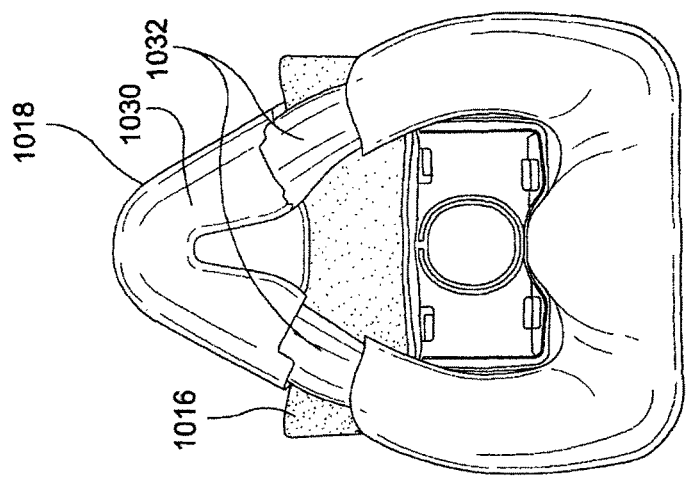
Figures 7, 33:
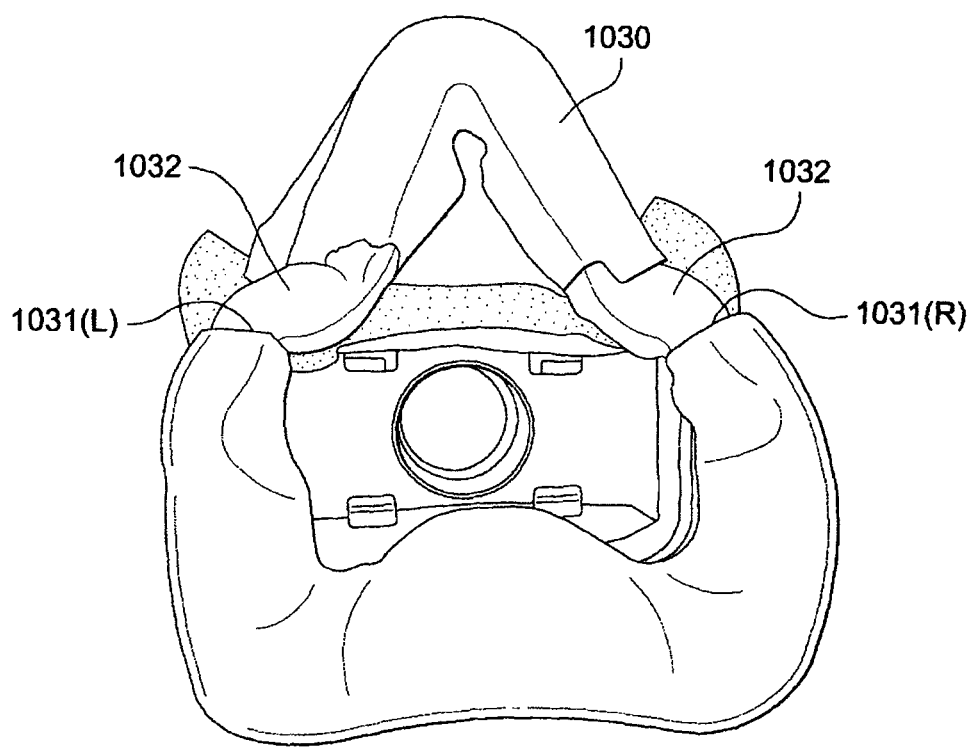
Figures 8, 33:
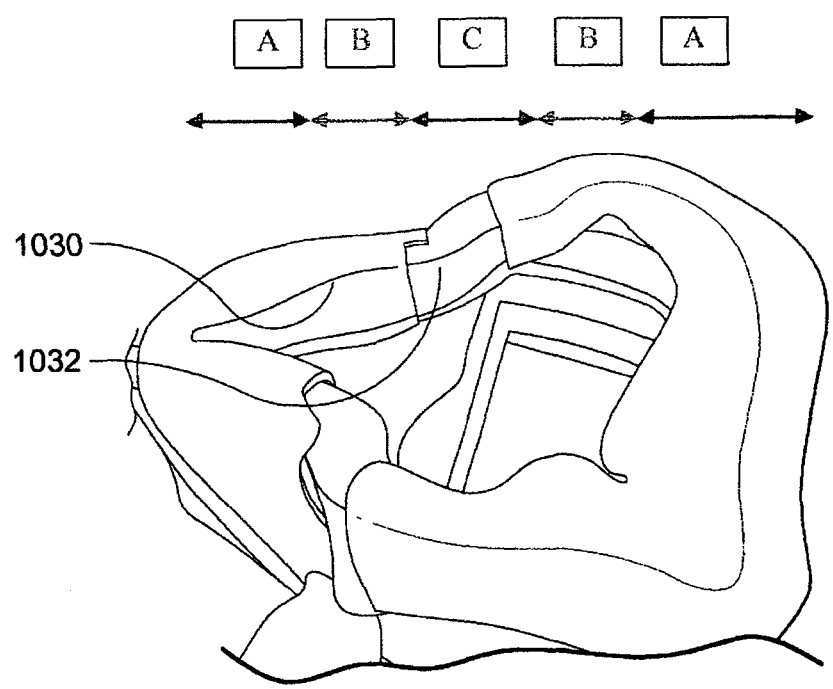
Figures 9, 33:
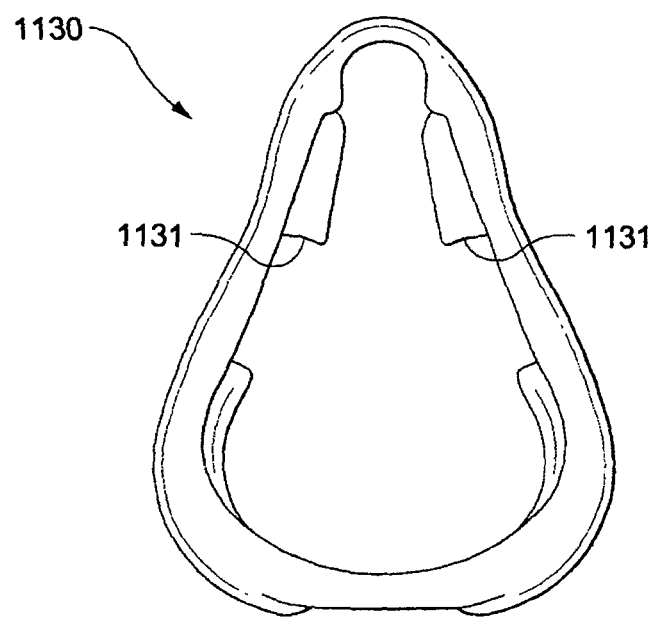
Figures 10, 33:
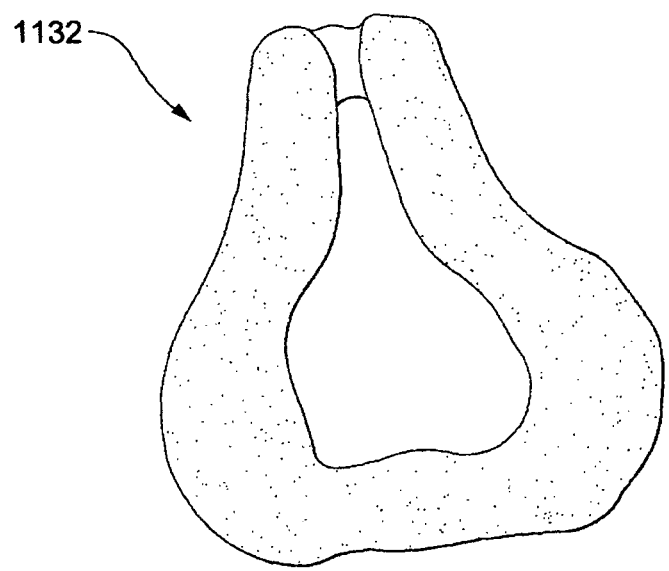
Figures 11, 33:
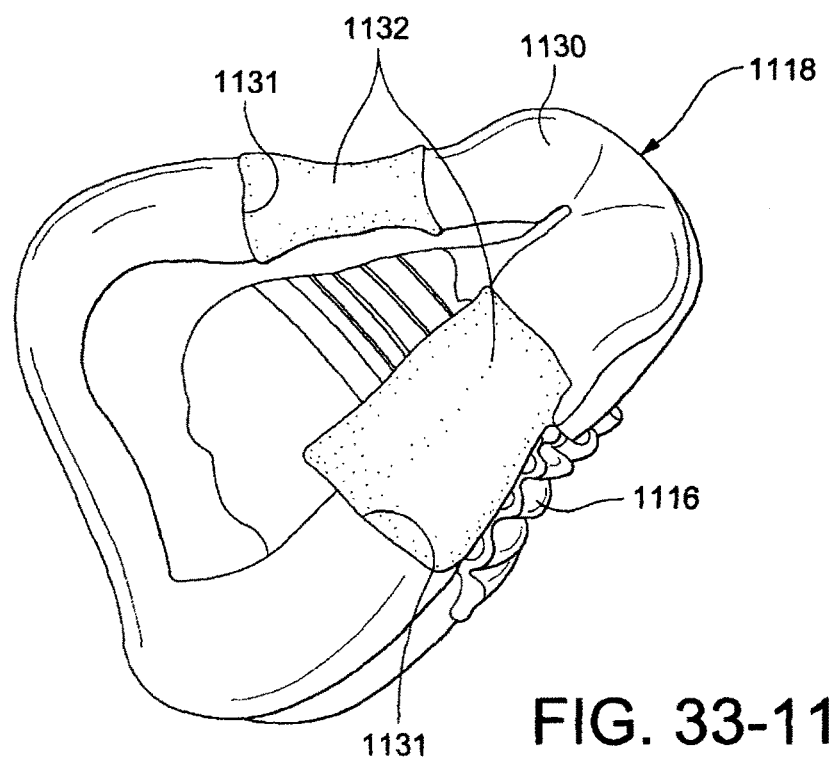
Figures 12, 33:
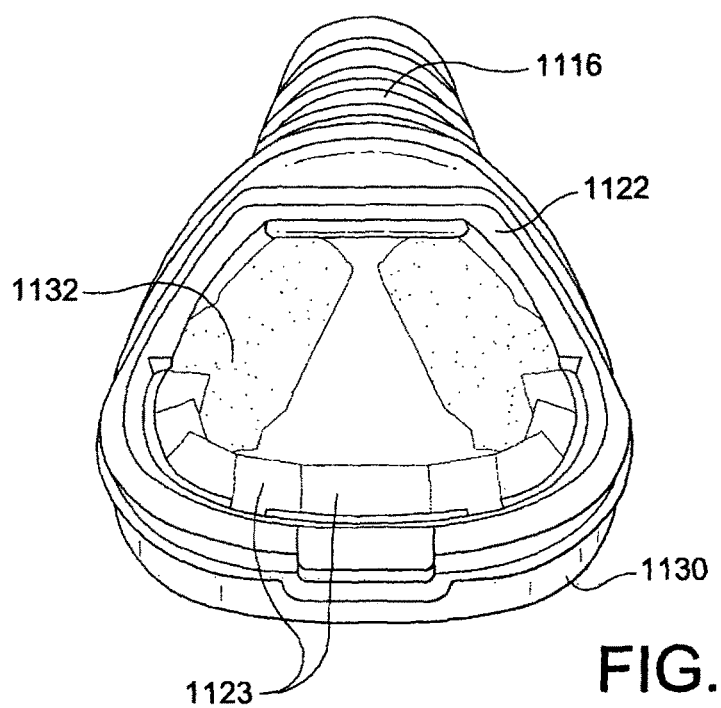
Figures 13, 33:
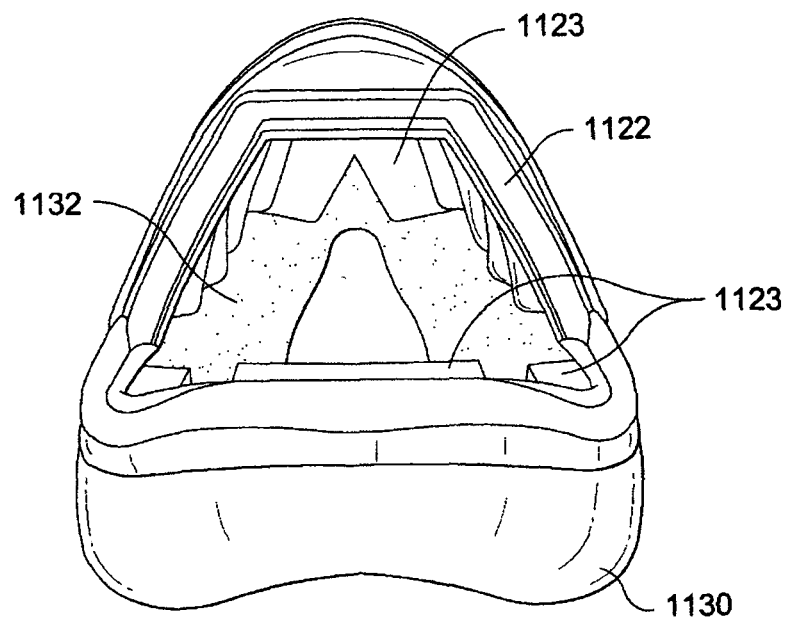
Figures 14, 33:
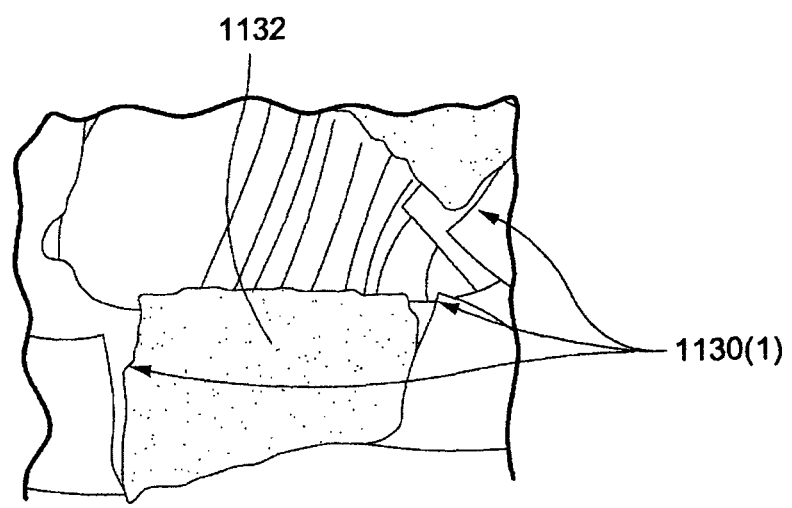
Figures 15, 33:
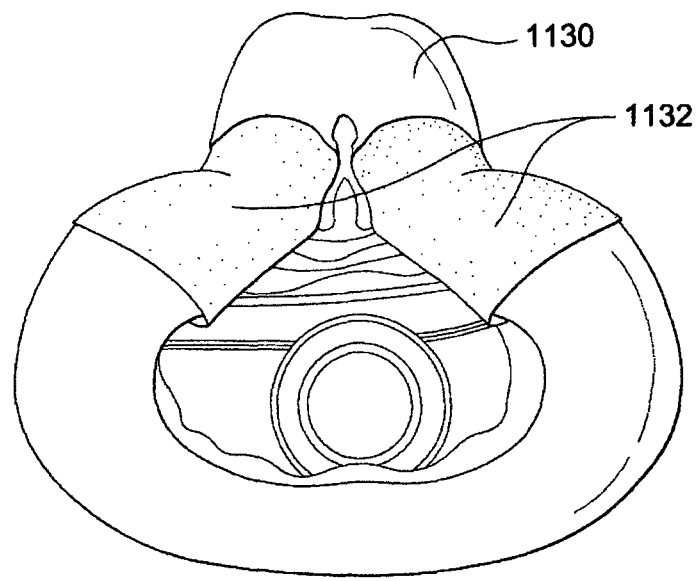
Figures 16, 33:
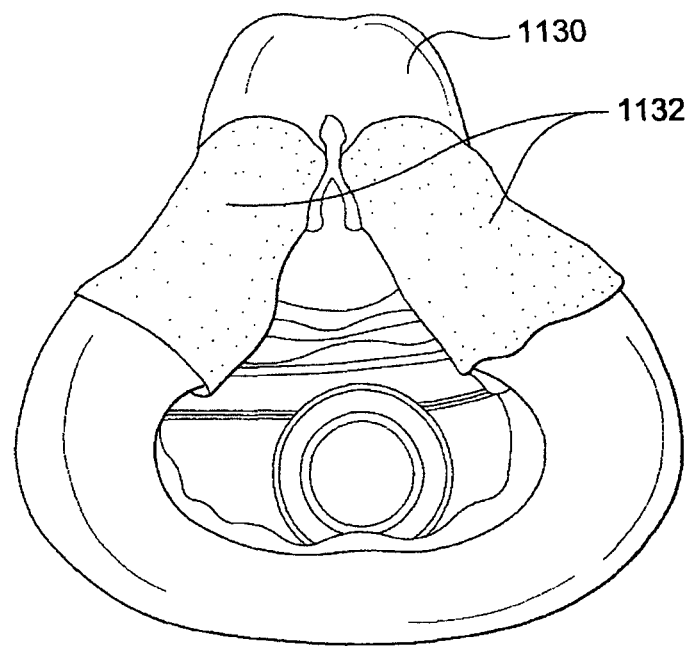
Figures 17, 33:
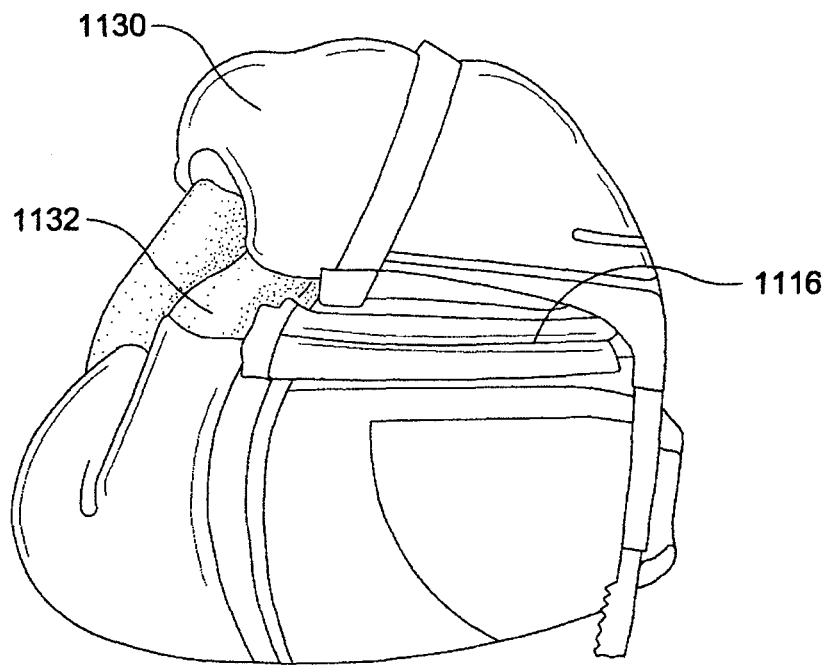
Figures 18, 33:
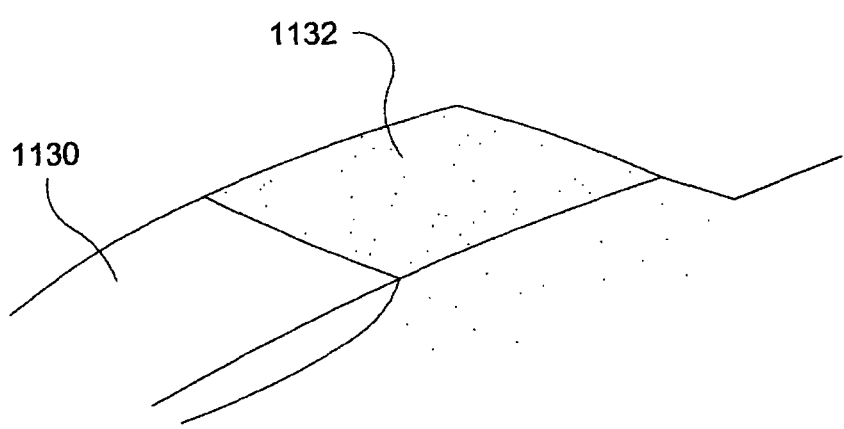
Figures 19, 33:
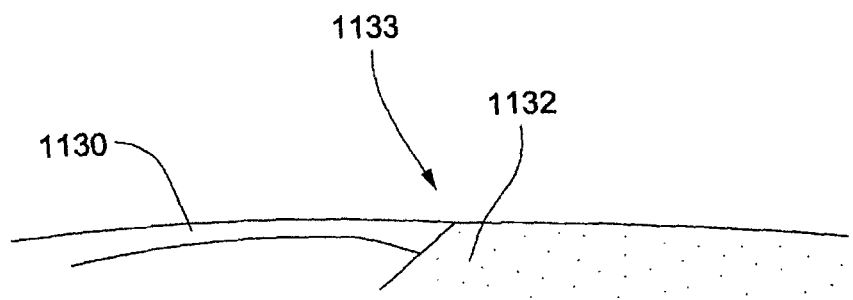
Figures 20, 33:
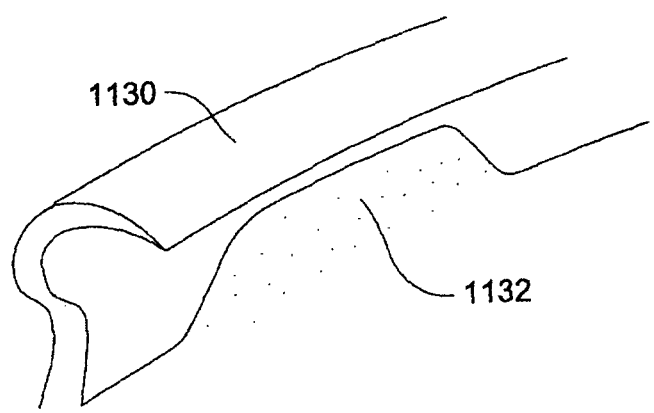
Figures 21, 33:
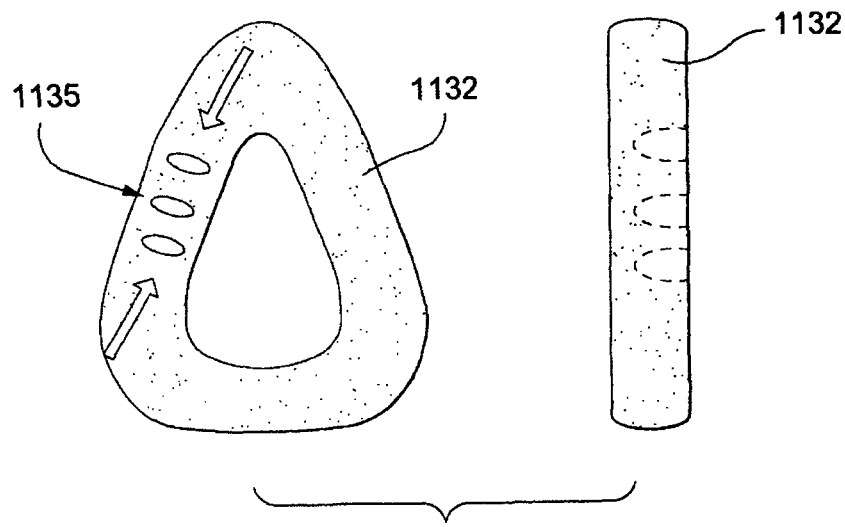

For example, FIGS. 21-1 and 21-2 illustrate a locking feature 300 that is slidable between engaged and disengaged positions. In the disengaged position, as shown in FIG. 21-1, the end portion 302 of the locking feature 300 is disengaged from the gears 155 of the gear 150 to allow rotation of the gear 150. In the engaged position, as shown in FIG. 21-2, the end portion 302 of the locking feature 300 is engaged with the gears 155 of the gear 150 to prevent unintentional rotation of the gear 150. The locking feature 300 may be spring loaded and manually movable between engaged/disengaged positions by a push button 304 as indicated by the arrow in FIG. 21-1.

Figures 22, 33:
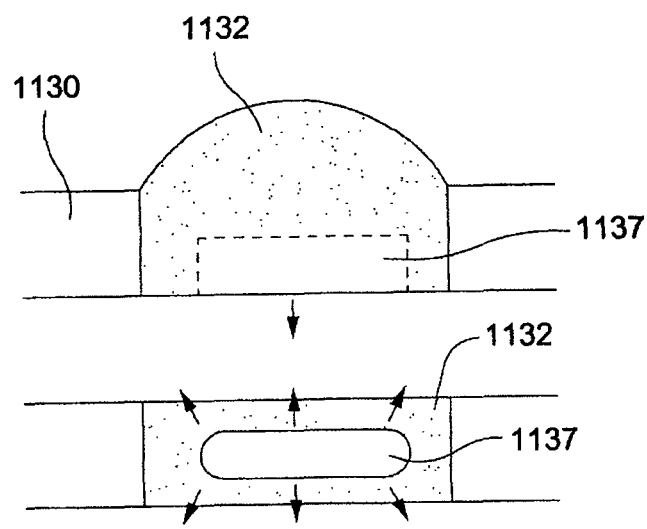

In another example as shown in FIG. 22, a locking feature 310 may be integrated (e.g., molded) as a part each guide 175 and movable between engaged and disengaged positions. In the engaged position, as shown in FIG. 22, the locking feature 310 provides a protrusion 312 adapted to engage with the gears 145 of the respective arm 140.1 to prevent movement of the arms. In the disengaged position (not shown), the protrusion 312 is disengaged from the gears 145 of the respective arm 140.1 to allow movement of the arms. The locking feature 310 may be manually movable between engaged/disengaged positions by a push button 314 as indicated by the arrows in FIG. 22.

Outer shroud 170 can be made from stiff materials such as molded plastics (such as polycarbonate or polypropylene), metal, etc. Outer shroud 170 may be incorporated into inner shroud 165 and as such made of the same material. Outer shroud 170 may be made as a permanent assembly with the rack and pinion mechanism and hence made of same or different material as this sub assembly.

2.3.4 Actuator

The adjustment mechanism may be set into motion using an actuator 134, as best seen in FIGS. 3-1 and 6-1 to 6-5. For example, actuator may take the form of a dial 190 coupled to the gear 150. When the dial 190 is rotated the gear 150 rotates. This rotational movement is transformed into vertical movement as the gear interacts with the rack 140. The dial 190 is located around the elbow aperture 135 but is large enough to be easily accessible and therefore allow adjustment by the patient while the mask is in use. The dial 190 may be operated while the mask system is worn, in situ. FIGS. 12-1 to 12-5 show isolated views of dial 190.

The dial 190 may include one or more visual design cues (e.g., arrows 195) that clearly indicate it is a rotatable element. Dial 190 may have one or more locking features, e.g., one or more recesses 200 that mate with the bumps 180 on the outer shroud 170 that prevent the dial from rotating unintentionally. For example, the underside 210 of the dial 190 (the side that contacts or faces the outer shroud 170) may have the recesses 200 that secure the bumps 180 of flexible arm(s) 185. Once past bump, the flexible arm 180 springs back to its original position and prevents the dial from turning back. The user would have to apply a force in the opposite direction to force the dial back the other way, i.e., push the same bump over the flexible arm.

Dial 190 can be made from stiff materials such as molded plastics (such as polycarbonate or polypropylene), metal, etc. Dial may be incorporated into the gear element and as such made of the same material. Dial may be made as a permanent assembly with the rack and pinion system and hence made of same or different material as this sub assembly. Dial may be overmolded with soft touch features to improve aesthetics, ease of use and intuitiveness.

The dial 190 may have additional features to make it easier to grip, for example molded gripping regions, roughened regions, tabs or other elements.

2.3.5 Mechanism Alternatives

While the rack and pinion mechanism have been discussed above, it is but one alternative as numerous other devices can be used for effecting adjustment of the size, dimensions and/or shape of the cushion/seal, e.g., a sliding mechanism, a lever, cam, etc. Also, the actuator 134 for causing the adjustment mechanism to change shape/size is described as a dial 190, but other forms are also possible. Moreover, it is possible that the mask system can be adjusted using an adjustment mechanism without an actuator, per se.

Figures 23, 33:
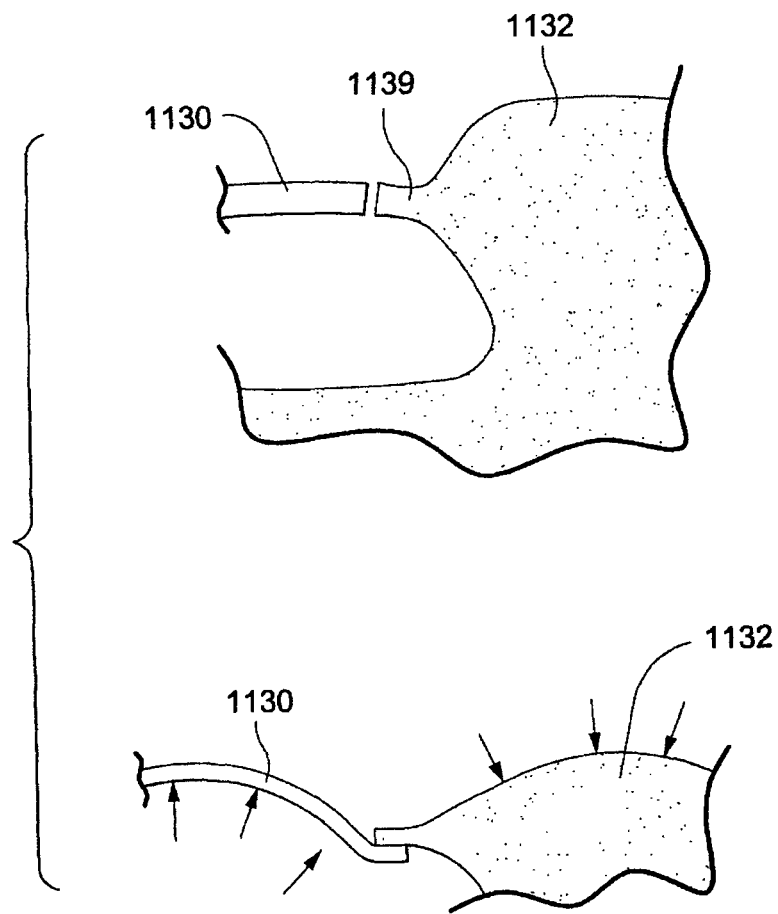
Figures 24, 33:
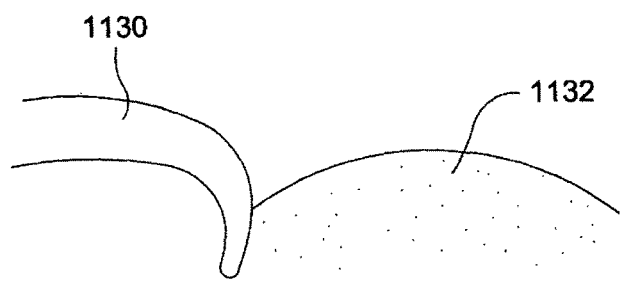
Figures 25, 33:
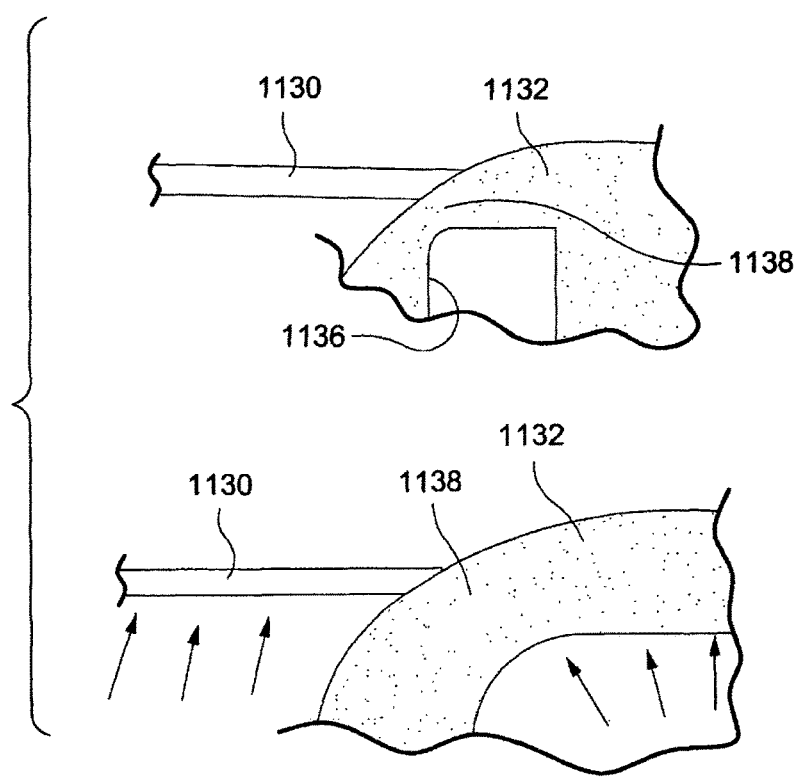

FIGS. 23-1 and 23-2 illustrate a worm gear mechanism that may be used for the adjustment of the dimensions or shape of the cushion seal. As illustrated, the guides 175 are structured to support respective worm gears 320, and each worm gear 320 includes gears 322 adapted to engage with the gears 145 of a respective arm 140.1. In use, rotation of the worm gears 320 translates into vertical movement of respective arms 140.1.

Figures 1, 24:
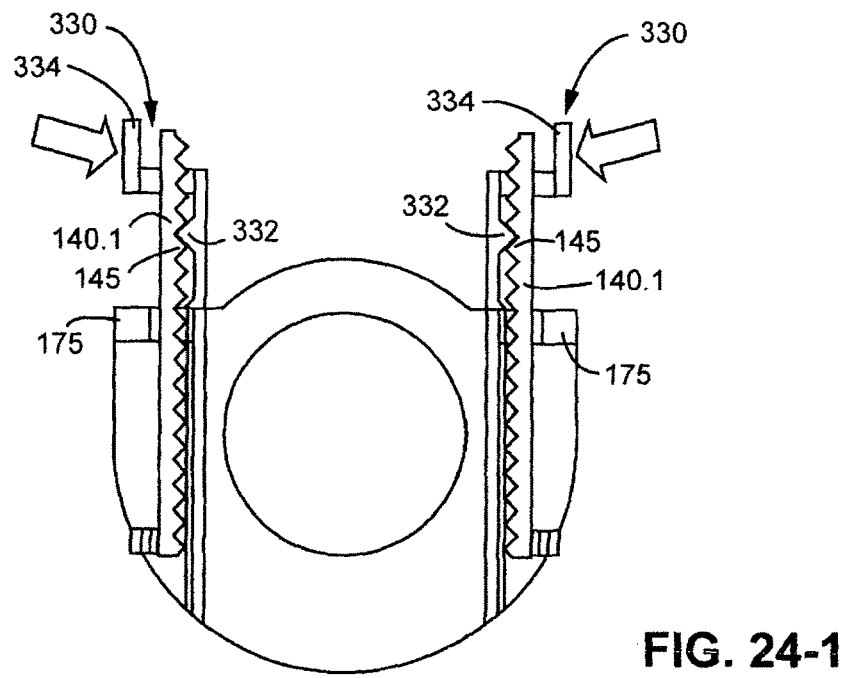
Figures 2, 24:
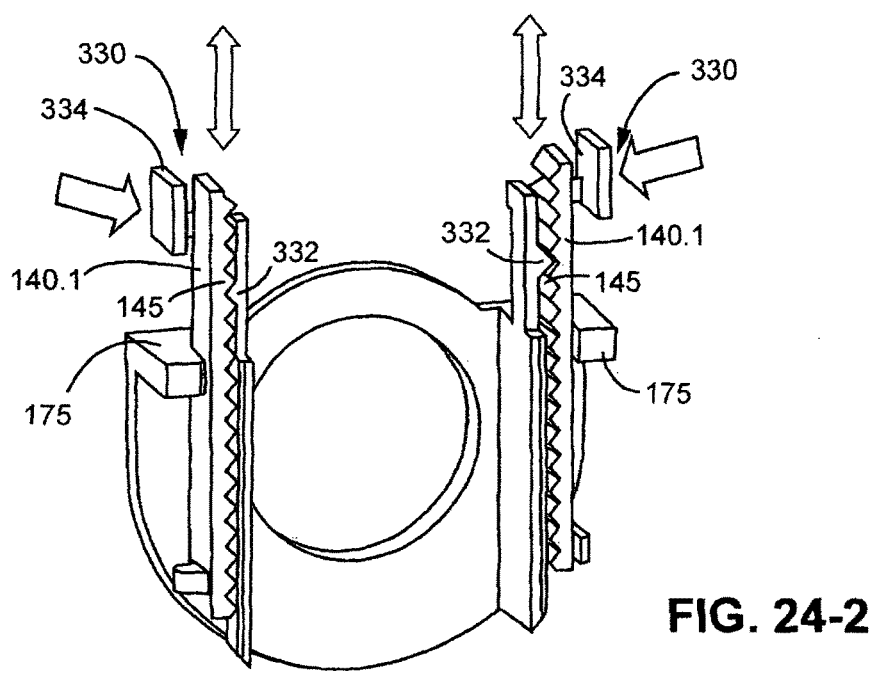

FIGS. 24-1 and 24-2 illustrate a sliding mechanism that may be used for the adjustment of the dimensions or shape of the cushion seal. Similar to the embodiment of FIG. 22, a locking feature 330 including a protrusion 332 is provided to each guide 175 (e.g., separate or molded as a part of the guide) and movable between engaged and disengaged positions. In the engaged position, as shown in FIGS. 24-1 and 24-2, the protrusion 332 engages with the gears 145 of a respective arm 140.1 to prevent movement of the arms. In the disengaged position (not shown), the protrusion 332 is disengaged from the gears 145 of the respective arm 140.1 to allow the arms 140.1 to slide vertically. The locking feature 330 may be manually movable between engaged/disengaged positions by a push button 334 as indicated by the arrows in FIGS. 24-1 and 24-2.

Pinch

Figure 74:
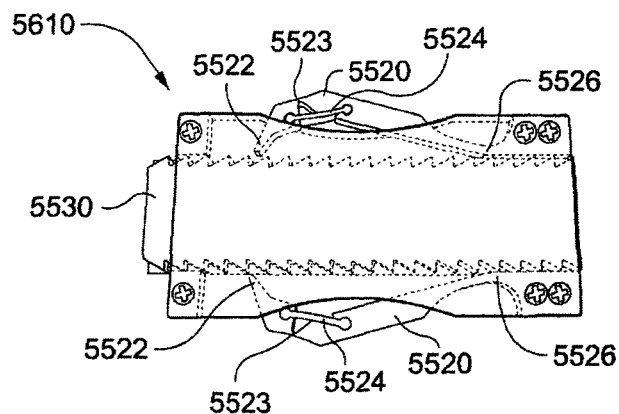
FIG. 74 shows a pinch type adjustment mechanism according to an embodiment of the technology.
Figures 1, 75:
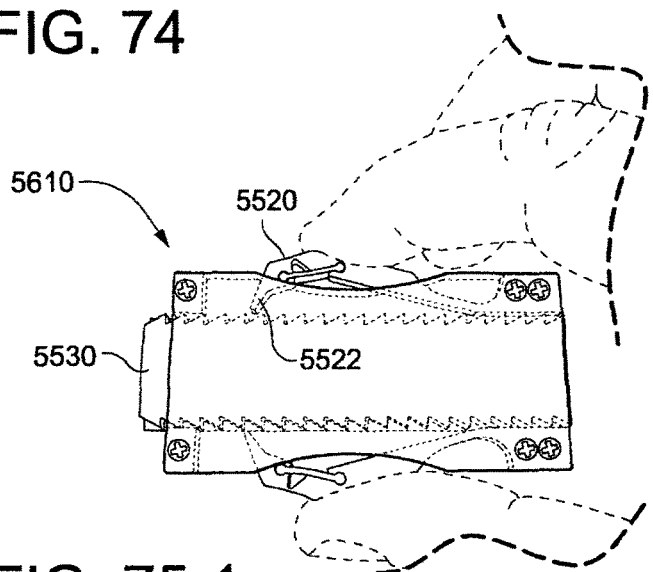
Figures 2, 75:
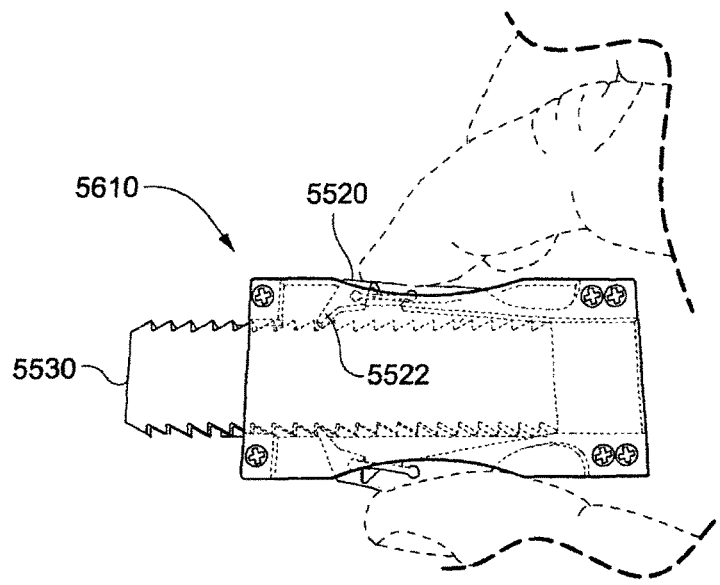

FIGS. 74, 75-1, and 75-2 illustrate a pinch type mechanism 5510 including flexible arm members 5520 on each side of a slider 5530 having gear teeth along the sides thereof. In the disengaged position as shown in FIG. 74, the flexible arm members 5520 are disengaged with the slider 5530. When the arm members 5520 are pinched towards one another as shown in FIG. 75-1, the arm members pivot about its base 5526 and allow end portion 5522 of each flexible arm member to engage with a respective tooth of the slider 5530. Further movement of the arm members 5520 towards one another pivots the end portion (about the flexible hinge 5523) which causes the arm members to push and adjust the position of the slider. Upon release, the end portions 5522 resiliently return to the position of FIG. 74 under biasing of elastic members 5524 and the arm members resiliently return to its starting position with respect to its base 5526.

Figure 76:
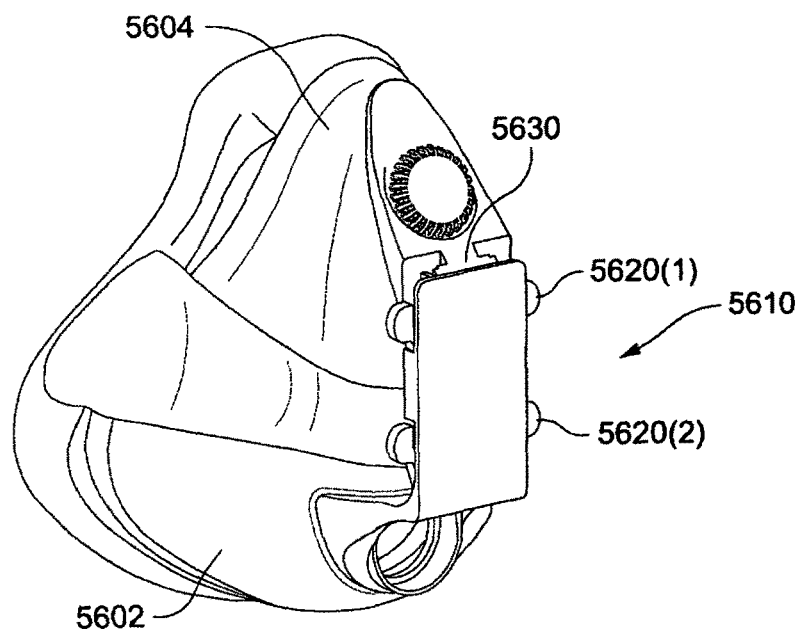
FIG. 76 shows a mask with a pinch type adjustment mechanism according to another embodiment of the technology.
Figure 77:
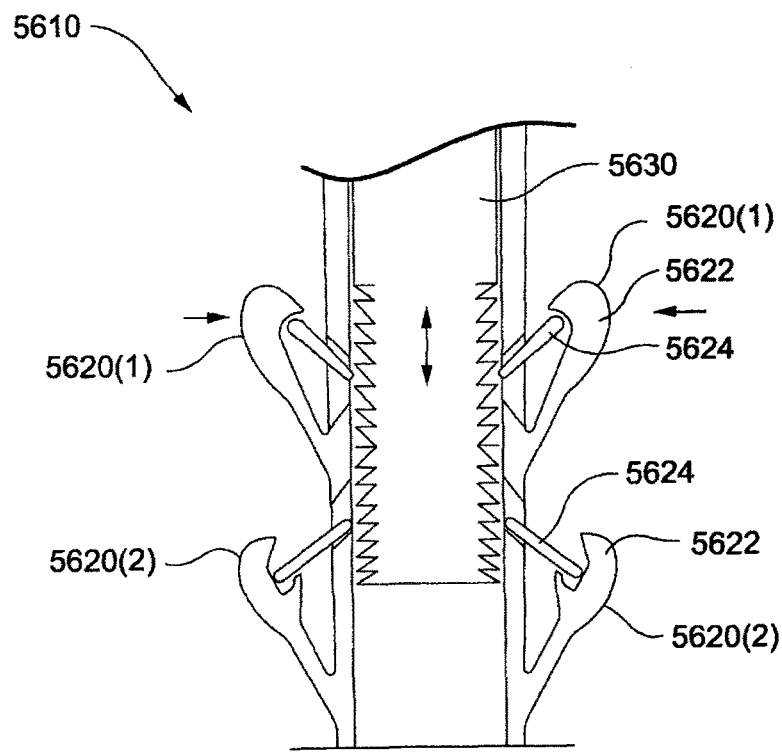
FIG. 77 is a schematic view of the pinch type adjustment mechanism of FIG. 76.

FIGS. 76 and 77 illustrate another pinch type mechanism 5610. In this embodiment, the mechanism includes a first set of arm members 5620(1) to move the slider 5630 in one direction and a second set of arm members 5620(2) to move the slider 5630 in the opposite direction. Each arm member includes a tab 5622 and an arm 5624 between the tab and slider. In use, selected tabs 5620(1) or 5620(2) are pinched towards one another, and the flexibility of the tabs pushes the arms into respective teeth of the slider which adjusts the position of the slider (i.e., up or down in a vertical direction as viewed in FIGS. 76 and 77). Upon release, the arm members resiliently return to their starting position in which the arms are disengaged with the slider teeth (e.g., FIG. 77). FIG. 76 shows the mechanism provided to a mask, with the arms members 5620(1), 5620(2) and its base provided to a lower frame portion 5602 and the slider 5630 provided to an upper frame portion 5604.

Angular Dial Adjuster

Figure 78:
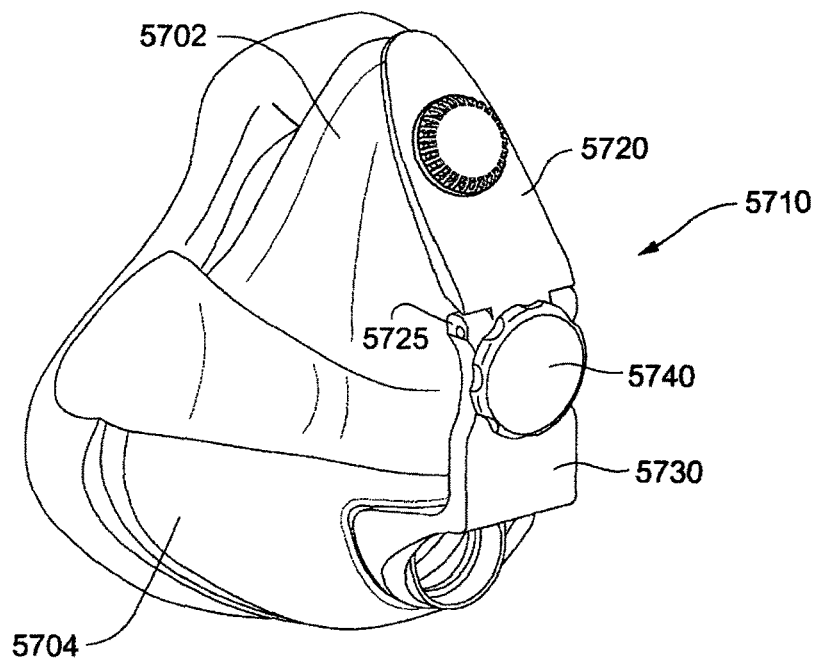
FIG. 78 shows a mask with an angular dial adjuster according to an embodiment of the technology.
Figure 79:
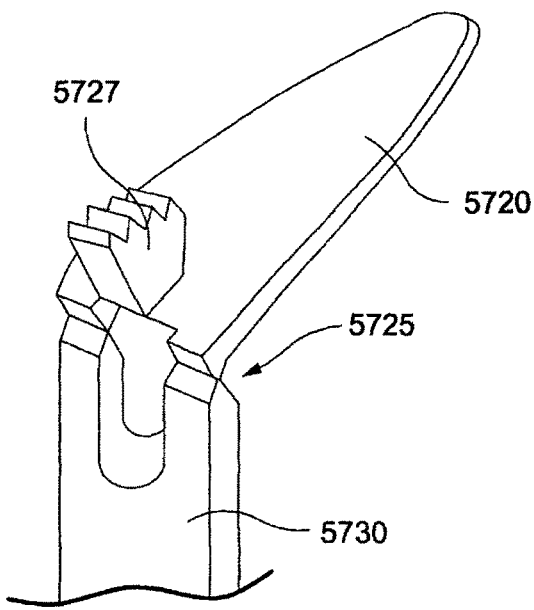
FIG. 79 is a perspective view of a portion of the adjuster of FIG. 78.
Figure 80:
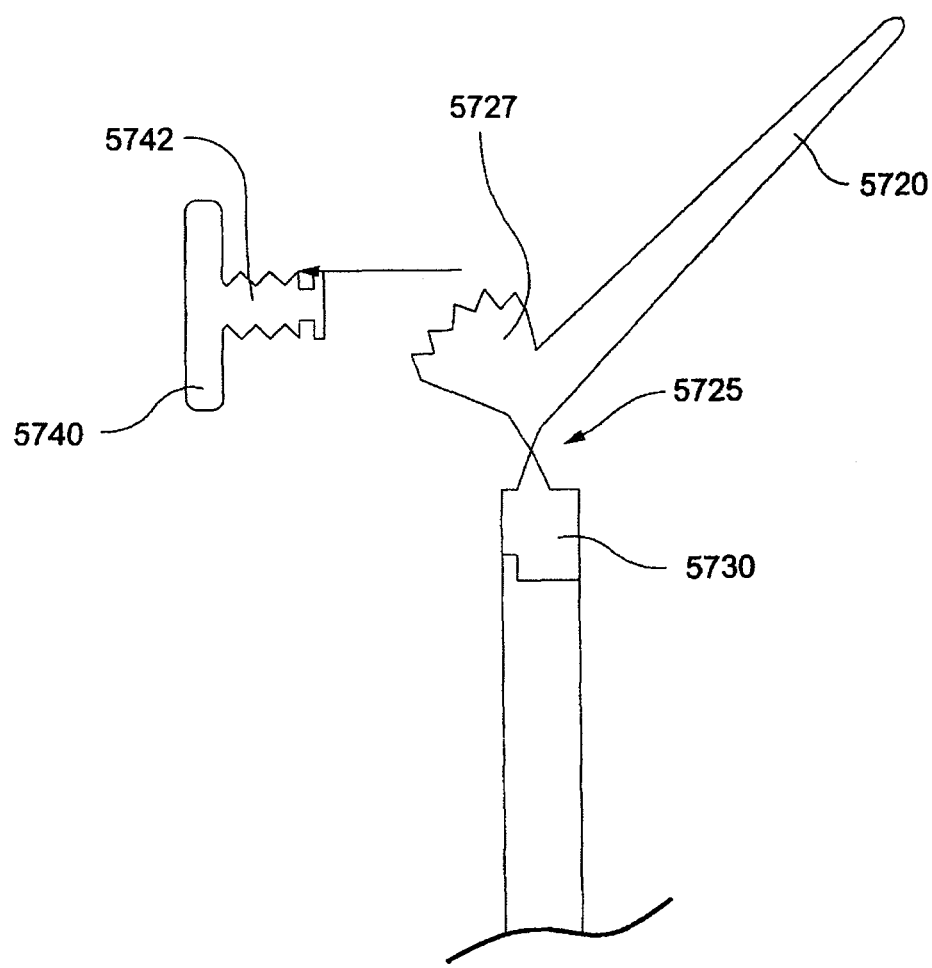
FIGS. 80 and 81 are schematic views of the adjuster of FIG. 78.
Figure 81:
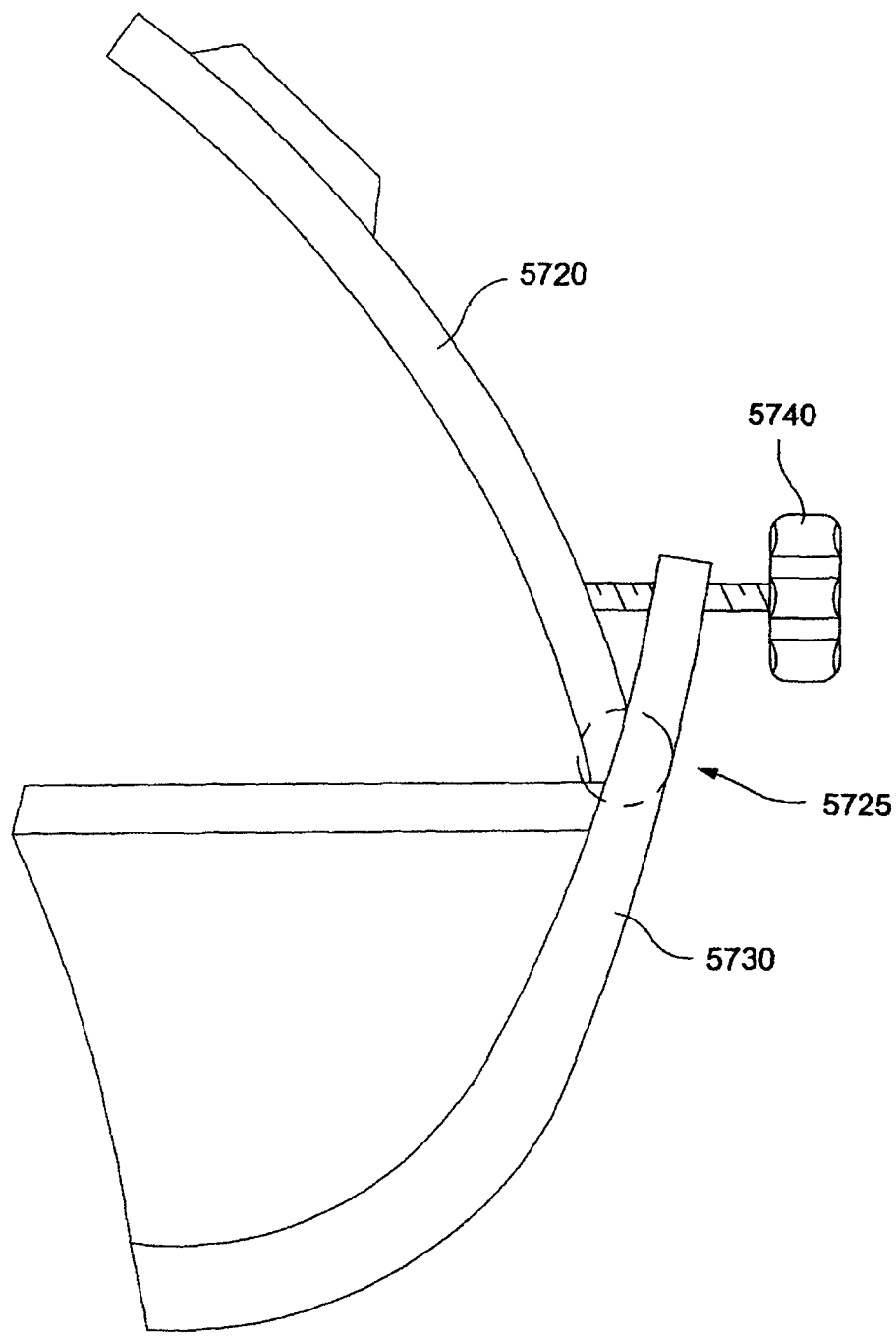

FIG. 78 shows an adjustment mechanism 5710 provided to a mask according to another embodiment of the technology. In this embodiment, the mechanism includes a first portion 5720 provided to an upper frame portion 5702 and a second portion 5730 provided to a lower frame portion 5704. The first and second portions 5720, 5730 are coupled to one another by a hinged portion 5725 which allows the first portion to rotate relative to the second portion. An actuator or dial 5740 is provided to effect angular adjustment of the first portion relative to the second portion. As schematically shown in FIGS. 79 to 81, the dial 5740 includes teeth 5742 structured to threadably engage teeth 5727 provided to the first portion 5720. In use, the dial 5740 may be rotated to adjust the position of the first portion relative to the second portion.

Figure 82:
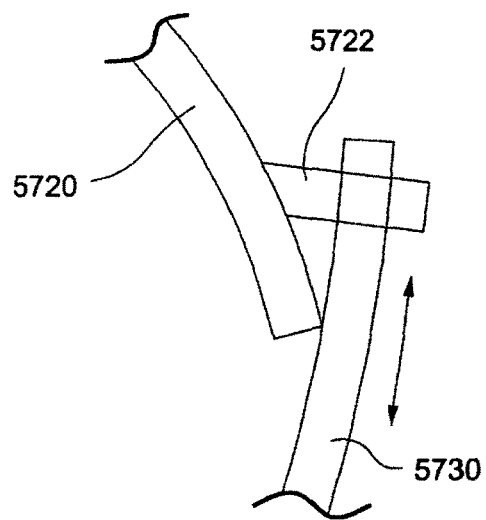
Figures 1, 82:
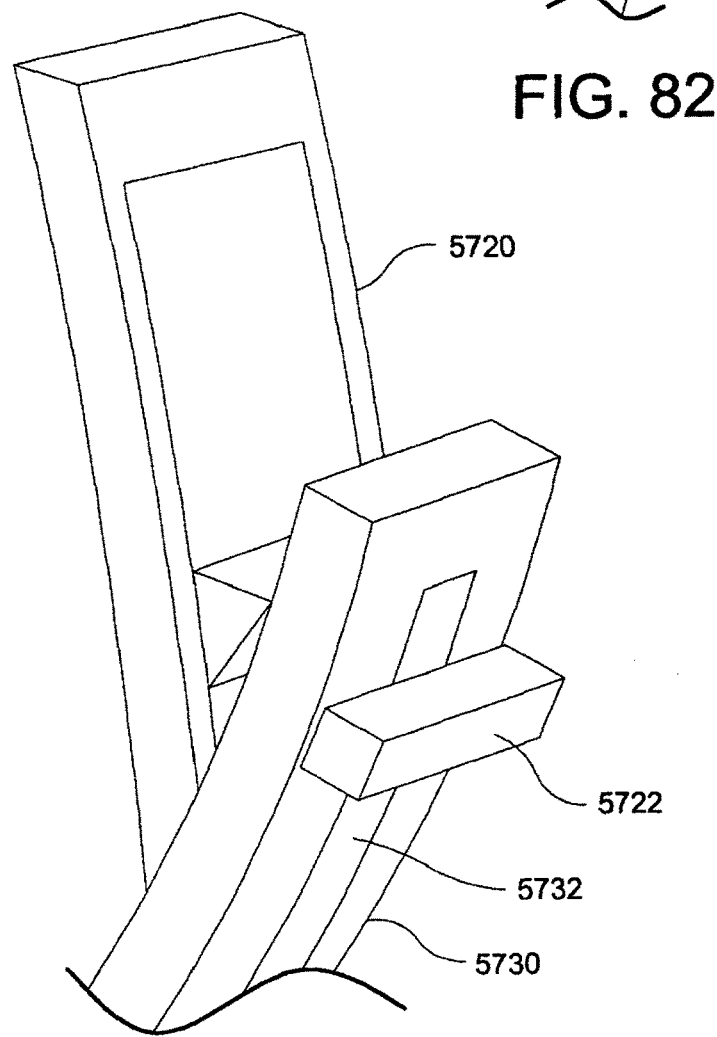

In an alternative embodiment, as shown in FIGS. 82 and 82-1, the first and second portions 5730, 5730 may be structured to slide relative to one another, e.g., second portion 5730 includes recess 5732 adapted to receive follower 5722 provided to the first portion 5720.

Over Center Latch

Figure 83:
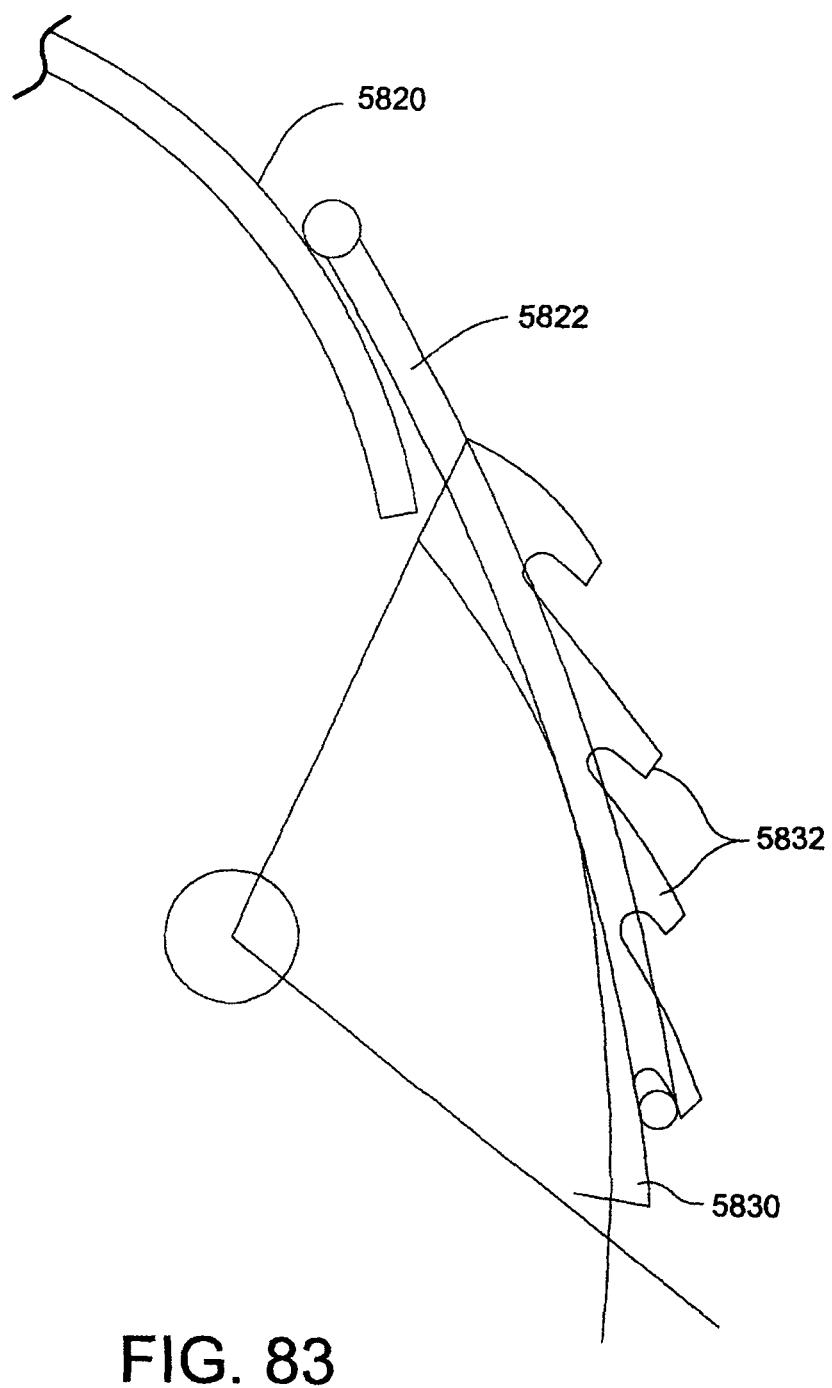
FIG. 83 is a schematic view of an over center latch mechanism according to an embodiment of the technology.

FIG. 83 illustrates an adjustment mechanism including an over center latch, e.g., like a ski boot. As illustrated, the mechanism includes a first portion 5820 provided to an upper frame portion and a second portion 5830 provided to a lower frame portion. The second portion includes a series of teeth 5832, and the first portion includes a latch 5822 that is selectively engageable with a one of the teeth to adjust the position of the first portion with respect to the second portion.

Vertical Dial Adjustment

Figure 84:
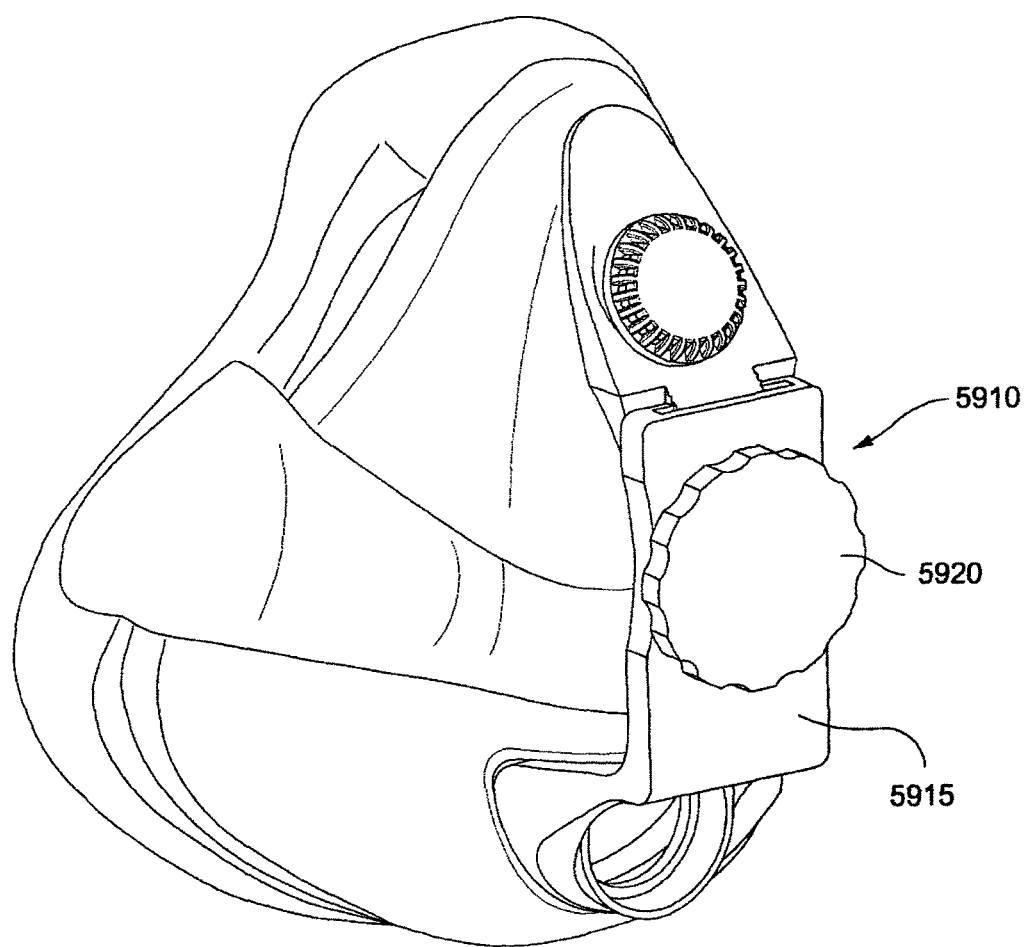
FIG. 84 shows a mask with a rack and pinion type mechanism according to an embodiment of the technology.
Figure 85:
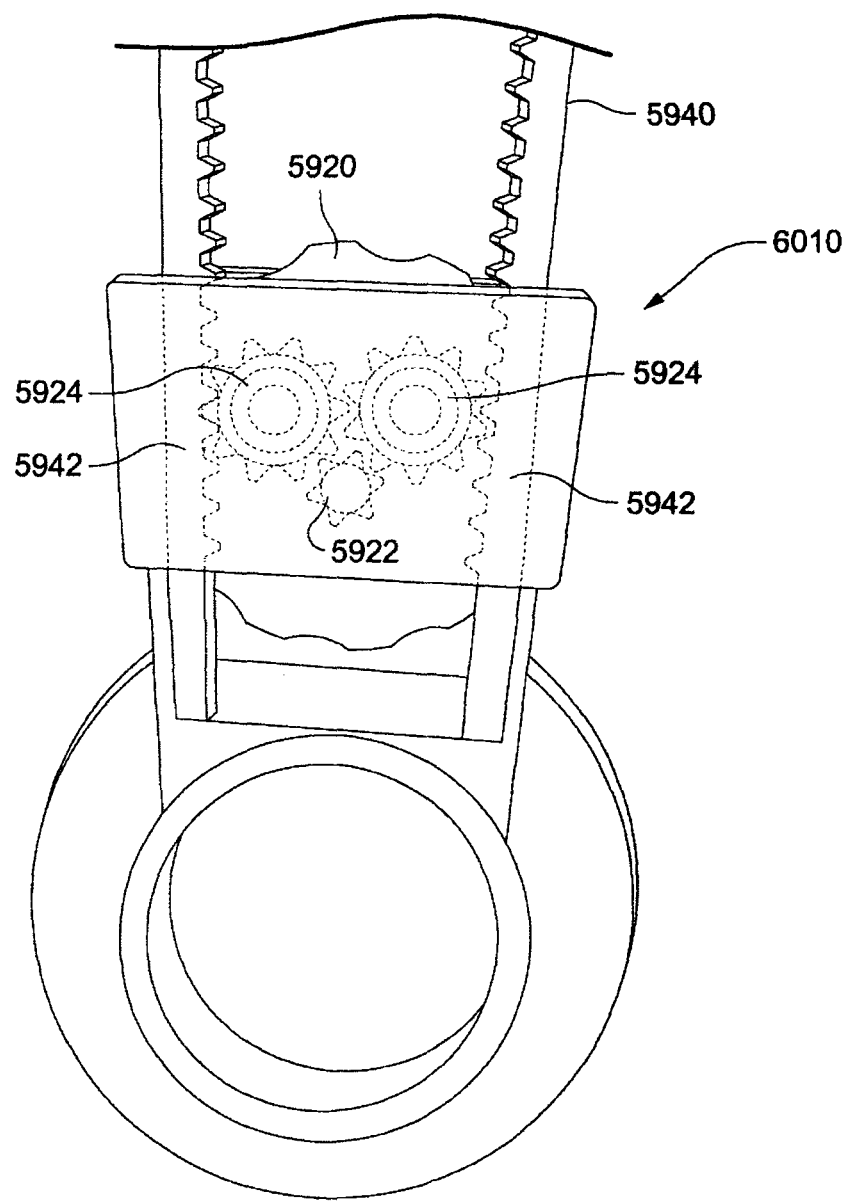
FIG. 85 is a perspective view of the rack and pinion type mechanism of FIG. 84.

FIGS. 84 and 85 show a rack and pinion type mechanism 5910 similar to that shown in FIG. 3-1 for example. As illustrated, the dial 5920 has an axis of rotation that extends horizontal and normal to the patient's face in use. In this embodiment, a shroud 5915 is provided to cover the rack. Also, in an embodiment, as shown in FIG. 85, the dial 5920 may include a gear 5922 that interacts with two gears 5924 on the dial, each gear 5924 engaged with the linear gear teeth 5942 of the rack 5940.

Figures 86, 87:
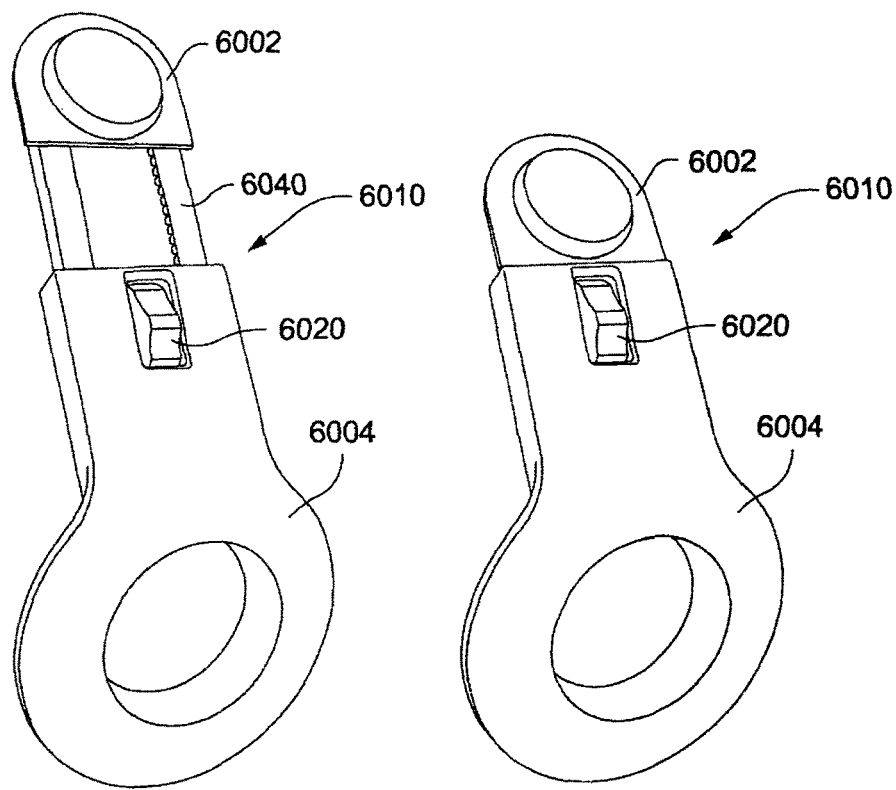
FIGS. 86 to 88 show various views of a rack and pinion type mechanism according to another embodiment of the technology.
Figure 88:
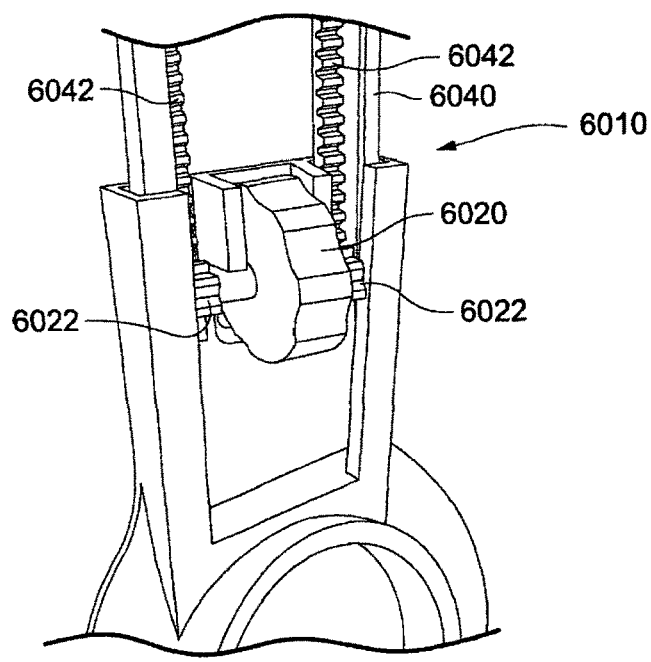

In an alternative embodiment, as shown in FIGS. 86 to 88, the dial 6020 of the rack and pinion type mechanism 6010 may be arranged such that is axis of rotation is horizontal and parallel to the plane of the patient's face in use. As illustrated, the rack 6040 is provided to the upper frame portion 6002 and the dial 6020 is provided to the lower frame portion 6004. As shown in FIG. 88, the dial 6020 includes gears 6022 that interact with the linear gear teeth 6042 of the rack 6040. FIGS. 86 and 87 show the mechanism in extended and retracted positions.

Figure 89:
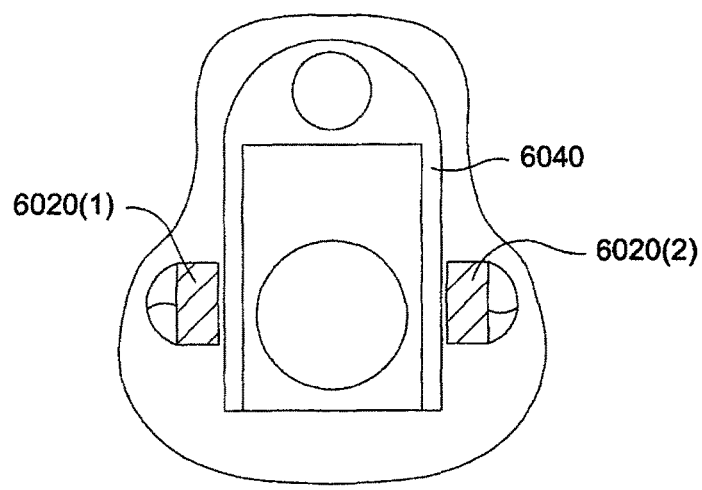
FIG. 89 shows a mask with a rack and pinion type mechanism according to another embodiment of the technology.

As shown in FIG. 89, the mechanism 6010 may include two dials 6020(1). 6020(2), each dial 6020(1), 6020(2) having a gear structured to interact with the linear gear teeth of the rack 6040. Similar to the embodiment of FIGS. 86 to 88, each dial includes an axis of rotation that is horizontal and parallel to the plane of the patient's face in use.

Figures 90, 91:
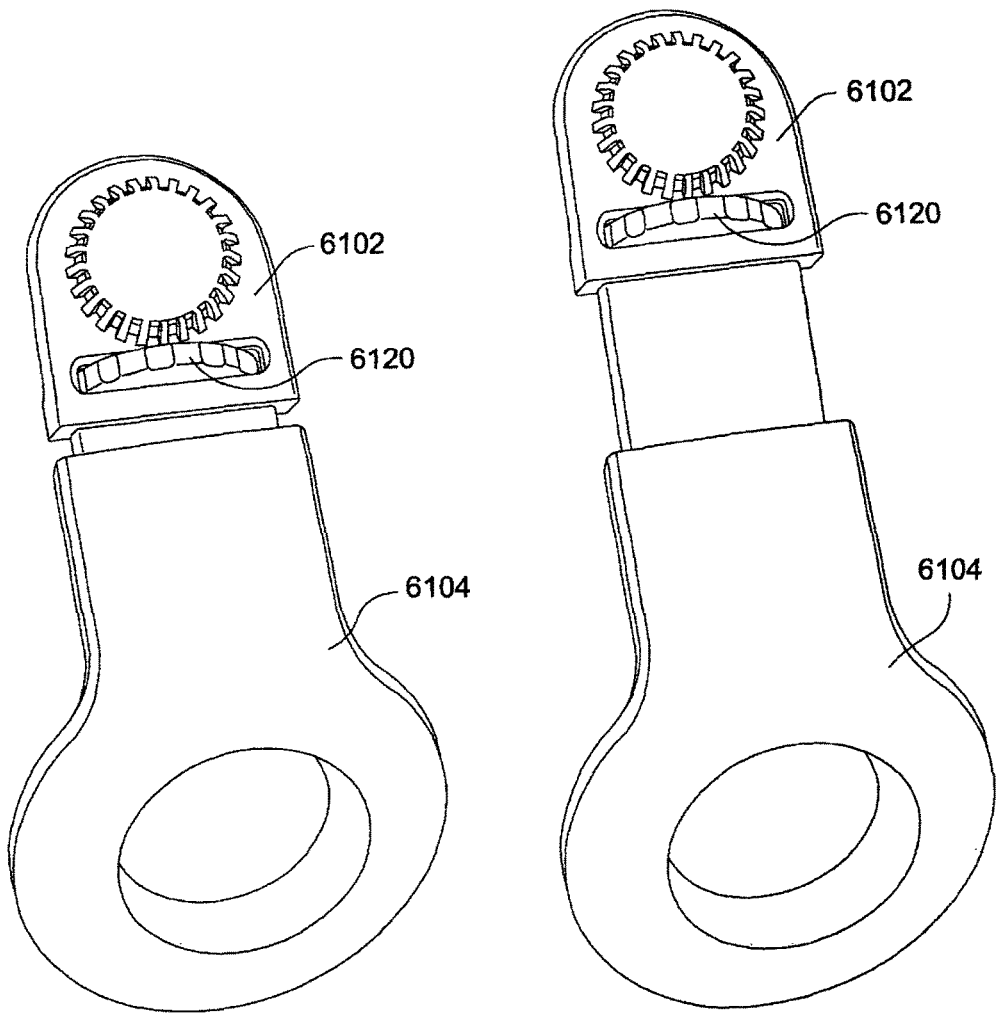
FIGS. 90 to 92 show various views of a rack and pinion type mechanism according to another embodiment of the technology.
Figure 92:
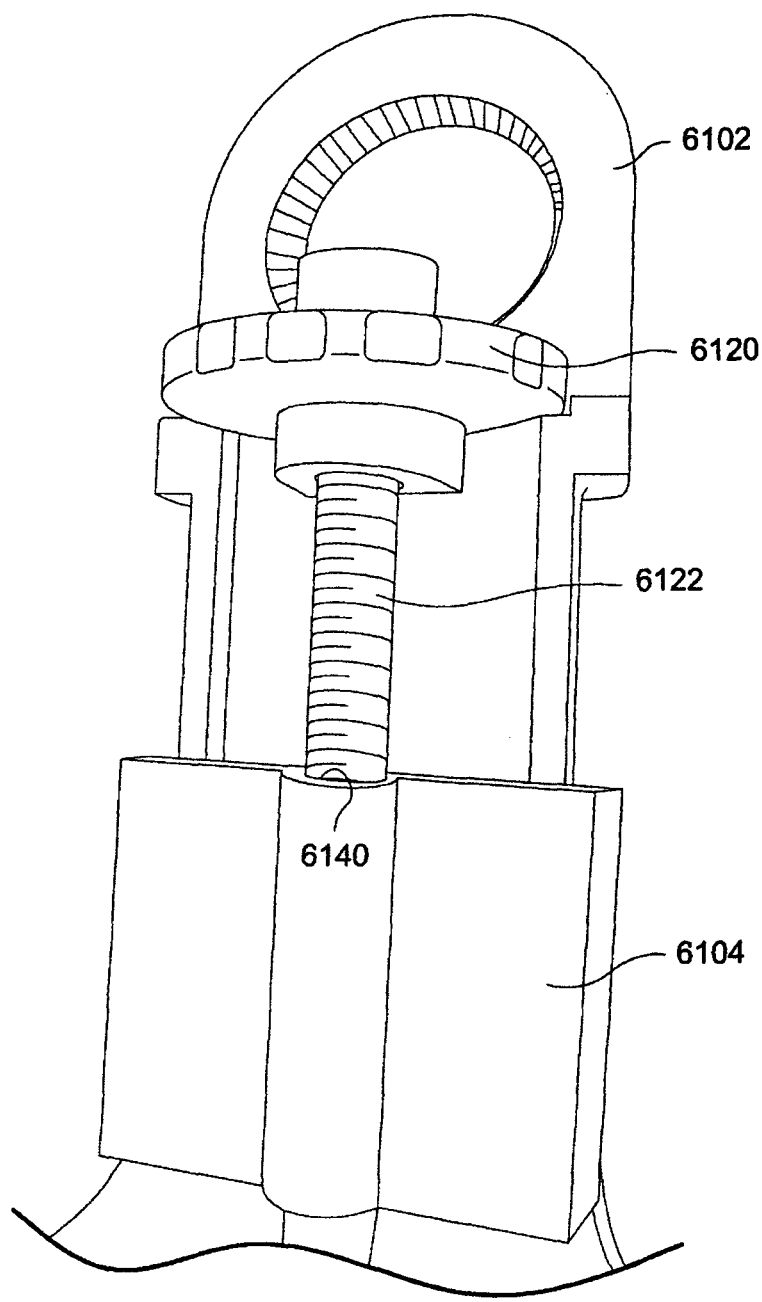

In another alternative embodiment, as shown in FIGS. 90 to 92, the dial of the adjustment mechanism may be arranged such that its axis of rotation is vertical and parallel to the plane of the patient's face in use. As illustrated, the upper frame portion 6102 supports the dial 6120, and the lower frame portion 6104 includes a threaded aperture 6140 adapted to threadably engage a threaded shaft 6122 provided to the dial 6120. In use, rotation of the dial causes the threaded shaft 6122 to move in and out of the threaded aperture 6140, which adjusts the position of the upper frame portion 6102 relative to the lower frame portion 6104. FIGS. 90 and 91 show the mechanism in retracted and extended positions.

Perimeter Crank

Figure 93:
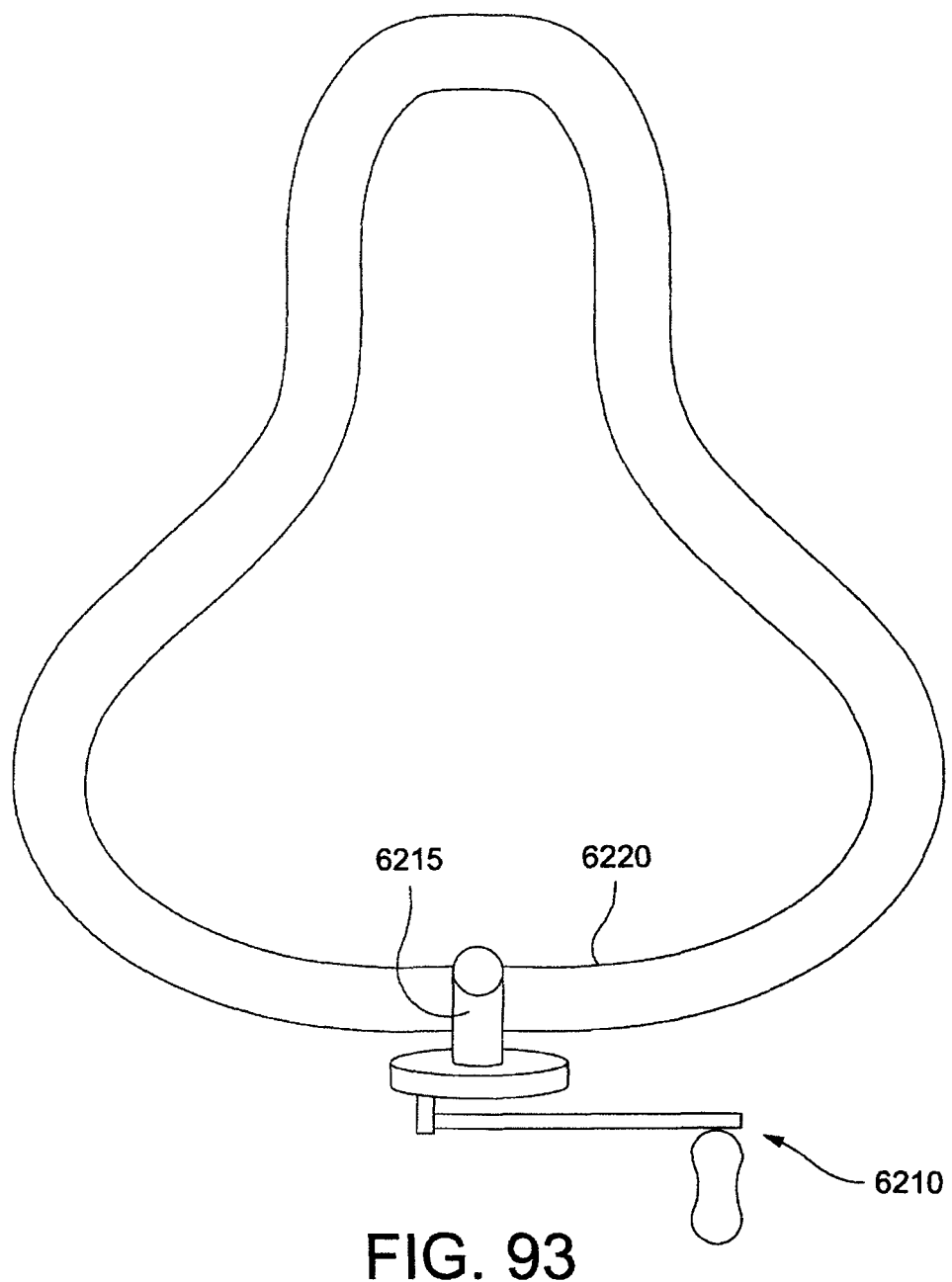
FIG. 93 is a schematic view of a mask with a crank mechanism according to an embodiment of the technology.

As shown in FIG. 93, a crank 6210 may be provided to the perimeter of the mask. The crank is engaged with a cord 6220 (e.g., constructed of polymeric and/or metallic material, etc.) that extends around at least a portion of the perimeter of the mask (e.g., around the entire perimeter). The crank axle 6215 is engaged with the cord 6220 which allows the crank to selectively wind the cord 6220 about the axle 6515 so as to change the shape of the mask.

Pull Out, Push In

Figure 94:
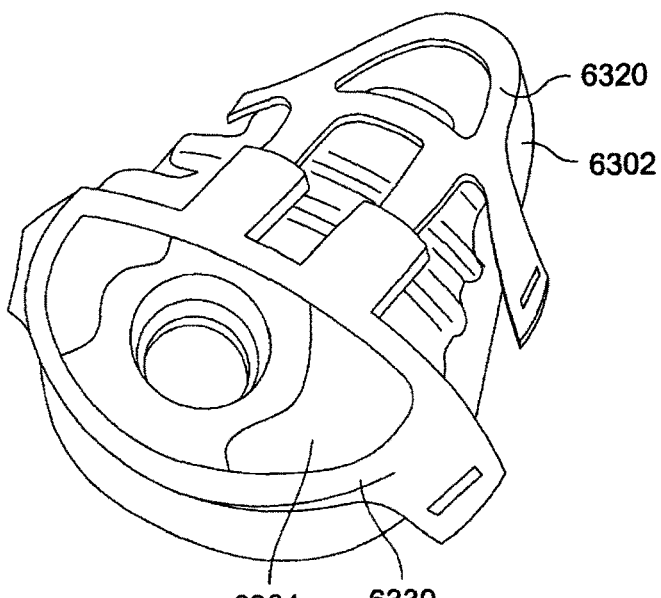
FIGS. 94 and 95 shows various views of an adjustment mechanism according to an embodiment of the technology.
Figure 95:
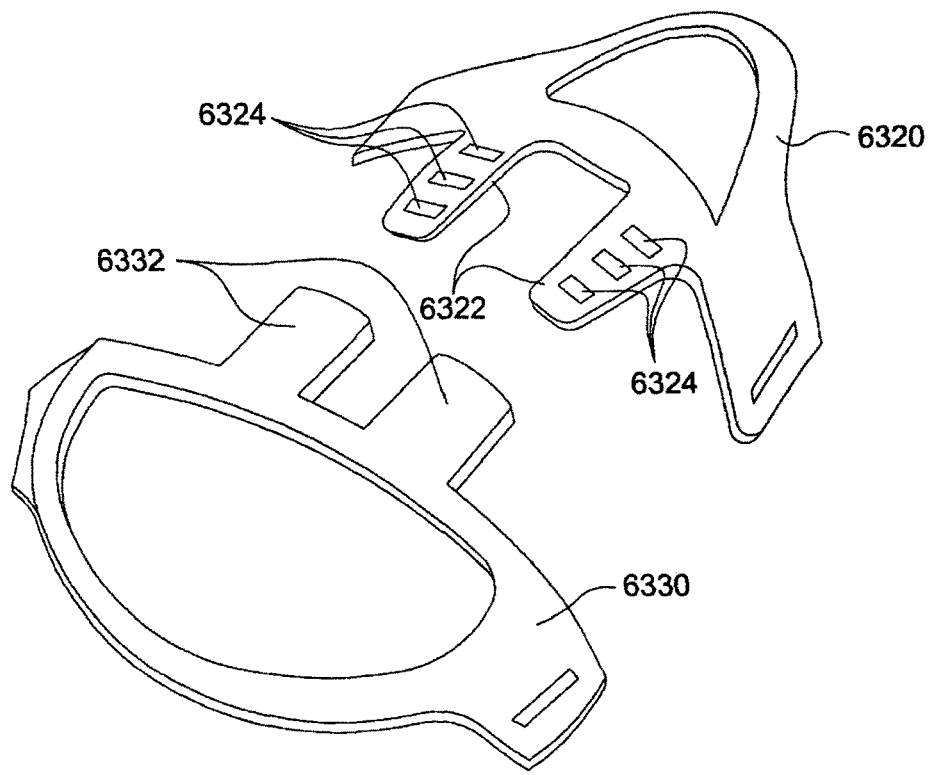

FIGS. 94 and 95 illustrate an adjustment mechanism including a first portion 6320 provided to an upper frame portion 6302 and a second portion 6330 provided to a lower frame portion 6304. The first and second portions 6320, 6330 are coupled to one another by a pin and hole arrangement to adjust the position of the first portion with respect to the second portion. In the illustrated embodiment, the second portion 6330 includes a pair of arms 6332 each including a pin or button (not visible), and the first portion 6320 includes a pair of arms 6322 each including a series of holes 6324. The pins may be releasably engaged with selected holes (e.g., push fit like a baseball cap) to adjust the relative position between the first and second portions. It should be appreciated that the positioning of the pins/holes may be reversed.

Figure 96:
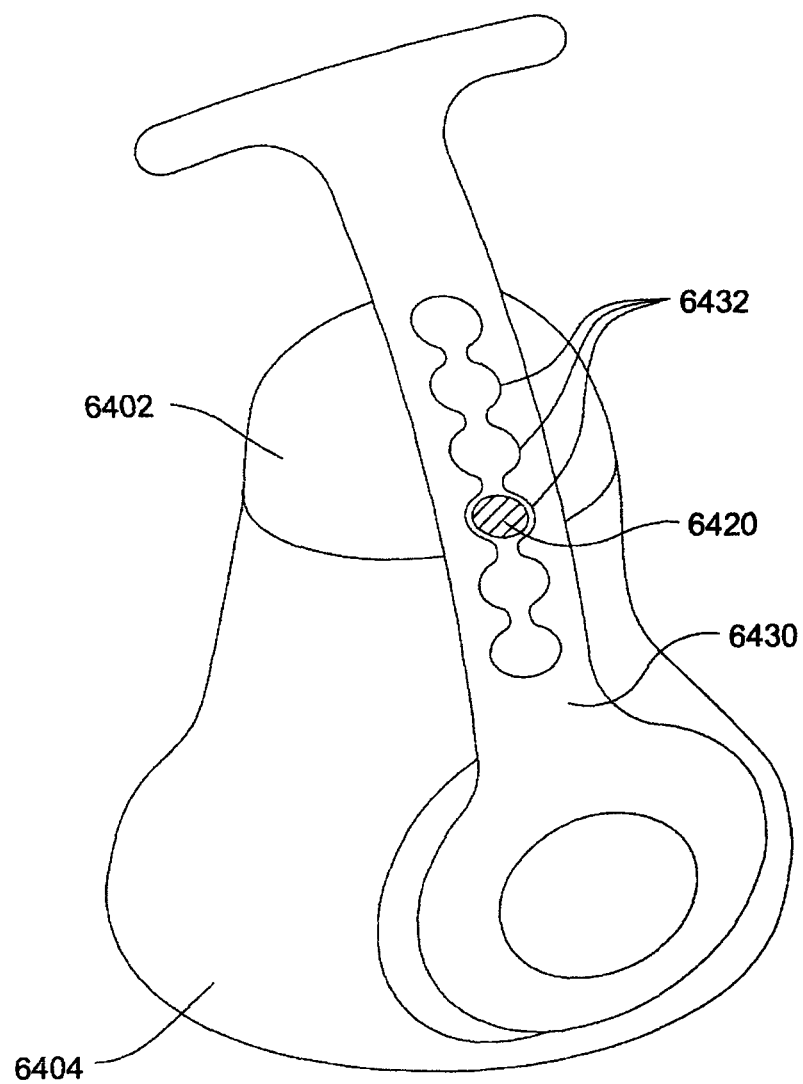
FIG. 96 shows a mask with an adjustment mechanism according to an embodiment of the technology.

In another embodiment, as shown in FIG. 96, the upper frame portion 6402 may include a pin 6420 and the lower frame portion 6404 may include a slider portion 6430 with a series of connected openings 6432. The pin 6420 may be releasably engaged with a selected one of the openings 6432 in the slider portion 6430 to adjust the relative position between the upper and lower frame portions 6402, 6404.

Side Sliders

Figure 97:
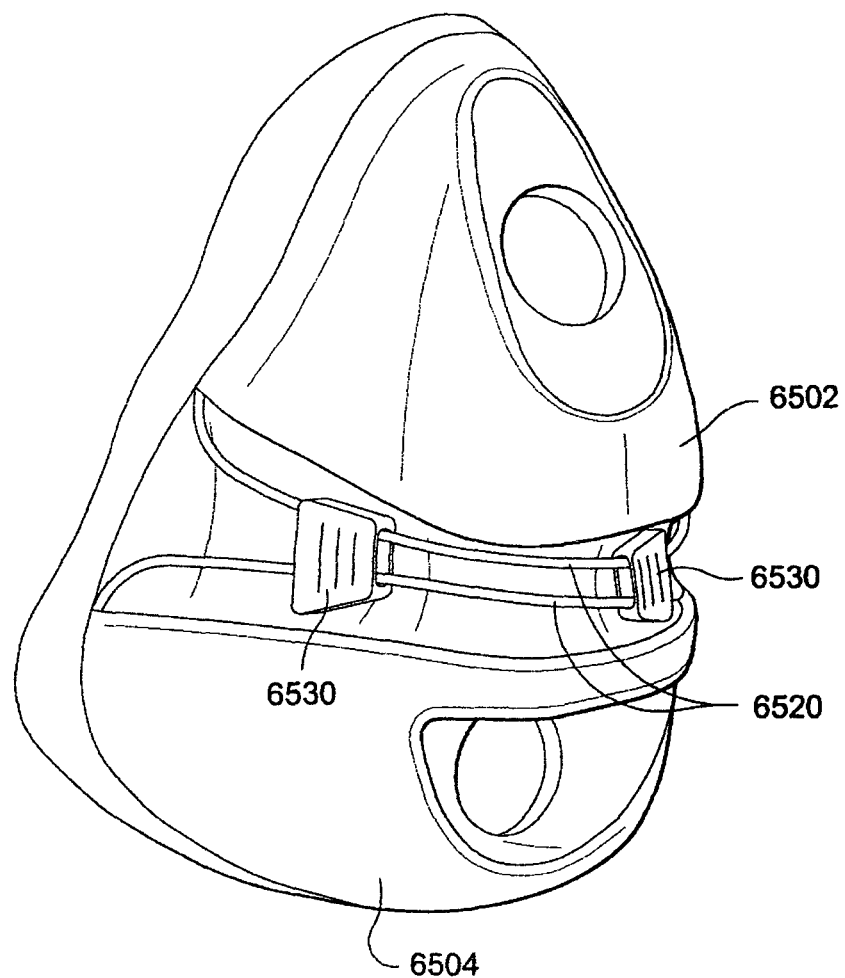
FIG. 97 is a perspective view of a mask including an adjustment mechanism with sliding adjusters according to an embodiment of the technology.
Figure 98:
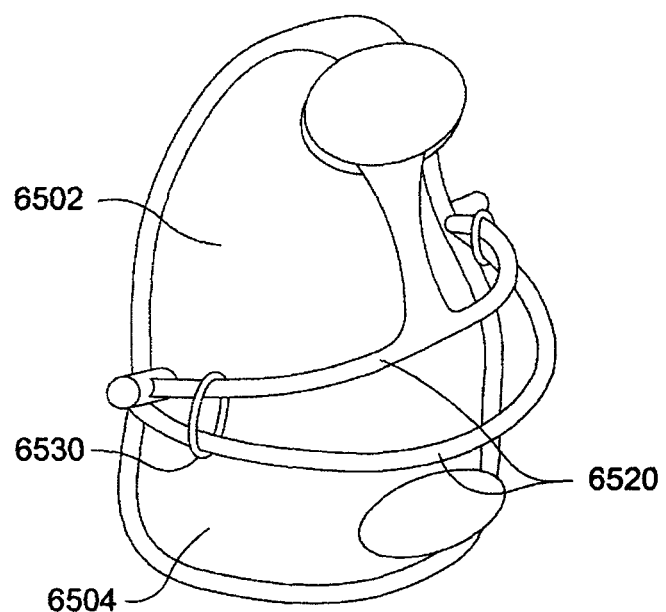
FIG. 98 is a perspective view of a mask including an adjustment mechanism with sliding adjusters according to another embodiment of the technology.

FIGS. 97 and 98 illustrate an adjustment mechanism including adjustment cords 6520 associated with upper and lower frame portions 6502, 6504, and sliders 6530 horizontally moveable along the adjustment cords to adjust the relative position between the upper and lower frame portions 6502, 6504 (e.g., pull the upper and lower frame portions together like a zipper). The mechanism may be arranged such that movement of the sliders from a center of the mask towards the perimeter is adapted to pull the upper and lower frame portions towards one another (FIG. 97), or the mechanism may be arranged such that movement of the sliders from the perimeter of the mask towards its center is adapted to pull the upper and lower frame portions towards one another (FIG. 98).

Side Arms

Figure 99:
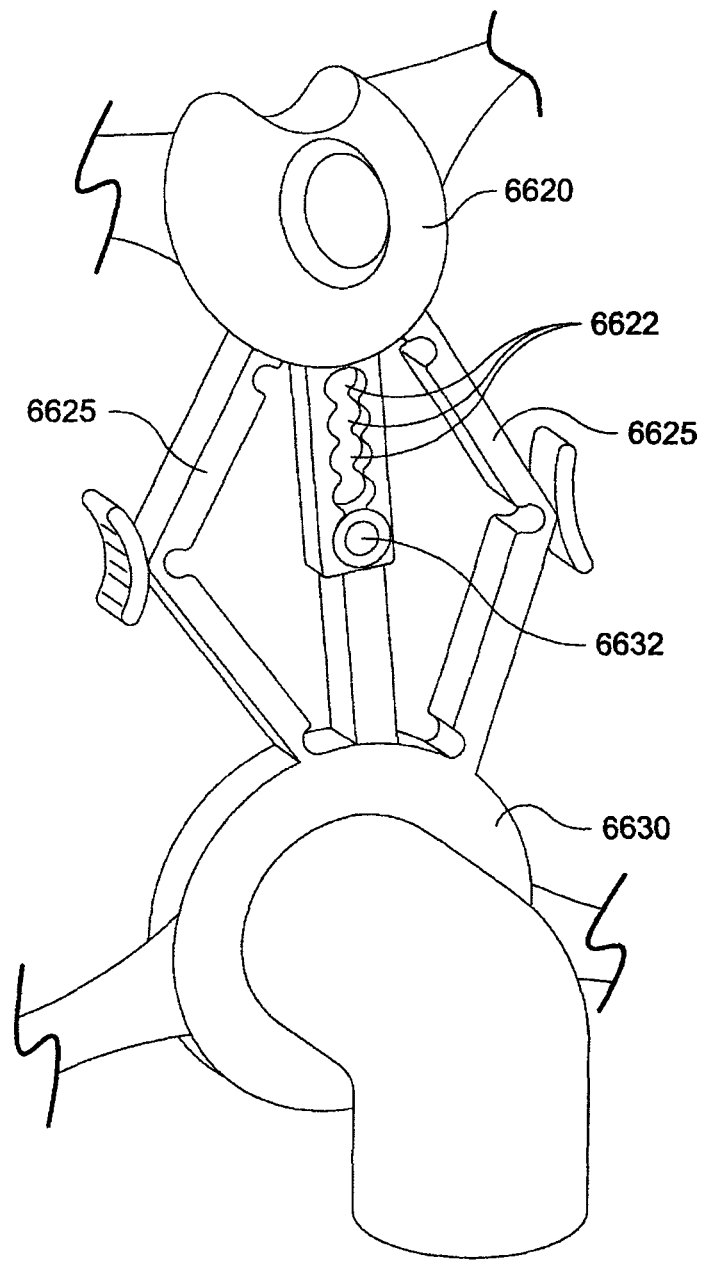
FIGS. 99 and 100 show an adjustment mechanism with adjustable side arms according to an embodiment of the technology.
Figure 100:
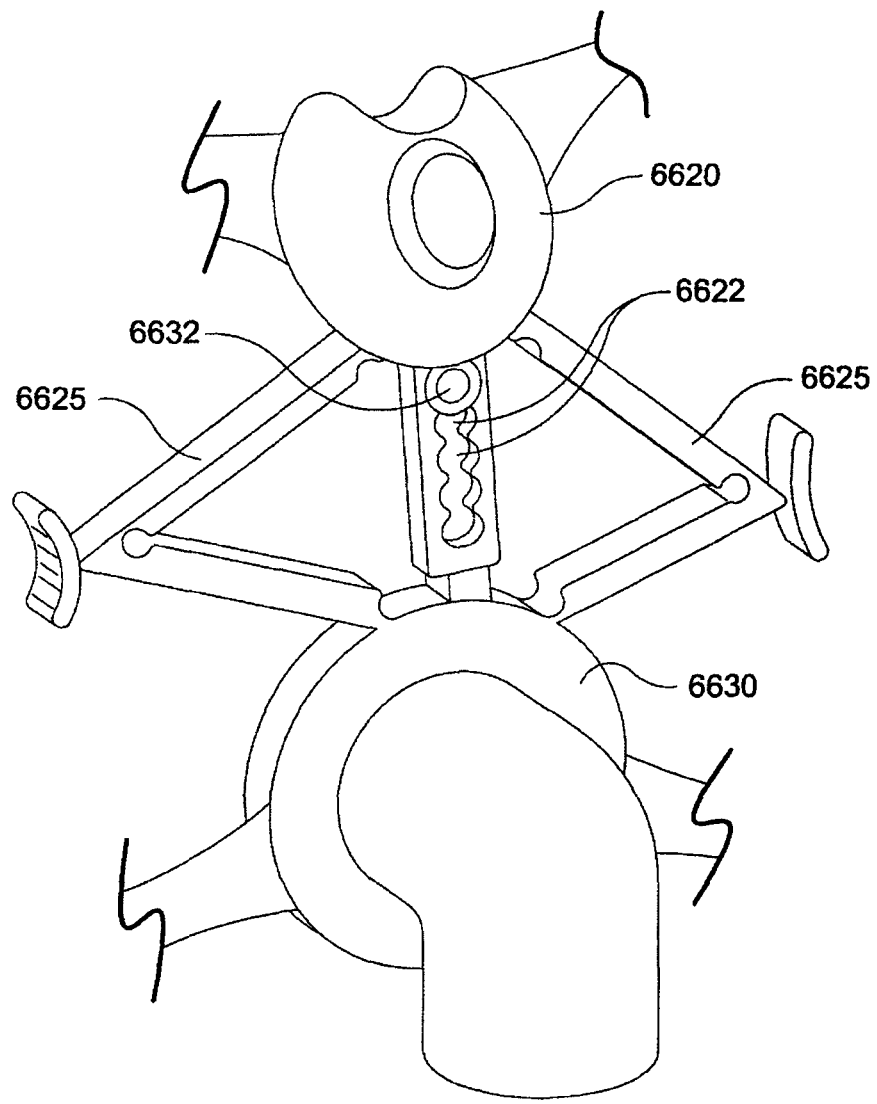

FIGS. 99 and 100 illustrate an adjustment mechanism including a first portion 6620 provided to an upper frame portion and a second portion 6630 provided to a lower frame portion. The first and second portions 6620, 6630 are coupled to one another by side arms 6625 each including hinge portions that allow relative movement between the first and second portions. A fixing arrangement is provided between the first and second portions to secure the first and second portions with respect to one another. As illustrated, the second portion 6630 includes an arm with a pin 6632, and the first portion 6620 includes an arm with a series of connected openings 6622. The pin 6632 may be releasably engaged with a selected one of the openings 6622 to pivot the side arms 6625 and adjust the relative position between the first and second portions.

Figure 101:
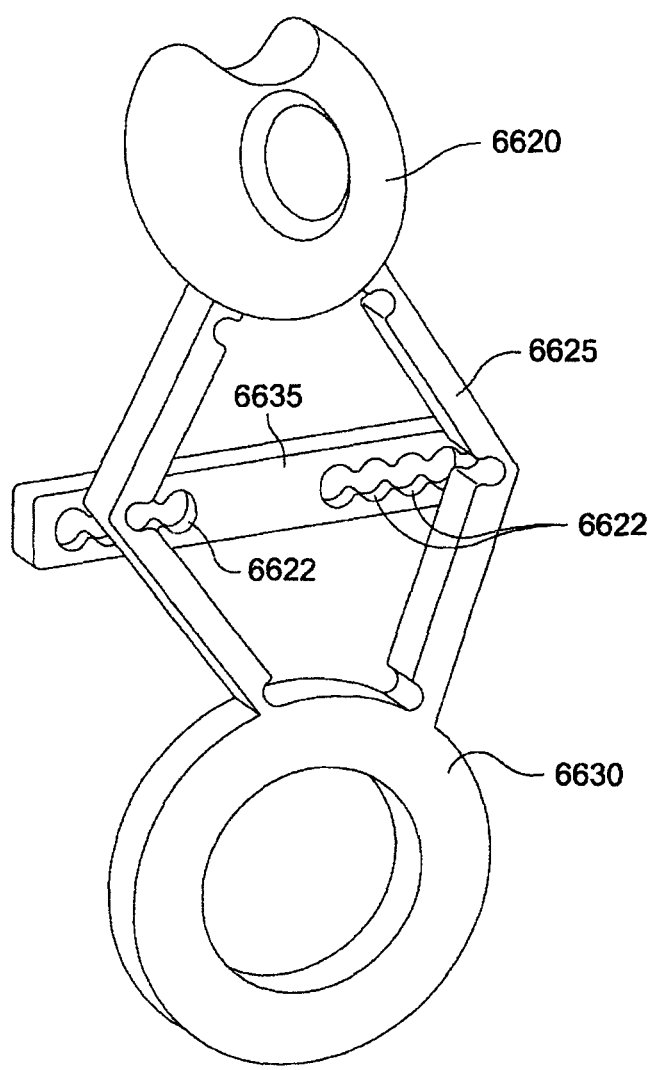
FIG. 101 shows an adjustment mechanism with adjustable side arms according to another embodiment of the technology.

In an alternative embodiment, as shown in FIG. 101, the fixing arrangement may extend between the arms so that the arms may be adjusted independent from one another. In this embodiment, each arm 6625 includes a pin (not visible) that is releasably engageable with a selected one of the openings 6622 provided at each end of arm 6635, so as to adjust the relative position between the first and second portions.

Headgear Connector Mechanism

Figure 102:
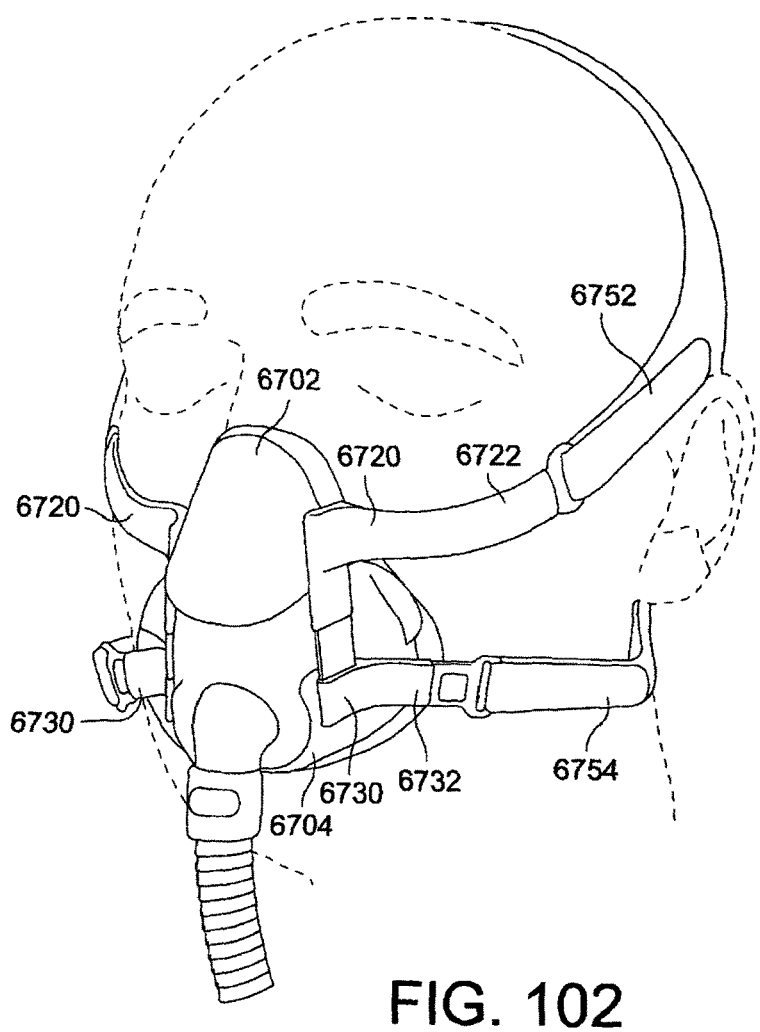
FIGS. 102 and 103 show an adjustment mechanism with headgear connectors according to an embodiment of the technology.
Figure 103:
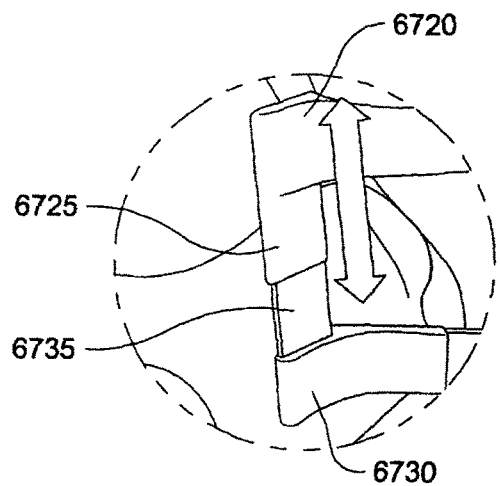

FIGS. 102 and 103 illustrate an adjustment mechanism including a first portion 6720 provided to an upper frame portion 6702 and a second portion 6730 provided to a lower frame portion 6704. The first portion 6720 provides an upper headgear connector 6722 adapted to engage an upper headgear strap 6752, and the second portion 6730 provides a lower headgear connector 6732 adapted to engage a lower headgear strap 6754. As shown in FIG. 103, the first and second portions include respective connector portions 6725, 6735 that are slidably engageable with one another (e.g., telescoping arrangement) so as to adjust the relative position between the first and second portions.

Shape Change Squish Together Mechanism

Figure 104:
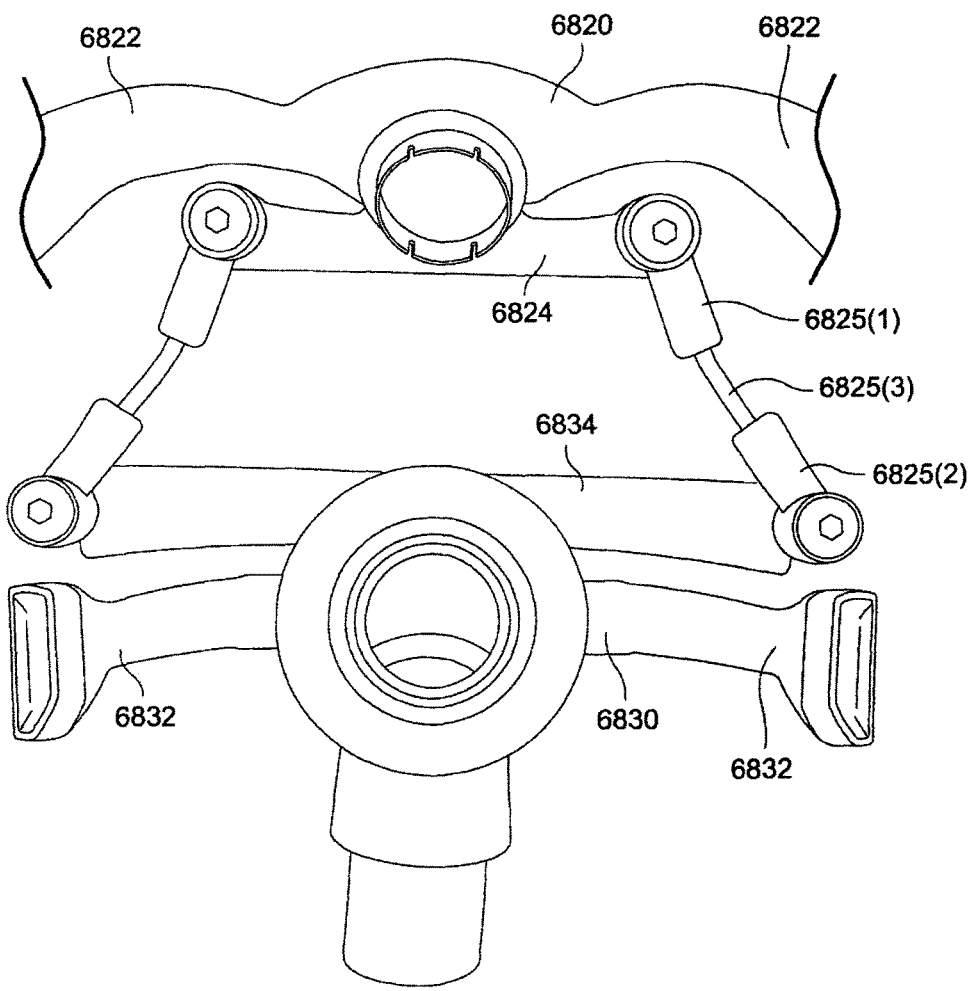
FIGS. 104 and 105 show an adjustment mechanism with adjustable side arms according to an embodiment of the technology.
Figure 105:
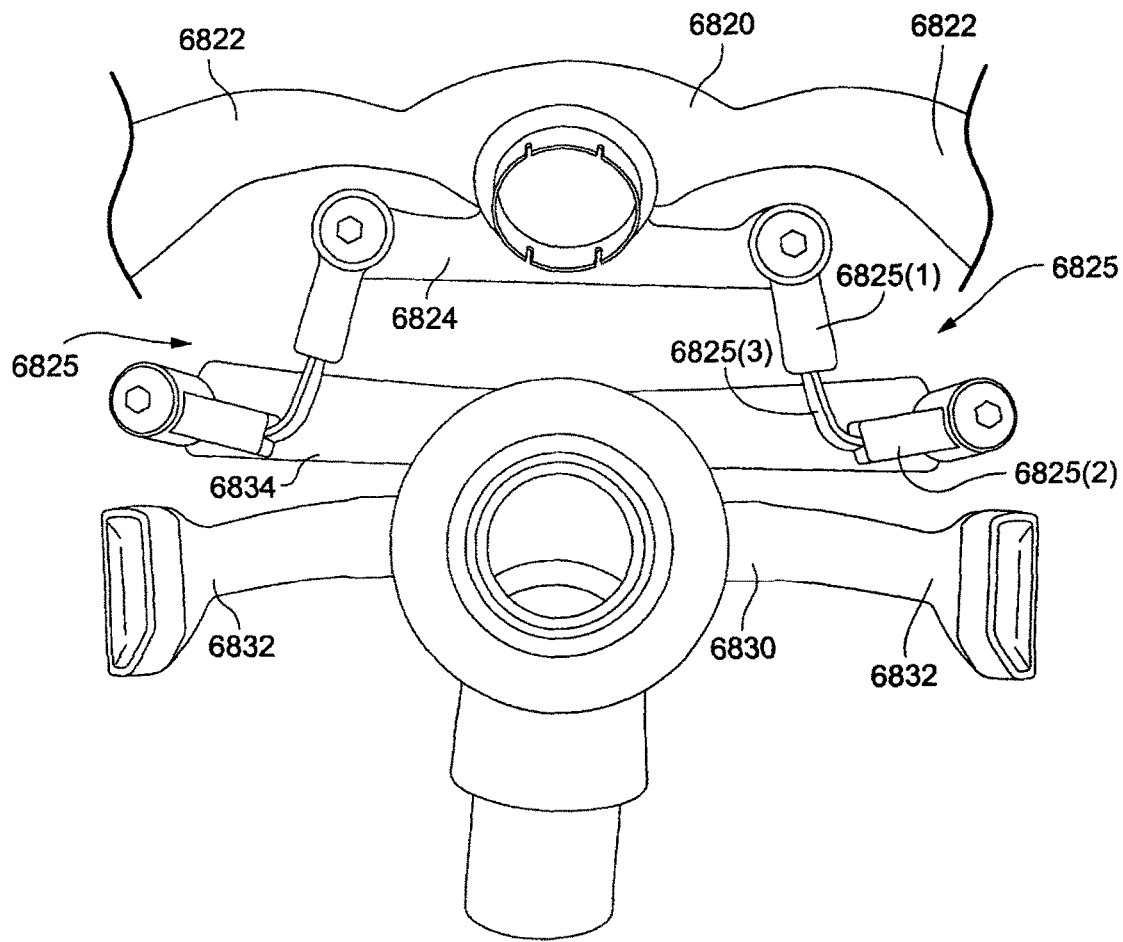

FIGS. 104 and 105 illustrate an adjustment mechanism including a first portion 6820 provided to an upper frame portion and a second portion 6830 provided to a lower frame portion. The first portion 6820 provides upper headgear connectors 6822 adapted to engage upper headgear straps, and the second portion 6830 provides lower headgear connectors 6832 adapted to engage lower headgear straps. The first and second portions 6820, 6830 are coupled to one another by side arms 6825. Each arm includes a first end 6825(1) pivotally mounted to a support arm 6824 of the first portion 6820, a second end 6825(2) pivotally mounted to a support arm 6834 of the second portion 6830, and a flexible member 6825(3) between the first and second ends. The pivotally mounted ends and flexible member allow the first and second portions to be moved relative to one another and then releasably fixed in position.

2.3.6 Modular Mask System

Another possibility is to provide a modular system 220 (FIG. 13) in which an upper frame portion 225 and a lower frame portion 230 are provided with respective upper and lower seal members 235, 240 provided to or otherwise affixed to the respective frame portion, e.g., co-molded. The combined frame portions with seal portions can be connected to one another directly via complementary linking elements 240, 245 to form a nasal mask or a full face mask for a small wearer, e.g., like pieces of a puzzle or a bayonet type fitting, magnetics, etc., to keep the adjacent seal portions in close contact with one another, such that the seal seam is as smooth, continuous and uninterrupted as possible.

If the size of the mask needs to be increased, the wearer can detach the upper and lower frame/seal portions, and insert an intermediate adapter member 250.1, 250.2, 250.3 between the upper and lower frame/seal portions. Preferably, the intermediate adapter has complementary linking elements 240, 245 that can only fit in one way to the upper and lower frame/seal portions. Several intermediate adapters can be provided, covering a whole range of different sizes and shapes. Each adapter will have a different height, and the shape and angle of such adapter member may change to allow a smooth transition between the upper and lower frame/seal portions.

In the above, frame portions 225, 230 and intermediate adapter members 250.1, 250.2, 250.3 may include respective seal portions. However, it is also possible to provide a single, one-piece seal 252 to cover frame portions 225, 230 and one of the adapter members. The seal 252 would have an initial compressed position suitable to cover the frame portions 225, but would be stretchable or expandable to also cover any of the adapter members as well. The seal could form an expandable channel 252.1 (see FIG. 13-1, a cross-section from FIG. 13) to receive the frame portions and optionally the adapter member. The natural flexibility of the seal, e.g., made of foam, TPE, silicone, hybrid of materials, etc., retains the seal onto the frame portions and adapter member.

2.3.7 Conformable Seal with Adaptor(s)

Figures 1, 2, 14:
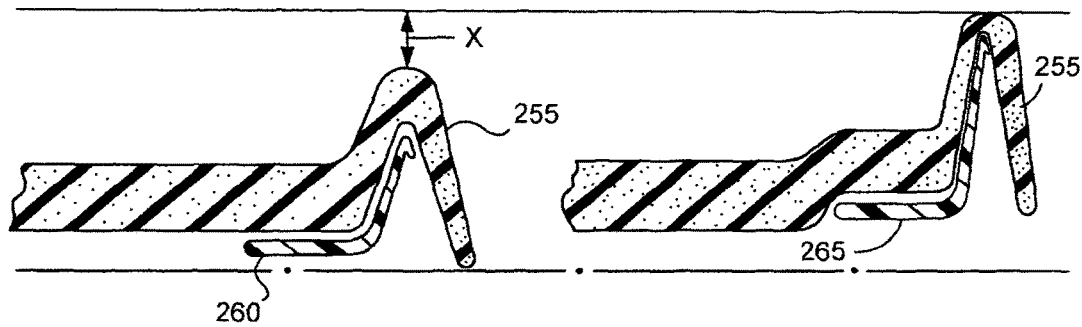

In another example, the frame 110 need not require two pieces to enable variability of the size and/or shape of the seal. For example, the seal, e.g., in the form of a foam seal, can be coupled or otherwise provided to a single piece frame. The seal 255, in its relaxed state (FIG. 14-1), is highly compressed to generally have the dimensions of the smallest wearer or patient intended for treatment or use. If the wearer or patient requires a change in the size and/or shape of the seal, e.g., by an amount X, the user may select from one or more adapters 260, 265 which may be provided to, e.g., inserted within the inside of, at least a part of the seal portion (FIG. 14-2). The adapters can come in different sizes and shapes, to which the foam seal will conform. The adapter 260, 265 may have a fixed shape, or it may be made of a malleable material that can maintain its shape. Once the adapter is removed or disassembled, the seal returns to its original (smallest) shape due to its own resiliency.

The adapter 260, 265 can also be adjusted when coupled with the seal/cushion by using an adjustment mechanism as discussed above, e.g., a dial can be used to change the size of the adaptor. Adjustment can take place in a manner similar to how a pipe clamp expands and contracts (overlapping band of material with grooves to interact with screw thread). However, only the size of the seal needs to be adjusted, e.g., by changing the size/shape of the adapter; it is not necessary to change the size of the frame or otherwise provide movable parts.

2.4 Cushion & Intermediate Member

The cushion 118 includes the seal 130, which may be formed in one piece with the cushion. Alternatively, the seal 130 may be a separate member that is coupled to or otherwise provided to the cushion 118. Cushion and intermediate member form a pressurized breathing chamber when combined.

Seal 130 may in one example be made of a foam material. The foam material may include silicone foam, higher density foam, lower density foam, open cell foam, closed cell foam, etc. Other exemplary foam materials and properties are disclosed in PCT Publication Nos. WO 2008/011683, WO 2008/011682, and WO 2008/070929, each of which is incorporated herein by reference in its entirety. In one example, when the cushion 118, or at least the seal thereof, assumes a relaxed state, it is dimensioned to accommodate larger size wearers. When it is desired to reduce the size or change the shape, the foam can be compressed or otherwise change shape as the facial height is reduced by the adjustment mechanism, e.g., rack and pinion system. Alternatively, the cushion can be dimensioned to start in the medium position and is stretched or compressed to the large and small size. In yet another alternative, the cushion starts in the small size and is stretched to the medium and large size. Foam is a good choice for these applications as it maintains its ability to seal when compressed or stretched. Similar alternatives apply to the adjustable region or gusset, in terms of its starting and ending positions (large, small or medium).

The intermediate member 116 (e.g., adjustable region or gusset) is designed to increase and decrease in height (in the vertical direction) but maintain the deliver of horizontal sealing force to the cushion to maintain the correct sealing vectors. As an alternative, the adjustable region or gusset 116 may be made of a stretchable or elastic material that changes its shape and dimensions upon application of a force, e.g., silicone. The adjustable region or gusset 116 can be made of a plastic material (including inherent or added spring force) which will then hold its shape when deformed to a new position. The shape and size of any such new position can be held by virtue of the shape retaining features of the adjustable region or gusset, or by additional structure that can hold the shape, e.g., clamps, etc. Intermediate member 116 may include one or more folds or undulations 116.1 (e.g., see FIGS. 16-1 to 16-5).

Cushion 118, or at least the seal 130, in one example is made from polyurethane (PU) foam. Intermediate member 116 may also be made from a PU foam of a higher density. The cushion 118 may include structure to connect the cushion to the frame, e.g., a cushion to frame member. The cushion to frame member can be produced by overmolding the rigid elements onto the soft foam cushion, e.g., as described in PCT/AU2009/000240, filed Feb. 27, 2009, incorporated herein by reference in its entirety.

Figures 1, 15:
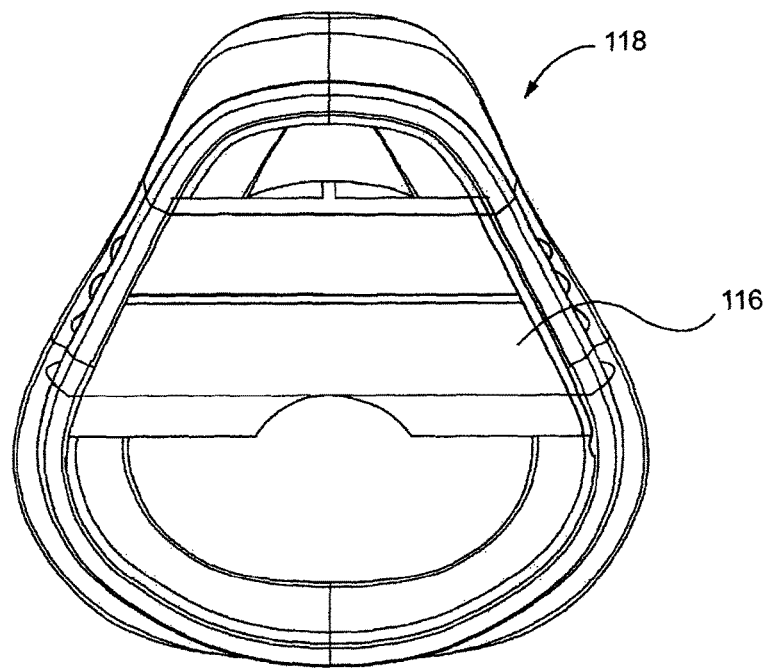
Figures 2, 15:
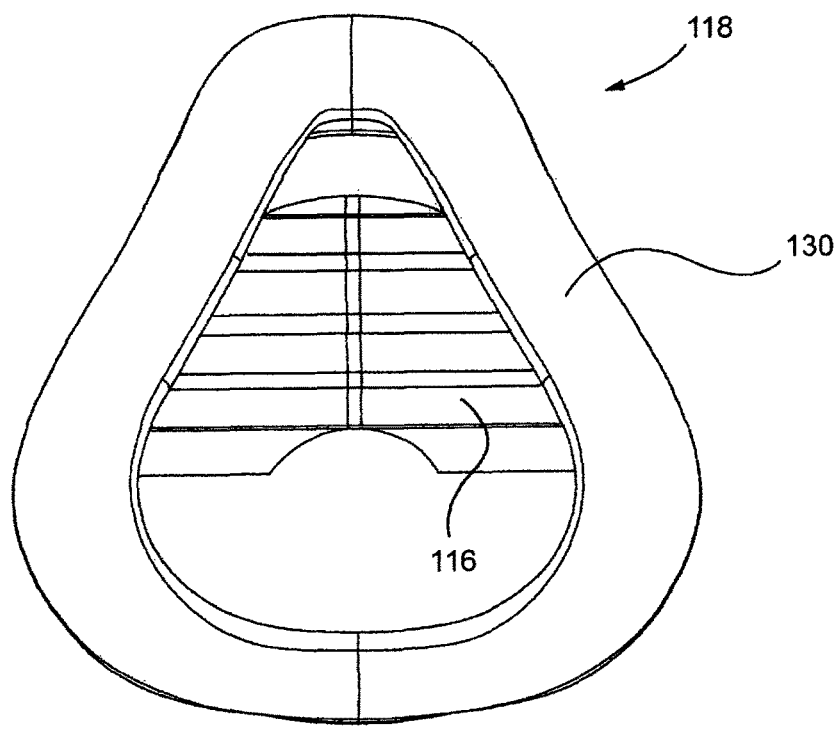
Figures 3, 15:
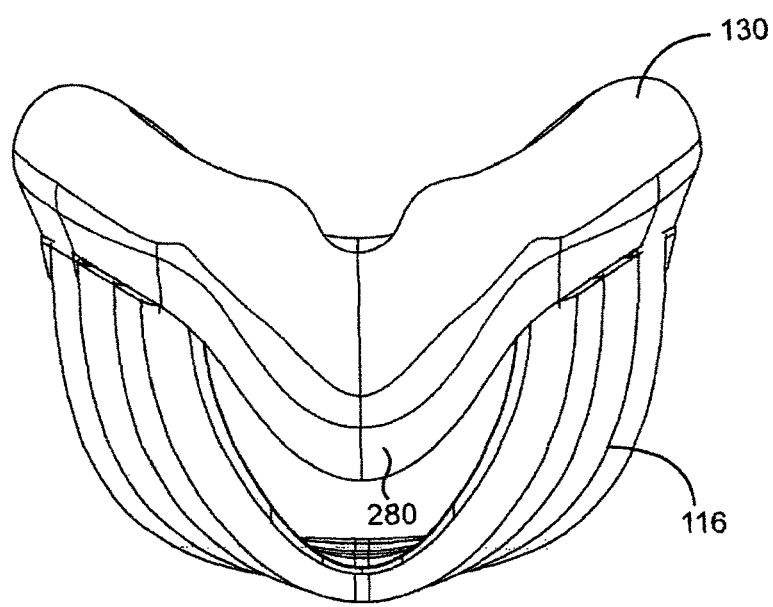
Figures 4, 15:
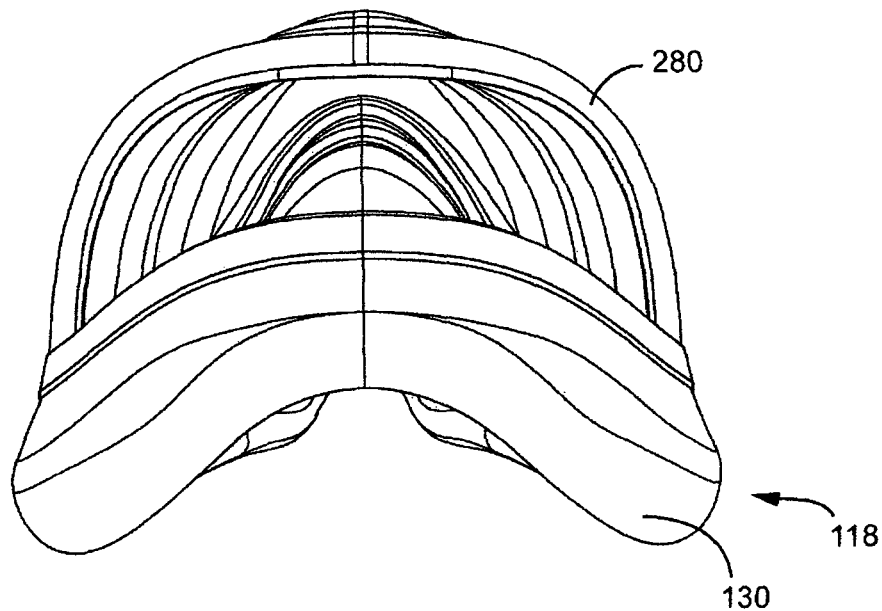
Figures 5, 15:
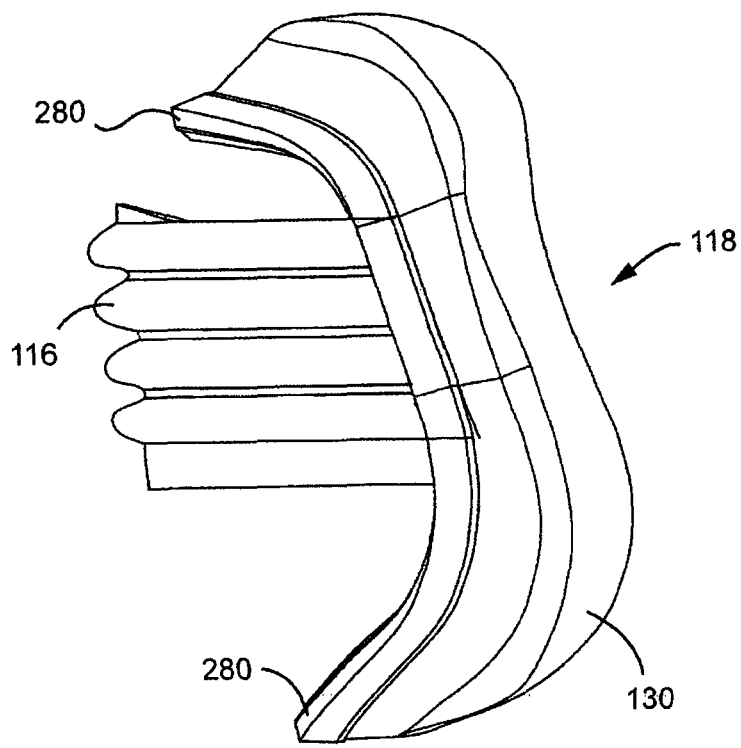
Figures 1, 16:
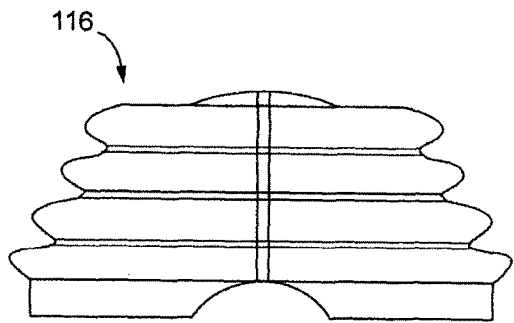
Figures 2, 16:
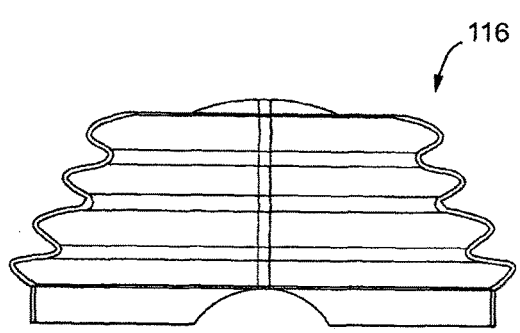
Figures 3, 16:
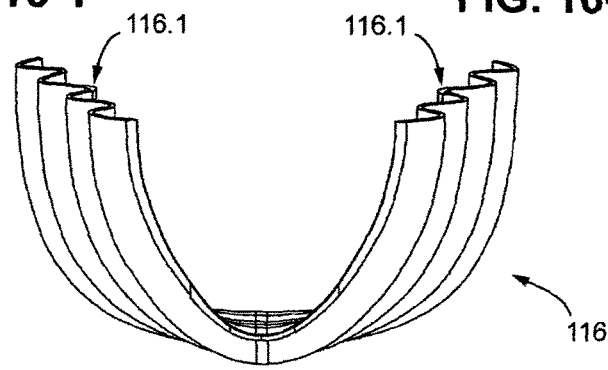
Figures 4, 16:
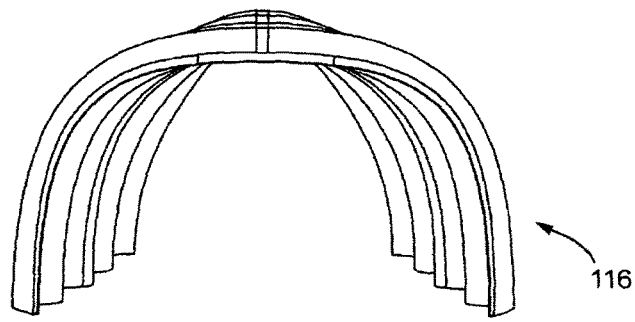
Figures 5, 16:
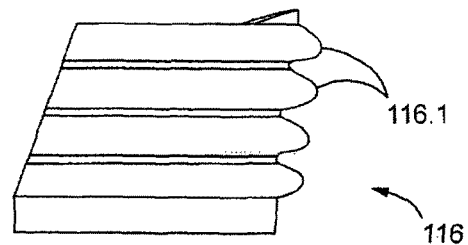

The cushion may include structure to commonly mate with both the intermediate member 116 and the upper and lower frame portions 112, 114. For example, the cushion may be coupled to the frame(s) 112, 114 and intermediate member using a tongue and groove system, e.g., the tongue 280 can be provided to the cushion 118 or the frame(s)/intermediate member, while the groove 285 can be provided to the other. FIGS. 15-1 to 15-5 show the sub-assembly of the adjustable region or gusset 116 and cushion 118, while FIGS. 16-1 to 16-5 show the adjustable region or gusset 116 in isolation. In an embodiment, the cushion 118 and adjustable region or gusset 116 may be integrally formed in one-piece, e.g., molded as a one-piece structure.

2.4.1 Sealing Profile

To adjust the shape and/or one or more dimensions (e.g., facial height) of the seal there are at least two options. First, as shown in FIGS. 17-1 to 17-2 the sealing profile can change in shape (rather than compress or stretch) in order to achieve the required adjustment in facial height, in which case the area within the perimeter is generally constant. FIGS. 17-1 shows the seal 130 having a perimeter 130.1, while FIG. 17.2 shows seal 130 having a perimeter 130.2 which has a different shape but the same length as the perimeter 130.1 In this case, the same overall sealing perimeter is maintained in the initial and changed shapes, and only the shape of the perimeter is changed to effect a change in the height of the seal. The size and shape of the top 130.3 and bottom 130.4 of the seal covering the nasal bridge region and the chin (full face mask) or upper lip region (nasal mask) preferably remains substantially constant; primarily the sides of the seal change in shape to allow for height adjustment.

Second, as shown in FIGS. 18-1 to 18-5, the sealing profile can be compressed (or contracted) or stretched (expanded) in order to achieve the required or desired adjustment in facial height in which case the area defined within the perimeter is variable. FIG. 18-1 shows the relaxed position of seal perimeter 131, while FIGS. 18-2 and 18-3, respectively, show compressed and stretched positions of seal perimeters 131' and 131". In the alternative of FIGS. 18-4 and 18-5, FIG. 18-4 shows a compressed position of seal perimeter 133, while FIG. 18-5 shows the stretched position of seal perimeter 133'. Stretching occurs as a result of movement of the four nodes 137.

A third alternative is to enable shape changing combined with some degree of stretch/compression. In these alternatives, again the shape and size of the top and bottom of the seal remains constant, over the entire range of adjustment.

The seal in the examples described is preferably a one piece member, having no interruptions or seams, etc., and generally forming a smooth continuous sealing surface with the wearer's skin.

3. Alternative Examples

The following provides alternative examples of a "one-size-fits-all" mask system, which may include one or more aspects of the examples described above. That is, the following examples may share one or more common characteristics and features to the examples described above.

3.1 Foam Example

The following provides alternative examples of a "one-size-fits-all" mask system, which uses foam to achieve the change in height. The following describes adjustable full-face mask systems, however it should be appreciated that aspects may be applied to other suitable mask systems, e.g., nasal mask systems. In an example, the orifice for receiving the patient's nose and mouth is to extend about 15-20 mm in height. In a preferred embodiment, the change in height of the cushion is about 10-20 mm. Alternatively, the change in height of the cushion may be about 12-16 mm. The change in height of the cushion may be about 16 mm. The change in height of the cushion may be about 12 mm.

Figure 25:
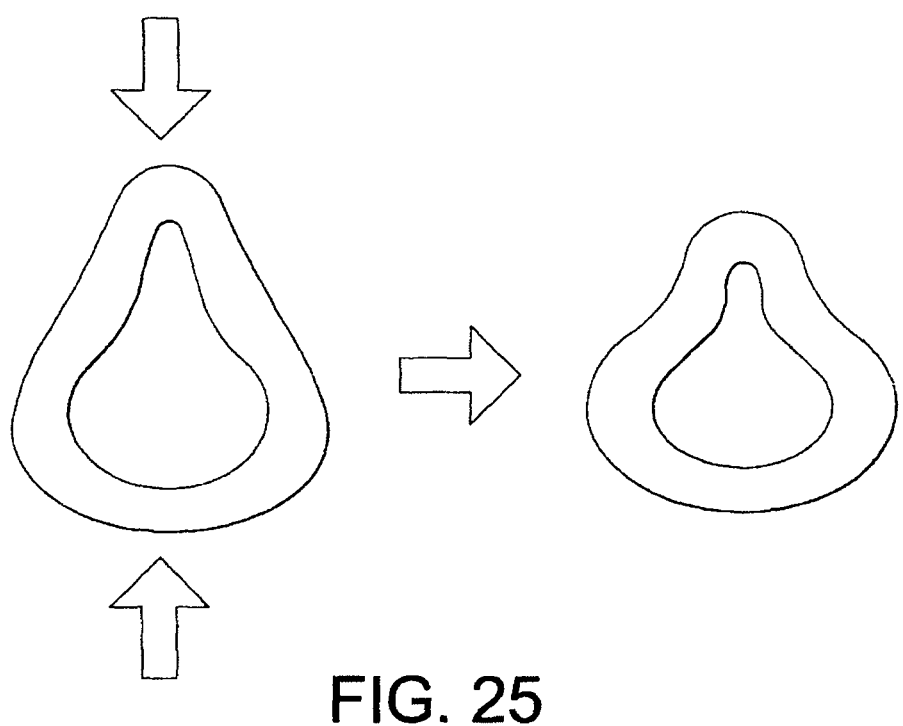
FIG. 25 is a schematic view showing height adjustment via material compression.

In embodiments, as shown in FIG. 25, the height adjustment may rely on material compression via a vertical adjustment mechanism, e.g., such as the rack and pinion type adjustment mechanism described above. However, it should be appreciated that height adjustment may include material tension or shape change.

3.1.1 Foam Example 1

Figures 1, 26:
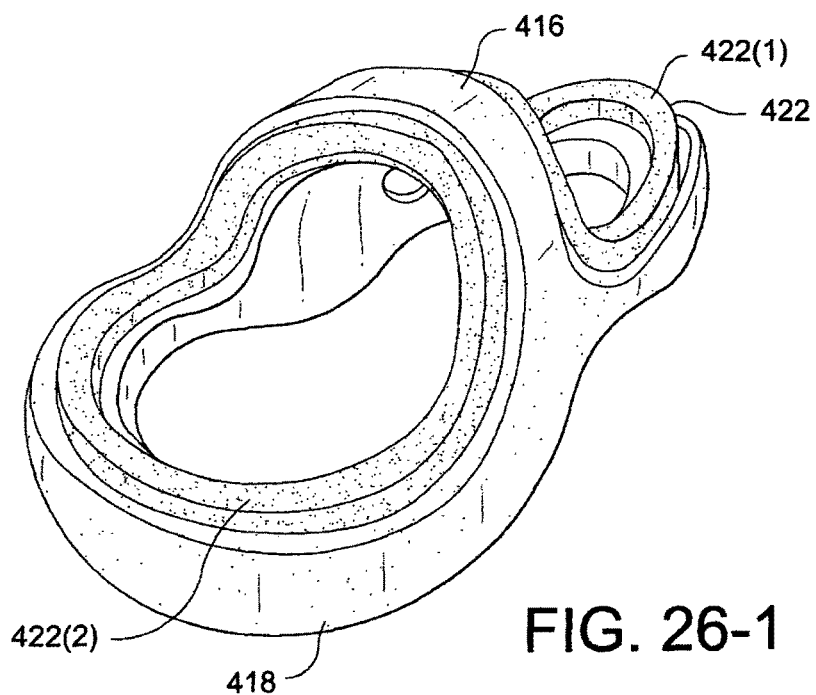
Figures 2, 26:
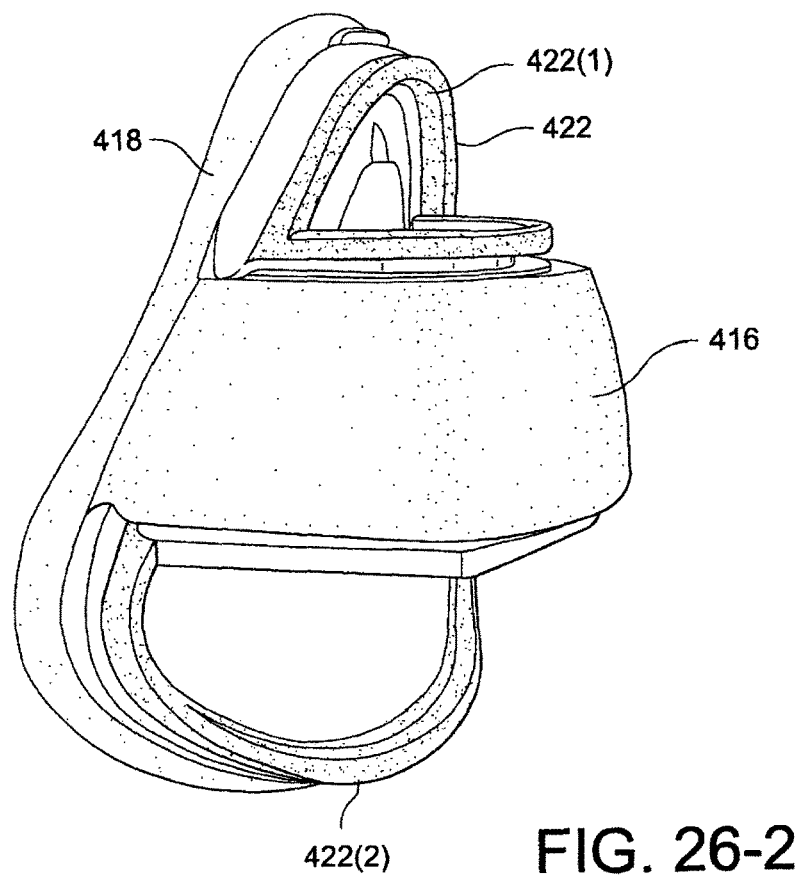
Figures 3, 26:
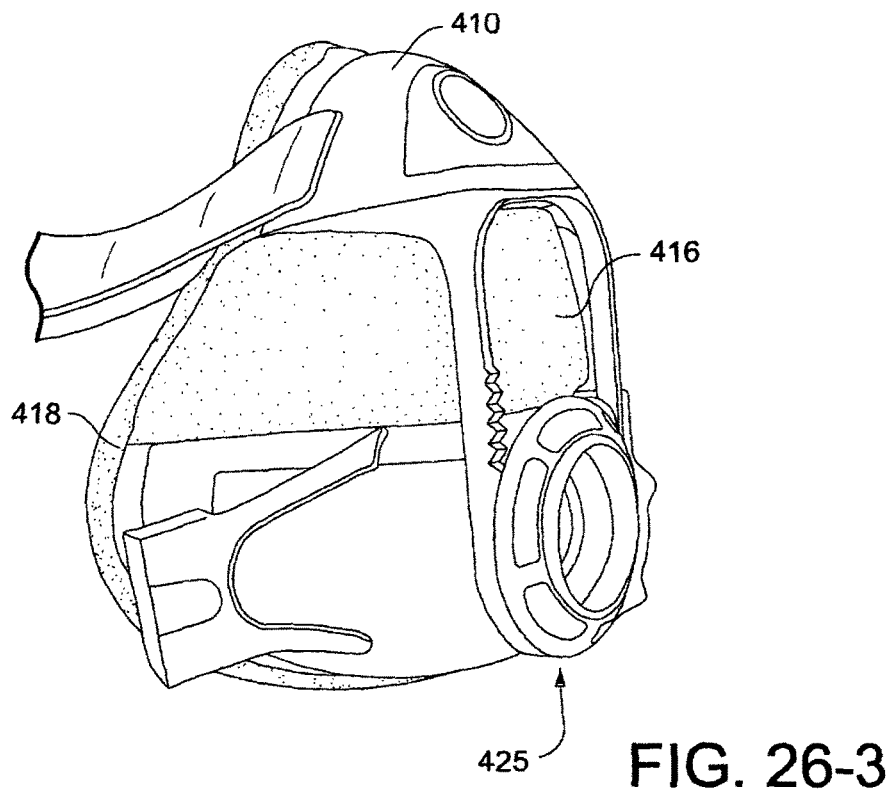
Figures 4, 26:
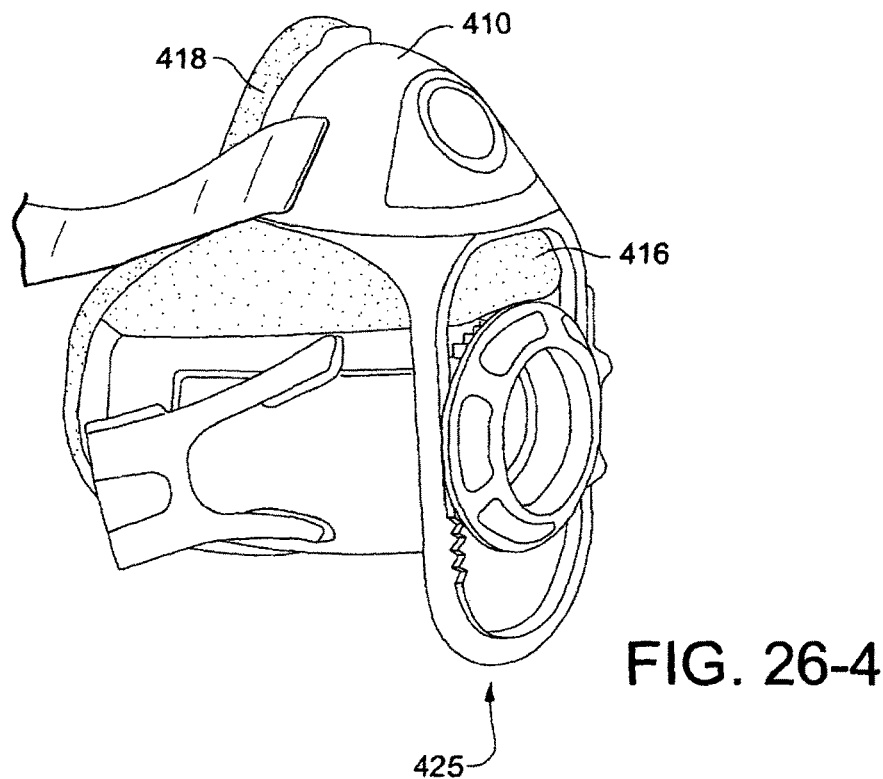
Figures 5, 26:
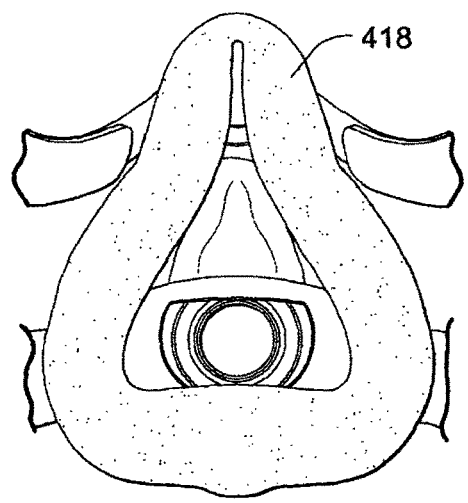
Figures 6, 26:
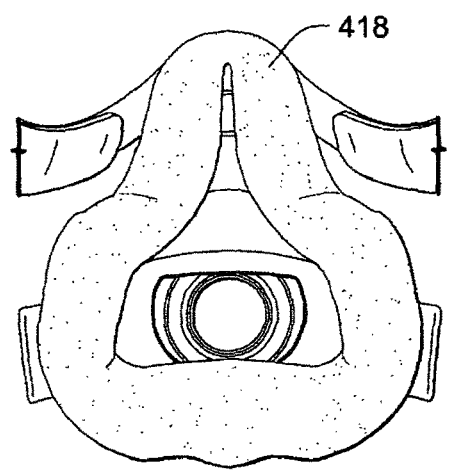
Figures 7, 26:
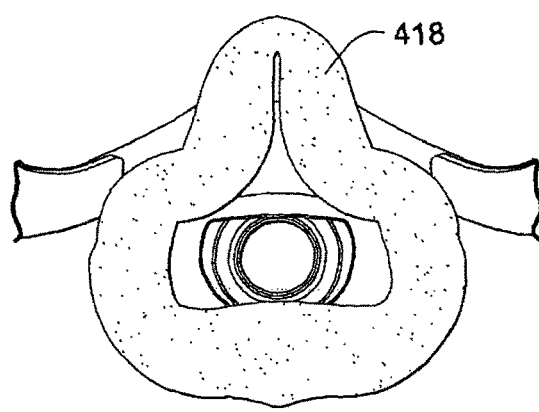
Figures 8, 26:
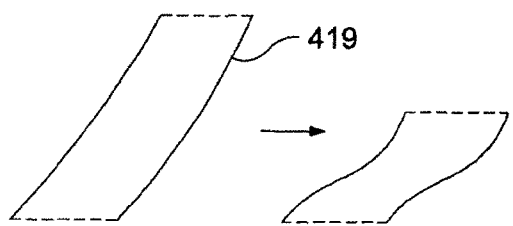
Figures 9, 26:
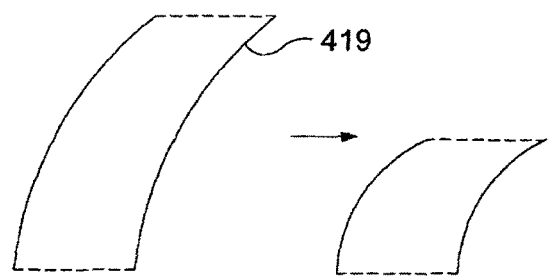
Figures 10, 26:
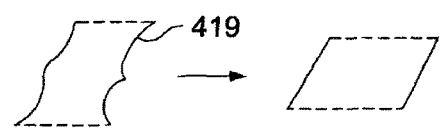
Figures 11, 26:
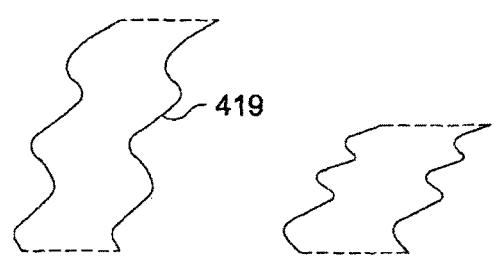

As shown in FIGS. 26-1 and 26-2, the cushion 418 and adjustable region or gusset 416 are constructed of a low density polyurethane foam, e.g., formed by compression cutting. A cushion clip 422 (including upper and lower portions 422(1), 422(2)) constructed of a higher density polyurethane foam is provided (e.g., over-molded, glued) to the cushion and adjustable region or gusset. As shown in FIGS. 26-3 and 26-4, the cushion clip 422 provides an interface for engagement with the frame 410 and adjustment mechanism 425.

In use, the cushion may be reduced in size by compression by the adjustment mechanism (e.g., from large size (FIGS. 26-3 and 26-5) to medium size (FIG. 26-6) to small size (FIGS. 26-4 and 26-7)).

In an embodiment, one or more portions of the foam adjustable region or gusset 416 may be provided with a sealant or skinned foam, e.g., to control leak. Also, in an alternative embodiment, an intermediate or medium size foam cushion may be provided which is structured to increase in size by tension and reduce in size by compression, e.g., +/− 10 mm compression/tension.

Figures 1, 11:
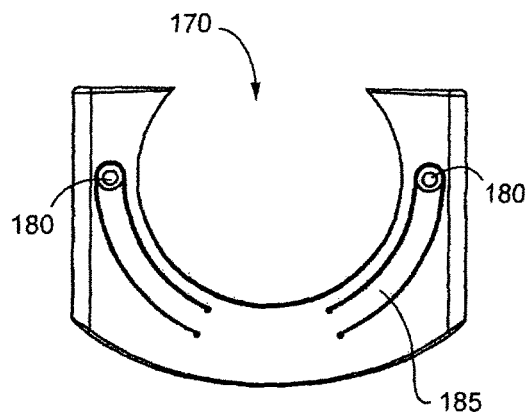
Figures 2, 11:
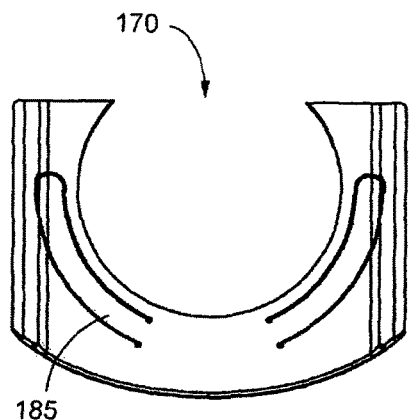
Figures 3, 11:
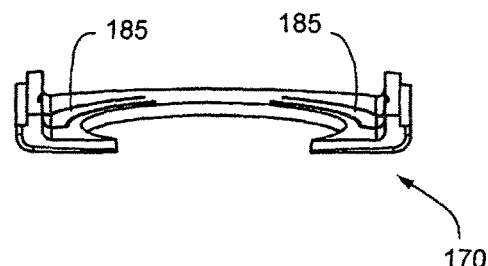
Figures 4, 11:
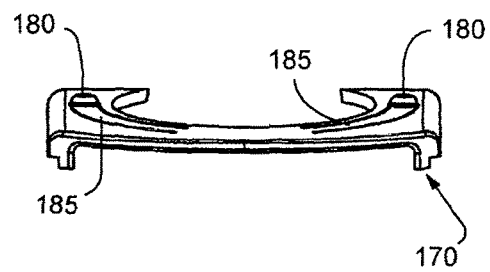
Figures 5, 11:
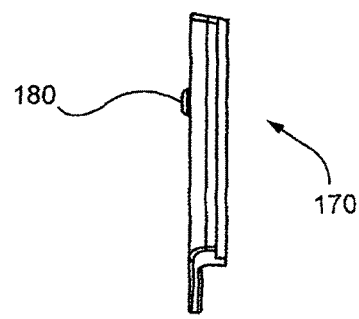

As shown in FIG. 26-8, the cushion/adjustable region or gusset may be structured such that it provides a generally flat or concave inwardly facing surface 419, which may collapse at least partially inwardly under compression. Alternatively, as shown in FIG. 26-9, the inwardly facing surface 419 may be generally concave to control the extent of inward collapse or bulge. FIGS. 26-10 and 26-11 show alternative examples for the inwardly facing surface 419 to control the extent of inward collapse, e.g., sequential concave surfaces (FIG. 26-10), adjustable region or gusset (FIG. 26-11). The collapsing of the inwardly facing surface needs to be controlled so as to prevent or minimize occlusion of the nasal passages.

3.1.2 Foam Example 2

Figures 1, 27:
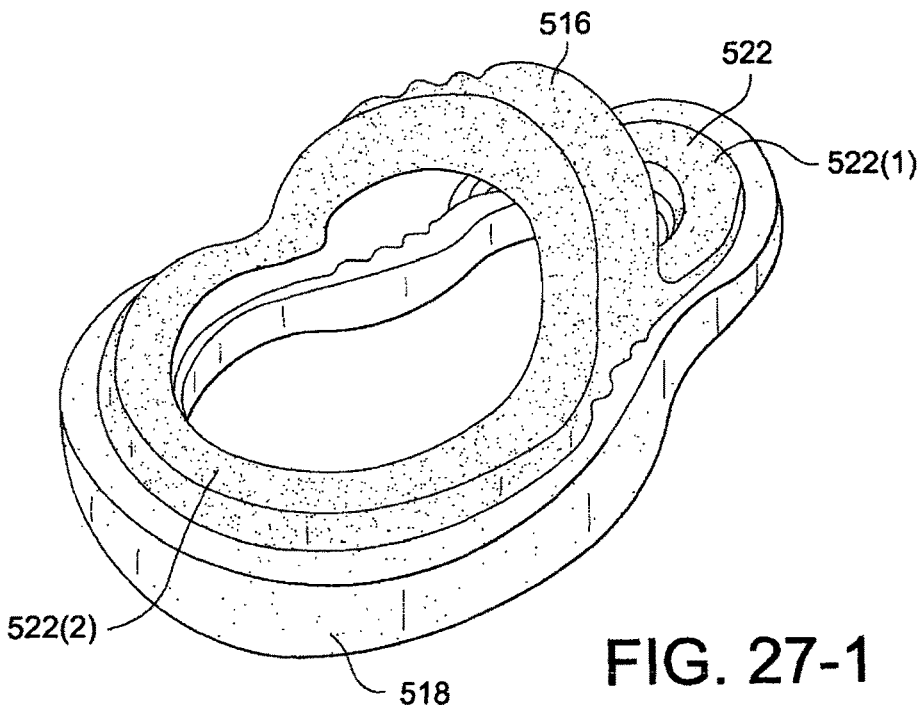
Figures 2, 27:
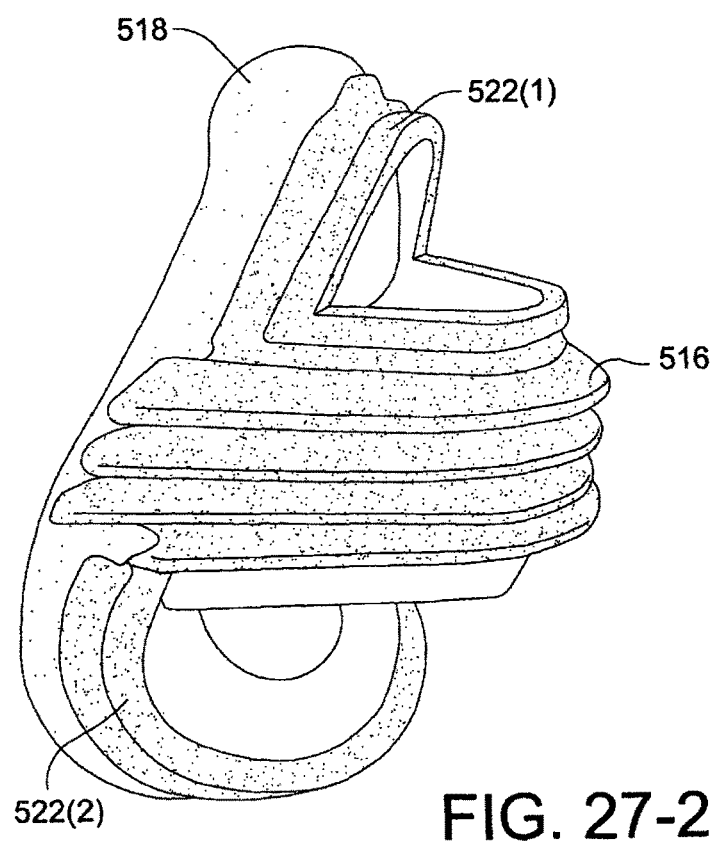
Figures 3, 27:
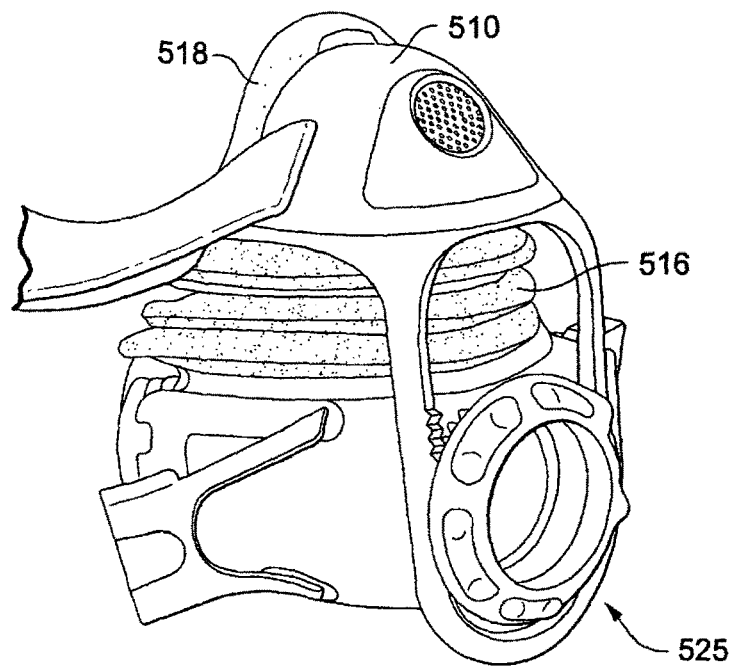
Figures 4, 27:
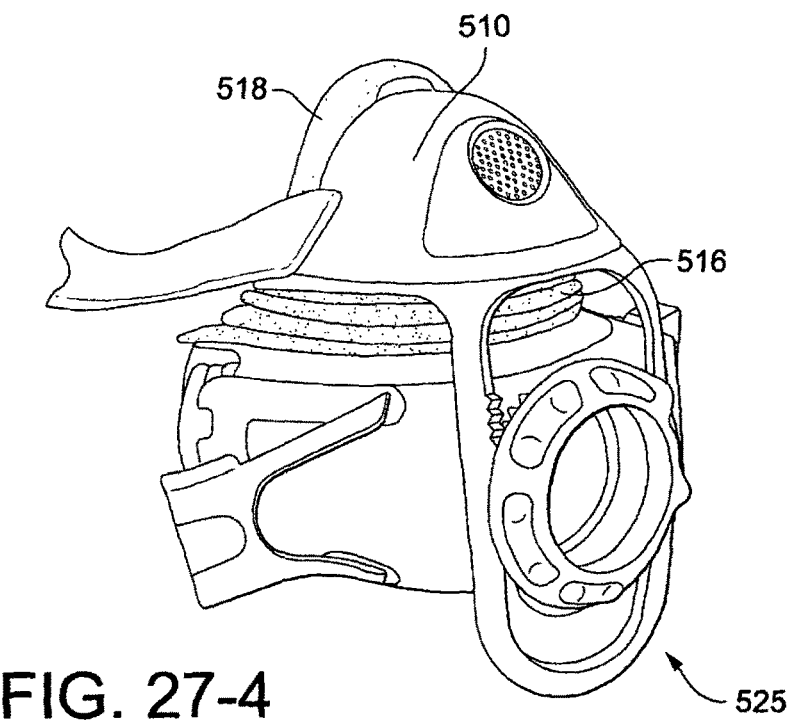
Figures 5, 27:
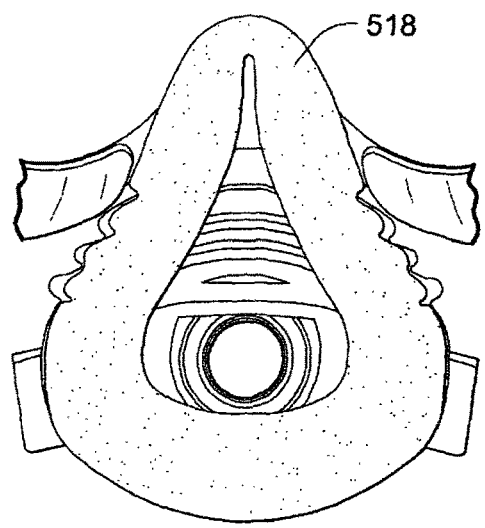
Figures 6, 27:
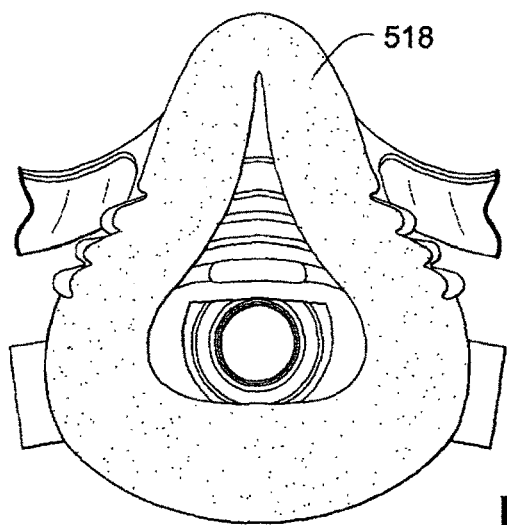
Figures 7, 27:
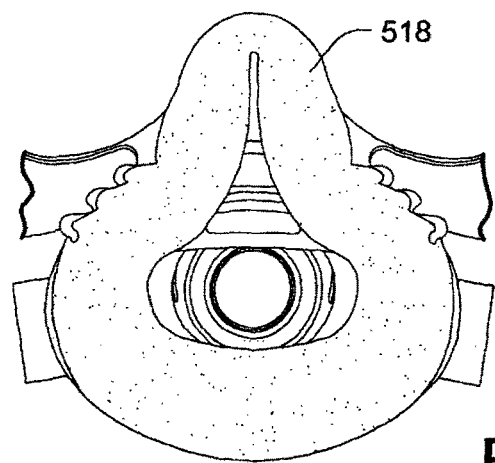
Figures 8, 27:
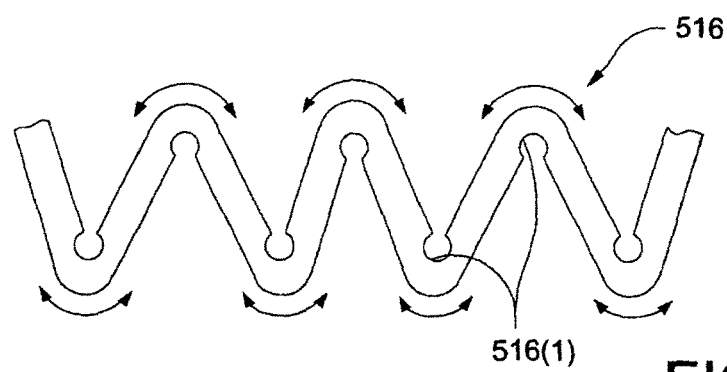
Figures 9, 27:
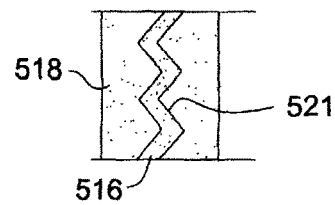
Figures 10, 27:
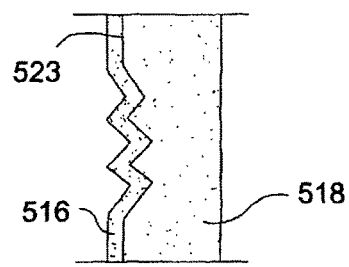
Figures 11, 27:
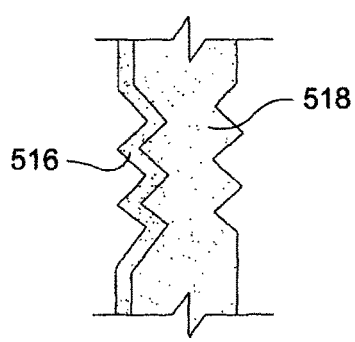
Figures 12, 27:
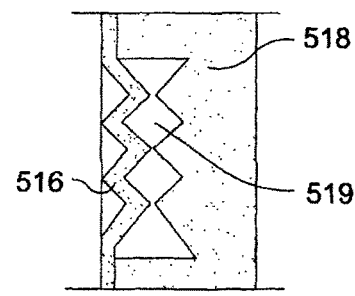

As shown in FIGS. 27-1 and 27-2, the cushion 518 is constructed of a low density polyurethane foam, e.g., formed by compression cutting. The adjustable region or gusset 516 and cushion clip 522 (including upper and lower portions 522(1), 522(2)) constructed of a higher density polyurethane foam are provided (e.g., over-molded, glued) to the cushion. As shown in FIGS. 27-3 and 27-4, the cushion clip 522 provides an interface for engagement with the frame 510 and adjustment mechanism 525.

In use, the cushion may be reduced in size by compression by the adjustment mechanism (e.g., from large size (FIGS. 27-3 and 27-5) to medium size (FIG. 27-6) to small size (FIGS. 27-4 and 27-7)). In an embodiment, the wall thickness (e.g., localized wall thinning) and/or geometry of the adjustable region or gusset may be structured to facilitate flexibility, e.g., more uniform compression.

In an alternative embodiment, an intermediate or medium size foam cushion may be provided which is structured to increase in size by tension and reduce in size by compression, e.g., +/− 10 mm compression/tension.

As shown in FIG. 27-8, the adjustable region or gusset 516 may include localized wall thinning, e.g., along the adjustable region or gusset hinges 516(1), to enhance flexibility for more uniform compression. Also, the inwardly facing surface of the cushion/adjustable region or gusset may be structured to control the extent of inward collapse or bulge, as described above. In addition, the cushion to adjustable region or gusset interface or attachment configuration may be structured to control collapse. For example, the adjustable region or gusset 516 may be attached to a front of the cushion 518 by a butt joint 521 (FIG. 27-9) or along sides 523 of the cushion 518 (FIG. 27-10). In another example, the inwardly facing surface of the cushion 518 may be an adjustable region or gusseted to enhance flexibility (FIG. 27-11). Also, the adjustable region or gusset 516 may be attached to the cushion 518 by a butt joint with relieved volume 519 along the adjustable region or gusset to enhance flexibility (FIG. 27-12). In this embodiment, additional bonding may be provided along the adjustable region or gusset points.

3.1.3 Foam Example 3

Figures 1, 28:
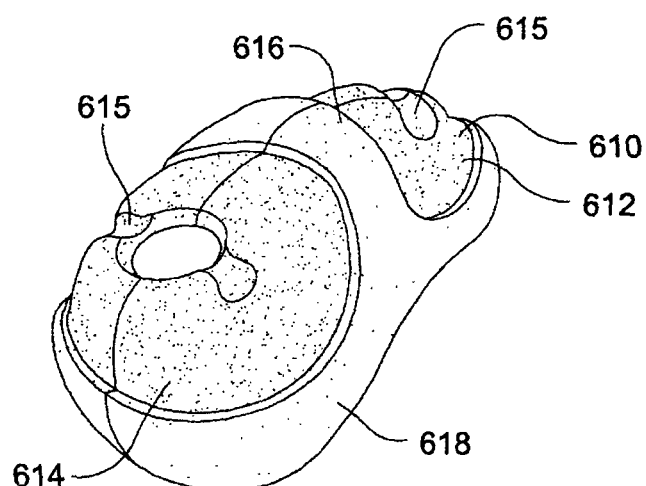

As shown in FIG. 28-1, the cushion 618 and adjustable region or gusset 616 are constructed of a low density polyurethane foam, e.g., formed by compression cutting. A frame 610 (including upper and lower frame portions 612, 614) constructed of higher density polyurethane foam is provided (e.g., over-molded, glued) to the cushion and adjustable region or gusset. As illustrated, the frame 610 may include one or more integrated features 615 that provide an interface for engagement with the adjustment mechanism. In use, the cushion may be reduced in size by compression by the adjustment mechanism.

3.1.4 Foam Example 4

Figures 1, 29:
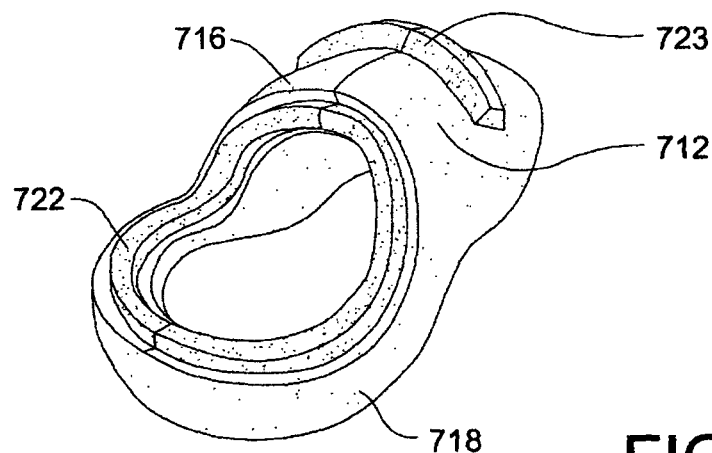

As shown in FIG. 29-1, the cushion 718, adjustable region or gusset 716, and upper frame portion 712 that extends over the patient's nose are constructed of a low density polyurethane foam, e.g., formed by compression cutting. A lower cushion clip 722 and upper interface structure 723 constructed of a higher density polyurethane foam is provided (e.g., over-molded, glued) to the cushion, adjustable region or gusset, and upper frame portion. The cushion clip 722 and interface structure 723 provide an interface for engagement with the frame and adjustment mechanism. In use, the cushion may be reduced in size by compression by the adjustment mechanism.

3.1.5 Foam Example 5

Figures 1, 30:
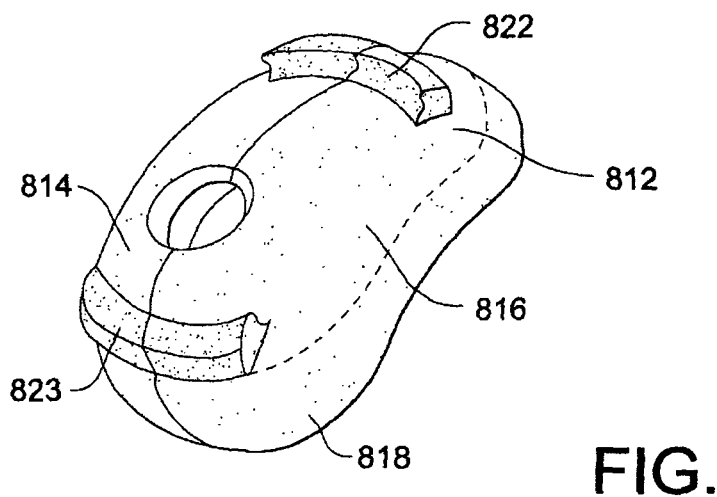

As shown in FIG. 30-1, the cushion 818, adjustable region or gusset 816, and upper and lower frame portions 812, 814 are constructed of a low density polyurethane foam, e.g., formed by compression cutting. Upper and lower interface structures 822, 823 constructed of a higher density polyurethane foam is provided (e.g., over-molded, glued) to the upper and lower frame portions. The interface structures 822, 823 provide an interface for engagement with the frame and adjustment mechanism. In use, the cushion may be reduced in size by compression by the adjustment mechanism.

3.1.6 Foam Example 6

Figures 1, 31:
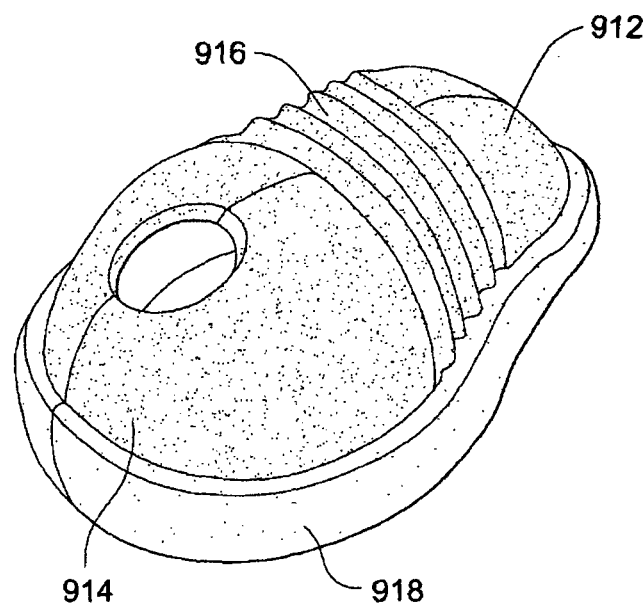

As shown in FIG. 31-1, the cushion 918 is constructed of a low density polyurethane foam, e.g., formed by compression cutting. The adjustable region or gusset 916 and upper and lower frame portions 912, 914 constructed of a higher density polyurethane foam are provided (e.g., over-molded, glued) to the cushion. The wall thickness (e.g., localized wall thinning) and/or geometry of the adjustable region or gusset 916 may be structured to facilitate flexibility or compression. The upper and lower frame portions 912, 914 may include interfaces for engagement with the frame and adjustment mechanism. In use, the cushion may be reduced in size by compression by the adjustment mechanism.

3.2 2-Part Cushion

The following provides alternative examples of a "one-size-fits-all" mask system, which uses a 2-part cushion to achieve the change in height. The following describes adjustable full-face mask systems, however it should be appreciated that aspects may be applied to other suitable mask systems, e.g., nasal mask systems.

Figure 32:
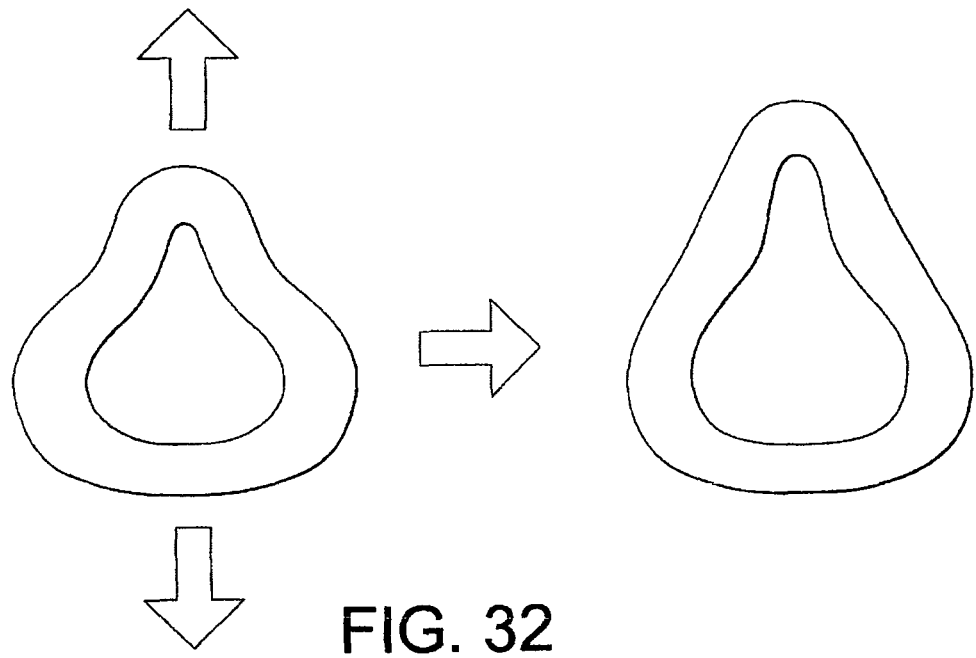
FIG. 32 is a schematic view showing height adjustment via material tension or stretch.

In embodiments, as shown in FIG. 32, the height adjustment may rely on material tension or stretch via a vertical adjustment mechanism, e.g., such as the rack and pinion type adjustment mechanism described above. However, it should be appreciated that height adjustment may include material compression or shape change.

3.2.1 2-Part Cushion Example 1

As shown in FIGS. 33-1 and 33-2, the cushion 1018 includes a single wall, silicone membrane part 1030 adapted to seal along the nasal bridge and around the mouth, and a separate undercushion part 1032 (e.g., PU foam, skinned foam, silicone foam, gel pocket) provided to the membrane part 1030. As illustrated, the membrane part 1030 includes cut-out regions 1031 along the sides of the patient's nose to reveal the undercushion part 1032. In use, the undercushion part 1032 provides support to the membrane part 1030 along the nasal bridge and around the mouth and the exposed portions of the undercushion part 1032 forms a compression-type seal along the sides of the nose.

As shown in FIG. 33-3, the cushion 1018 is provided to a frame including upper and lower frame portions 1012, 1014. A foam adjustable region or gusset 1016 is provided between the upper and lower frame portions 1012, 1014.

An adjustment mechanism 1025 (e.g., adjustable screw arrangement) is provided between the upper and lower frame portions 1012, 1014 for height adjustment. In use, the cushion may be reduced in size by compression by the adjustment mechanism (e.g., from large size (FIG. 33-4) to medium size (FIG. 33-5) to small size (FIG. 33-6)).

In an example embodiment, one or more portions of the undercushion part 1032 may be adhered (e.g., glued) to the membrane part 1030, e.g., to enhance the seal between the parts and prevent leak. In such embodiment, the size of the cut out region 1031 may be selected to control bending characteristics of the undercushion part 1032 in use, i.e., when compression force from frame transferred through the membrane part to the undercushion part. For example, FIG. 33-7 shows a cushion having a larger cut out region 1031(L) on the left side than the cut out region 1031(R) on the right side. As illustrated, since the membrane part 1030 sits higher and more medially on the undercushion part 1032 for the left side than the right side, a different mode of bending is experienced causing a larger S-shaped bend of the undercushion part 1032 on the left side.

FIG. 33-8 shows a compression seal zone (C) of the cushion, expanding seal zones (A) of the cushion, and transition zones (B) between the compression seal and expanding seal zones. In an embodiment, to enhance comfort, the height of the undercushion part 1032 in the compression seal zone (C) may be increased so that a compression seal may be provided while allowing the membrane part 1030 to expand outwards in the expanding seal zones (A) thereby reducing the amount of overall strap tension.

FIGS. 33-9 and 33-10 illustrate a cushion including a silicone membrane part 1130 and an undercushion part 1132 constructed (e.g., molded) of two part polyurethane foam (e.g., porous foam) and insertable to the membrane part 1130. In an embodiment, the foam undercushion part 1132 may be skinned or unskinned. As described above, the membrane part 1130 includes cut-out regions 1131 to reveal the undercushion part 1132. However, in an alternative embodiment, the membrane part may be continuous with no cut-outs.

In an example embodiment, one or more portions of the undercushion part 1132 may be adhered (e.g., glued) to the membrane part 1130, e.g., to ease transition of compression force from membrane part to undercushion part. In an embodiment, as shown in FIG. 33-14, edge segments 1130(1) of the membrane part 1130 adjacent the undercushion part 1132 may be unglued to the undercushion part 1132, e.g., left free moving to allow membrane more freedom in sealing against the patient's face in use.

Figure 13:
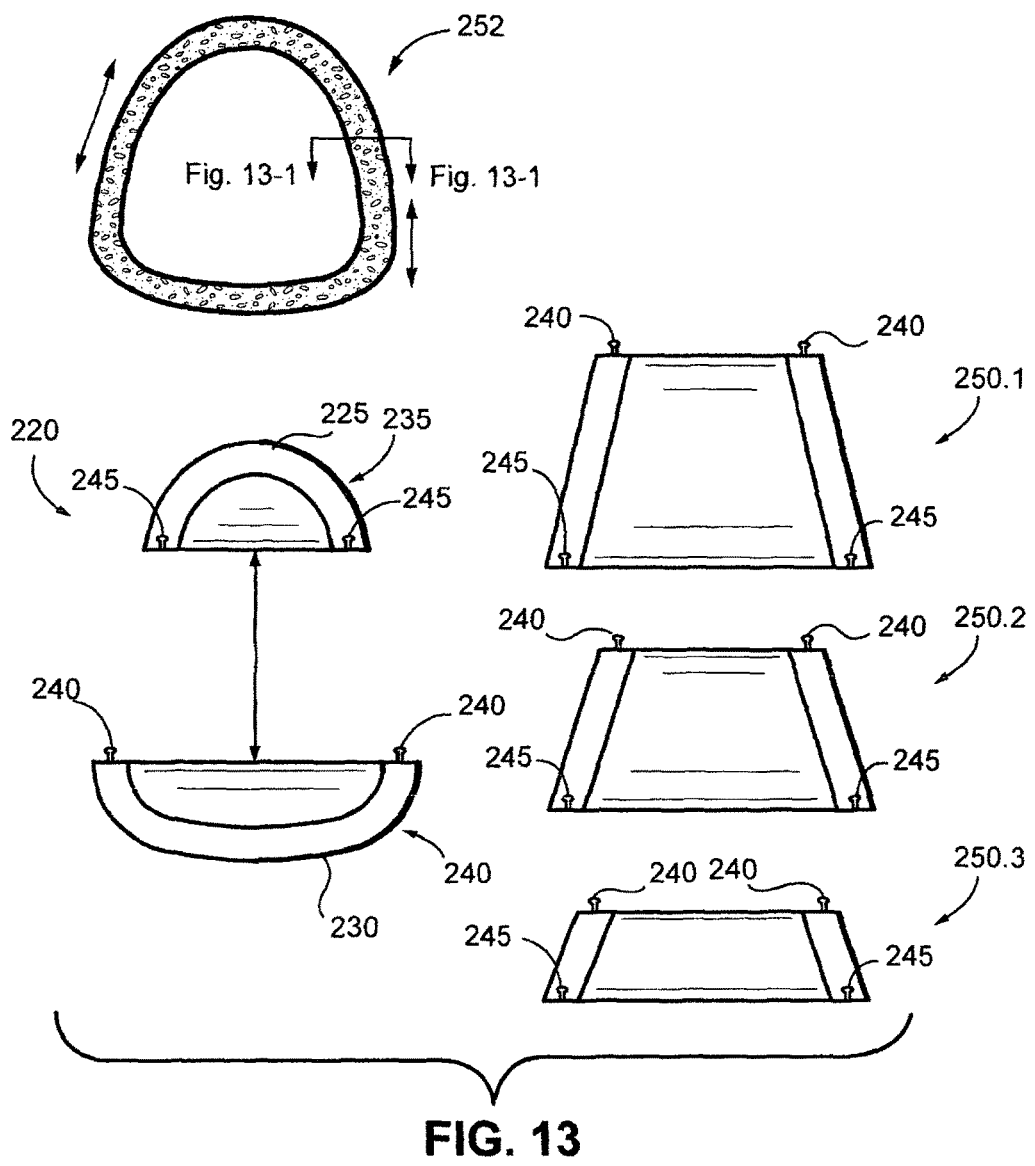
Figures 1, 13:
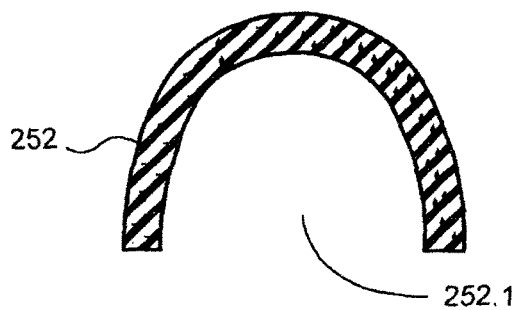

FIG. 33-11 shows an adjustable region or gusset 1116 (e.g., constructed of silicone (e.g., 28 Shore A silicone)) provided to the cushion 1118, and FIGS. 33-12 and 33-13 show clip portions 1122 that provide an interface for engagement with the frame and adjustment mechanism. In addition, FIGS. 33-12 and 33-13 show support portions 1123 (e.g., constructed of a semi-rigid material) provided to the clip portions (e.g., glued) and adapted to support the foam undercushion part 1132 in use. FIGS. 33-15 to 33-17 show the cushion reduced in size by the adjustment mechanism (e.g., FIG. 33-15 shows small size and FIG. 33-16 shows medium size).

In an example embodiment, the silicone membrane part and the foam undercushion part may include similar stiffnesses, e.g., to better distribute load across the silicone and foam during changes in size and reduce the size of valleys, or reduce the surface discontinuity of the patient sealing surface. In an example embodiment, the cushion may be structured such that the shape change in the cushion (e.g., where valleys in the cushion may occur) occurs in non-sensitive regions of the patient's face.

In this embodiment, the foam undercushion part relies on compression while the silicone membrane part relies on air pressure to seal on the patient's face. This provides opposite sealing mechanisms, which includes a transition period between the two. The illustrated embodiment bridges the opposite sealing mechanisms, e.g., by making the foam act more like a silicone seal and vice versa.

FIGS. 33-18 to 33-25 provide alternative examples of a cushion with a silicone membrane part and a foam undercushion part. In FIG. 33-18, the foam undercushion part 1132 may be substantially flush with the silicone membrane part 1130. As shown in FIG. 33-19, the interface 1133 between parts 1130, 1132 may be disposed at an angle. When the foam is compressed in use, the silicone may slightly compress as well. In FIG. 33-20, the silicone membrane part 1130 is continuous which avoids contact of the foam undercushion part 1132 with the patient's face and avoids foam/silicone interface on the sealing surface. In FIG. 33-21, the foam undercushion part 1132 includes cut-outs 1135 (e.g., one or more cut-outs along one or more portions of the cushion perimeter) within the foam itself, which facilitates compression/shape change, i.e., lessens rigidity so that the membrane does not absorb substantially all deformation. In FIG. 33-22, the foam undercushion part 1132 protrudes from the silicone membrane part 1130, i.e., foam has a gentle curve which allows transition between compression and membrane seal. The foam may include a cut-out 1137 within the foam that allows the foam to deform over a larger area to seal and allows for easier compression, e.g., lessens rigidity so that membrane does not absorb substantially all deformation. In FIG. 33-23, the foam undercushion part 1132 protrudes from the silicone membrane part 1130 as described above and also includes a flexible flap 1139 to provide a flexible element for the membrane part 1130 to join. The flap provides a smoother transition between seal types, allowing the membrane to join to the foam at a stage when the curvature is smoother, e.g., prevents wrinkles and valleys. The foam and silicone fight to obtain equilibrium between compression/expansion and the flap may overlap the membrane part to enhance the seal between foam and silicone parts. In FIG. 33-24, the silicone membrane part 1130 is attached (e.g., glued) as an arch against the foam undercushion part 1132 to provide two hills with a valley therebetween. As the foam compresses and the membrane expands, the valley between them will decrease, thereby achieving seal between the two interfaces. In FIG. 33-25, cut-outs 1136 may be provided within the foam 1132 itself that are large enough so that it leaves a thin wall section 1138 of foam at the interface between the membrane 1130 and foam 1132. In use, the foam compresses, but the thin wall section 1138 of foam due to air pressure will expand, helping transition between the compression and membrane seal.

3.2.2 2-Part Cushion Example 2

Figures 4, 34:
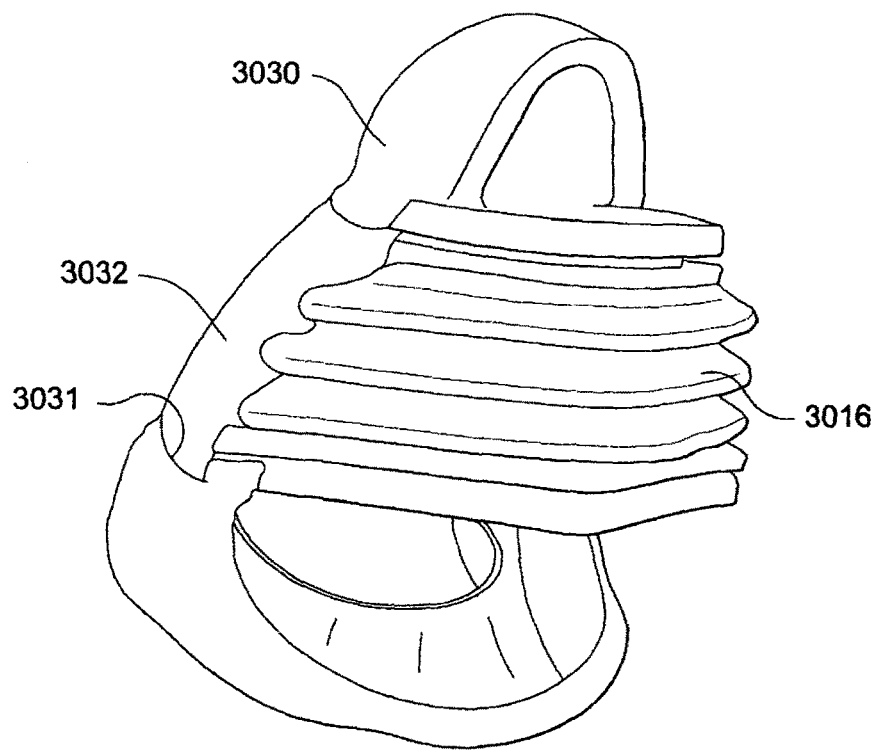
Figures 5, 34:
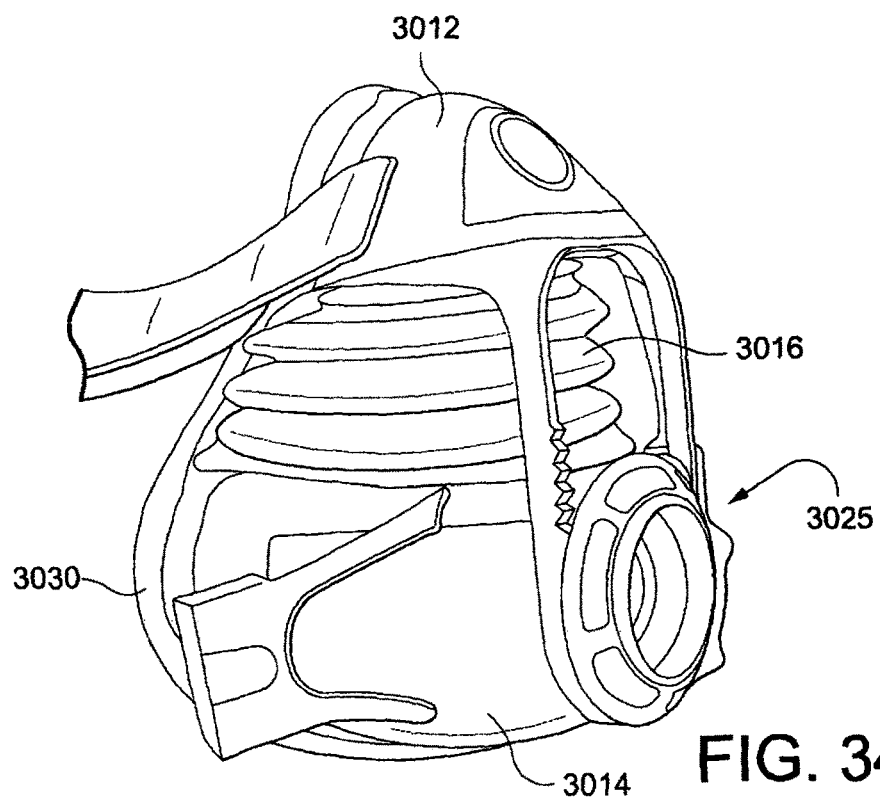
Figures 6, 34:
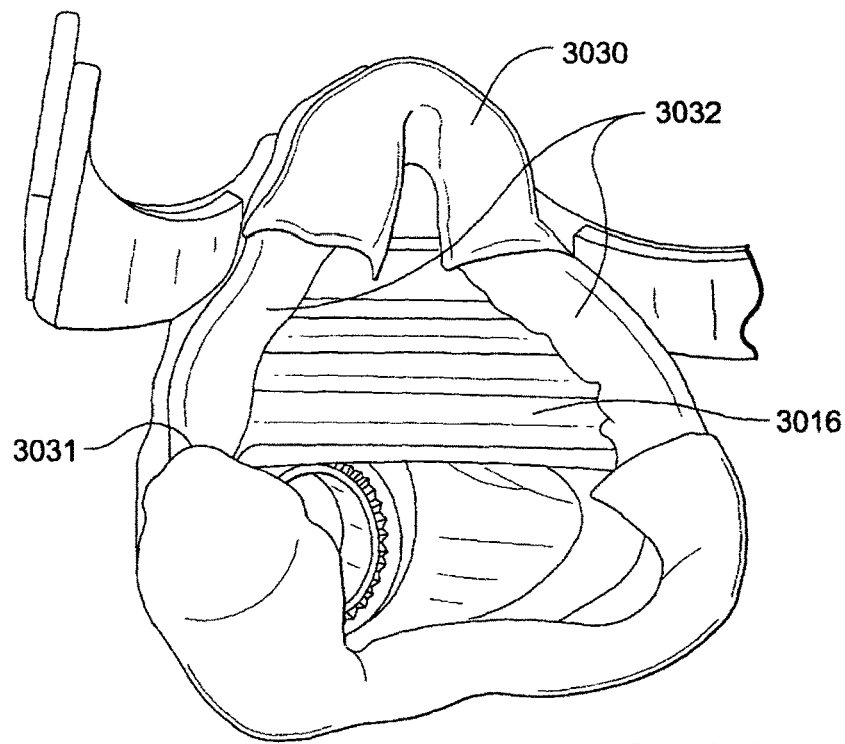
Figures 7, 34:
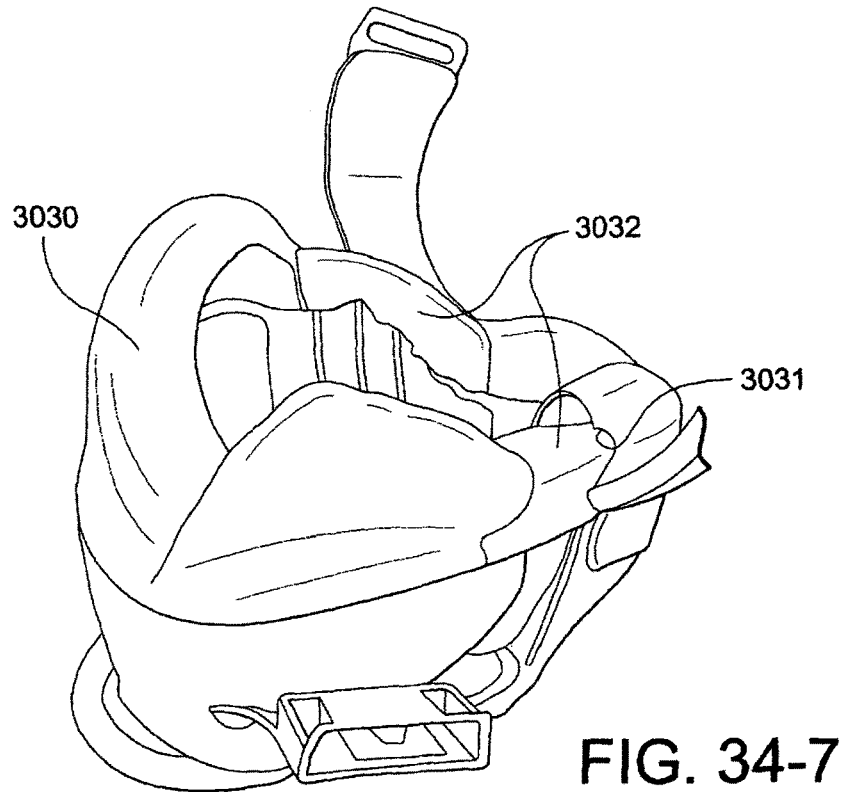

FIGS. 34-1 and 34-2 show a cushion 1218 including a single wall, silicone membrane part 1230 adapted to seal along the nasal bridge and around the mouth and a frame part 1212 integrated with the membrane part 1230. A separate undercushion part 1232 (e.g., PU foam, skinned foam, silicone foam, gel bladder, TPE, low durometer silicone) is provided to the membrane part 1230. As illustrated, the membrane part 1230 includes cut-out regions 1231 along the sides of the patient's nose to reveal the undercushion part 1232. In use, the undercushion part 1232 provides support to the membrane part 1230 along the nasal bridge and around the mouth and the exposed portions of the undercushion part 1232 forms a compression-type seal along the sides of the nose.

In an embodiment, adjustment may be accommodated through shape change, i.e., material is not substantially stretched or compressed to change the length of the perimeter of a large size cushion to fit a smaller user. The missing membrane allows the undercushion to shape change without stretching or compressing and deforming the membrane and hence interrupting the seal. Rather, adjustment is accommodated by buckling or deformation of the material to deform the cushion into the required shape. In an example, the cushion may provide a 20 mm height change from large to small size.

FIG. 34-3 shows various small cushion shapes constructed by maintaining the same length of perimeter of the large cushion shape. As illustrated, upper and lower portions of the cushion remain substantially the same across sizes, while a transition region or mouth width 8000 of the cushion increases. Preferably, the transition region compromises the amount of curvature with sufficient clearance below the eyes. In addition, sharp corners or tight radii are preferably avoided, e.g., to avoid undesired deformation of the cushion.

In an exemplary embodiment, the cushion may be molded into a "medium" size, and then stretched to a "large" size or shape-changed to a "small" size. However, it should be appreciated that height adjustment may include aspects of material stretch, compression, and/or shape change.

FIGS. 34-4 and 34-7 illustrate an exemplary cushion including a silicone membrane part 3030 and gel parts 3032 provided to the membrane part 3030. The membrane part 3030 includes cut-out regions 3031 to reveal the gel parts 3032. The gel parts 3032 may be provided in the cut-out regions only, or the gel parts may be part of a gel undercushion that extends around the entire cushion perimeter. Upper and lower frame portions 3012, 3014, an adjustable region or gusset 3016 between the upper and lower frame portions, and an adjustment mechanism 3025 is provided to the cushion.

FIGS. 34-8 to 34-10 show the cushion reduced in size by the adjustment mechanism (e.g., FIG. 34-8 shows large size, FIG. 34-9 shows medium size, and FIG. 34-10 shows small size). The gel may squash outwards and may stretch to reduce in size. In an embodiment, the gel part may be attached to the silicone part with a convex shape so that the gel part deforms outwardly away from the breathing chamber when reduced in size, e.g., to prevent occlusion of the nasal passages. Also, in an embodiment, the gel part may protrude above the silicone part (in the cut-out regions), e.g., to maintain continuous sealing contact in use. In an embodiment, top straps of headgear may be arranged to constrain the cushion profile when around the gel parts and provide additional localized compression for a seal.

3.2.3 2-Part Cushion Example 3

Figures 1, 35:
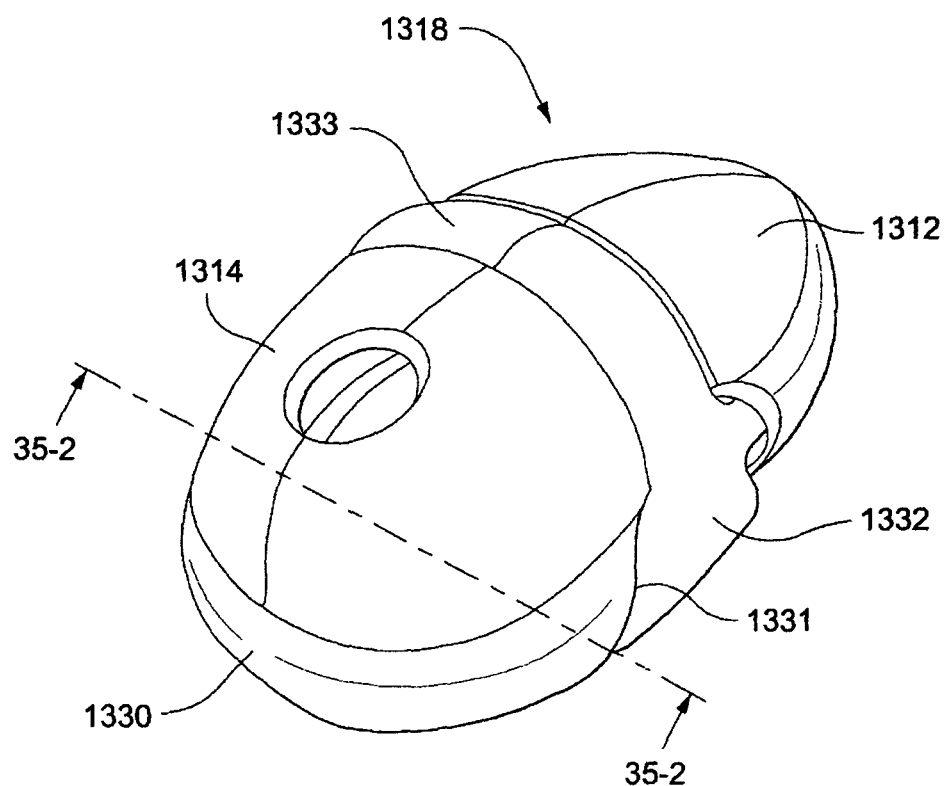
Figures 2, 35:
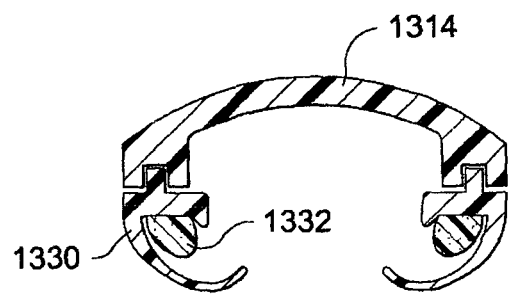
Figures 3, 35:
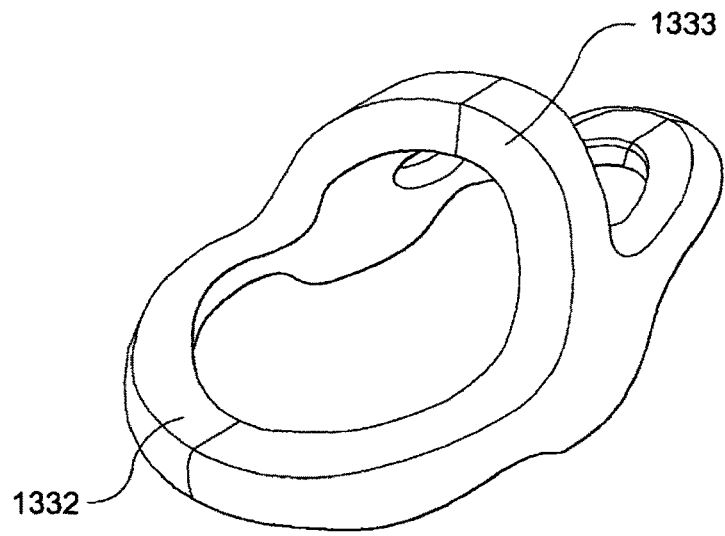

FIGS. 35-1 to 35-3 show a cushion 1318 including a single wall, silicone membrane part 1330 adapted to seal along the nasal bridge and around the chin and a separate undercushion part 1332 (e.g., PU foam, skinned foam, silicone foam, gel pocket) provided to the membrane part 1330. Separate upper and lower frame portions 1312, 1314 are provided to the cushion. As illustrated, the undercushion part 1332 includes a bridge portion 1333 (also called an adjustable portion) which bridges the upper and lower frame portions 1312, 1314 to accommodate stretch. As illustrated, the membrane part 1330 includes cut-out regions 1331 along the sides of the patient's nose to reveal the undercushion part 1332. In use, the undercushion part 1332 provides support to the membrane part 1330 along the nasal bridge and around the mouth and the exposed portions of the undercushion part 1332 forms a compression-type seal along the sides of the nose.

3.2.4 2-Part Cushion Example 4

Figures 1, 36:
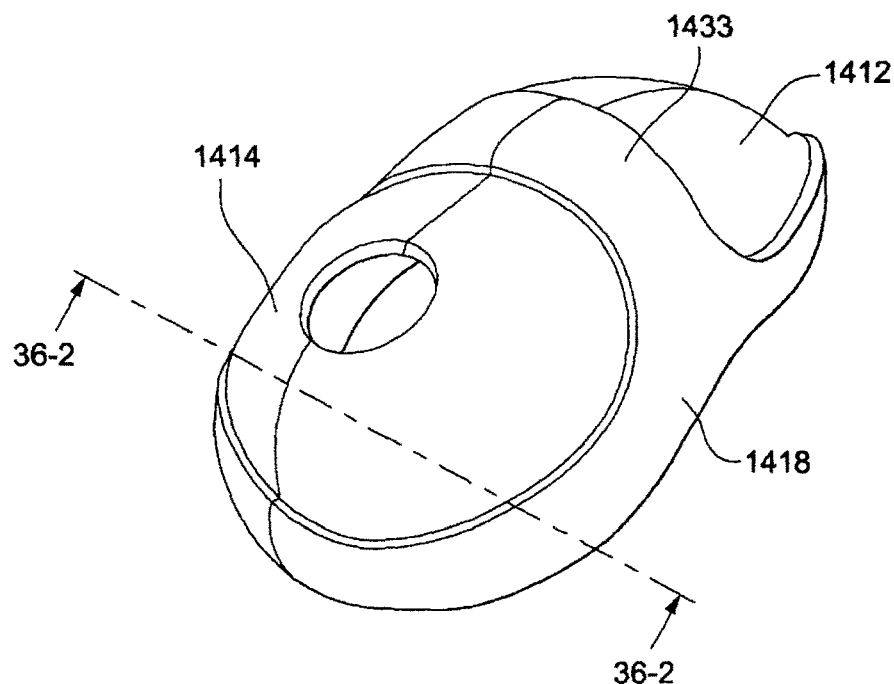
Figures 2, 36:
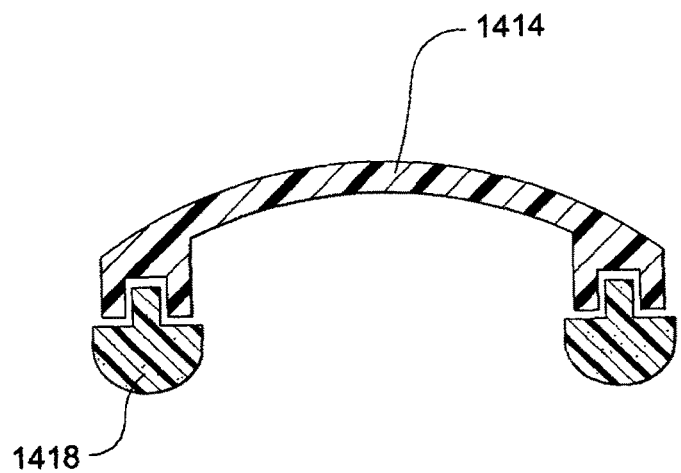

FIGS. 36-1 and 36-2 show a cushion 1418 (e.g., constructed of a low durometer TPU/TPE/PUR or low durometer silicone/silicone foam) adapted to provide a continuous compression type seal around the mask perimeter. Separate upper and lower frame portions 1412, 1414 are provided to the cushion. As illustrated, the cushion 1418 includes a bridge portion 1433 (adjustable portion) which bridges the upper and lower frame portions 1412, 1414 to accommodate stretch. The bridge portion 1433 may be constructed from the same material as the cushion.

3.2.5 2-Part Cushion Example 5

Figures 1, 37:
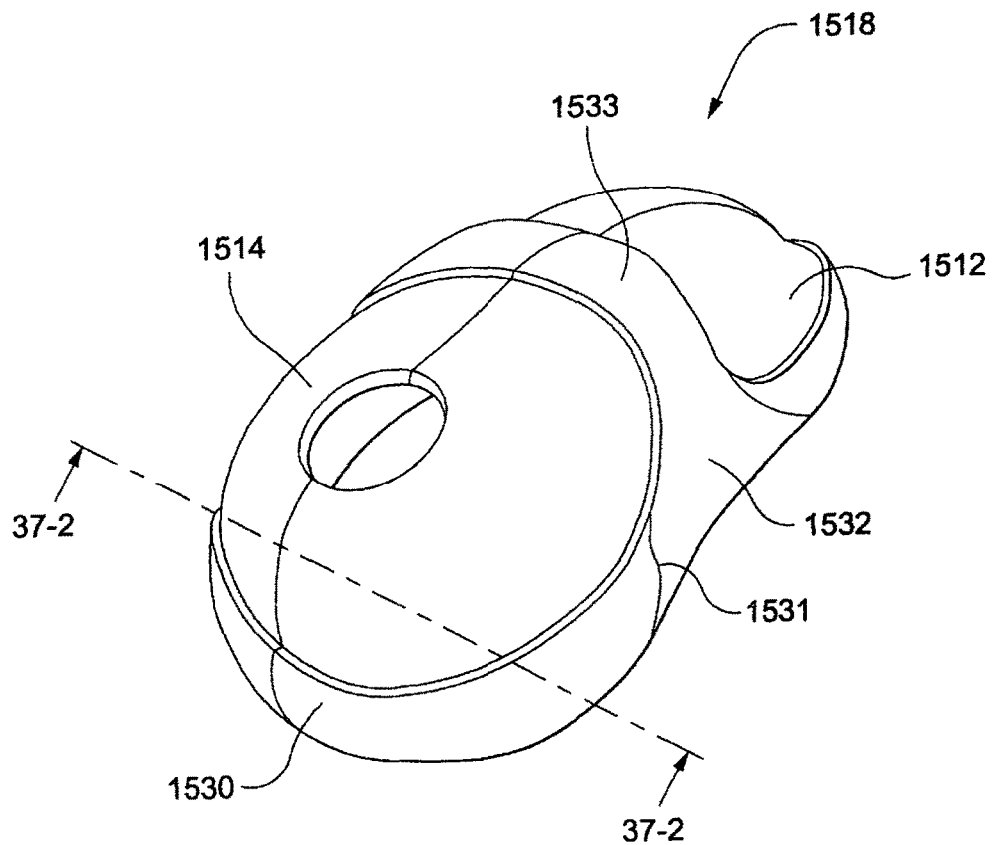
Figures 2, 37:
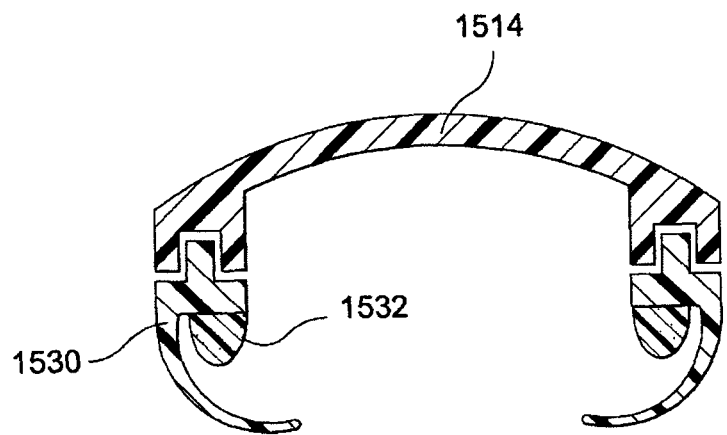

FIGS. 37-1 and 37-2 show a dual durometer cushion 1518 including a single wall, membrane part 1530 adapted to seal along the nasal bridge and around the chin and a low durometer undercushion part 1532 overmolded to the membrane part 1530. Separate upper and lower frame portions 1512, 1514 are provided to the cushion. As illustrated, the undercushion part 1532 includes a bridge portion 1533 which bridges the upper and lower frame portions 1512, 1514 to accommodate stretch. As illustrated, the membrane part 1530 includes cut-out regions 1531 along the sides of the patient's nose to reveal the undercushion part 1532. In use, the undercushion part 1532 provides support to the membrane part 1530 along the nasal bridge and around the chin and the exposed portions of the undercushion part 1532 forms a compression/membrane seal along the sides of the nose. Thus, the parts 1530, 1532 cooperate to provide a continuous membrane seal.

3.2.6 2-Part Example 6

Figures 1, 38:
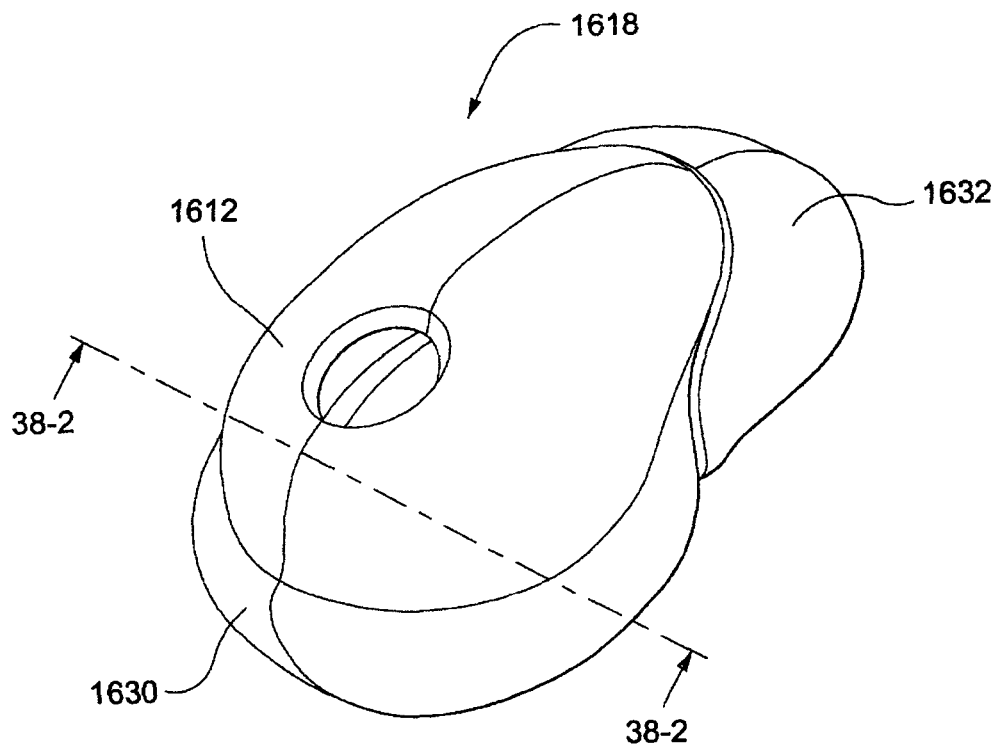
Figures 2, 38:
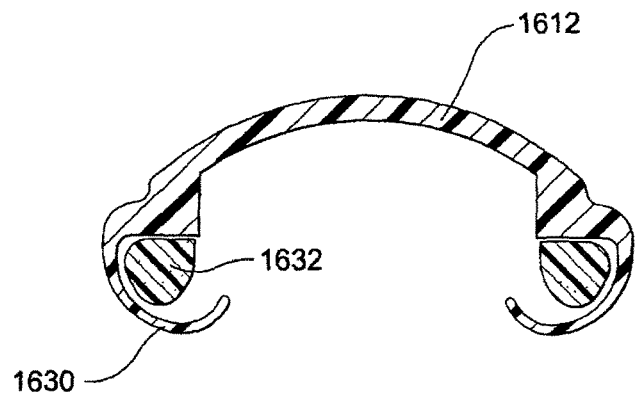
Figures 3, 38:
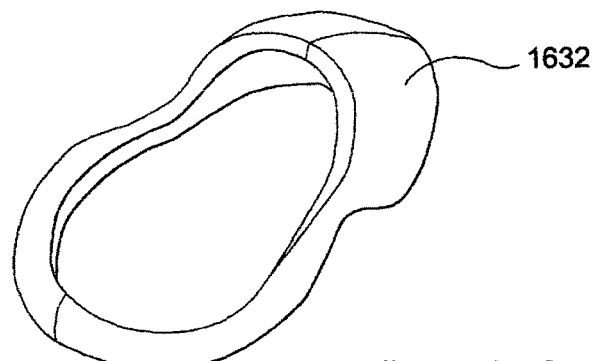
Figures 4, 38:
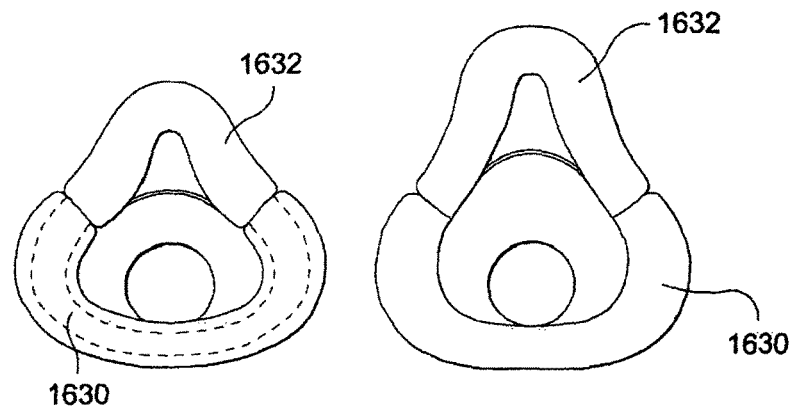

FIGS. 38-1 to 38-4 show a cushion 1618 including a single wall, membrane part 1630 adapted to seal around the chin region and a frame part 1612 integrated with the membrane part 1630. As shown in FIG. 38-3, a separate low durometer undercushion part 1632 (e.g., molded foam, PU foam, skinned foam, silicone foam, gel pocket) is provided to the membrane part 1630. In use, the undercushion part 1632 provides support to the membrane part 1630 around the chin region and the undercushion part 1632 forms a compression-type seal along the nasal bridge and the sides of the nose. As shown in FIG. 38-4, adjustment of the cushion (e.g., stretch/deformation for size change) is localized to the undercushion part 1632. The membrane part and frame part may be interference fit together, or molded together.

3.3 Accordion Style Adjustable Region of Gusset Example

Figures 1, 2, 39, 40:
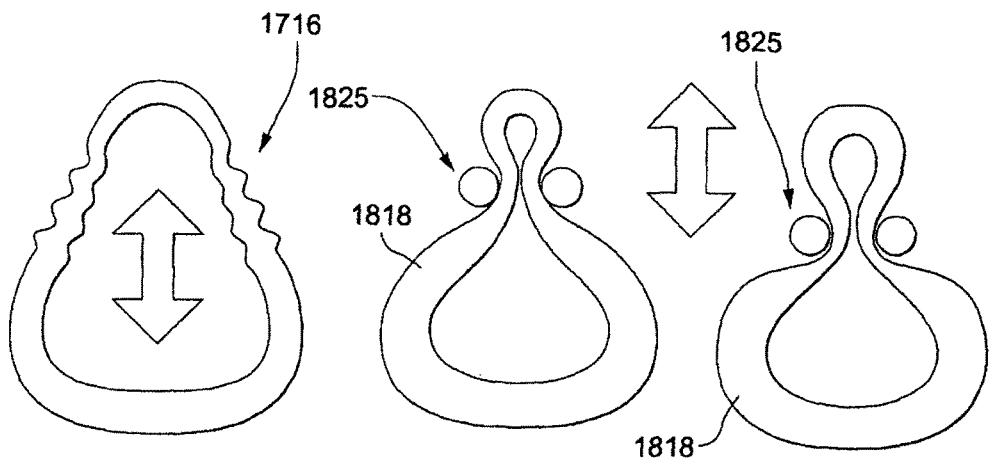

FIG. 39 shows a cushion with an accordion style adjustable region or gusset 1716. The adjustable region or gusset 1716 allows the sealing profile to change shape (rather then compress or stretch) in order to achieve the required adjustment in facial height.

3.4 Pinch Example

FIGS. 40-1 and 40-2 illustrate a soft cushion 1818 (e.g., silicone, TPE) with an integrated frame adapted to form a continuous compression type seal with the patient's face. An independent roller mechanism 1825 (e.g., including rolling pins) is provided to the cushion and structured to adjust the sealing profile. That is, the roller mechanism pinches the cushion together around the nasal bridge region and may be adjusted vertically to adjust the geometry of the sealing profile and cover the size range (e.g., small, medium, and large).

In this example, the cushion is changed in shape from a first size to a second size. The length of the perimeter remains constant, and the proportions of each portion of the cushion change for example to make the cushion smaller, the lower part of the cushion is widened out.

3.5 Stretch Sealing Profile (Frame Point Contact) Example

Figures 1, 2, 41:
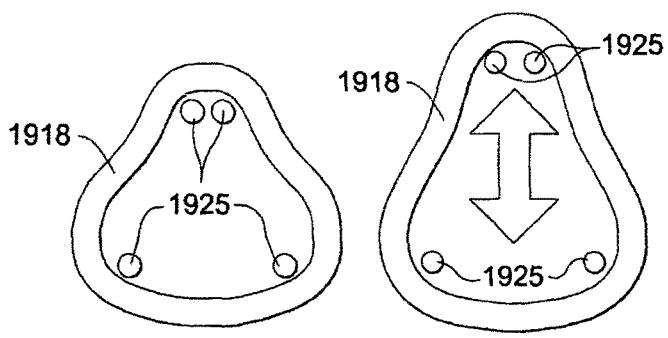

FIGS. 41-1 and 41-2 illustrate a cushion 1918, e.g., constructed of TPE, TPU. The frame includes pin members 1925 that provide point contact with the cushion. The pin members are adjustable by an adjustment mechanism to stretch the sealing profile of the cushion for larger sizes, e.g., from small to medium and from medium to large.

3.6 Stretch Sealing Profile (Frame Adjustable Region or Gusset) Example

Figures 1, 2, 42:
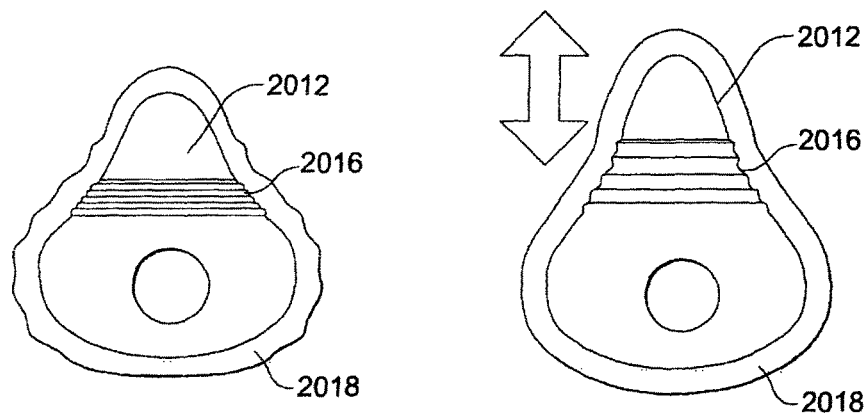

FIGS. 42-1 and 42-2 illustrate a cushion 2018, e.g., constructed of TPE, TPU. A frame 2012 with an adjustable region or gusset 2016 has continuous contact with the cushion. The frame is adjustable by an adjustment mechanism to stretch the sealing profile of the cushion for larger sizes, e.g., from small to medium and from medium to large.

3.7 Module Example

Figures 7, 43:
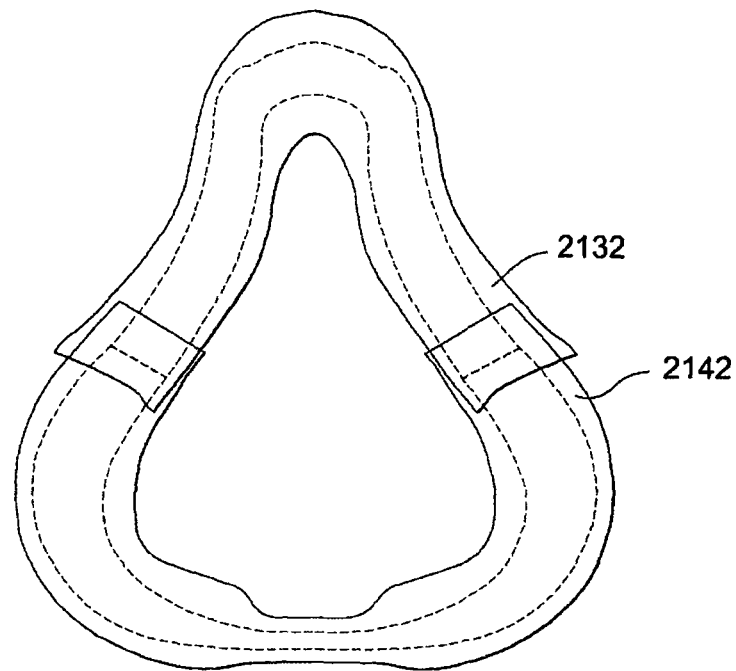
Figures 8, 43:
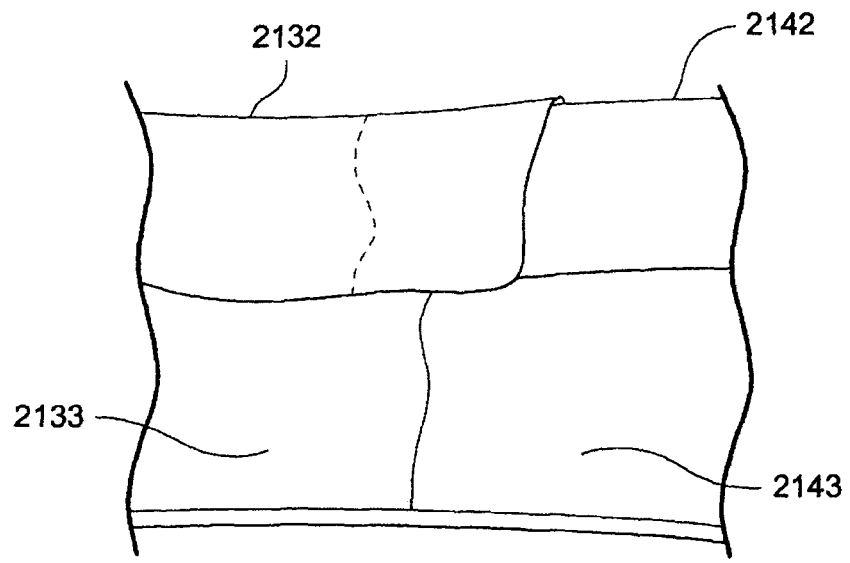

FIGS. 43-1 to 43-3 show a modular sealing arrangement including a universal base section 2118 adapted to accommodate an interchangeable top section, e.g., a large size top section 2120(1), a medium size top section 2120(2), or a small size top section 2120(3). The base section 2118 includes a cushion/frame adapted to seal around the mouth and sides of the nose. Each top section 2120(1), 2120(2), 2120(2) is fixable to the base section and includes a cushion/frame adapted to seal around the nose and nasal bridge. In an embodiment, each cushion/frame may be molded of silicone to reduce part count, e.g., frame portion may be a thicker silicone than cushion portion.

FIGS. 43-4 to 43-6 shows an exemplary arrangement for fixing a top section 2120 to the base section 2118. As illustrated, the top section 2120 includes a frame 2130 and sealing membrane 2132 (FIGS. 43-4 and 43-5), and the base section 2118 includes a frame 2140 and sealing membrane 2142 (FIG. 43-6). A pin/groove arrangement (e.g., pins 2130(1) on frame 2130 and grooves 2140(1) on frame 2140) is provided to align and locate the frames 2130, 2140 to one another, and a latch arrangement (e.g., latch 2140(2) on frame 2140 and groove 2130(2) on frame 2130) is provided to secure the frames to one another, e.g., with a snap-fit.

As illustrated, the membranes 2132, 2142 protrude past respective frames so that the membranes overlap and seal against one another when the top and bottom sections are fixed to one another. FIG. 43-7 illustrates the membranes 2132, 2142 overlapping one another. As shown in FIG. 43-8, thicker silicone sections 2133, 2143 supporting the membranes 2132, 2142 may lie flush with one another, e.g., to prevent leak and allow assembly into a channel of the frame.

3.8 Hinged External Skeleton Example

Figures 1, 44:
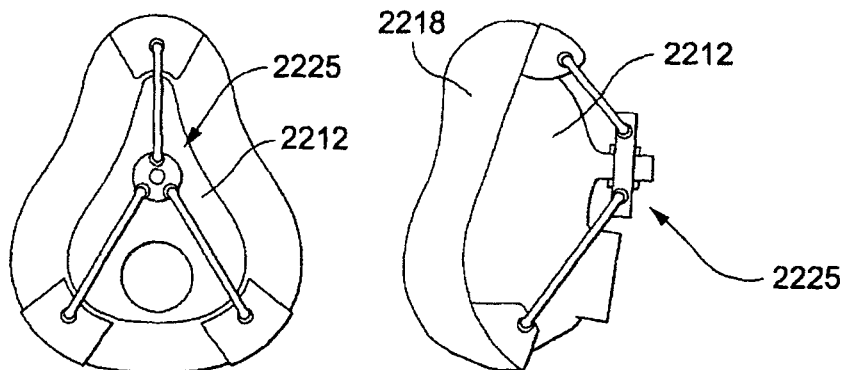
Figures 2, 44:
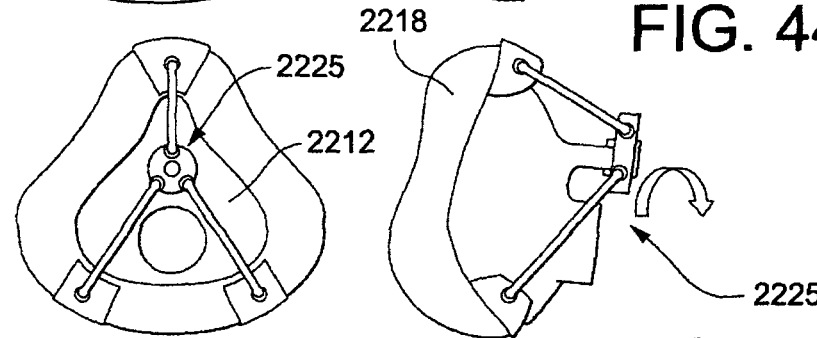
Figure 45:
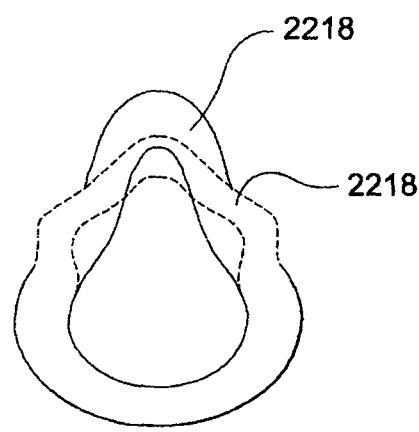

FIGS. 44-1 to 44-2 and 45 show a cushion 2218 (e.g., constructed of silicone, TPE/TPU, foam, etc.) supported by a flexible frame 2212 (e.g., constructed of silicone, TPE, treated textiles). A skeleton style adjustment mechanism 2225 is coupled to the frame and structured to adjust the sealing profile, e.g., adjustment mechanism is adjusted towards/away from face to vertically adjust the frame and hence the cushion. That is, the adjustment mechanism includes a base and pivotal adjustment members mounted between the base and the frame 2212. In use, the position of the base may be adjusted to adjust the position of the adjustment members, which adjusts the frame and hence the shape of the cushion. As shown in FIG. 45, adjustment is accommodated through shape change, i.e., material is not stretched or compressed.

FIG. 44-1 shows the mask system adjusted to a large size, where the adjustment mechanism 2225 is supporting the cushion to stretch to a larger height.

FIG. 44-2 shows the mask system adjusted to a small size, where the adjustment mechanism 2225 is maintaining the cushion in its relaxed or starting position.

3.9 Thermoformed Cushion and Skeleton Frame

FIGS. 54 to 73 show alternative arrangements of a mask system according to an alternative embodiment of the present technology. Preferably, the mask system may comprise a skeleton or inextensible frame portion. The skeleton may provide the structure or shape of the mask system so that the nose of the patient may fit within the cavity or breathing chamber of the mask system. Preferably the skeleton may be adjustable or re-positionable from a first position to a second position by stretching and/or shape change of a membrane or flexible member, where the membrane connects or attaches to the skeleton. The membrane may attach one or more portions of the skeleton while also sealing or otherwise covering the mask system to enable delivery of therapy to the patient. The skeleton and/or the membrane may also act as an anchoring or attachment portion, for connection of additional elements of the patient interface such as a headgear, elbow, air delivery tube, vent system, etc.

The skeleton and membrane may be assembled by thermoforming. Preferably, a cushion or sealing member is connected to the skeleton and/or membrane to affect a seal between a patient and the mask system. The cushion may be removably attachable to the skeleton and/or membrane. Preferably, the cushion is assembled with the skeleton and membrane by thermoforming.

Beneficially, by thermoforming portions or the whole mask system, the number of parts of the mask system may be reduced, may be easier to clean, may be cheaper to manufacture and/or may be more flexible, less obtrusive and user friendly.

Most preferably, the cushion may be a conformable material capable of providing a compression seal with the patient. Preferably, the cushion may be constructed of a foam, gel, fabric or other deformable material. The membrane may be constructed from a flexible and substantially elastic material such as fabric. The skeleton may be constructed from a substantially inextensible material such a polycarbonate, polypropylene, nylon, aluminum, steel. Alternatively, the skeleton may be made from a flexible material such as a silicone or thermoplastic urethane (TPU). The skeleton may be substantially resilient such that it returns to its intended shape after loading.

3.9.1 Thermoformed Embodiment 1

Figure 54:
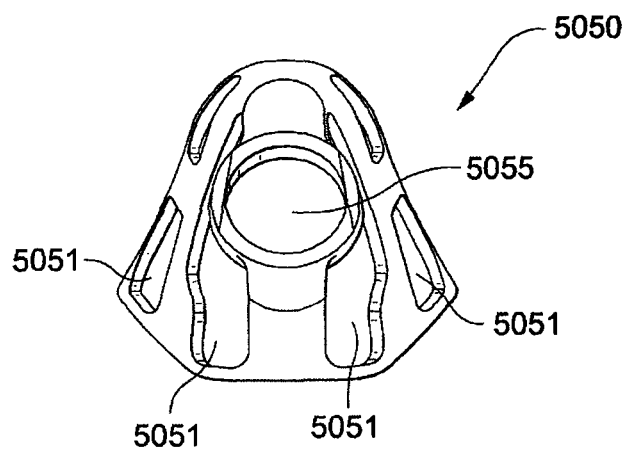
FIG. 54 shows a front view of a portion of a skeleton according to an embodiment of the present technology.
Figure 55:
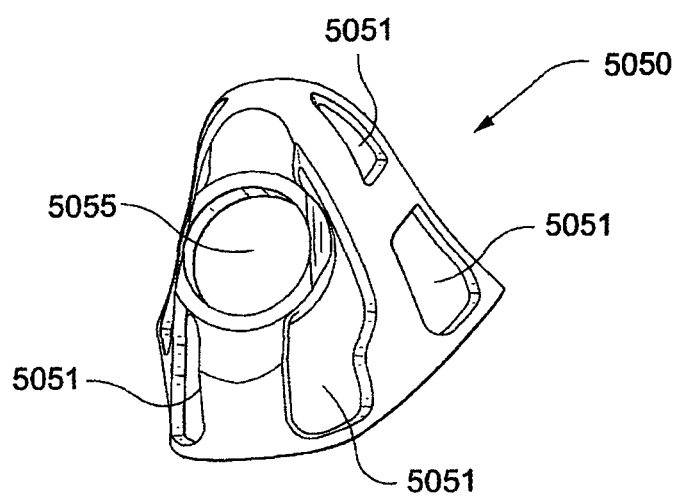
FIG. 55 shows an isometric view of a portion of a skeleton according to an embodiment of the present technology.

FIGS. 54 and 55 show an upper or top portion 5050 of a skeleton that may be positioned generally over the nose of the patient when in use. The upper portion 5050 may include an orifice 5055 adapted to receive, for example, an adjustment mechanism, a vent, an elbow, or an air delivery tube. Upper portion 5050 may be without aperture or orifices for structural integrity or strength. Preferably, upper portion 5050 may include one or more apertures 5051 to minimize material and thus weight and cost of the upper skeleton portion. Apertures 5051 may also enable the skeleton to at least partially flex or bend.

Figure 56:
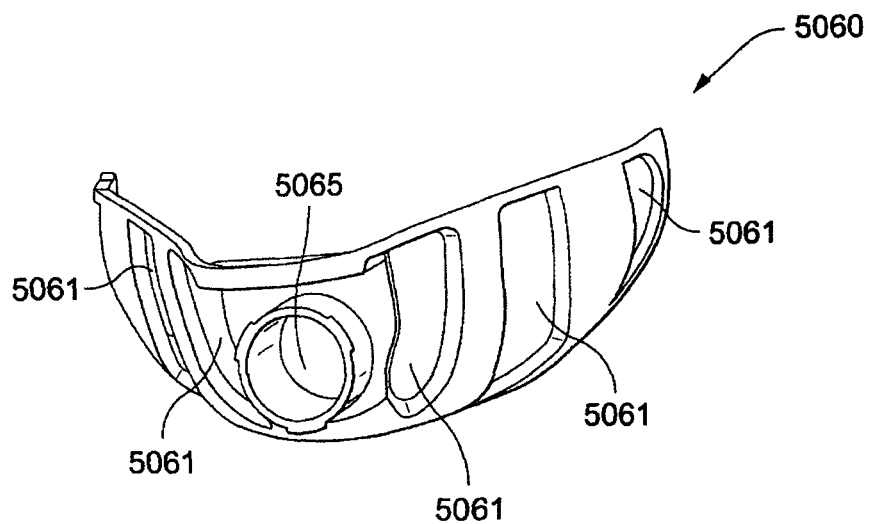
FIG. 56 shows an isometric view of a portion of a skeleton according to an embodiment of the present technology.

FIG. 56 shows a lower or bottom portion 5060 of a skeleton that may be positioned generally over the mouth or chin of the patient when in use. The lower portion 5060 may include an orifice 5065 adapted to receive, for example, an adjustment mechanism, a vent, an elbow, or an air delivery tube. Lower portion 5060 may be without aperture or orifices for structural integrity or strength. Preferably, the lower portion 5060 may include one or more apertures 5061 to minimize material and thus weight and cost of the lower skeleton portion. Apertures 5061 may also enable the skeleton to at least partially flex or bend.

Figure 59:
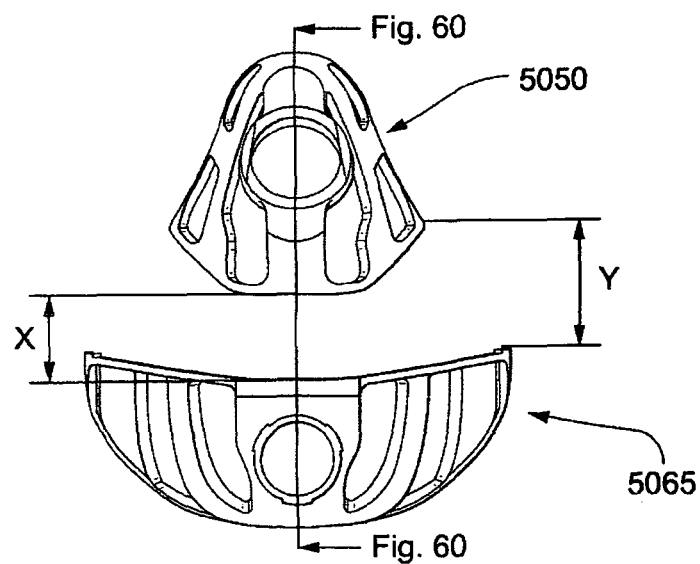
FIG. 59 shows a front view of a skeleton of a mask according to an embodiment of the present technology.

FIG. 59 shows upper portion 5050 in its relative position to lower portion 5060. Preferably, the distance X between the upper portion 5050 and lower portion 5060 at the center region may be 10-30 mm, e.g., 12-20 mm, 18 mm. Preferably, the distance Y between the upper portion 5050 and lower portion 5060 at the corners or outermost region may be 15 to 40 mm, e.g., 20-30 mm, 26 mm.

Figure 57:
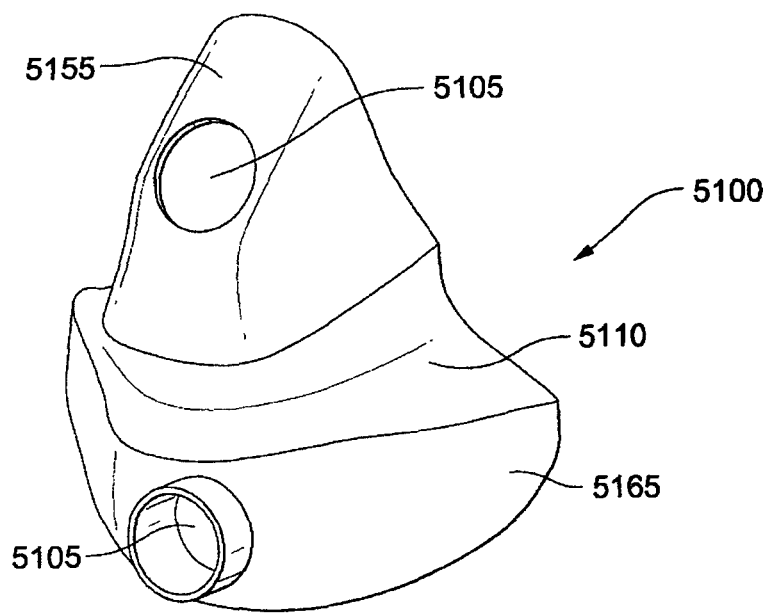
FIG. 57 shows an isometric view of a portion of a mask according to an embodiment of the present technology.

FIG. 57 shows a membrane 5100 that may be connected or otherwise formed with the skeleton. Membrane 5100 may include an upper portion 5155 and a lower portion 5165 for alignment with upper skeleton portion 5055 and lower skeleton portion 5065, respectively. Membrane 5100 may further include an adjustment region 5110 that may be able to flex, stretch, fold and/or bend to adjust the distance or alignment of the upper portion 5155 and lower portion 5165 and hence the positions of the upper skeleton 5055 and lower skeleton 5065. Adjustment region 5110 may be more flexible than the upper portion 5155 and lower portion 5165. Alternatively, the adjustment region 5110 may have the same flexibility as upper portion 5155 and lower portion 5165. The membrane 5100 may include apertures 5105 for alignment with respective apertures on upper skeleton portion 5055 and lower skeleton portion 5065.

Figure 58:
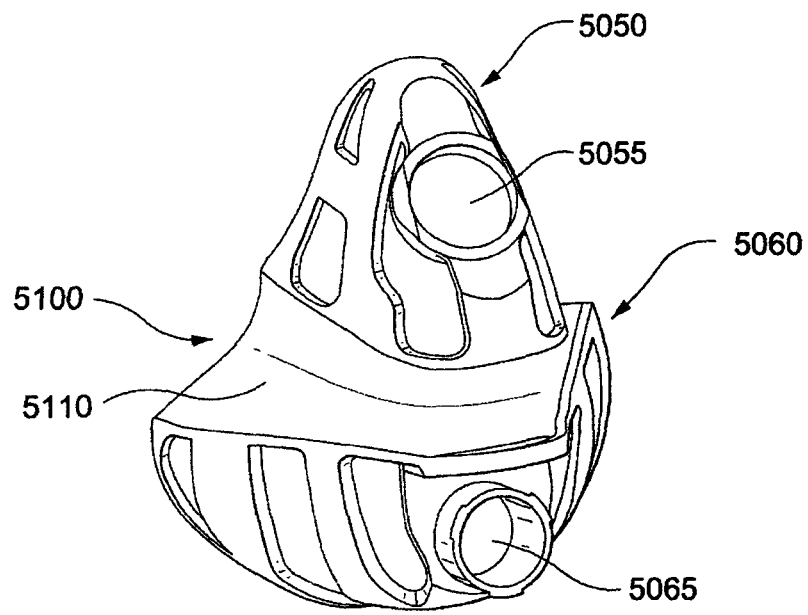
FIG. 58 shows an isometric view of a mask according to an embodiment of the present technology.
Figure 60:
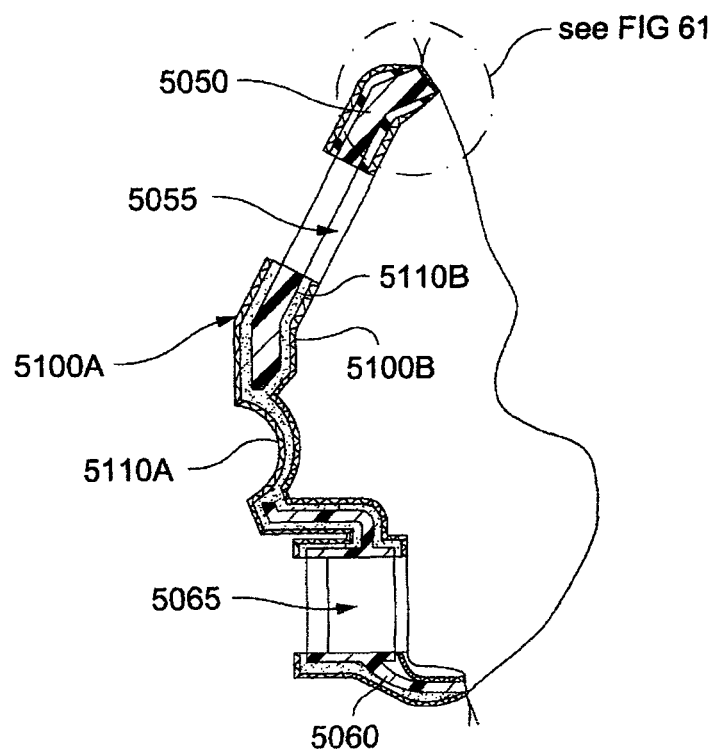
FIG. 60 shows a section view of a mask according to an embodiment of the present technology.

FIG. 58 shows the relative positions of the upper portion 5050 of the skeleton and the lower portion 5060 of the skeleton when positioned with the membrane 5100. The adjustment region 5110 is positioned generally between the upper portion 5050 and lower portion 5060 to facilitate repositioning or adjustment of the distance or alignment of the skeleton portions. FIG. 60 shows a section through the mask system, where the upper and lower portions 5050 and 5060 of the skeleton are positioned within the membrane 5100. Adjustment region 5110 may be substantially between upper portion 5050 and lower portion 5060.

Figure 61:
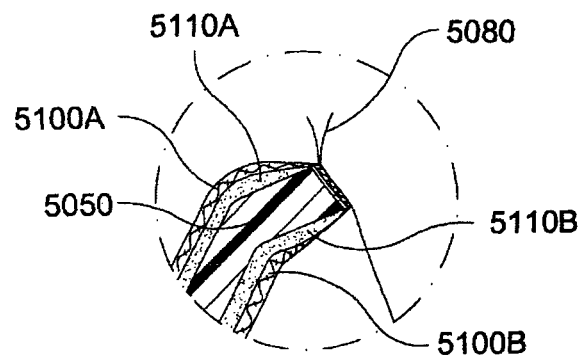
FIG. 61 shows a portion of a section view of a mask according to an embodiment of the present technology.

FIG. 61 shows a portion of the section shown in FIG. 60. Upper portion 5050 may be positioned or encapsulated within membrane 5100. In addition, a compliant material 5180 may be positioned between the skeleton portion and the membrane portion to soften the appearance and increase the comfort of the mask system. The compliant material may be, for example, foam, fabric, 3D weaves, felt, gel.

Preferably, the skeleton, membrane and compliant material may be formed by lamination and/or thermoforming. For example, there may be a patient contacting side membrane 5100B that may be laminated or otherwise attached to compliant material 5110B. There may also be a non-patient contacting side membrane 5100A that may be laminated or otherwise attached to compliant material 5110A. Upper portion 5050 and lower portion 5060 may be positioned between the laminations of membranes 5100A and 5100B in a tool. Heat may be applied to the tool to thermally form or join the membranes 5100A and 5100B together. Excess material 5080 may appear at the join of the membranes that may be trimmed by hand cutting, die cutting, ultrasonic die cutting or welding.

In an exemplary embodiment as shown in FIGS. 60 and 61, the upper and lower portions 5050, 5060 are constructed of nylon, the compliant material 5110A and 5110B is a foam material (e.g., open cell polyurethane foam with thickness of about 1-10 mm, e.g., 5 mm), and the membrane 5100A and 5100B is constructed of a fabric material (e.g., thickness of about 0.1-1.0 mm, e.g., 0.5 mm). However, it should be appreciated that other suitable materials as noted above may be possible. As shown in FIG. 60 for example, the foam/fabric materials finish at the inner and outer edges of the orifices 5055, 5065.

3.9.2 Thermoformed Embodiment 2

In an embodiment, a skeleton may be sealed or covered with a membrane to form a first portion, and a cushion may be sealed or covered with a membrane to form a second portion, where the first and second portions may be coupled or attached to form a mask system.

Figure 62:
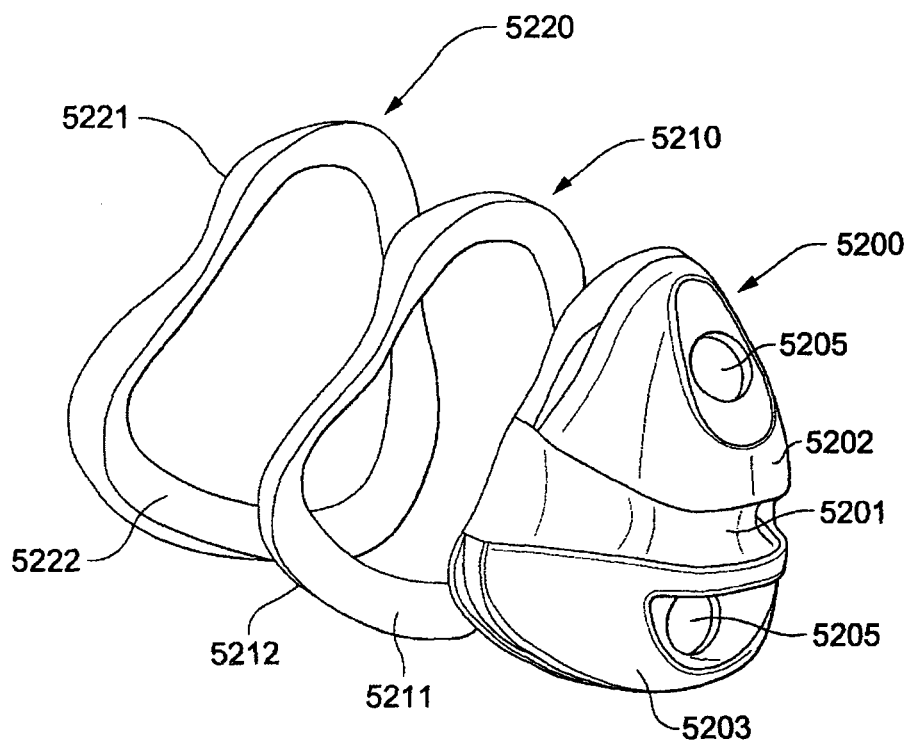
FIG. 62 shows an exploded isometric view of a portion of a mask according to an embodiment of the present technology.

FIG. 62 shows a structural element 5200, positioning element 5210, and a conforming element 5220. Structural element 5200 may provide the mask system with a generally dome or hemispherical shape to avoid contacting the patient's nose in use. The positioning element 5210 may provide shape and support to a conforming element 5220. Positioning element 5210 may also connect the conforming element 5220 to the structural element 5200. Conforming element 5220 may contact the patient and/or provide a comfortable compression region with the patient so that they may sealingly engage with the mask system.

Skeleton or structural element 5200 may be resilient, elastic and/or flexible. Skeleton may include one or more orifices 5205 adapted for engagement with an adjustment mechanism, vent, elbow, air delivery tube, etc. Skeleton 5200 may include an adjustment region 5201 that may be flexible or deformable to allow an upper region 5202 to be realigned or repositioned with respect to a lower portion 5203 of skeleton 5200. Preferably, skeleton 5200 may be constructed of a resilient material such as silicone, nylon, TPU, thermoplastic elastomers (TPE). Preferably, adjustment region 5201 may be more flexible than upper region 5202 and lower region 5203. This may be achieved by using a different material for adjustment region 5201 and attaching it to upper region 5202 and lower region 5203. Preferably, skeleton 5200 may be formed from the same material, with adjustment region 5201 having a thickness less than at least a portion of the upper region 5202 and lower region 5203. Preferably, adjustment region may be positioned between upper region 5202 and lower region 5203.

Figure 63:
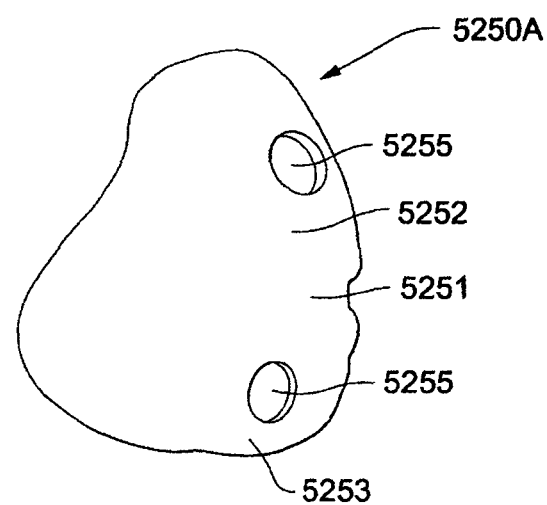
FIG. 63 shows a portion of a mask according to an embodiment of the present technology.
Figure 64:
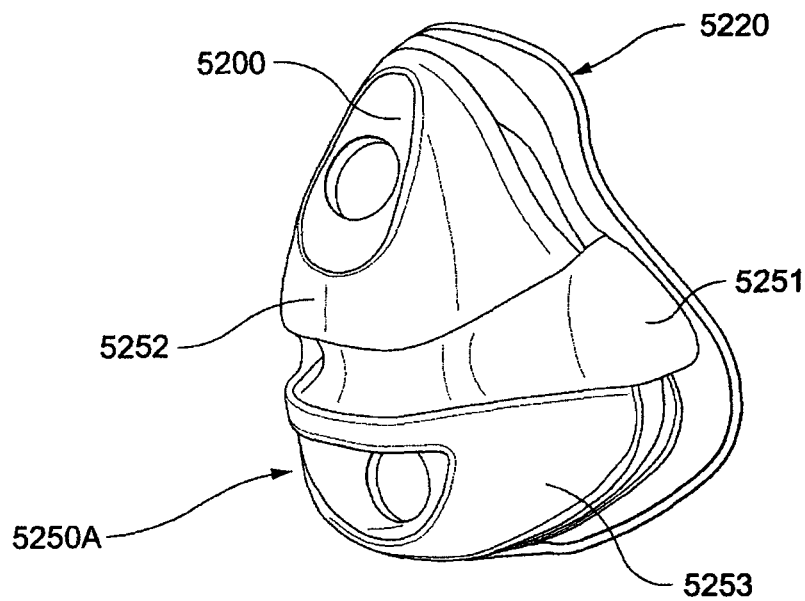
FIG. 64 shows a front isometric view of a mask according to an embodiment of the present technology.
Figure 65:
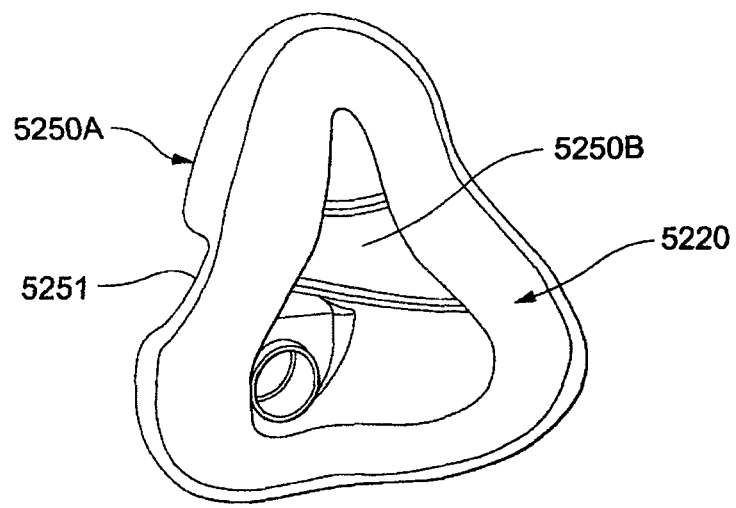
FIG. 65 shows a rear isometric view of a mask according to an embodiment of the present technology.
Figure 66:
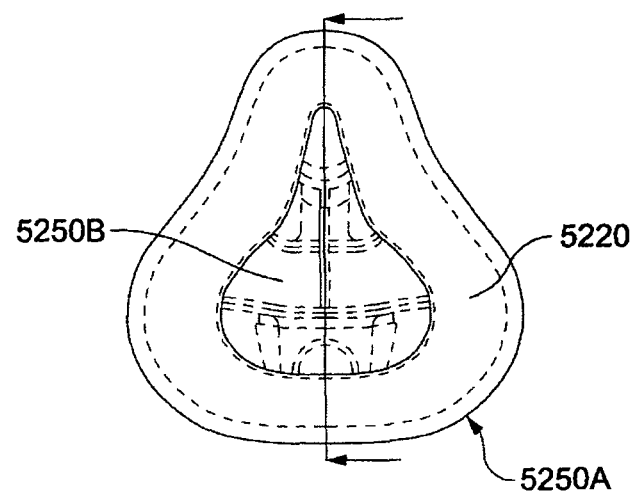
FIG. 66 shows a rear view of a mask according to an embodiment of the present technology.
Figure 67:
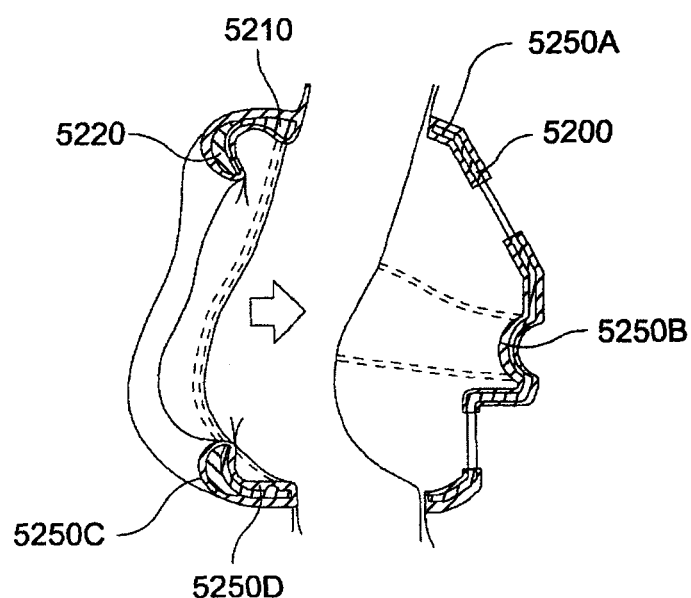
FIG. 67 shows an exploded section view of a mask according to an embodiment of the present technology.

Skeleton 5200 may be encapsulated or coated with a membrane having a first portion 5250A and a second portion 5250B as shown in FIGS. 63-69. First portion 5250A (as shown in FIG. 63) may be positioned on the outer or non-patient contacting side of the skeleton, with upper portion 5252 to align with upper region 5202 and lower portion 5253 to align with lower region 5203. First portion 5250A may have one or more orifices 5255 to align with the orifices on the skeleton, e.g., orifices 5255 sealed at respective orifices on skeleton so first portion 5250A does not cover orifices on skeleton. First portion 5250A may additionally include an adjustment region 5251 that may align with the adjustment region on the skeleton. Second portion 5250B may be positioned on the inner or patient contacting side of the skeleton. Second portion 5250B may be joined to first portion 5250A around the perimeter of structural element 5200. This joint may be created by thermoforming, gluing, stitching etc. This arrangement is shown in FIG. 67.

Positioning element 5210 may engage, attach, and/or be formed with conformable element 5220. Positioning element 5210 may have a first side 5211 and a second side 5212, where one of these sides may be aligned next to the structural element 5200 and the other side aligned or positioned proximal to the conforming element 5220. Positioning element may be shaped to curve inwards in order to position the conforming structure into an effective sealing position. Conforming element 5220 may have a first side 5222 and a second side 5221, where one of these sides may be aligned next to the positioning element 5210 and the other side aligned or positioned proximal to the patient.

Figure 68:
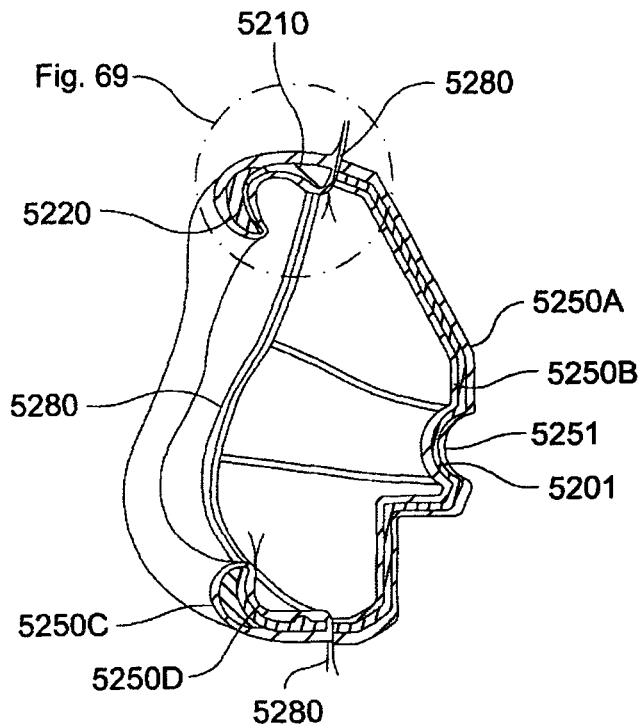
FIG. 68 shows a section view of a mask according to an embodiment of the present technology.
Figure 69:
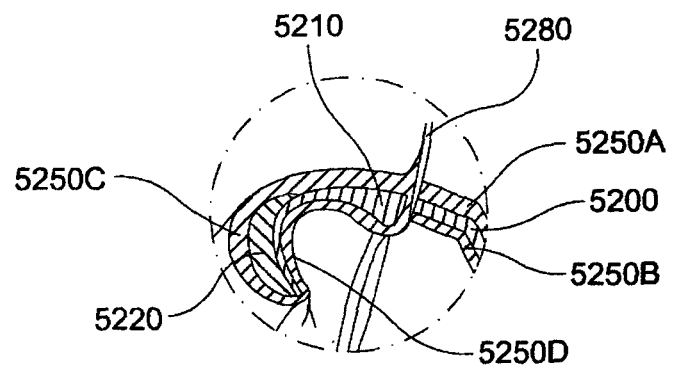
FIG. 69 shows a portion of a section view of a mask according to an embodiment of the present technology.
Figure 70:
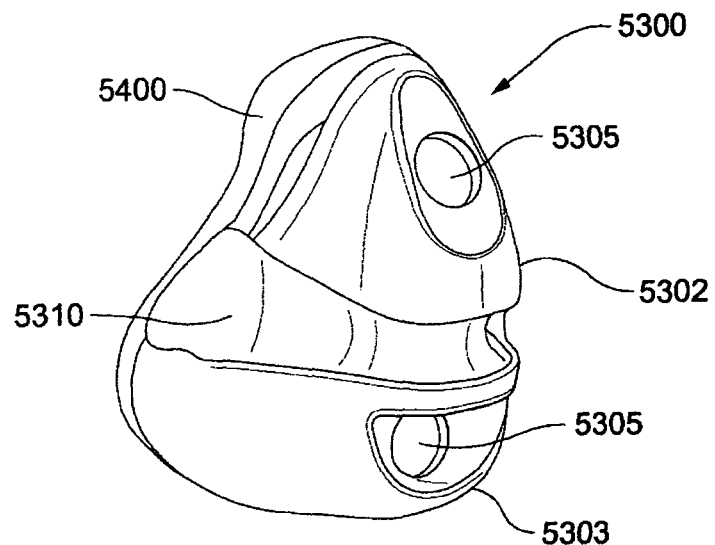
FIG. 70 shows a portion of a mask according to an embodiment of the present technology.
Figure 71:
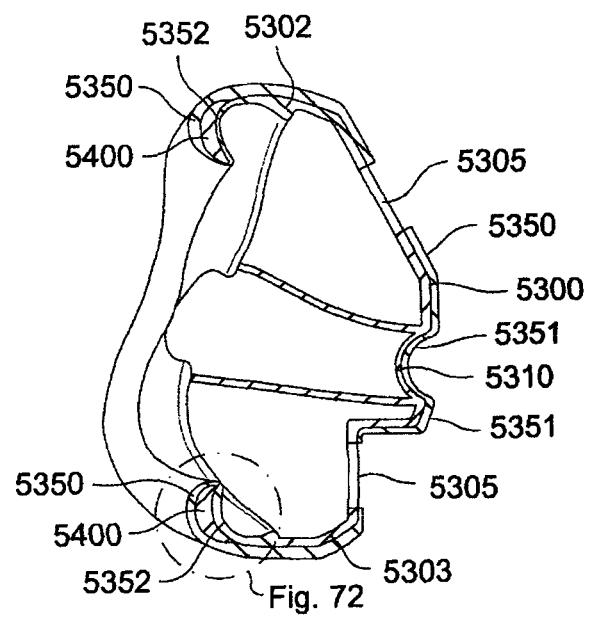
FIG. 71 shows a section view of a mask according to an embodiment of the present technology.

In a preferred embodiment, conforming element 5220 may interface with the positioning element 5210 to form an internal portion. The internal portion may be encapsulated or covered by a membrane or coating. The membrane may comprise a first portion 5250C and a second portion 5250D as shown in FIGS. 67-69. First portion 5250C may be positioned on the outer portion or patient contacting portion of the mask system. Second portion 5250D may be positioned within or on the inner surface of the mask system. Second portion 5250D may be joined to first portion 5250C around the perimeter of inner portion. This joint may be created by thermoforming, gluing, stitching etc. This arrangement is shown in FIG. 67.

Preferably, membranes 5250A, 5250B, 5250C and 5250D may be constructed of a woven or non-woven fabric. In an embodiment, the conforming element 5220 may be constructed of foam (e.g., open cell polyurethane foam with thickness of about 1-10 mm, e.g., 5 mm), and the positioning element 5210 may be constructed of TPU, silicone, etc. However, it should be appreciated that other suitable materials may be used.

FIG. 68 shows the assembly of the structural element 5200 with the sub-assembly of the positioning element 5210 and conforming element 5220. That is, structural element 5200 and the positioning/conforming element sub-assembly 5210, 5220 are separately covered with membrane layers (e.g., fabric), and then the membrane covered structural element and the membrane covered positioning/conforming element sub-assembly are attached to one another. The membrane layers from the structural element 5200 and the sub-assembly (positioning element 5210 and conforming element 5220) may connect at region 5280. The membrane layers may be attached by gluing, welding, hook and loop, press stud or other connecting mechanism. Preferably, the connecting mechanism is air tight to prevent leak between the surfaces. FIG. 69 shows the connecting region 5280 in more detail.

3.9.3 Thermoformed Embodiment 3

FIGS. 70 to 73 show an alternative embodiment of the present technology. Supporting structure or structural element 5300 may form the body or frame of the mask system. Supporting structure 5300 may include upper region 5302 and lower region 5303. Upper region 5302 and lower region 5303 may be spaced or separated by an adjustable region 5301. Adjustable region 5310 may allow upper region 5302 to be movably positionable in relation to lower region 5303. Supporting structure 5300 may also include one or more orifices or apertures 5305 for connection with a vent, adjustment mechanism, elbow, air delivery tube, etc.

Supporting structure 5300 may include positioning portion 5352 that may be on the patient contacting side of the supporting structure, and may have a generally C-shaped cross section or curve inwards towards the inner region of the supporting structure. Positioning portion 5352 may enable conforming portion 5400 to be in a position or alignment that may enable or enhance the seal of the mask to the patient.

Supporting structure 5300 may be constructed of a single material, such as silicone, TPU or TPE. Regions requiring greater flexibility than other regions of the mask system (such as adjustable region 5310 or positioning portion 5352) may have a reduced thickness to allow greater flexibility. Alternatively, supporting structure may be constructed of various materials to enable different flexibility and elasticity of each region.

Conforming portion 5400 may be comfortable, flexible and deformable. Conforming portion 5400 may be constructed of a foam (e.g., open cell polyurethane foam), gel, silicone, TPE, TPU, fabric, etc. Conforming portion may interface or otherwise align with positioning portion 5352 of supporting structure 5300.

Membrane or covering 5350 may be adapted to wrap or coat supporting structure 5300 and conforming portion 5400. Preferably, membrane 5350 may be a fabric that may be thermoformed onto the supporting structure 5300 and conforming portion 5400. Preferably, the supporting structure may be coated or constructed of a TPU or other material that may adhere to the covering 5350.

Figure 72:
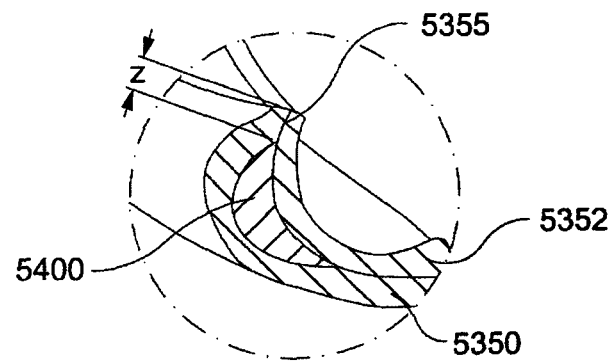
FIG. 72 shows a portion of a section view of a mask according to an embodiment of the present technology.
Figure 73:
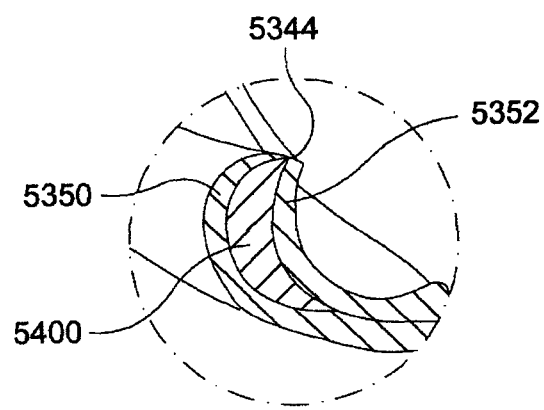
FIG. 73 shows a portion of a section view of a mask according to an embodiment of the present technology.

As shown in FIGS. 72 and 73, membrane 5350 may attach to the supporting structure 5300 along a surface 5355. As shown in FIG. 72, the length Z of surface 5355 may be 1-10 mm, e.g., 3-8 mm, 5 mm. Surface 5355 may increase the integrity and longevity of the seal and adhesion between covering 5350 and supporting structure 5300. Alternatively, covering 5350 may attach to conforming portion 5400. In a further alternative, covering 5350, conforming portion 5400 and supporting structure 5300 may join at a point or knife edge 5344 (see FIG. 73). This may be sealed or otherwise joined by die cutting, ultrasonic die cutting, sowing, adhesive or other method.

In the illustrated embodiment, the membrane 5350 is only provided along the outer side of the supporting structure 5300 and the patient contacting side of the conforming portion 5400, i.e., not along the inner side of the supporting structure 5300 and the non-patient contacting side of the conforming portion 5400. The membrane 5350 includes one or more orifices to align with the orifices 5305 on the supporting structure 5300, e.g., orifices of membrane sealed at respective orifices on supporting structure so membrane does not cover orifices on supporting structure.

3.9.4 Alternative Cushion Embodiments

FIGS. 106-114 illustrate alternative embodiments of a cushion constructed of a combination of materials, e.g., foam, fabric, semi-rigid element, and/or silicone. These materials provide an adjustable cushion that provides a robust seal by limiting the deformation at the sealing surface throughout size adjustment. A combination of foam and fabric on top of a silicone spring allows for minimal deformation through compression and stretch as the foam fabric is very pliable. The silicone spring provides a relatively large amount of travel to accommodate the different contours of the patient's face without adding bulk to the mask and also provides some structure for cushion size adjustment to occur accurately.

Figure 106:
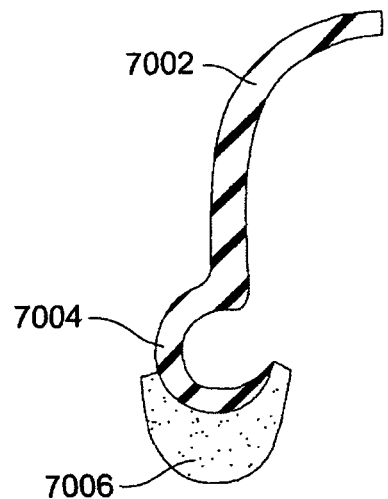
FIGS. 106 to 114 are cross-sectional views showing alternative cushion embodiments.

FIG. 106 shows a cushion including a silicone frame portion or fascia 7002, a silicone undercushion 7004, and a foam sealing portion 7006. The silicone fascia provides flexibility to the front of the mask and allows cushion size adjustability. The silicone undercushion minimizes overall bulk, allows for gross spring adjustment, and minimizes leak through the foam sealing portion. The foam sealing portion minimizes distortion at the sealing surface when adjusting the cushion size using the pliable material properties of foam, fills small creases/wrinkles on the patient's face, and provides comfort on initial contact.

The silicone undercushion may be provided along one or selected portions of the cushion perimeter. For example, the silicone undercushion may be provided along the entire perimeter of the cushion, or the silicone undercushion may be removed in one or more portions of the cushion perimeter (e.g., silicone undercushion not provided in nasal bridge and chin or upper lip regions so only foam sealing portion provides sealing force in these regions).

Figure 107:
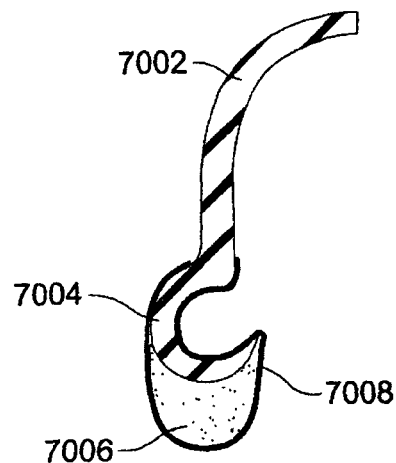

FIG. 107 shows a cushion similar to that of FIG. 106. In contrast, the cushion of FIG. 107 includes a fabric layer 7008 over the silicone undercushion 7004 and the foam sealing portion 7006. The fabric layer improves the durability of the foam, may improve comfort (smooth surface finish, soft to touch, etc.), and improves aesthetics.

Figure 108:
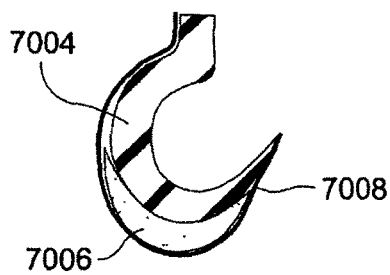

FIG. 108 shows an arrangement without the fascia, i.e., silicone/TPE undercushion or spring element 7004, foam portion 7006, and fabric layer 7008 along the outer side of the foam portion and undercushion.

Figure 109:
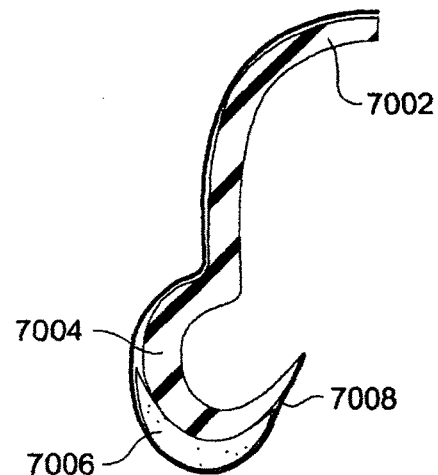

FIG. 109 shows a silicone/TPE fascia 7002 and undercushion 7004, a foam portion 7006, and a fabric layer 7008 only along the outer side of the foam portion, undercushion, and fascia.

Figure 110:
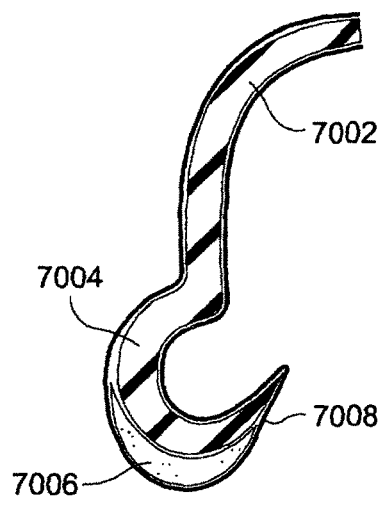

FIG. 110 shows a silicone/TPE fascia 7002 and undercushion 7004, a foam portion 7006, and a fabric layer 7008 along the outer side of the foam portion, undercushion, and fascia and the inner side of the undercushion and fascia.

Figure 111:
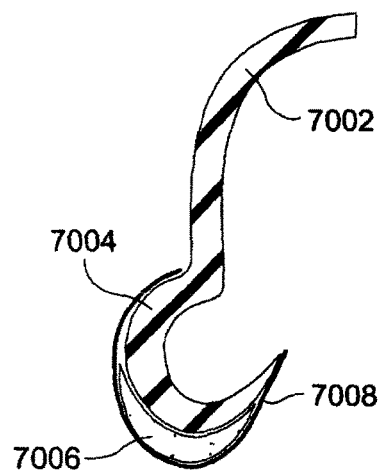

FIG. 111 shows a silicone/TPE fascia 7002 and undercushion 7004, a foam portion 7006, and a fabric layer 7008 only along the outer side of the foam portion and undercushion.

Figure 112:
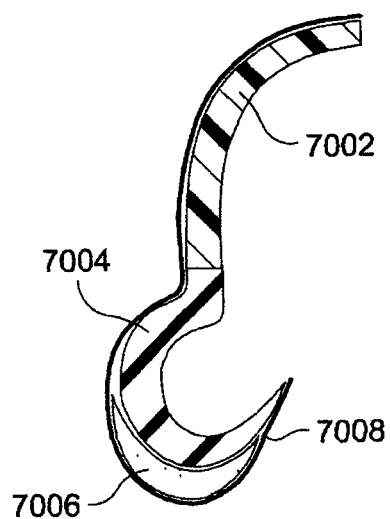

FIG. 112 shows a semi-rigid fascia 7002, a silicone/TPE undercushion 7004, a foam portion 7006, and a fabric layer 7008 only along the outer side of the foam portion, undercushion, and fascia.

Figure 113:
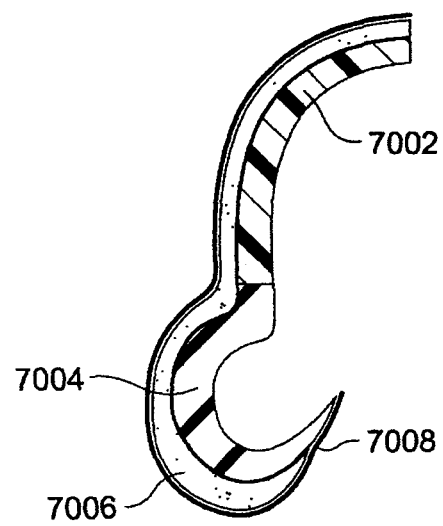

FIG. 113 shows a semi-rigid fascia 7002, a silicone/TPE undercushion 7004, a foam portion 7006 that extends along the outer side of the undercushion and fascia, and a fabric layer 7008 that extends along the foam portion along the outer side of the undercushion and fascia.

Figure 114:
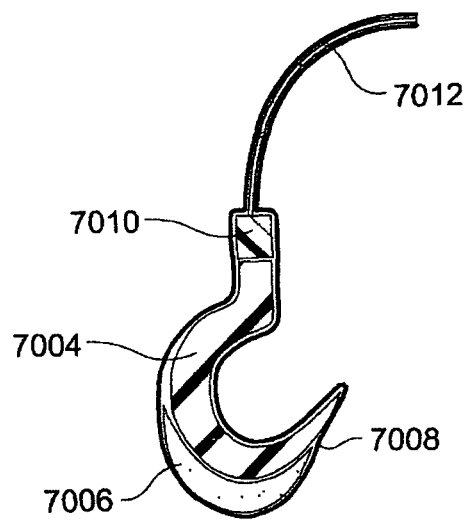
Figure 115:
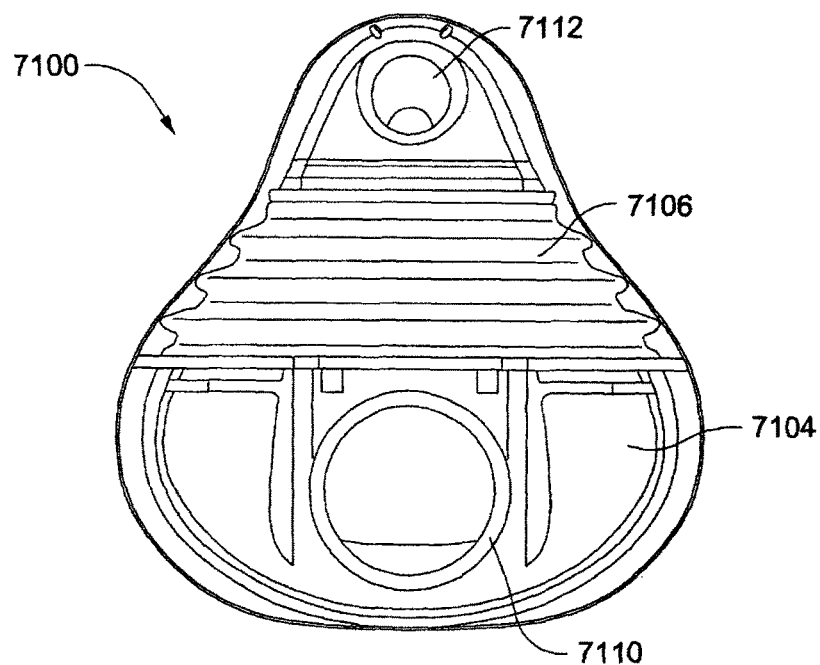
FIGS. 115 and 116 are front and rear views of an integrated cushion and frame according to an embodiment of the technology.
Figure 116:
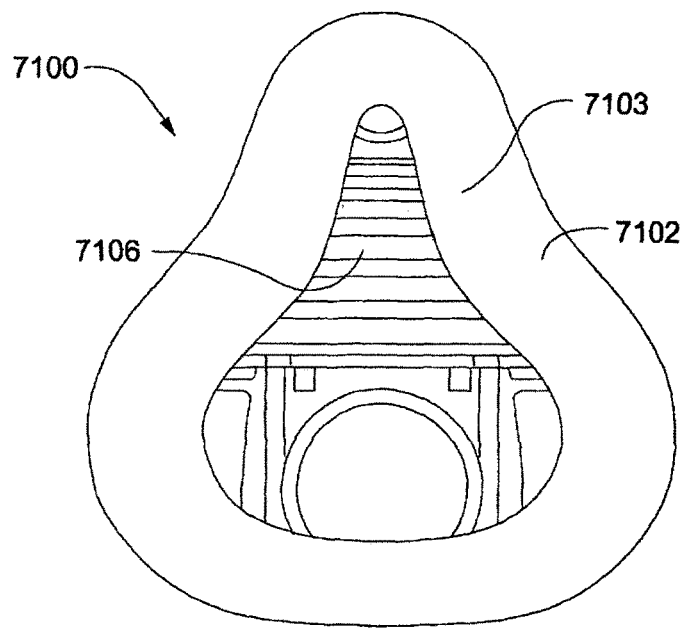
Figure 117:
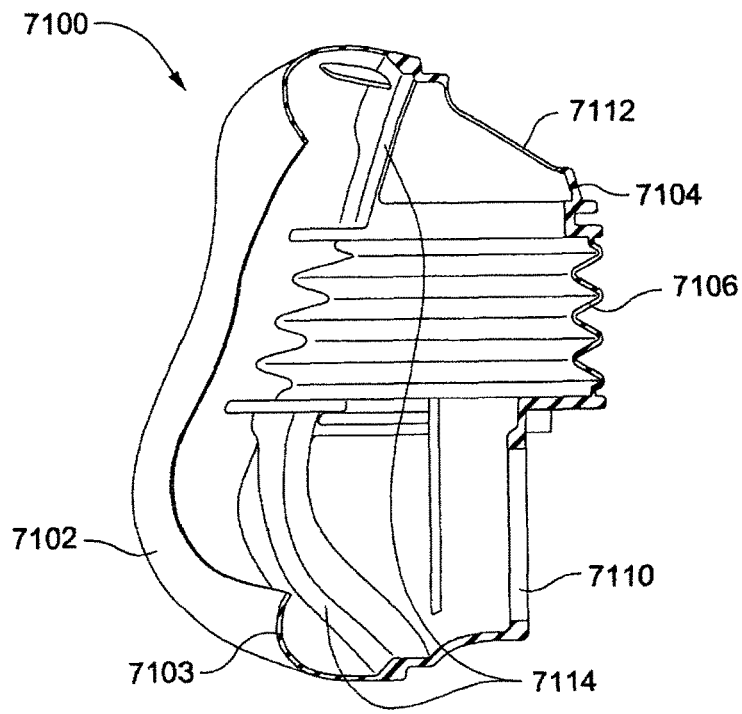
FIGS. 117 and 118 are cross-sectional views of the integrated cushion and frame of FIGS. 115 and 116.
Figure 118:
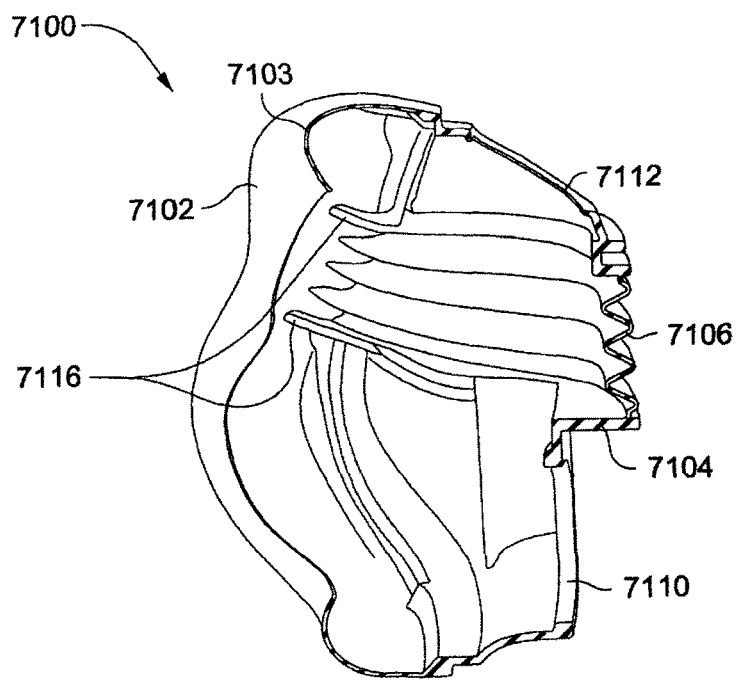
Figure 119:
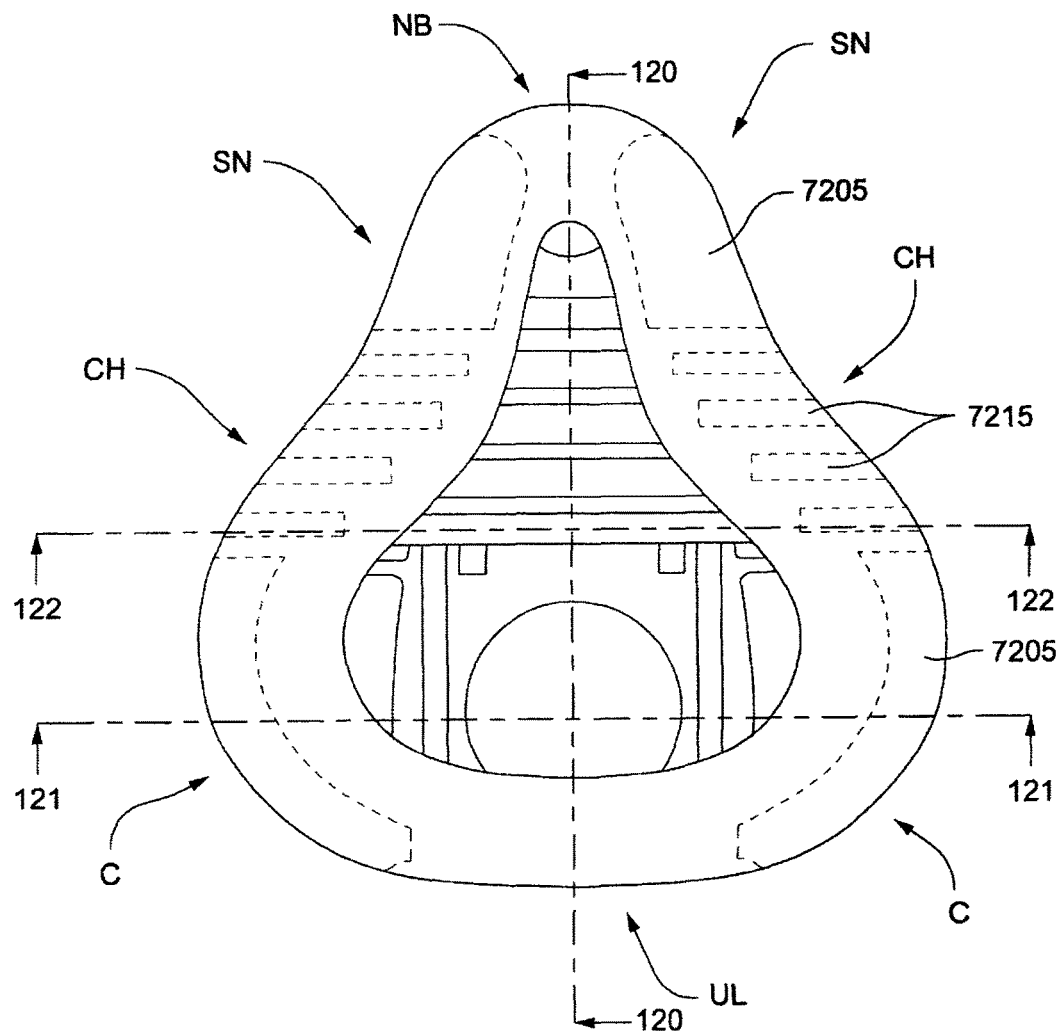
FIG. 119 is a rear view of an integrated cushion and frame according to another embodiment of the technology.
Figure 120:
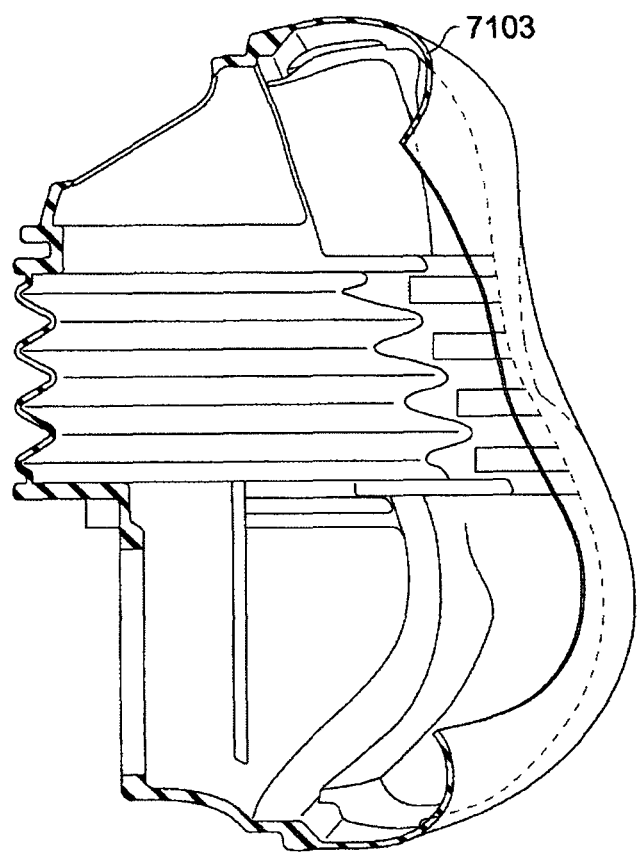
FIGS. 120 to 122 are cross-sectional views through the integrated cushion and frame of FIG. 119.
Figure 121:
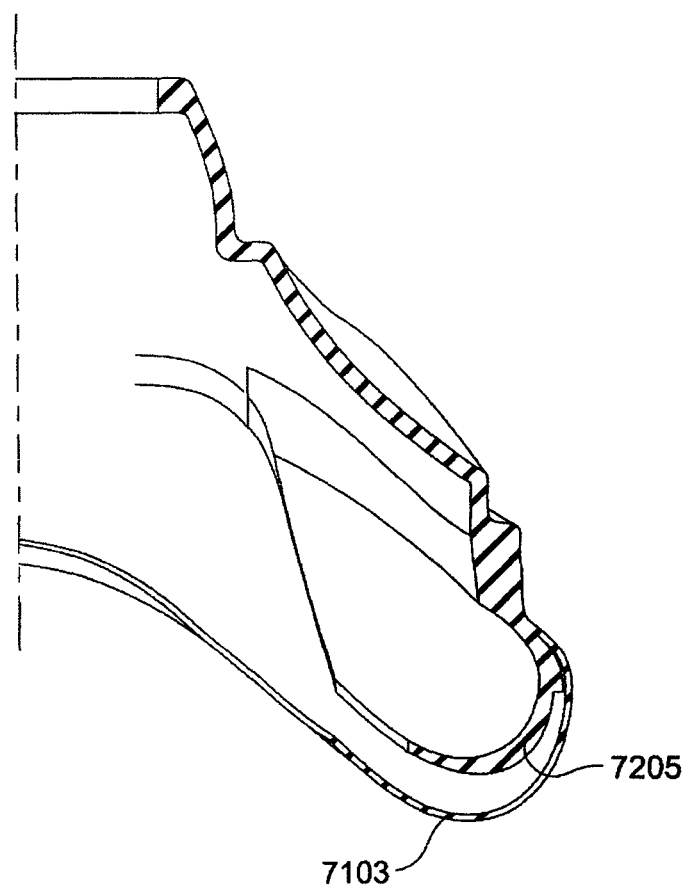
Figure 122:
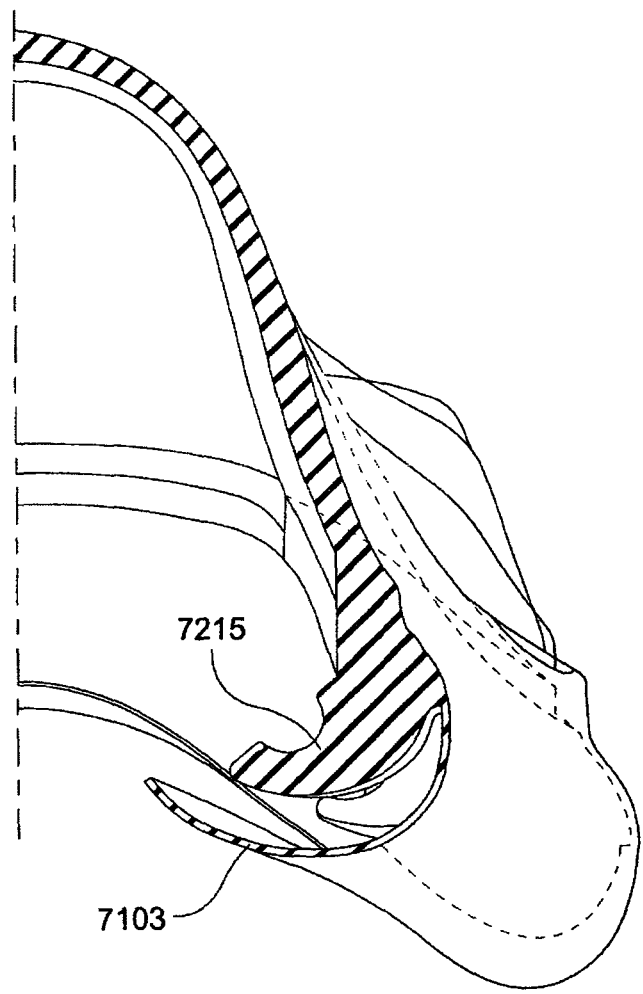

FIG. 114 shows a laminated foam/fabric (air tight) fascia 7012, a semi-rigid skeleton frame 7010, a silicone/TPE undercushion 7004, a foam portion 7006, and a fabric layer 7008 along the outer side of the foam portion, undercushion, skeleton frame, and fascia, and the inner side of the undercushion, skeleton frame, and fascia.

3.10 Pocket (Insert) Example

Figures 4, 46:
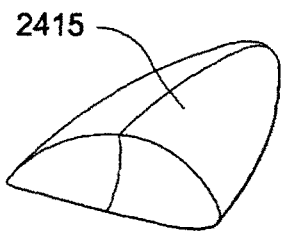
Figures 5, 46:
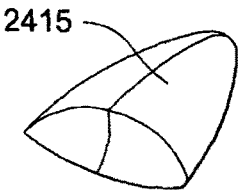
Figures 6, 46:
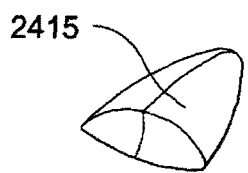

FIGS. 46-1 to 46-6 show a cushion 2418 supported by a flexible frame 2412 (e.g., constructed of silicone). The frame 2412 is molded as a "small" size and includes one or more integrated pockets 2414 each adapted to receive different size inserts 2415 (e.g., hard molded inserts, air/gel bladders, etc.). In use, a selected insert (e.g., a large size (FIG. 46-4), medium size (FIG. 46-5), or small size (FIG. 46-6)) is inserted into the frame pockets to stretch the frame and thereby adjust the size of the cushion. FIG. 46-3 shows the frame without an insert, and FIG. 46-4 shows the frame with an insert.

In this example, the cushion 2148 is stretched from a first size to a second size.

3.11 Pocket (pump) Example

As an alternative to the embodiment of FIGS. 46-1 to 46-6 described above, gas or liquid (rather than a separate insert) may be used to fill the pocket 2414, e.g., via a pump.

3.12 Flexible Trunk Example

Figure 47:
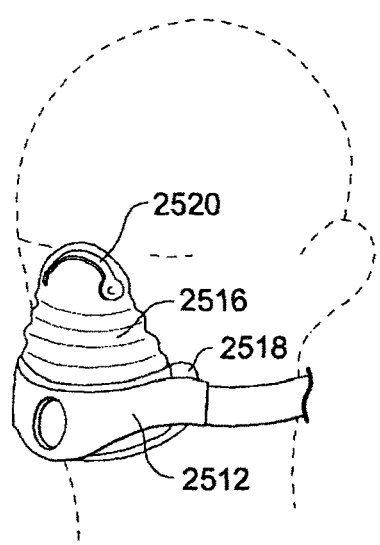
FIG. 47 shows a cushion according to an embodiment of the present technology.

FIG. 47 shows a rigid base section 2512 with a cushion 2518 adapted to seal around the patient's mouth. A flexible adjustable region or gusset structure 2516 (e.g., constructed of silicone, TPE) extends upwardly from the cushion and base section to form a seal around the patient's nose and nasal bridge region. The seal provided by the adjustable region or gusset structure may be maintained around the patient's nose through adhesive or a malleable clip 2520, for example.

The malleable clip 2520 clamps or pinches the cushion onto the patient's nose.

3.13 Scrolling Example

Figures 1, 48:
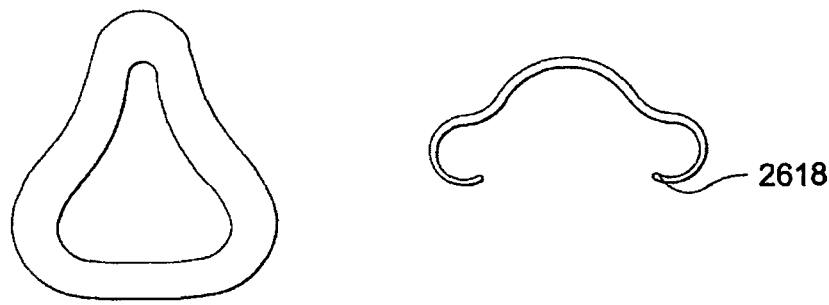
Figures 2, 48:
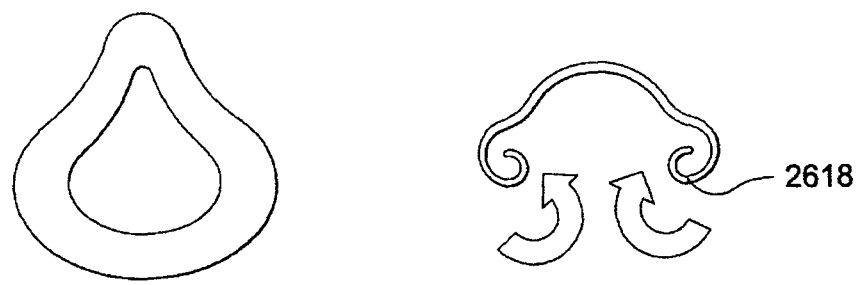
Figures 3, 48:
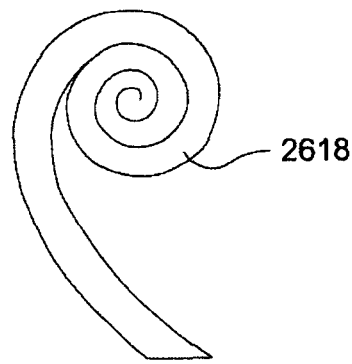

FIGS. 48-1 to 48-3 show a flexible frame with integrated cushion. As illustrated, the membrane 2618 of the cushion is inverted and can be scrolled or coiled to change the overall size of the cushion, e.g., from the configuration of FIG. 48-1 to the configuration of FIG. 48-2. That is, the membrane may be coiled in on itself to reduce the outer perimeter of the cushion and thus adjust the mask size. FIG. 48-3 is an isolated view of the membrane 2618 coiled in on itself.

3.14 Malleable Example

Figure 49:
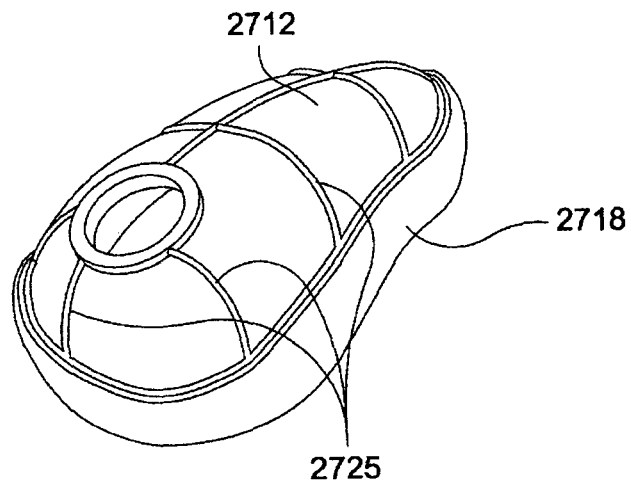
FIG. 49 shows a cushion according to an embodiment of the present technology.

FIG. 49 shows a cushion 2718 supported by a flexible frame 2712 (e.g., constructed of silicone). The flexible frame 2712 is provided (e.g., overmolded) with integrated memory components 2725, e.g., stainless steel wire matrix, wire mesh, thermoformable component, shape memory polymer. The integrated memory components allow the shape of the frame and hence the sealing profile of the cushion to be adjusted in all planes and retain such shape in use. Adjustment is accommodated through shape change, i.e., material is not stretched or compressed.

3.15 Under Nose Example

Figure 50:
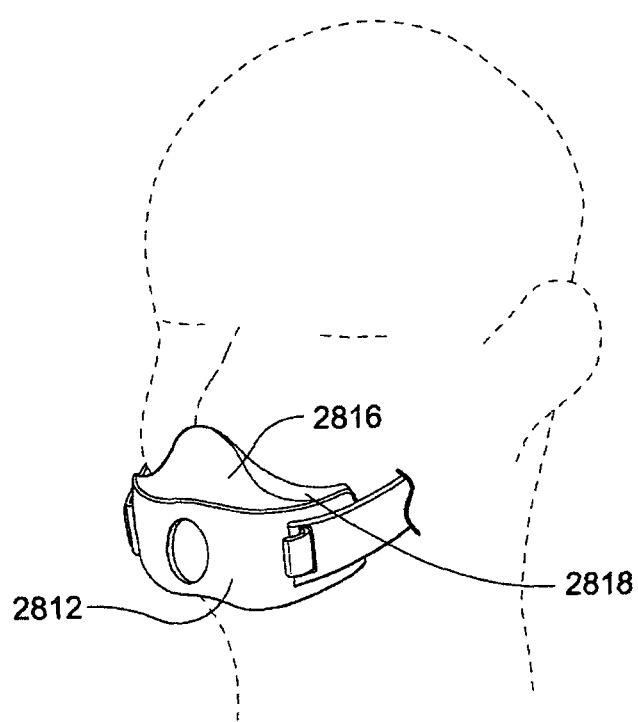
FIG. 50 shows a cushion according to an embodiment of the present technology.

FIG. 50 shows a rigid base section 2812 with a cushion 2818 adapted to seal around the patient's mouth. A separate seal structure 2816 extends upwardly from the cushion and base section to form a seal underneath the nose or form a nasal cradle around the base of the nose. Size variation may be accommodated by flexibility of the seal structure 2816.

3.16 Shape Change Examples

FIGS. 51-1 to 51-5 show various arrangements to "shape-change" into different sizes of cushion. In FIG. 51-1, one or more slits 3102 may be provided to the cushion, which allows a relatively large angular change without greatly affecting regions away from the slit. In FIG. 51-2, one or more generally U-shaped cuts 3202 may be provided to the cushion in areas that will compress during buckling of the cushion. The U-shaped cuts allow material to bend in required locations with less force. In FIG. 51-3, one or more generally U-shaped slots may be provided to the cushion to allow material to bend in required locations with less force. This arrangement is similar to the slits described above, however movement in either direction is possible due to the larger clearance between the two sides. In FIG. 51-4, the cushion 3301 may have mixed or varying curvature along its length. In such embodiment, more material may be provided in locations where flare-ups may occur, the extra material helping prevent loss of seal against the face as the material will not flare outwards as much. In FIG. 51-5, a cut 3302 may be provided a bottom of the membrane, which causes the wall to bend into the face, creating tension along the outer membrane. This tension will allow the membrane to keep its shape when the cushion is compressed into the smaller size.

Figures 1, 52:
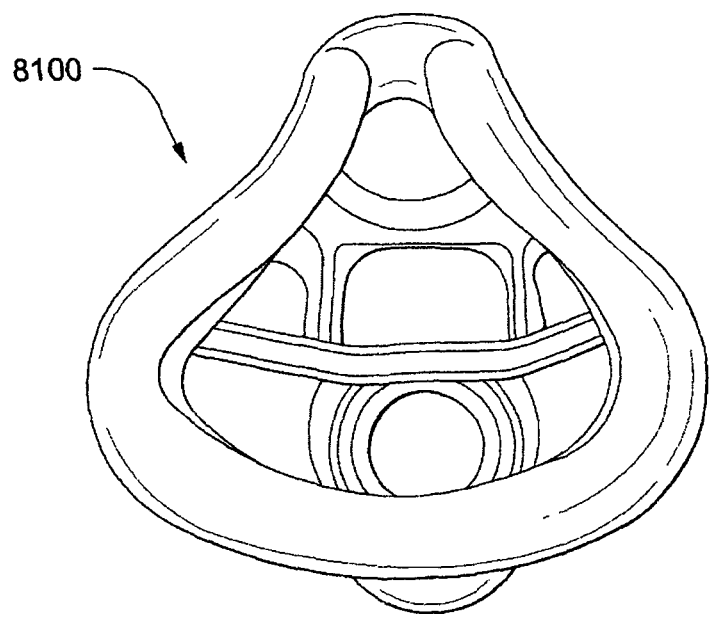
Figures 2, 52:
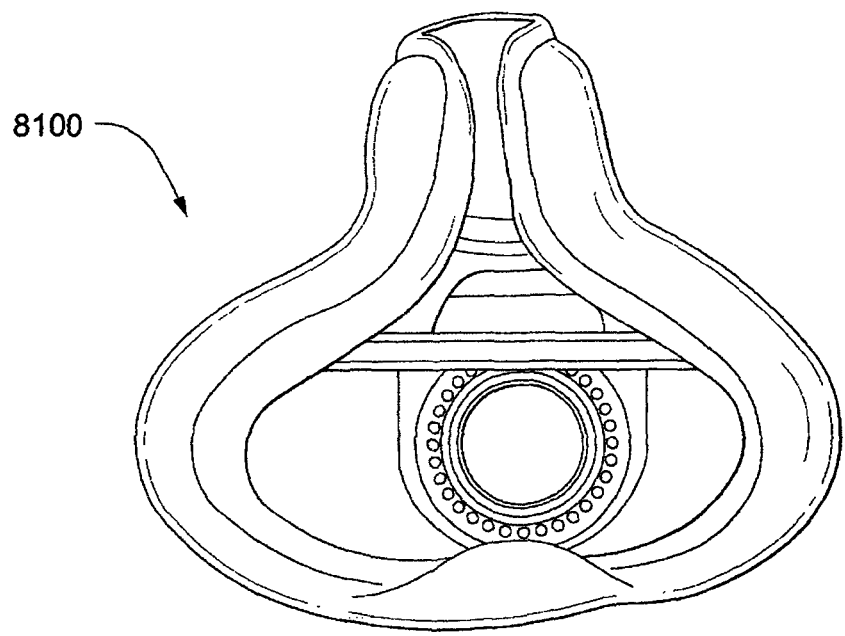
Figures 3, 52:
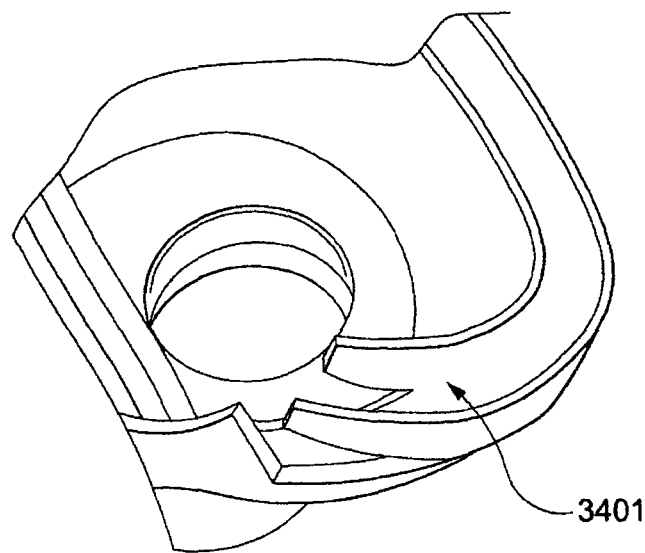
Figures 4, 52:
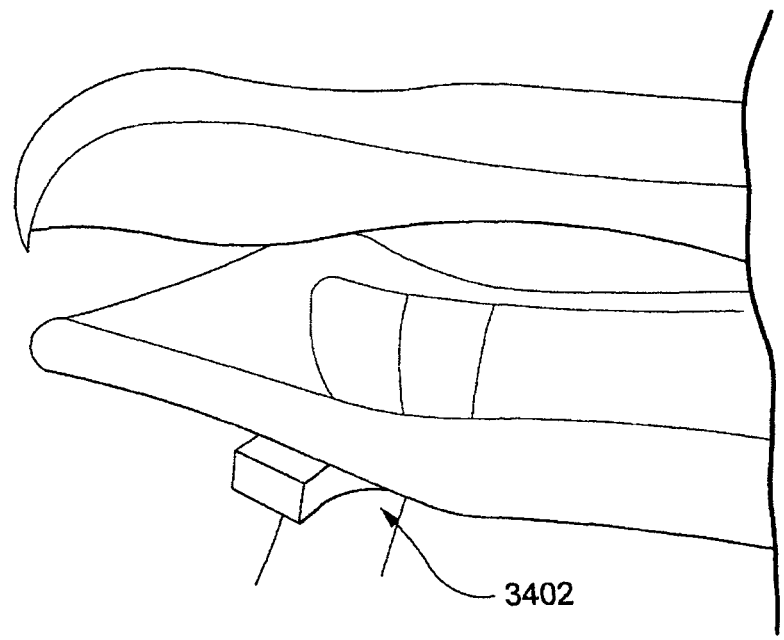
Figures 6, 52:
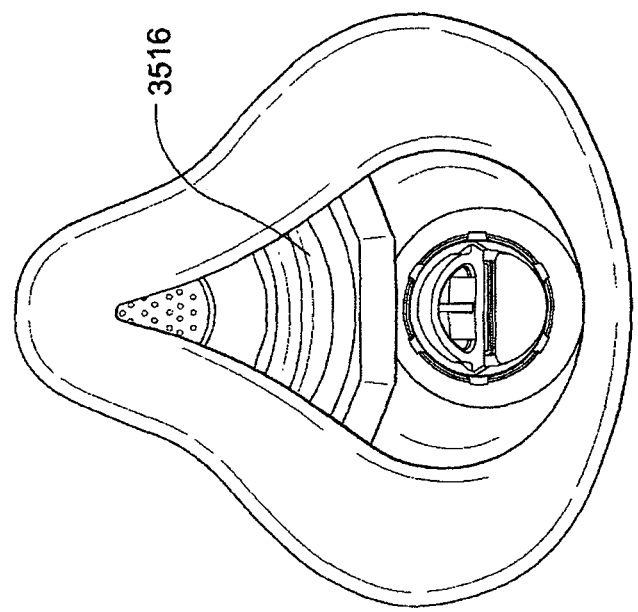
Figures 5, 52:
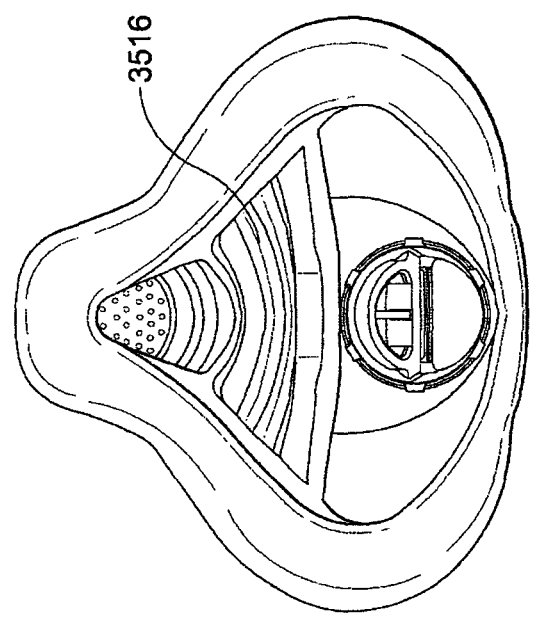
Figures 7, 52:
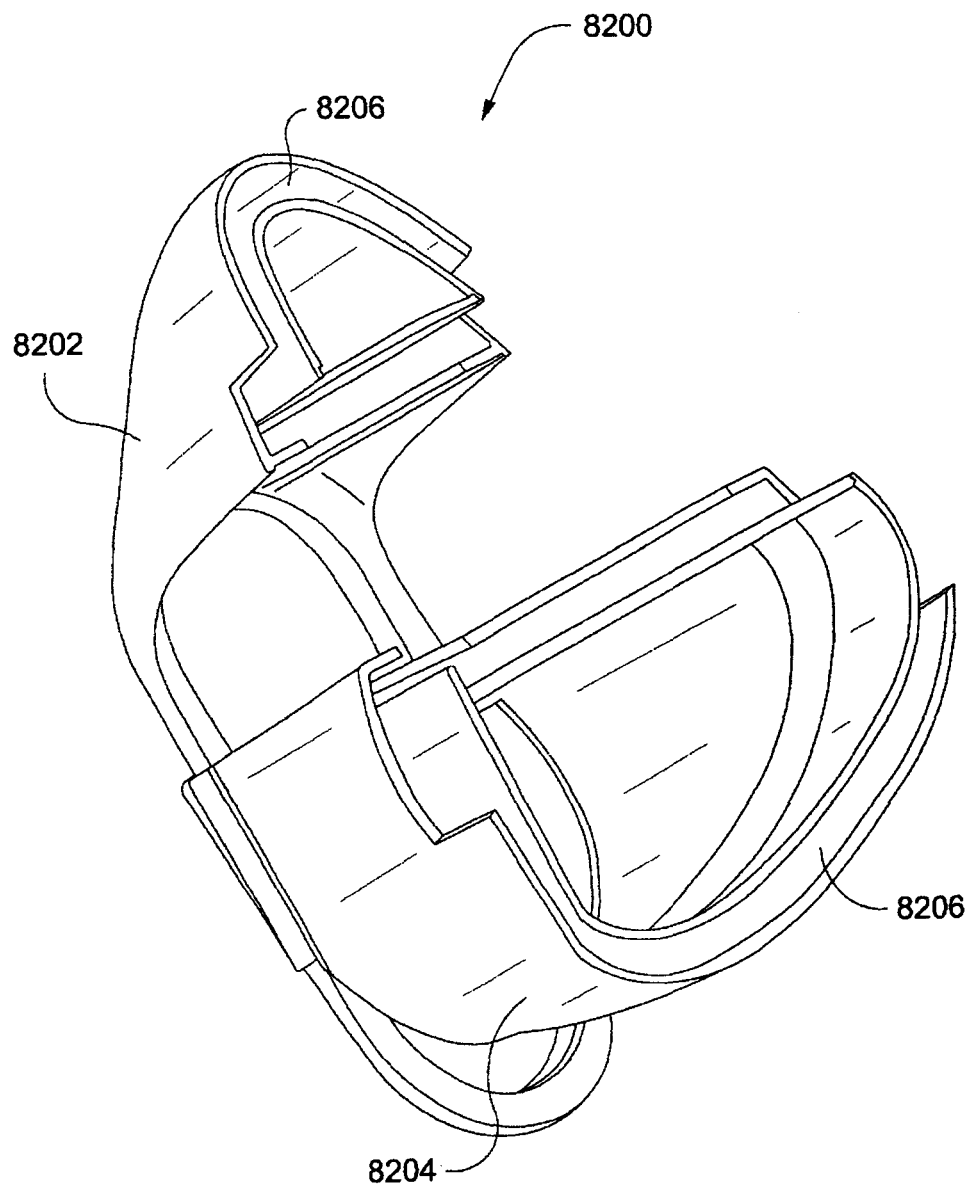
Figures 8, 52:
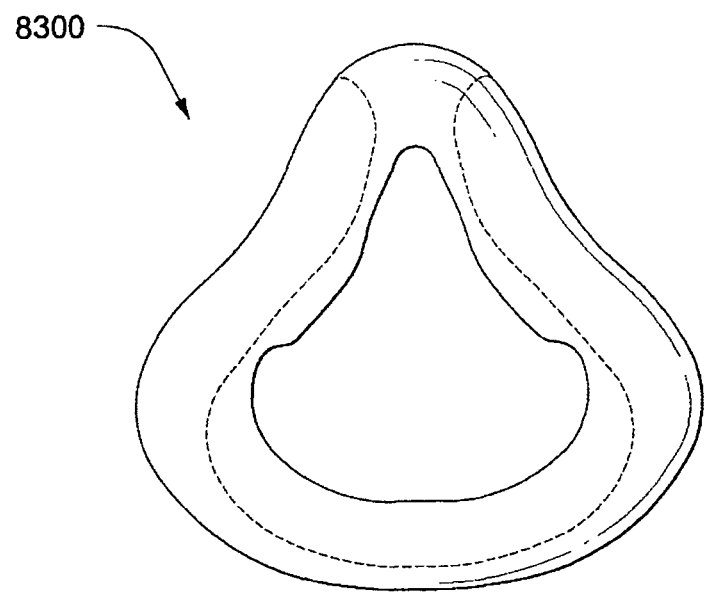
Figures 9, 52:
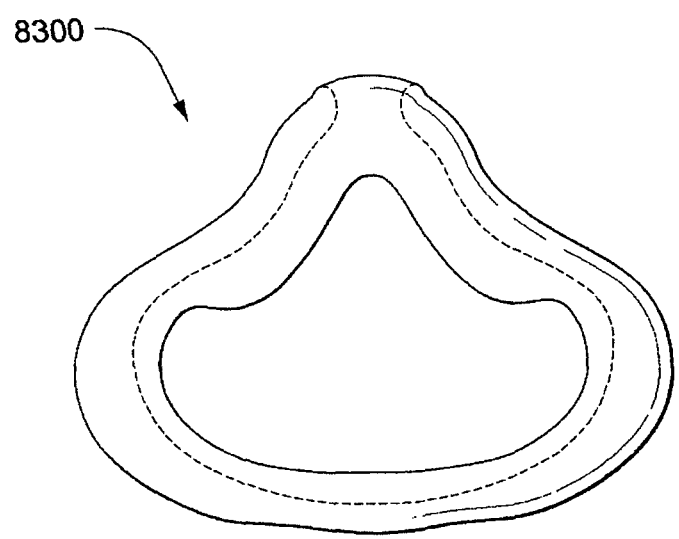
Figures 10, 52:
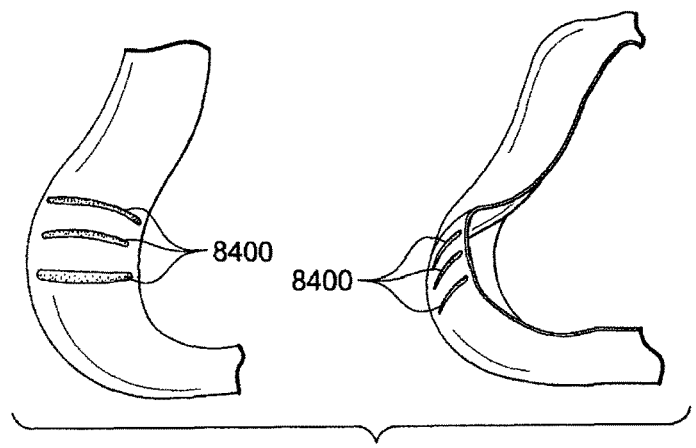
Figures 11, 52:
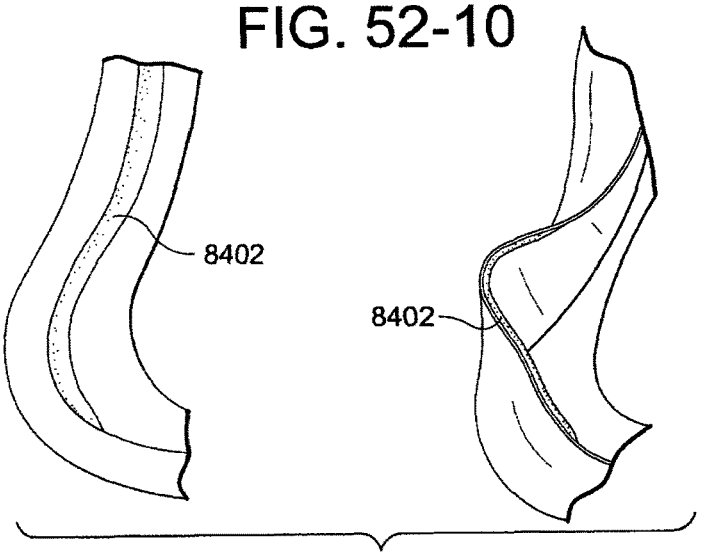
Figures 12, 52:
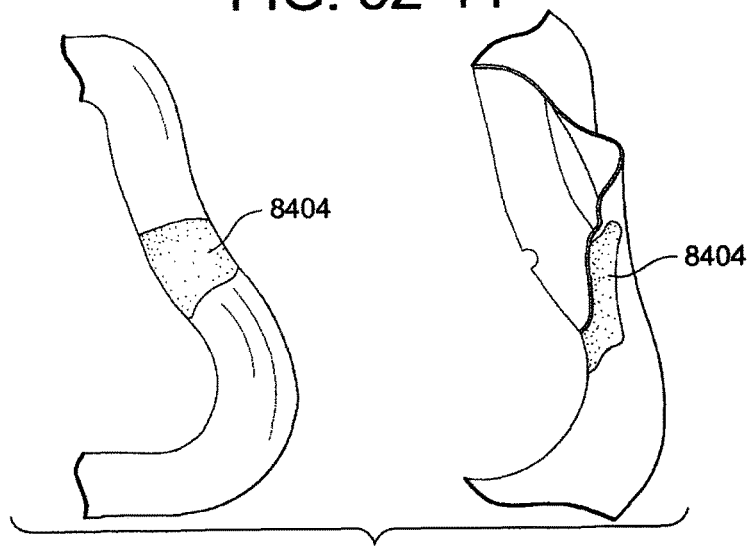
Figures 13, 52:
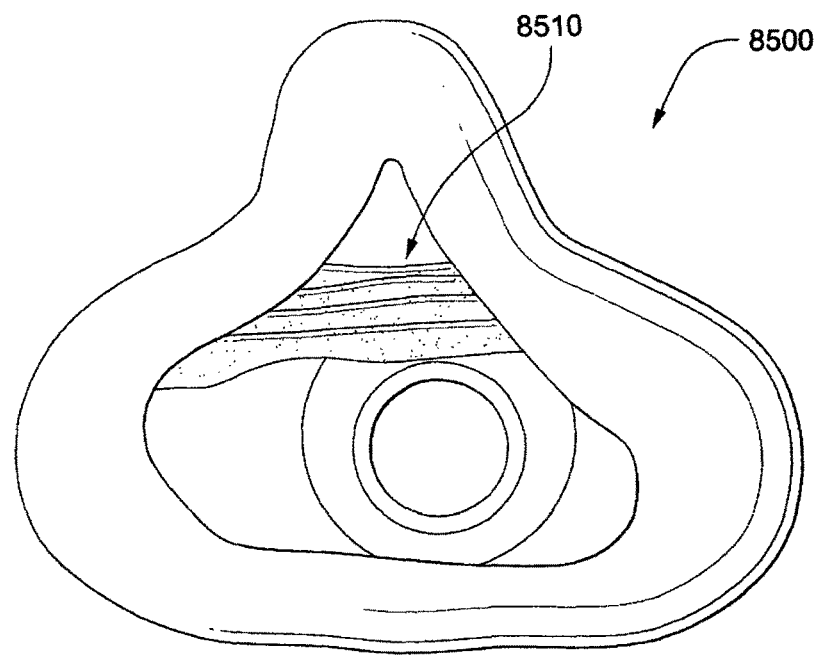
Figures 14, 52:
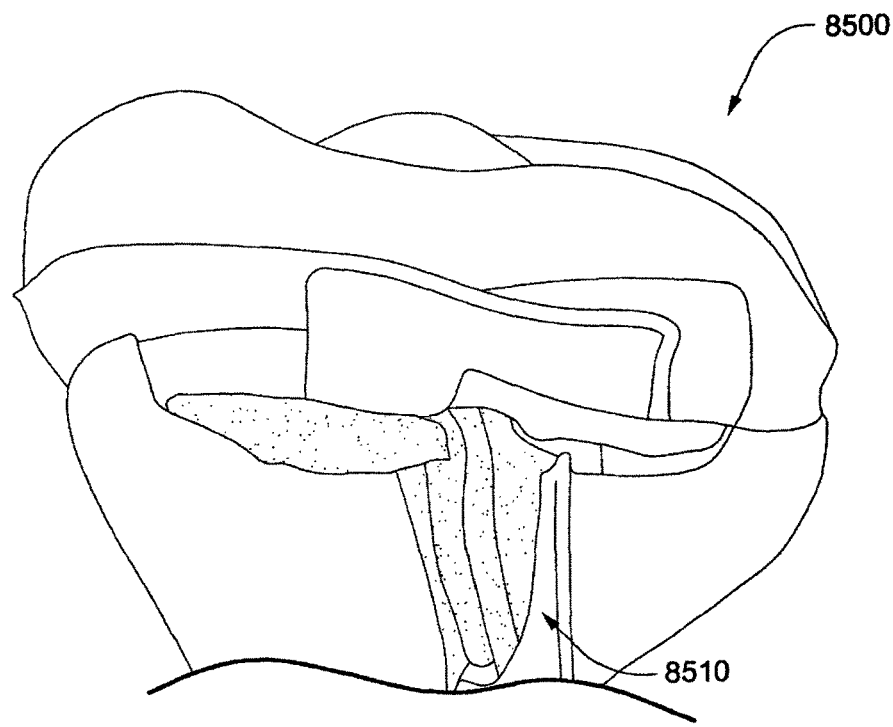
Figures 15, 52:
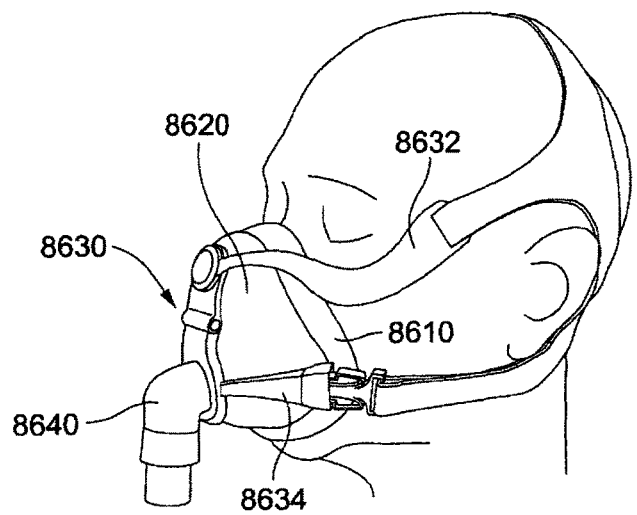
Figures 16, 52:
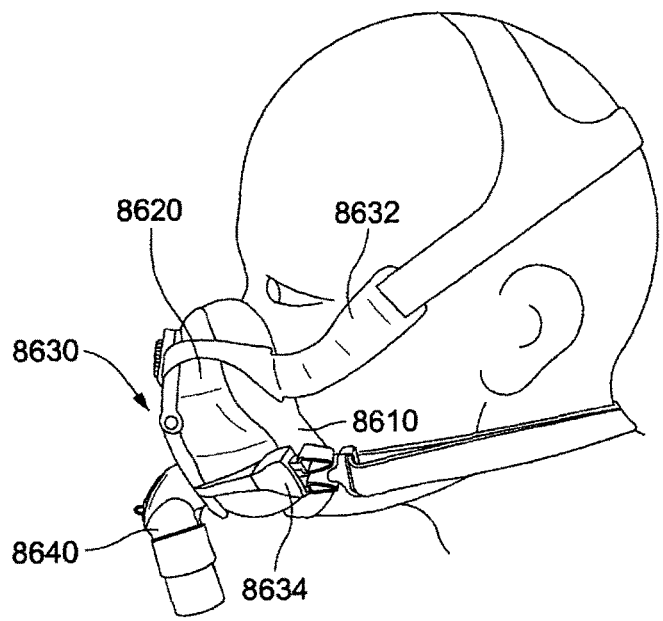
Figures 17, 52:
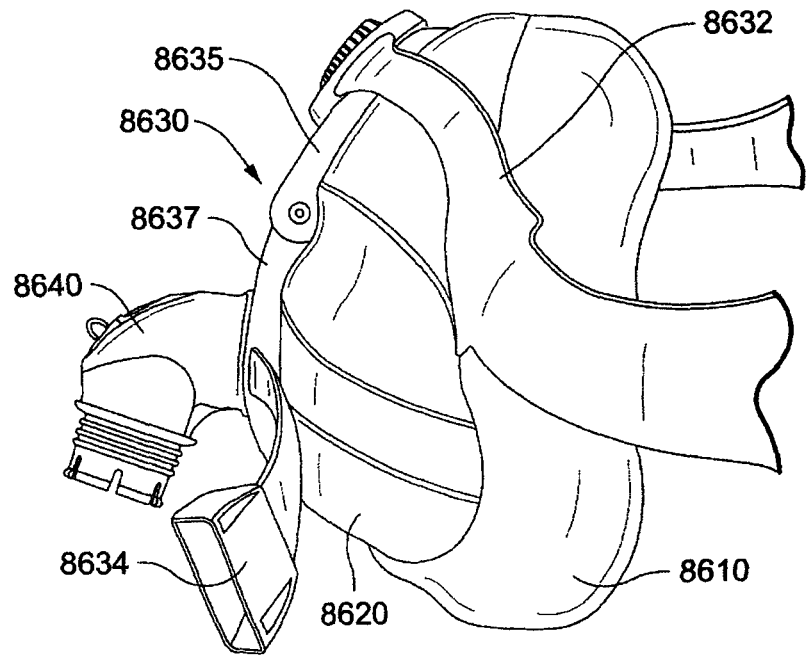
Figures 18, 52:
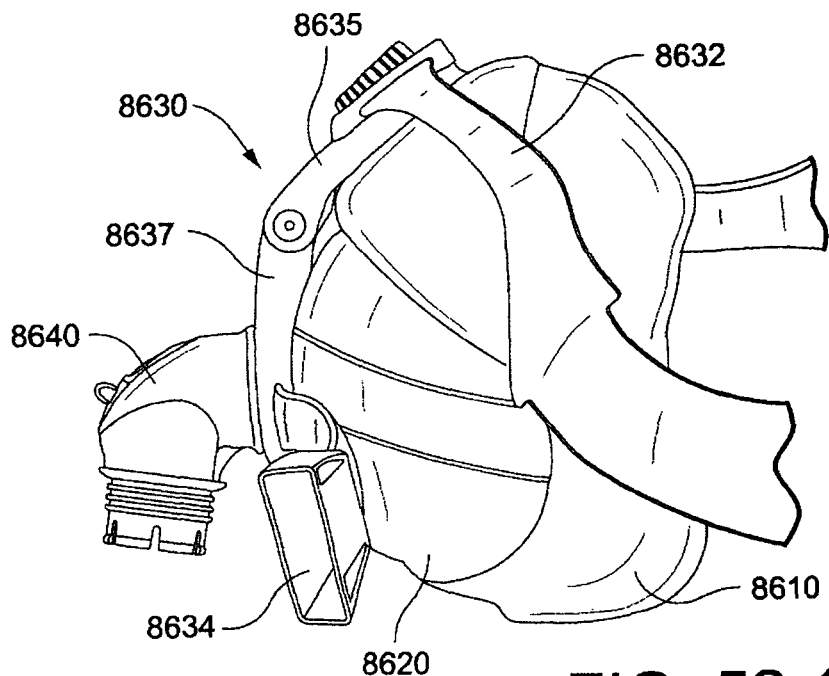
Figures 19, 52:
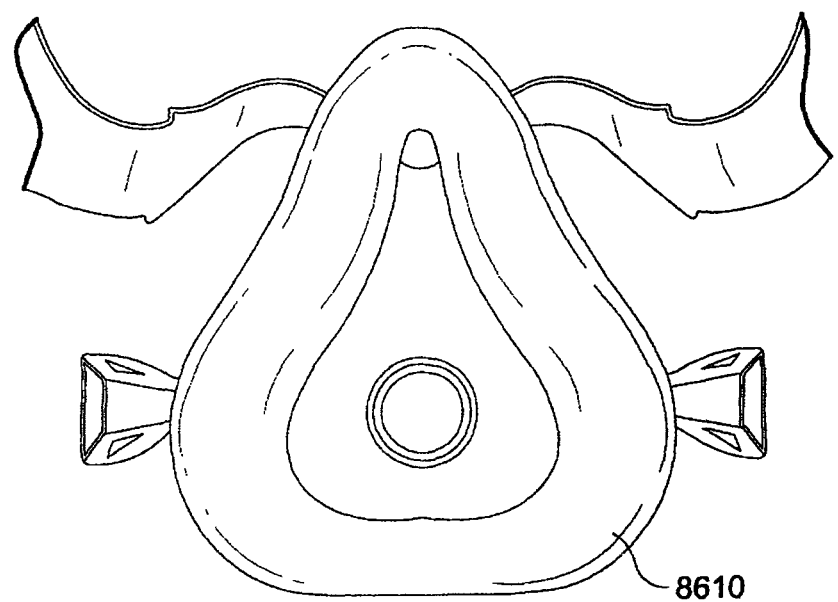
Figures 20, 52:
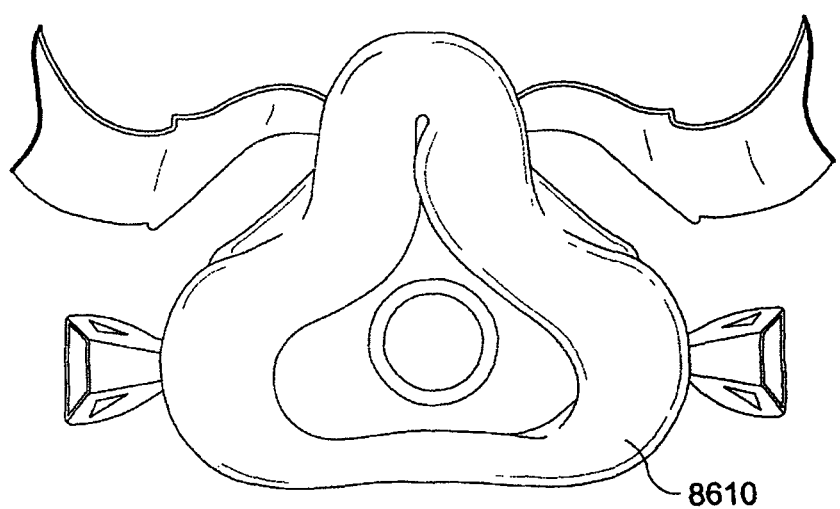
Figures 21, 52:
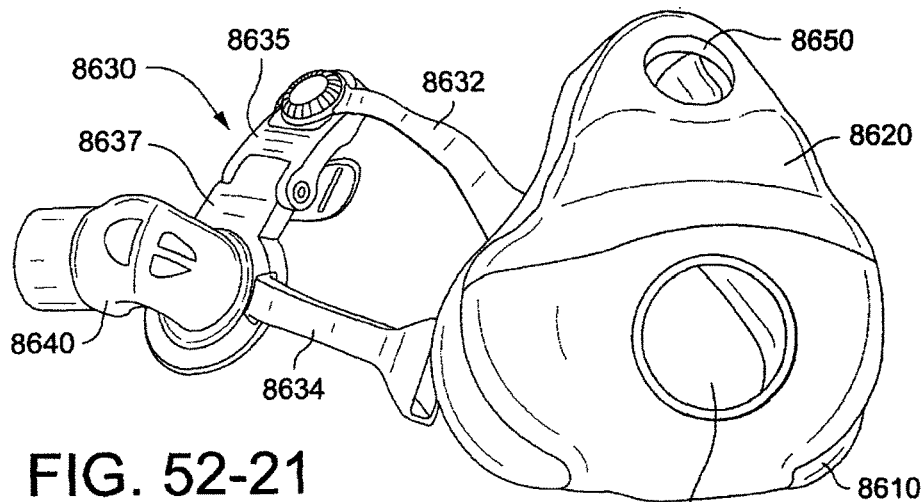
Figures 22, 52:
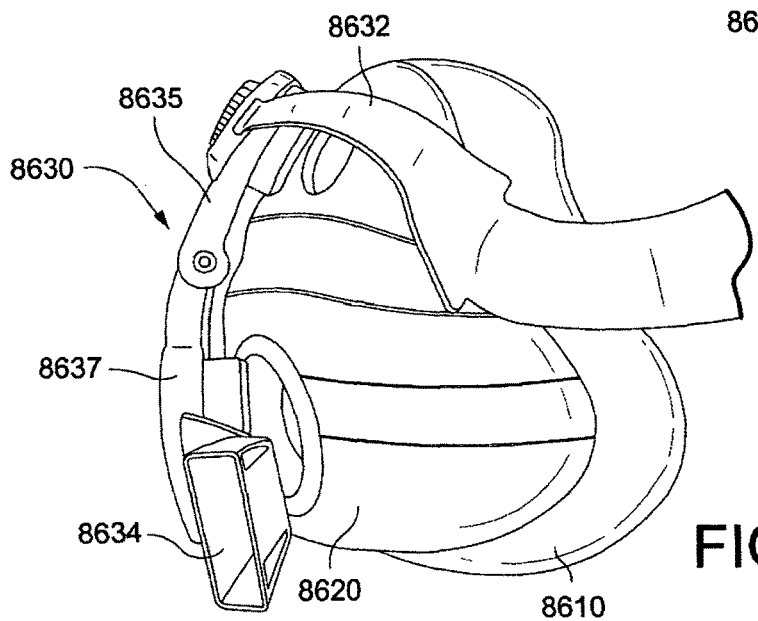

FIGS. 52-1 and 52-2 illustrate a cushion 8100 including a general "bike-seat" type shape that may be shape-changed between sizes. FIG. 52-1 shows a medium size of the cushion and FIG. 52-2 shows a small size of the cushion. In this embodiment, the mouth width is kept generally constant across sizes, and the nose width is minimized to adjust size. As shown in FIG. 52-3, the bottom half of frame may be modified so that the cushion-to-frame interface 3401 guides the cushion towards the center of the mask, thereby assisting in the shape change.

In an embodiment, the side wall of the cushion in the shape changing or transition region of the cushion may thinned out, which provides the cushion with more flexibility. This may allow the cushion to predominately deform into the nose rather than deform away from the frame.

In an embodiment, as shown in FIG. 52-4, supports 3402 may be provided to the frame in the nasal bridge region, e.g., to prevent the walls of the cushion from rolling into the nose and hence occluding the patient's nares.

In an embodiment, as shown in FIGS. 52-5 and 52-6, an adjustable region or gusset 3516 may be provided to the cushion, e.g., to add stiffness to the cushion wall and prevent the wall from deforming away from the frame. FIG. 52-5 shows a small size of the cushion and FIG. 52-6 shows a medium size of the cushion.

FIG. 52-7 illustrates an exemplary frame 8200 including upper and lower frame portions 8202, 8204 to accommodate the cushion and allow the cushion to deform into the desired shape. As illustrated, the upper and lower frame portions 8202, 8204 may each provide a cushion channel 8206 to receive the cushion.

FIGS. 52-8 and 52-9 illustrate a cushion 8300 including a general "pear" shape that may be shape-changed between sizes. FIG. 52-8 shows a medium size of the cushion and FIG. 52-9 shows a small size of the cushion. In this embodiment, the mouth width is increased to adjust size.

During compression of the cushion to a small size, a flare out of the outer and inner membrane may occur. The following provides alternative examples to prevent flare outs. For example, as shown in FIG. 52-10, one or more ribs 8400 (e.g., silicone beads) may be provided to the membrane to increase stiffness and reduce or prevent the membrane from flaring out. FIGS. 5-10 to 5-12 shows membrane flaring outwards to some extent—the additional stiffening elements have reduced the flaring outwards. To further reduce or prevent flaring out, the stiffeners may increase in size or be combined so as to maintain the membrane in an inwardly curved position. In FIG. 52-11, the outer membrane may be extra curled, e.g., strips of silicone 8402 provided to the membrane in flare out areas. The strips may be placed on an angle to extend the membranes curvature and help constrain the membrane to prevent flare out. In FIG. 52-12 the outer membrane may include thickened regions 8404 on flare out areas.

FIGS. 52-13 and 52-14 illustrate a general "pear" shaped cushion 8500 provided with an adjustable region or gusset 8510, e.g., to add stiffness to the cushion.

FIGS. 52-15 to 52-22 show a cushion 8610 supported by a flexible frame 8620, and an adjustment mechanism 8630 (including upper and lower headgear connectors 8632, 8634 and supporting an elbow 8640) coupled to the frame and structured to adjust the sealing profile. For example, the adjustment mechanism include upper and lower portions 8635, 8637 that are pivoted to one another to allow relative movement between the portions for adjustment. FIGS. 52-15, 52-17, and 52-19 show the cushion adjusted to a larger size, and FIGS. 52-16, 52-18, 52-20 show the cushion adjusted to a smaller size. As shown in FIGS. 52-21 and 52-22, "high value" components (e.g., adjustment mechanism 8630, headgear connectors 8632, 8634, and elbow 8640) separate as a sub-assembly from a disposable/interchangeable cushion 8610/frame 8620. This arrangement allows choice of cushion/frame materials, e.g., silicone, foam, gel, etc. As illustrated, two circular openings 8650, 8652 (e.g., see FIG. 52-21) are provided in the cushion frame to accommodate the adjustment mechanism with easy fit, removal, and sealing. The cushion frame is relatively rigid to allow the adjustment mechanism to snap in and also provide rigidity in non-shape changing areas.

Figure 53:
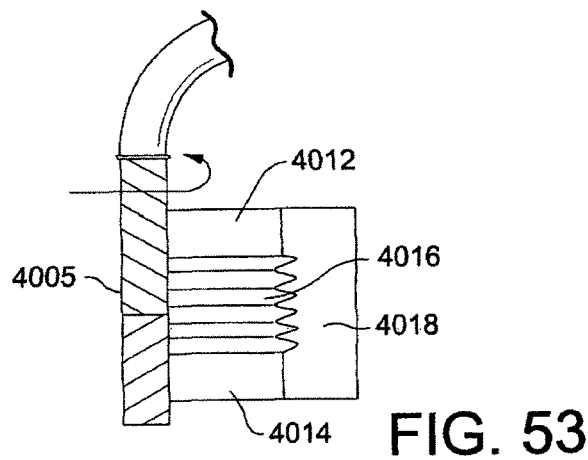
FIG. 53 shows a cushion and adjustment mechanism according to an embodiment of the present technology.

FIG. 53 shows another arrangement in which the cushion is supported by over-the-head tubing. As illustrated, upper and lower frame portions 4012, 4014 are provided to the cushion 4018, with an adjustable region or gusset 4016 between the frame portions. The over-the-head tubing includes a tube portion 4005 threadably engaged with one or both of the upper and lower frame portions 4012, 4014 such that rotation of such tube portion 4005 effects relative movement of the upper and lower frame portions and hence height adjustment of the cushion 4018.

3.17 Integrated Cushion and Frame Region (Fascia)

In an embodiment, the cushion and frame components may be integrally formed as a one-piece structure, i.e., a single molded part. This arrangement eliminates a cushion to frame interface (e.g., thereby eliminating potential leaks at the interface between the cushion and frame) and eliminates multiple parts. In an exemplary embodiment, the integrated cushion and frame may be molded of an elastomeric material such as silicone (e.g., 40 Shore A silicone).

FIGS. 115 to 118 illustrate an integrated cushion and frame 7100 according to an embodiment of the technology. As illustrated, the integrated cushion and frame 7100 includes a cushion region 7102, a frame region 7104, and an adjustable region or gusset region 7106. As described above, the cushion region provides membrane 7103 adapted to form a seal with the patient's face in use, and the cushion region is flexible, compressible and/or stretchable so as to allow the length and/or shape of the cushion region to change. The frame region defines a mask interior breathing chamber and is adapted to support or otherwise shape at least a portion of the cushion region. The adjustable region provides a substantially flexible region adapted to alleviate the mechanical resistance of the cushion and frame regions to stretching and compression which changes cushion sizing. The adjustable region transitions into the cushion membrane profile resulting in a series of 'scooped out' regions along the side. The location of this 'scoop out' has been optimized to reduce stress on the cushion profile during shape change without affecting seal performance.

The front of the frame region includes two apertures, e.g., a lower aperture 7110 to accommodate an elbow and an upper aperture 7112 to accommodate a vent insert.

In use, the integrated cushion and frame may be provided to an external skeleton which provides a rigid support structure, an actuation or adjustment mechanism to adjust the size, and structure for attaching headgear.

3.17.1 Undercushion Support Structure

The following provides alternative embodiments of an undercushion support structure to support the membrane.
Separately Formed and Attached In the exemplary embodiment of FIGS. 117 and 118, an undercushion support structure (not shown) to support the membrane 7103 is molded separately from the integrated cushion and frame 7100 and then attached thereto (e.g., by grafting). To aid location of the undercushion support structure, the integrated cushion and frame 7100 includes a defined shoulder 7114 running along an inside surface thereof and one or more integrated rib features 7116. However, it should be appreciated that an undercushion support structure may be integrally formed in one piece with the integrated cushion and frame 7100.
Undercushion Fingers FIGS. 119 to 122 illustrate an arrangement wherein a continuous flap-type undercushion 7205 is provided along side of nose SN and corner regions C of the cushion, and individual spaced part undercushion fingers 7215 are provided along cheek regions CH of the cushion. In this embodiment, no undercushion is provided in the nasal bridge region NB and upper lip or chin regions UL, i.e., membrane 7103 only. This arrangement of no undercushion along a longitudinal axis of the cushion enhances flexibility of the cushion along its longitudinal axis.

The undercushion fingers provide sufficient support to the cushion in the sealing direction without inhibiting the stretch or compression of the cushion in this region during size change. This is achieved by locating the fingers at the peaks of the gusset geometry where deformation is minimal during size change. The undercushion fingers 7215 include a similar curvature to the undercushion 7205, however the undercushion fingers are thicker in profile to compensate for the non-continuous structure of the fingers.

Figure 123:
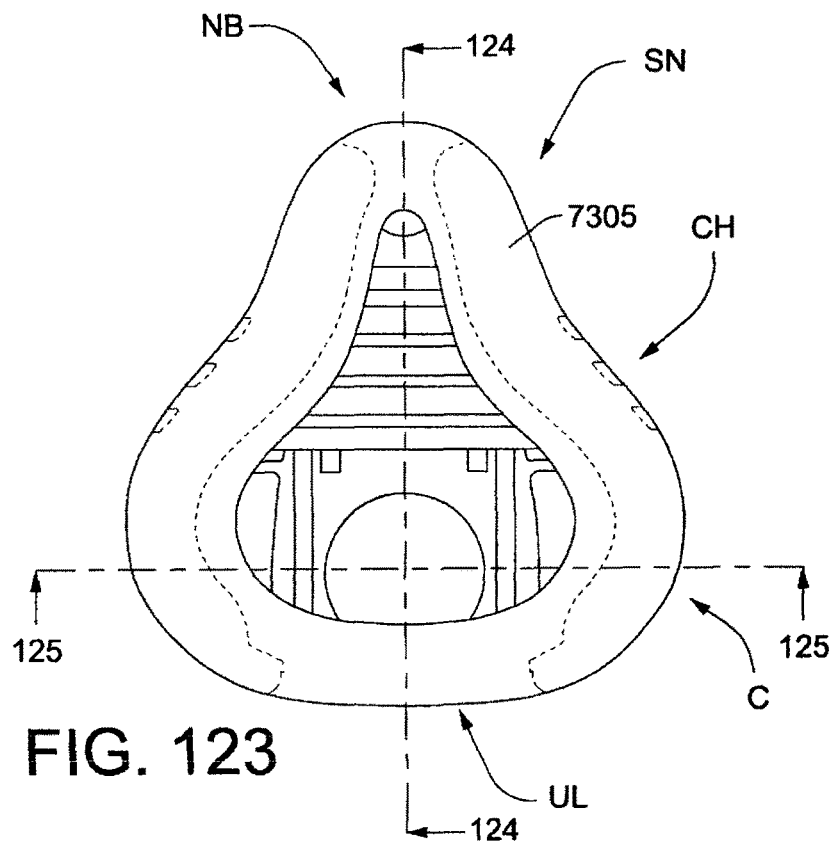
FIG. 123 is a rear view of an integrated cushion and frame according to another embodiment of the technology.
Figure 124:
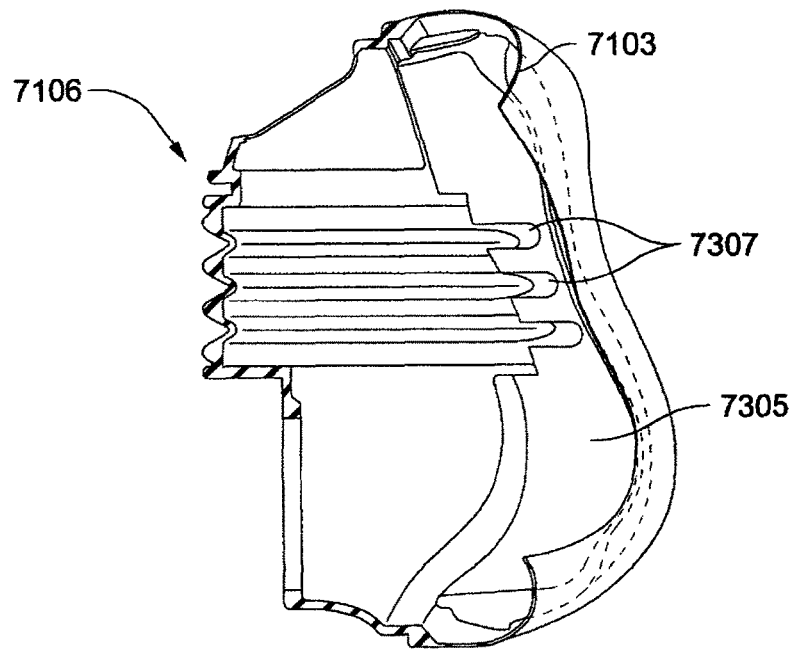
FIGS. 124 and 125 are cross-sectional views through the integrated cushion and frame of FIG. 123.
Figure 125:
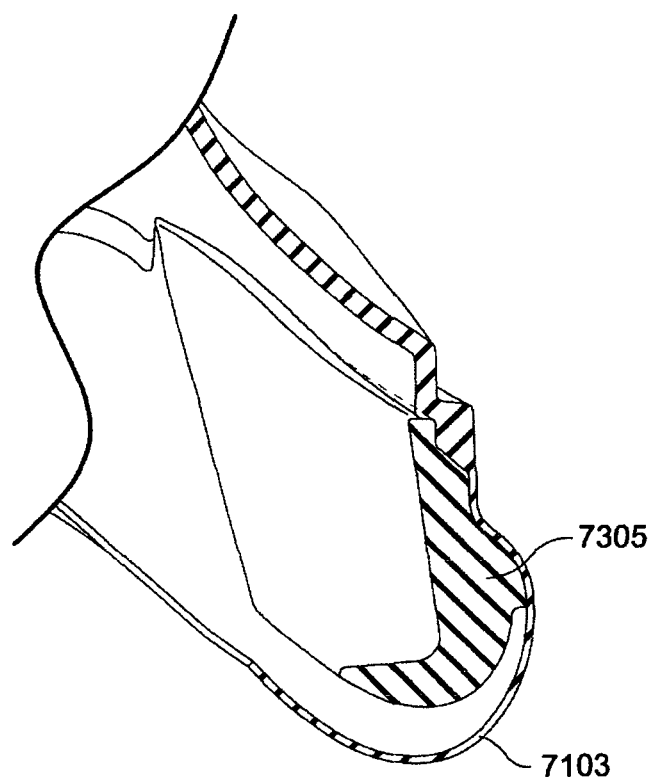

In an embodiment, the undercushion and undercushion fingers may be integrally molded in one piece (e.g., 40 Shore A or similar silicone) along with the integrated cushion and frame 7100.
Low Duro Undercushion FIGS. 123 to 125 illustrate an arrangement wherein a low durometer undercushion 7305 (e.g., 2-10 Shore A hardness material) is provided along the side of nose SN, cheek CH, and corner regions C of the cushion. In this embodiment, no undercushion is provided in the nasal bridge region NB and upper lip or chin regions UL, i.e., membrane 7103 only. This arrangement of no undercushion along a longitudinal axis of the cushion enhances flexibility of the cushion along its longitudinal axis. As shown in FIG. 125, the undercushion 7305 is thicker in profile to compensate for the lower hardness material.

The undercushion 7305 provides sufficient support to the cushion in the sealing direction while reducing the force required to adjust the cushion size by using a soft and flexible undercushion structure and also optimizing geometry in the gusset region. As shown in FIG. 124, stress reliefs 7307 are provided to the undercushion 7305 in the gusset region 7106 to allow stretch and compression in this region with minimal force.

In an embodiment, the undercushion (e.g., 2-10 Shore A hardness silicone or TPE) may be molded in one piece along with the integrated cushion and frame 7100 (e.g., 40 Shore A hardness silicone or TPE), e.g., dual durometer molding.

Low Duro

Figure 126:
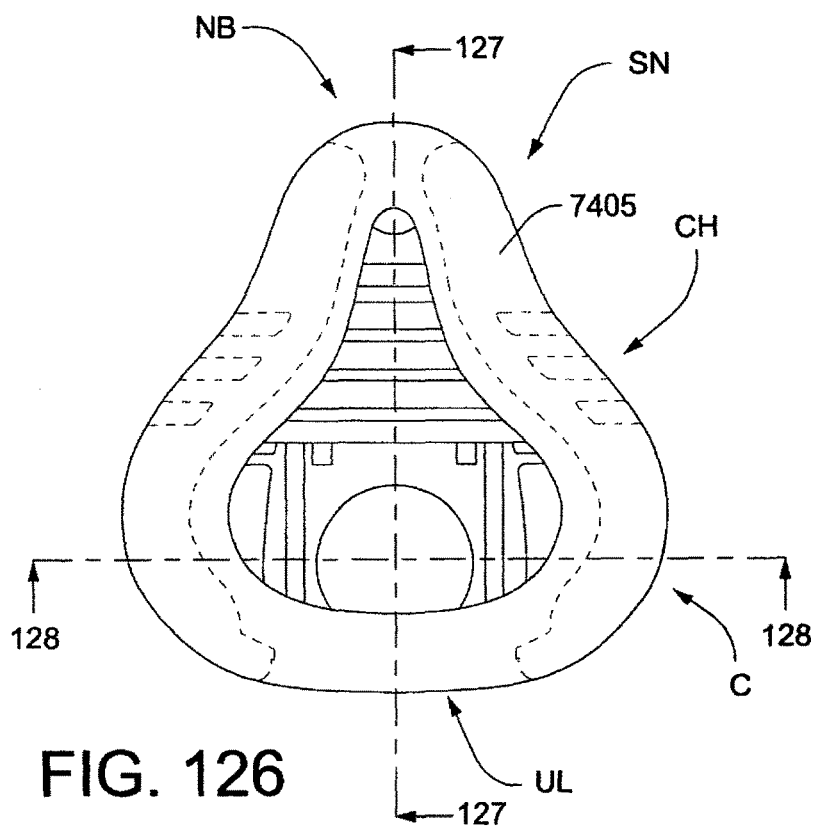
FIG. 126 is a rear view of an integrated cushion and frame according to another embodiment of the technology.
Figure 127:
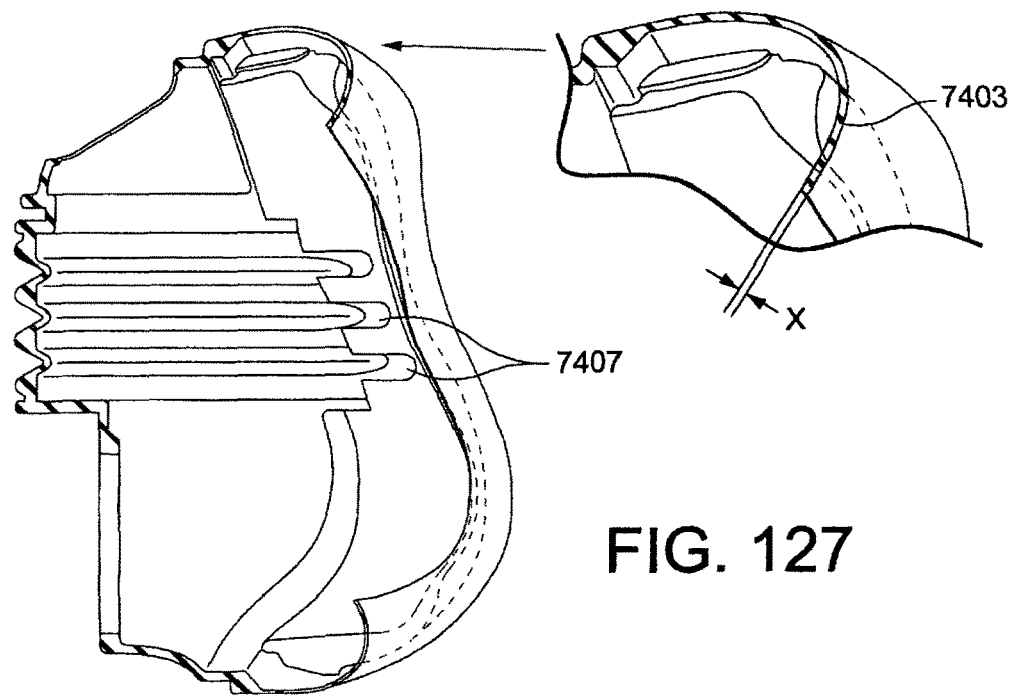
FIGS. 127 and 128 are cross-sectional views through the integrated cushion and frame of FIG. 126.
Figure 128:
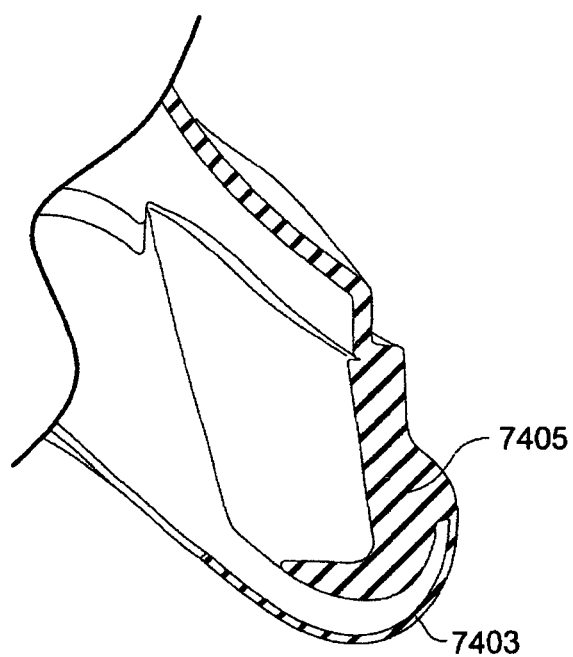

FIGS. 126 to 128 illustrate an arrangement wherein a low durometer material (e.g., 2-10 Shore A hardness material) is utilized for both the undercushion 7405 and the membrane 7403. In this embodiment, the undercushion is provided along the side of nose SN, cheek CH, and corner regions C of the cushion, and no undercushion is provided in the nasal bridge region NB and upper lip or chin regions UL. This arrangement of no undercushion along a longitudinal axis of the cushion enhances flexibility of the cushion along its longitudinal axis.

This arrangement allows the cushion to be molded with conventional molding technology, e.g., dual durometer molding not required. This arrangement provides sufficient support to the cushion in the sealing direction while reducing the force required to adjust the cushion size by using a soft and flexible material for the entire cushion. Similar to the embodiment of FIGS. 123 to 125, stress reliefs 7407 may be provided to the undercushion in the gusset region to allow stretch and compression in this region with minimal force (see FIG. 127).

Similar to the embodiment of FIGS. 123 to 125, the undercushion 7405 is thicker in profile to compensate for the lower hardness material (see FIG. 128). In this embodiment, the membrane 7403 has been made thicker (e.g., than the membrane of FIGS. 115 to 125) to compensate for the lower hardness material. For example, as shown in the enlarged detailed view of FIG. 127, the thickness X of the membrane 7403 is about 0.7-1.0 mm. In contrast, such thickness in the previous embodiments of FIGS. 115 to 125 is about 0.3-0.5 mm.

3.17.2 Single Wall Cushion

The following provides alternative embodiments of single wall cushion, i.e., membrane only with no undercushion support structure.

First Exemplary Embodiment of Single Wall Cushion

Figure 129:
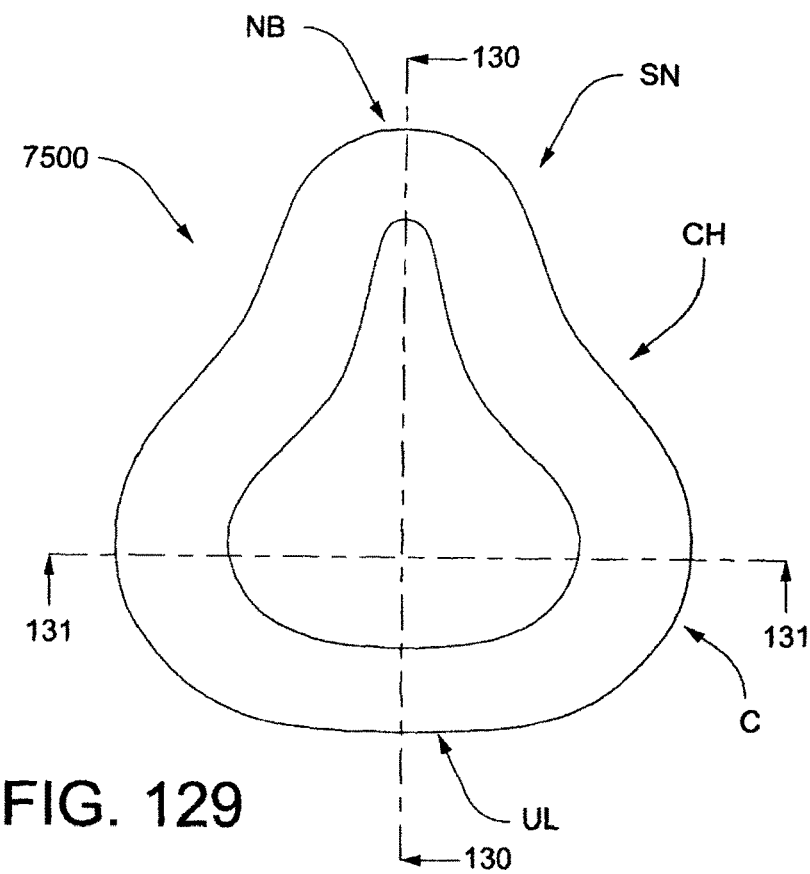
FIG. 129 is a front view of a cushion according to another embodiment of the technology.
Figure 130:
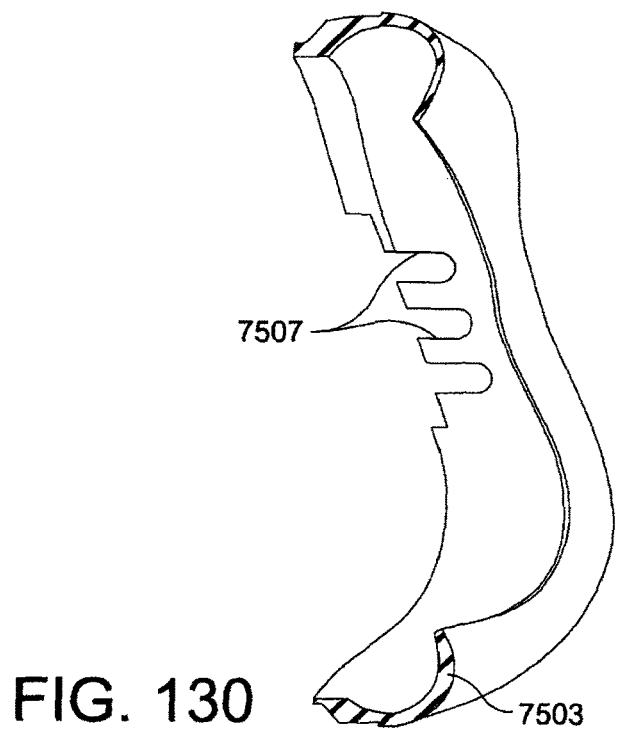
FIGS. 130 and 131 are cross-sectional views through the cushion of FIG. 129.
Figure 131:
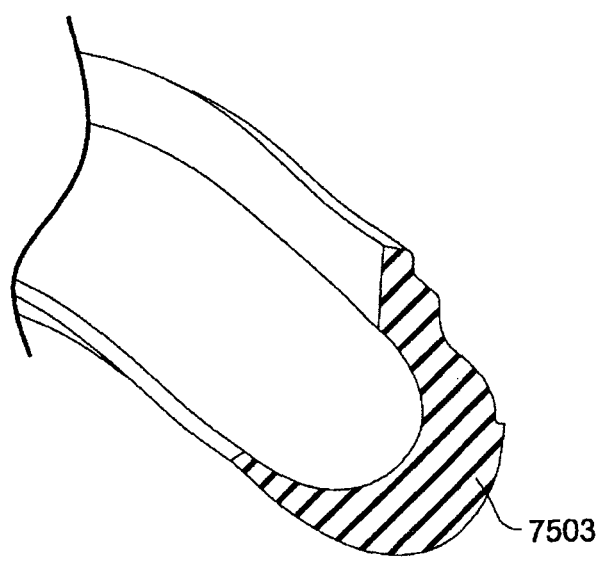
Figure 132:
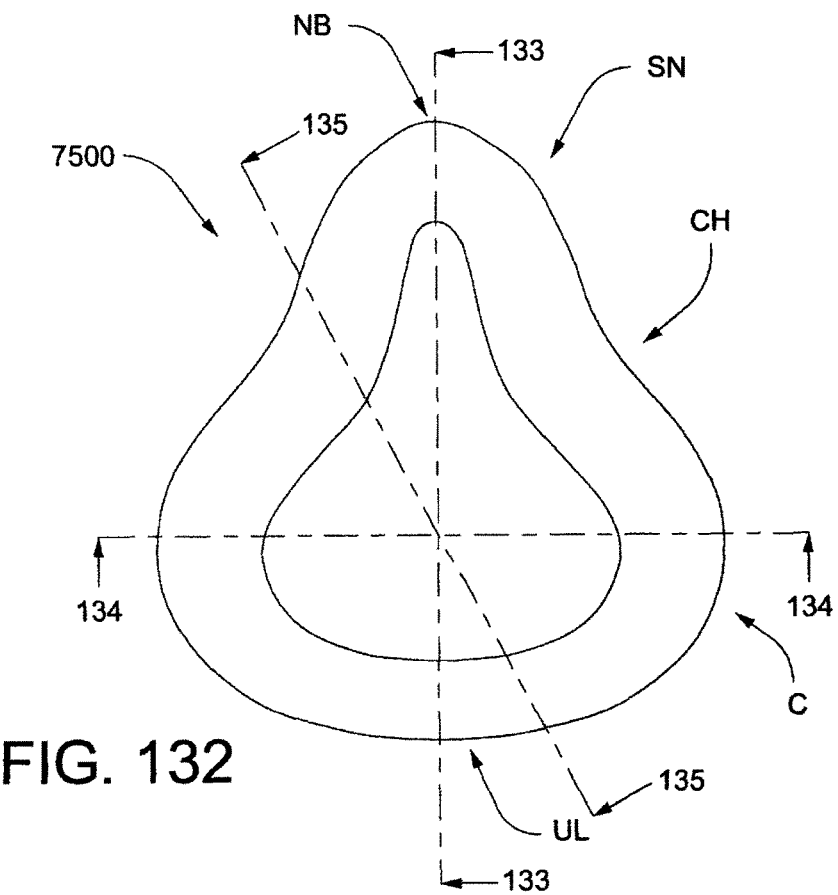
FIG. 132 is a front view of a cushion according to another embodiment of the technology.

FIGS. 129 to 131 illustrate a cushion 7500 including only a membrane 7503 about its perimeter, i.e., no undercushion support structure. The cushion is constructed of a low durometer material (e.g., 2-10 Shore A hardness material), and the thickness of the membrane is varied in different regions of the cushion to provide similar functionality to a dual wall cushion, i.e., membrane and undercushion.

By using a soft and flexible low durometer material (e.g., 2-10 Shore A silicone) instead of a traditional higher durometer material (e.g., 40 Shore A silicone), the force required to adjust the cushion size is lowered. Additionally, a low durometer material accommodates a similar degree of flexibility and conformance with a significantly thicker wall section when compared to a 40 Shore A silicone. An exemplary benefit of having a thicker cushion section is that it is more resistant to pinching and buckling which may occur during size change.

In an embodiment, the cushion cross-sections are varied such that the membrane is thickest in the corner regions C of the cushion, thicker in the side of nose and cheek regions SN, CH, and thinnest in the nasal bridge region NB and upper lip or chin regions UL.

FIG. 130 shows a cross section of the membrane in its thinnest regions, which provides the cushion with sufficient flexibility to inflate to optimize seal and comfort. FIG. 131 shows a cross section of the membrane along one of its thicker regions, which region may function as a support structure and resist bottoming out while maintaining a degree of conformity.

As shown in FIG. 130, stress reliefs 7507 may be provided in the gusset region to aid size adjustment. The cushion 7500 may be attached (e.g., grafted) to a frame region or fascia or the cushion may be integrated or molded in one piece with a fascia.

Second Exemplary Embodiment of Single Wall Cushion

FIGS. 132 to 135 illustrate a single wall cushion 7600 according to another embodiment of the technology. As with the embodiment of FIGS. 129-131, the cushion 7600 only includes a membrane 7603 about its perimeter, and the thickness of the membrane varies about the perimeter to provide similar functionality to a dual wall cushion.

In this embodiment, the geometry or curvature of the membrane 7603 may be similar to the geometry of the undercushion in cushions disclosed in PCT Application No. PCT/AU2010/000657, entitled Nasal Mask System filed May 28, 2010, which claims the benefit of U.S. Provisional Application Nos. 61/213,326, filed May 29, 2009, 61/222,711, filed Jul. 2, 2009, 61/272,162, filed Aug. 25, 2009, 61/272,250, filed Sep. 4, 2009, 61/263,175, filed Nov. 20, 2009, and 61/282,693, filed Mar. 18, 2010, and Australian Provisional Application Nos. 2009902524, filed 2 Jun. 2009, and 2009906101, filed 15 Dec. 2009, each of which is incorporated herein by reference in its entirety. In the embodiment of FIGS. 129 to 131, the geometry or curvature of the membrane 7503 may be similar to the geometry of the membrane in cushion disclosed in such PCT application.

As illustrated, a thin lip of material 7609 extends off the membrane 7603. This thin lip 7609 extends around the entire perimeter of the cushion and is configured to seal through inflation.

Figure 133:
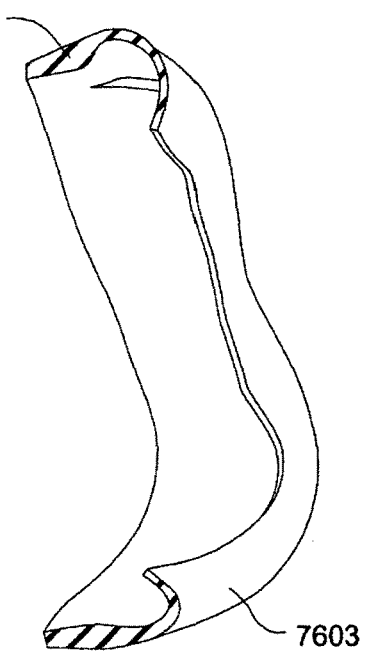
Figure 134:
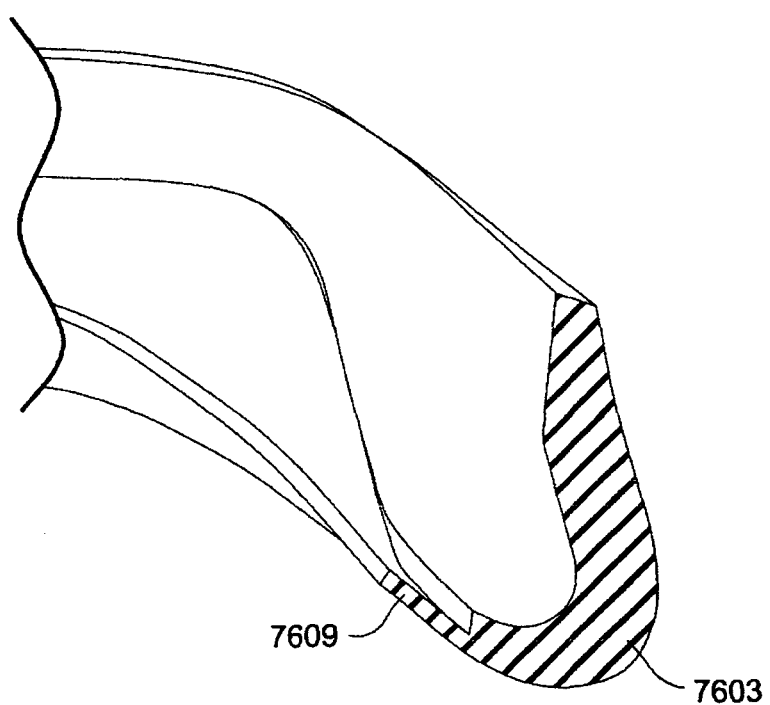
Figure 135:
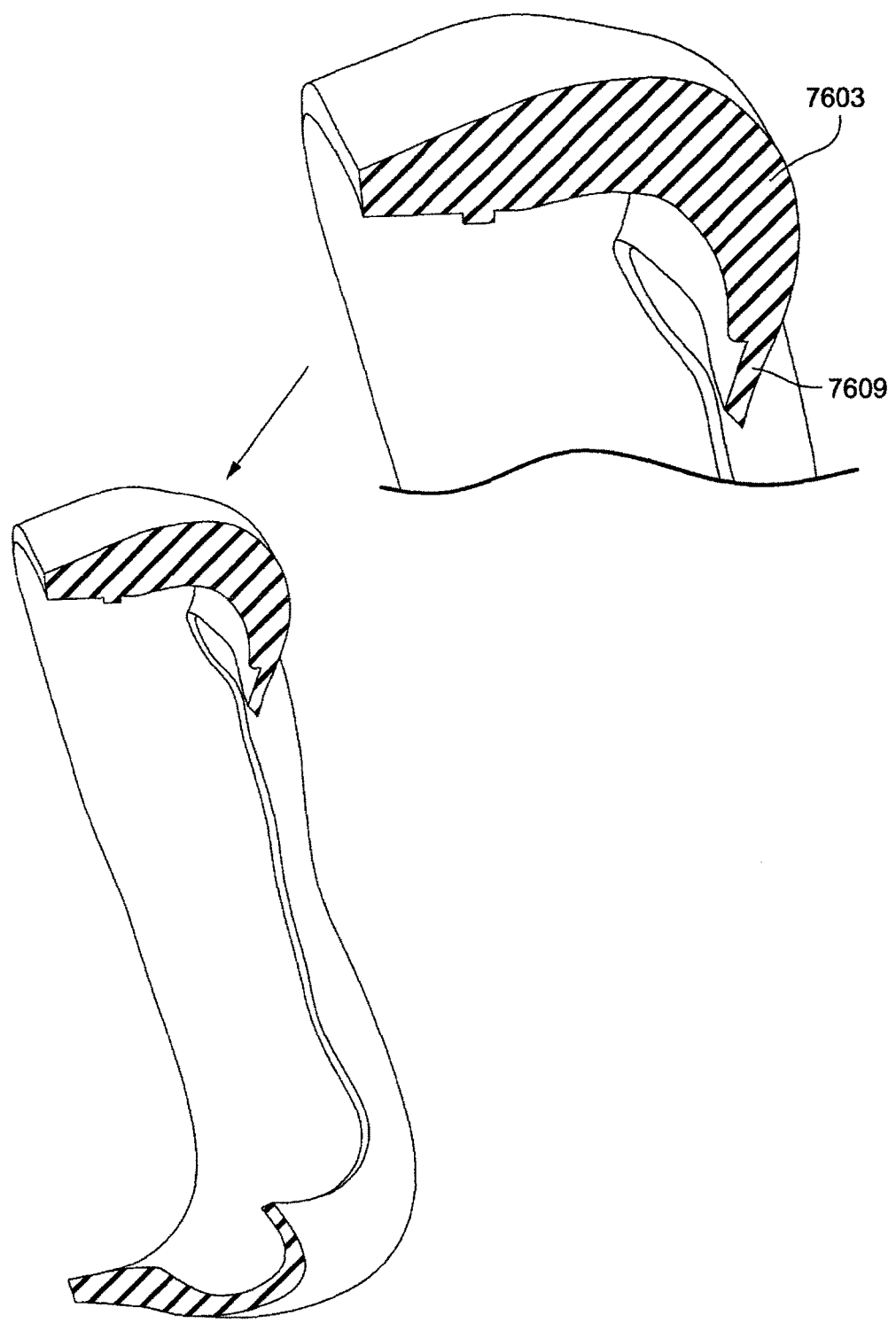
Figure 136:
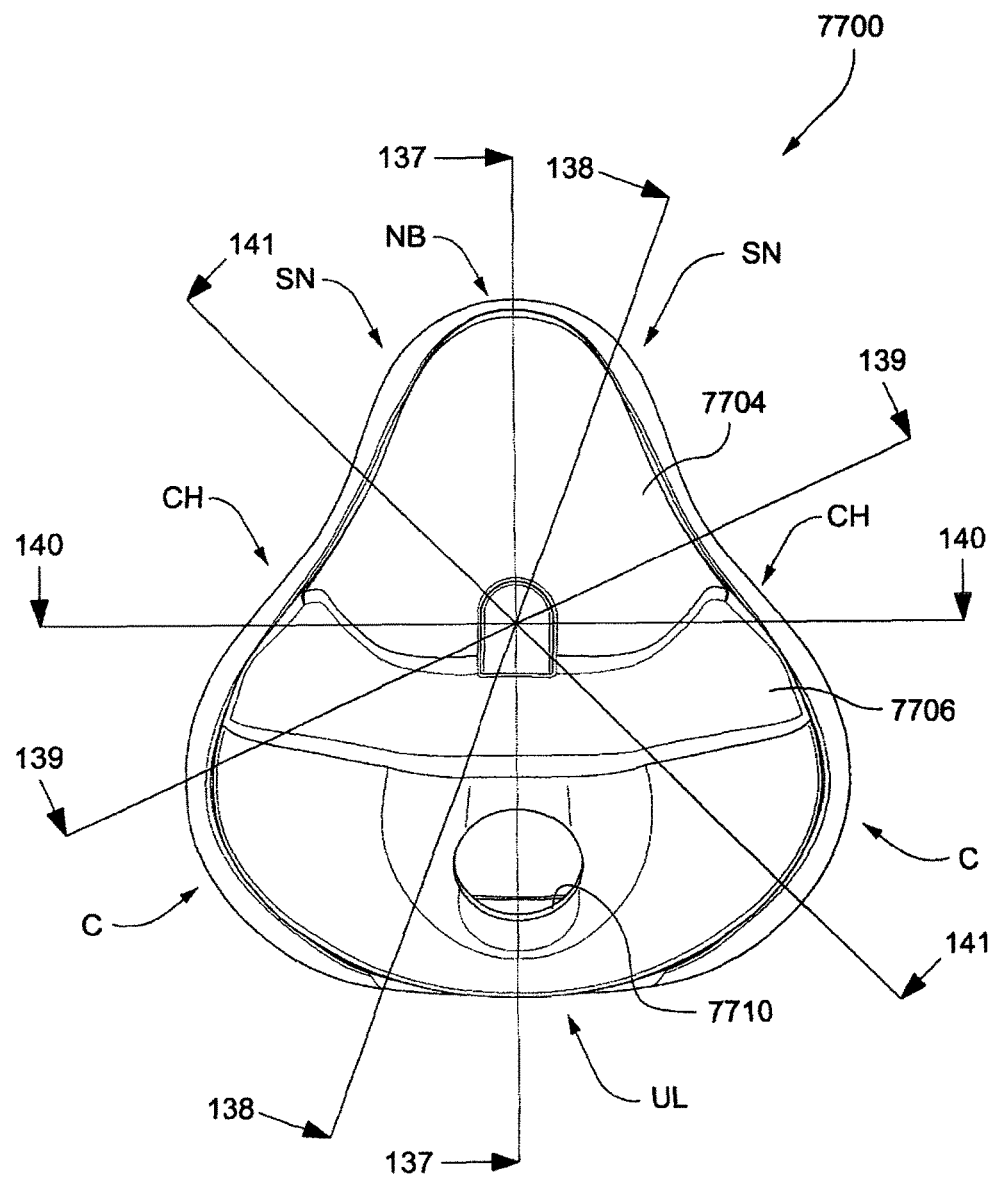

FIG. 133 shows that a tapering wall section 7611 is employed at the top and base of the cushion to enhance flexibility so the membrane can inflate to optimize seal and comfort. FIG. 134 shows a cross section of the membrane along one of its thicker regions, which region may function as a support structure and resist bottoming out while maintaining a degree of conformity.

As with the embodiment of FIGS. 129-131, the cushion 7600 is constructed of a low durometer material (e.g., 2-10 Shore A hardness material). By using a soft and flexible material instead of traditional 40 Shore A silicone, the relative force required to adjust the cushion size can be lowered. Additionally, a low durometer material accommodates a similar degree of sealing flexibility and conformance with a significantly thicker wall section when compared to a 40 Shore A silicone. An exemplary benefit of having a thicker cushion section is that it is more resistant to pinching and buckling which will occur during size change.

Third Exemplary Embodiment of Single Wall Cushion

FIGS. 136 to 141 illustrate an integrated cushion and frame 7700 according to an embodiment of the technology. As illustrated, the integrated cushion and frame 7700 includes a cushion region 7702, a frame region 7704, and an adjustable region or gusset region 7706. The front of the frame region includes an aperture 7710 to accommodate an elbow.

As described above, the cushion region includes only a membrane 7703 about its perimeter. The integrated cushion and frame may be constructed of a low durometer material (e.g., 2-10 Shore A hardness material), and the thickness of the membrane is varied in different regions of the cushion to provide similar functionality to a dual wall cushion, i.e., membrane and undercushion. For example, the cushion cross-sections are varied such that the membrane is thinnest in the nasal bridge region NB and upper lip or chin regions UL (see FIG. 137) and thicker in the side of nose, cheek, and corner regions SN, CH, C.

Figure 137:
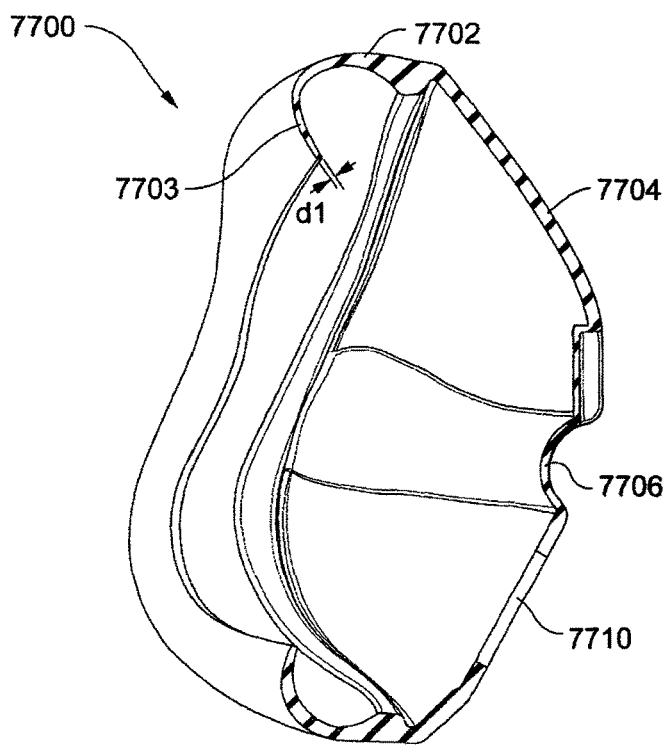
Figure 138:
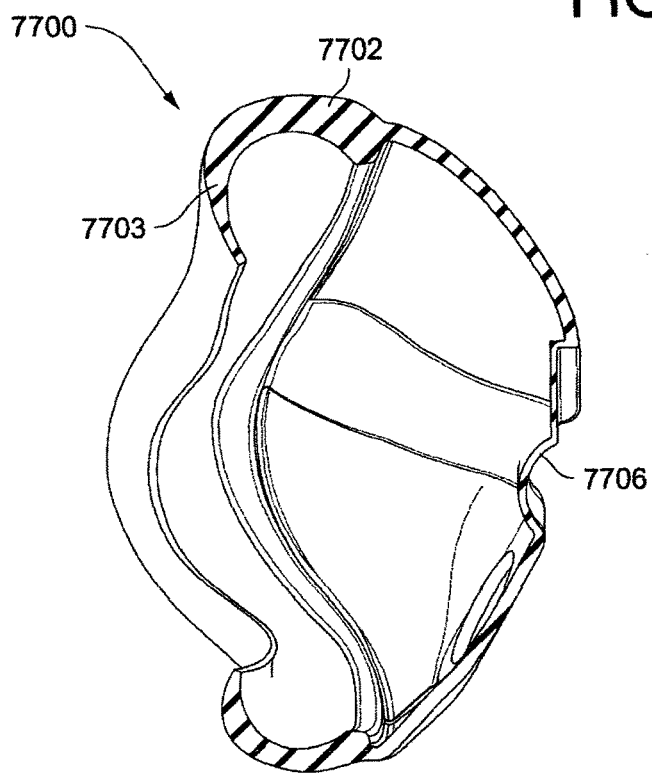
Figure 139:
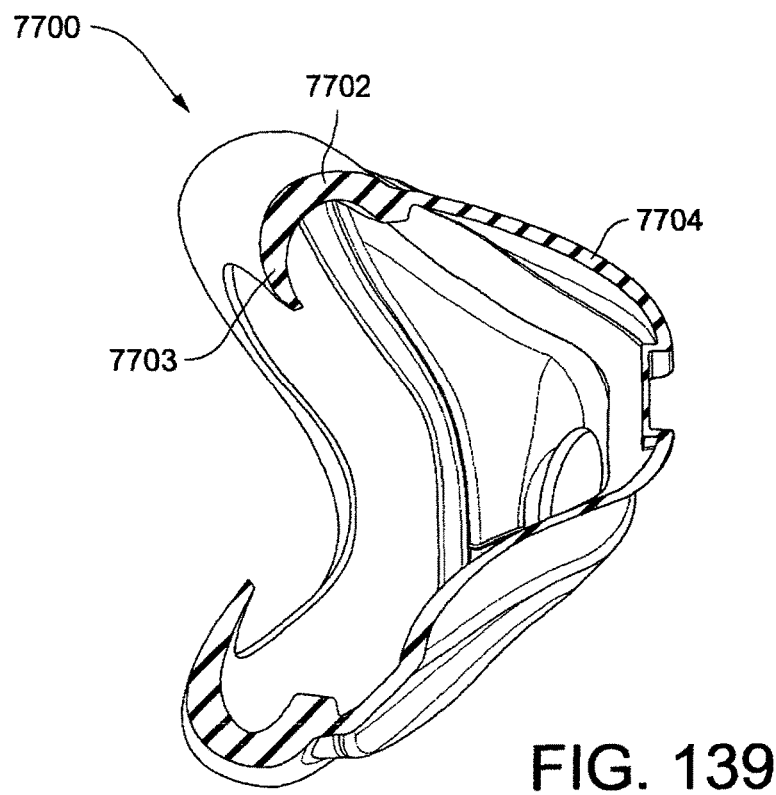
Figure 140:
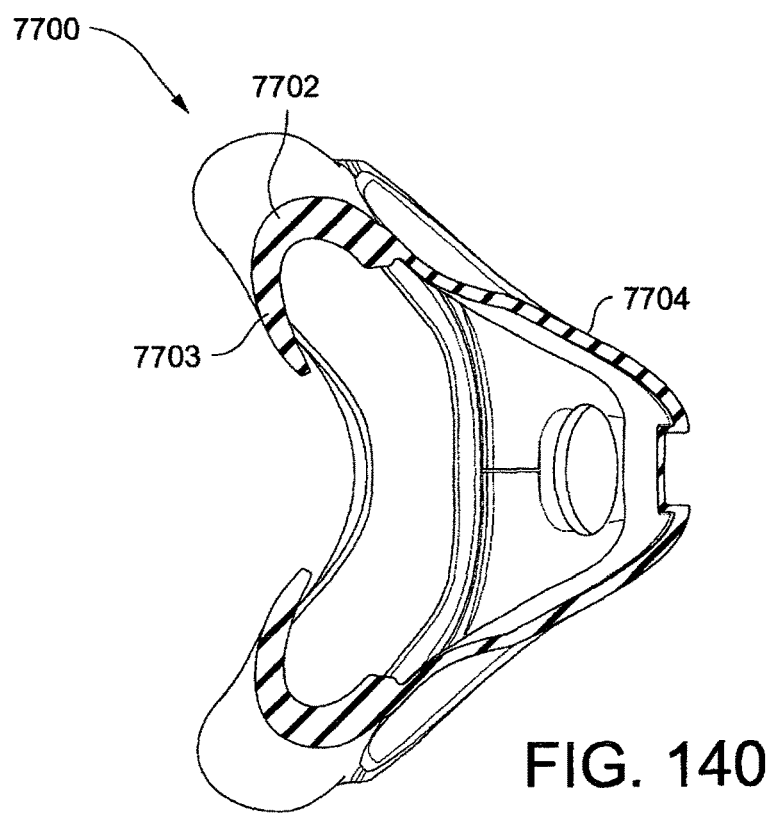
Figure 141:
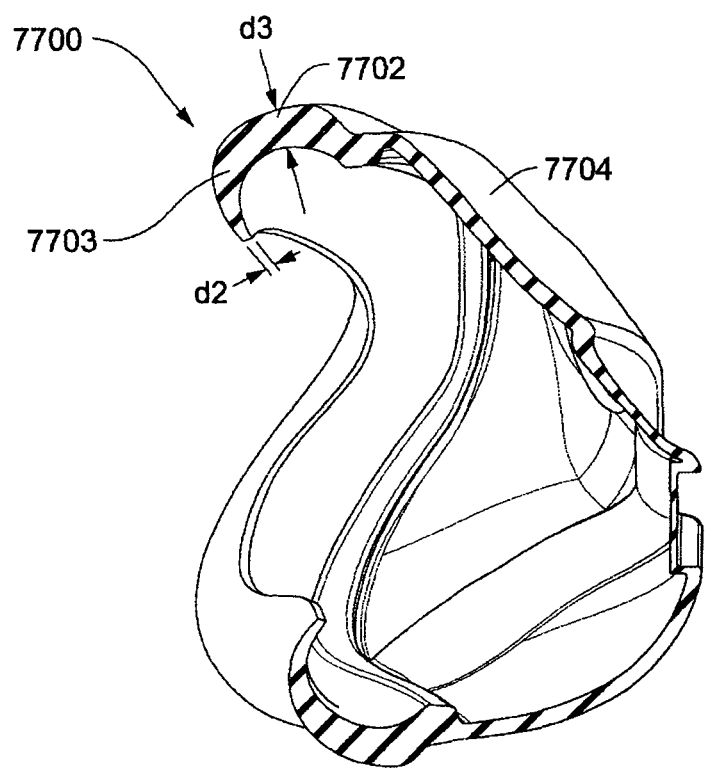

The membrane has been made thicker (e.g., than the membrane of FIGS. 115 to 125) to compensate for the lower hardness material. For example, as shown in FIG. 137, the thickness d1 of the membrane is about 0.7-1.0 mm (e.g., 0.8 mm). In contrast, such thickness in the previous embodiments of FIGS. 115 to 125 is about 0.3-0.5 mm. Also, as shown in FIG. 141, the thickness d2 of the membrane is about 1.0-1.5 mm (e.g., 1.2 mm), and the thickness d3 is about 1.5-3.5 mm (e.g., 2.5 mm).

One advantage of a mask system in accordance with the present technology is that it may be adjusted and that it can form a seal on a face of a patient so that positive pressure therapy may be provided to the patient. A further advantage of the present technology is that it may be adjusted while on a patient's face making it simpler and or easier to fit a patient. A further advantage of the present technology is that the mask system will maintain a seal while being adjusted. Another advantage of the present technology is that it permits fine adjustment, e.g. less than about 1 mm, as well as coarse adjustment, e.g. greater than about 2 to 3 mm. Another advantage of a mask system in accordance with the present technology is that the mask system may be adjusted via one adjustment point, simplifying and improving ease of use. An advantage of a mask system in accordance with the present technology is that it provides an mechanism to facilitate controlled adjustment of a first part of mask system relative to a second part of a mask system without skewing the relative positions of the two parts of the mask system. An advantage of a mask system in accordance with the present technology is that it provides an adjustment mechanism which is relatively easy to clean, for example by avoiding overlapping regions, recessed regions, closed away regions and other locations in which dirt or bacteria may accumulate. An advantage of a mask system in accordance with an aspect of present technology is the avoidance of leak paths in a seal forming portion, for example as may be provided by creases or overlapping sections. An advantage of a mask system in accordance with an aspect of present technology is that it provides an adjustment mechanism which can provide adjustment without impingement of facial features, e.g. a nose region, and which is readily adjustable without being impinged upon by other mask features, e.g. an elbow. An advantage of the present technology is that it provides a mask system that includes first and second mask portions which may be adjusted relative to one another, and the mask system further includes in one form headgear attachment points on the first and on the second mask portions While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A mask system for delivery of a flow of air at a continuously positive pressure to an entrance to a patient's airways, wherein the mask system is configured to maintain a therapy pressure in a range of about 2-30 cmH$_2$O to ameliorate sleep disordered breathing, the mask system comprising:
   a sealing portion including:
      a sealing surface that is continuous along a perimeter of the sealing portion, the sealing surface adapted to form a seal that is continuous around the patient's nose or the patient's nose and mouth in use;
      an opening configured to receive the patient's nose or the patient's nose and mouth in use;
      an upper region configured to seal at or near the patient's nasal bridge region; and
      a lower region configured to seal at or near the patient's chin region or the patient's top lip region, and the sealing portion comprising a deformable material;
   a supporting portion connected to the sealing portion to support the sealing portion in a sealing position on the patient in use;
   an adjustable portion adapted to adjust the supporting portion to modify a length dimension of the sealing portion from a first position to a second position by deforming the sealing portion, the length dimension measured between the upper region and the lower region; and
   an adjustable breathing chamber defined at least in part by the sealing portion and configured to communicate the flow of air to the patient's airways,
   wherein the sealing portion is adapted to form the seal around the patient's nose or the patient's nose and mouth in the first position and the second position to maintain the therapy pressure, and
   wherein the sealing portion is configured such that the opening increases in width at the upper region as the length dimension of the sealing portion increases.

2. The mask system of claim 1, wherein the sealing portion comprises one continuous piece of material.

3. The mask system of claim 1, wherein the supporting portion is configured to be moved by the adjustable portion.

4. The mask system of claim 1, wherein the supporting portion is configured to at least partially define the adjustable breathing chamber.

5. The mask system of claim 1, wherein the supporting portion is configured to abut the sealing portion and change the length dimension of the sealing portion when the adjustable portion is adjusted.

6. The mask system of claim 1, wherein the supporting portion is configured to be positioned within the sealing portion.

7. The mask system of claim 1, wherein the sealing portion comprises a patient-contacting surface that is configured to conform to the patient's face.

8. The mask system of claim 1, wherein the supporting portion is configured to be detachably assembled with the sealing portion.

9. The mask system of claim 1, wherein the adjustable portion comprises a one piece construction with the sealing portion.

10. The mask system of claim 1, wherein the sealing portion further comprises a middle section, and the adjustable portion is connected integrally with the middle section of the sealing portion.

11. The mask system of claim 1, wherein the sealing portion comprises an upper sealing section, a lower sealing section, and a middle adjustable section.

12. The mask system of claim 1, wherein the sealing portion further comprises a non-patient-contacting side, and the supporting portion comprises a frame configured to be installed on the non-patient-contacting side of the sealing portion.

13. The mask system of claim 1, further comprising a mask body coupled to the sealing portion.

14. The mask system of claim 1, wherein the adjustable portion is configured such that the flow of air passes through the adjustable portion to provide the flow of air to the adjustable breathing chamber.

15. The mask system of claim 1, wherein the supporting portion includes a pair of upper headgear connectors and a pair of lower headgear connectors to connect headgear straps to the supporting portion.

16. A mask system for delivery of a flow of air at a continuously positive pressure to an entrance to a patient's airways, wherein the mask system is configured to maintain a therapy pressure in a range of about 2-30 cmH$_2$O to ameliorate sleep disordered breathing, the mask system comprising:
   a sealing portion including:
      a sealing surface that is continuous along a perimeter of the sealing portion, the sealing surface adapted to form a seal that is continuous around the patient's nose or the patient's nose and mouth; and
      an opening configured to receive the patient's nose or the patient's nose and mouth in use;
   a supporting portion connected to the sealing portion to support the sealing portion in a sealing position on the patient in use;
   an adjustable portion integrated with and part of the supporting portion such that the adjustable portion is configured to adjust the supporting portion; and
   an adjustable breathing chamber defined at least in part by the sealing portion and configured to communicate the flow of air to the patient's airways during use;
   wherein the sealing portion is constructed and arranged to be deformed by adjustment of the supporting portion by the adjustable portion to change a length dimension of the sealing portion,
   wherein the length dimension is measured between a first region of the sealing portion configured to seal at or near the patient's nasal bridge region and a second region of the sealing portion configured to seal at or near the patient's chin region or the patient's top lip region, and
   wherein the sealing portion is configured such that the opening increases in width at the first region as the length dimension of the sealing portion increases.

17. The mask system of claim 16, wherein the supporting portion includes a pair of upper headgear connectors and a pair of lower headgear connectors to connect headgear straps to the supporting portion.

18. A mask system for delivery of a flow of air at a continuously positive pressure to an entrance to a patient's airways, wherein the mask system is configured to maintain a therapy pressure in a range of about 2-30 cmH$_2$O to ameliorate sleep disordered breathing, the mask system comprising:
   a sealing portion including:
      a sealing surface that is continuous along a perimeter of the sealing portion, the sealing surface adapted to form a seal that is continuous around the patient's nose or the patient's nose and mouth; and
      an opening configured to receive the patient's nose or the patient's nose and mouth in use;
   a supporting portion connected to the sealing portion to support the sealing portion in a sealing position on the patient in use;
   a mechanism adapted to adjust the supporting portion to modify a height dimension of the sealing portion from a first position to a second position by deforming the sealing portion, the height dimension measured in a direction parallel to the patient's facial height when the mask system is worn by the patient; and
   an adjustable breathing chamber defined at least in part by the sealing portion and configured to receive communicate the flow of air to the patient's airways during use and when the sealing portion is in the first position and the second position,
   wherein the sealing portion is adapted to form the seal around the patient's nose or the patient's nose and mouth in the first position and the second position to maintain the therapy pressure within the adjustable breathing chamber, and
   wherein the sealing portion is configured such that the opening increases in width at a nose region of the sealing portion that is configured to seal at or near the patient's nasal bridge region as the height dimension of the sealing portion increases.

19. The mask system according to claim 18, wherein the supporting portion includes at least one intermediate member, an upper supporting portion, and a lower supporting portion, the upper supporting portion and the lower supporting portion connected by the at least one intermediate member.

20. The mask system according to claim 19, wherein the at least one intermediate member comprises an adjustable region having at least one fold to allow expansion or contraction.

21. The mask system according to claim 19, wherein the height dimension of the at least one intermediate member is variable due to adjustment of the mechanism, while a shape of a lower chin region or an upper lip region of the sealing portion remains generally constant.

22. The mask system according to claim 18, further comprising a locking member to prevent inadvertent actuation of the mechanism.

23. The mask system according to claim 18, wherein the supporting portion comprises a frame including an upper frame portion and a lower frame portion, and the mechanism is provided between the upper frame portion and the lower frame portion.

24. The mask system according to claim 18, wherein the sealing portion is configured to be compressed or stretched to adjust the height dimension of the sealing portion.

25. The mask system according to claim 18, wherein the sealing portion comprises a foam and/or a gel.

26. The mask system according to claim 18, wherein the mask system comprises at least one thermoformed portion.

27. The mask system according to claim 18, wherein the mechanism comprises parts that are selectively movable from the first position to the second position, either by a person or a machine.

28. The mask system according to claim 27, wherein the mechanism is structured to be operated by an actuator.

29. The mask system of claim 28, wherein the actuator is configured such that the flow of air passes through the actuator to provide gas to the adjustable breathing chamber.

30. The mask system according to claim 29, wherein the actuator comprises a dial.

31. The mask system according to claim 18, further comprising a headgear with a plurality of headgear straps adapted to anchor the mask system to the patient.

32. The mask system according to claim 18, further comprising a rotatable dial to adjust the mechanism.

33. The mask system according to claim 32, further comprising an elbow coupled to the supporting portion, the elbow passing through the center of the rotatable dial such that the elbow and dial are independently rotatable relative to one another about a common axis of rotation.

34. The mask system according to claim 18, wherein the sealing portion is adapted to be adjusted between a nasal mask configuration that seals around the patient's nose in use and a full-face mask configuration that seals around the patient's nose and mouth in use.

35. The mask system according to claim 18, wherein the sealing portion is adapted to be adjusted along the patient's top lip region.

36. The mask system according to claim 18, wherein the sealing portion is adapted to seal over different nasal bridge geometries of the patient.

37. The mask system according to claim 18, wherein the sealing portion further comprises a transition region, a mouth width, an upper sealing portion, and a lower sealing portion, the lower sealing portion configured to remain substantially constant in at least one aspect while the transition region or the mouth width of the sealing portion varies due to adjustment of the mechanism.

38. The mask system according to claim 18, wherein the sealing portion further comprises a mouth width, the sealing portion configured such that the mouth width remains substantially constant while the height dimension of the sealing portion increases.

39. The mask system of claim 18, wherein the supporting portion includes a pair of upper headgear connectors and a pair of lower headgear connectors to connect headgear straps to the supporting portion.

* * * * *